US006204388B1

(12) United States Patent
Danishefsky et al.

(10) Patent No.: US 6,204,388 B1
(45) Date of Patent: Mar. 20, 2001

(54) SYNTHESIS OF EPOTHILONES, INTERMEDIATES THERETO AND ANALOGUES THEREOF

(75) Inventors: Samuel J. Danishefsky, Englewood, NJ (US); Peter Bertinato, Old Lyme, CT (US); Dai-Shi Su; DongFang Meng, both of New York, NY (US); Ting-Chao Chou, Paramus, NJ (US); Ted Kamenecka, New York, NY (US); Erik J Sorensen, San Diego, CA (US); Aaron Balog; Kenneth A. Savin, both of New York, NY (US); Scott Kuduk, Harleysville, PA (US); Christina Harris; Xiu-Guo Zhang, both of New York, NY (US); Joseph R. Bertino, Branford, CT (US)

(73) Assignee: Sloan-Kettering Institute For Cancer Research, New York, NY (US)

( * ) Notice: Subject to any disclaimer, the term of this patent is extended or adjusted under 35 U.S.C. 154(b) by 0 days.

(21) Appl. No.: 09/257,072

(22) Filed: Feb. 24, 1999

Related U.S. Application Data

(63) Continuation-in-part of application No. 08/986,025, filed on Dec. 3, 1997.
(60) Provisional application No. 60/075,947, filed on Feb. 25, 1998, provisional application No. 60/092,319, filed on Jul. 9, 1998, provisional application No. 60/097,733, filed on Aug. 24, 1998, provisional application No. 60/032,282, filed on Dec. 3, 1996, provisional application No. 60/033,767, filed on Jan. 14, 1997, provisional application No. 60/047,566, filed on May 22, 1997, provisional application No. 60/047,941, filed on May 29, 1997, and provisional application No. 60/055,533, filed on Aug. 13, 1997.

(51) Int. Cl.[7] .................. C07D 213/127; C07D 277/22; C07D 209/10; C07D 307/38
(52) U.S. Cl. ...................... 546/340; 548/204; 548/510; 549/494; 549/498; 560/174
(58) Field of Search ............................ 546/340; 548/204, 548/510; 549/494, 498; 560/174

(56) References Cited

U.S. PATENT DOCUMENTS

| 5,021,430 | * | 6/1991 | Ksander | ................................ | 514/332 |
| 5,917,084 | * | 6/1999 | Jiang | ..................................... | 560/174 |
| 5,969,145 | * | 10/1999 | Schinzer et al. | ..................... | 548/110 |

* cited by examiner

Primary Examiner—Joseph McKane
Assistant Examiner—Sonya N Wright
(74) Attorney, Agent, or Firm—A. David Joran

(57) ABSTRACT

The present invention provides convergent processes for preparing epothilone A and B, desoxyepothilones A and B, and analogues thereof, useful in the treatment of cancer and cancer which has developed a multidrug-resistant phenotype. Also provided are intermediates useful for preparing said epothilones.

9 Claims, 102 Drawing Sheets

1: RαH: epothilone A
2: RxCH₃: epothilone B

Convergent strategy for a total synthesis of epothilone A (I).

P = unspecified protecting group

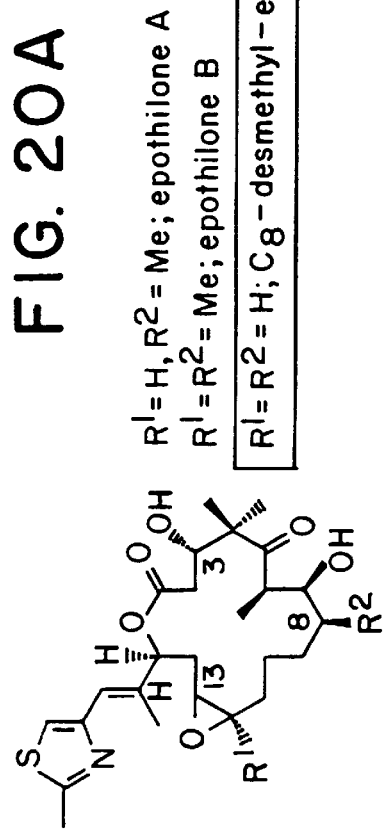
FIG. 19C
FIG. 20A
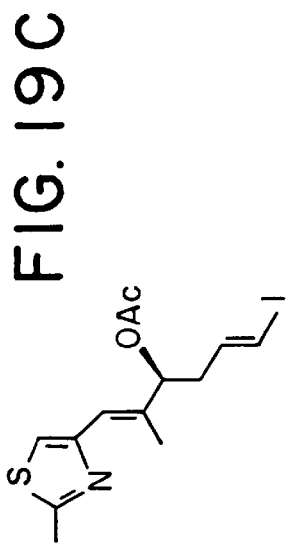
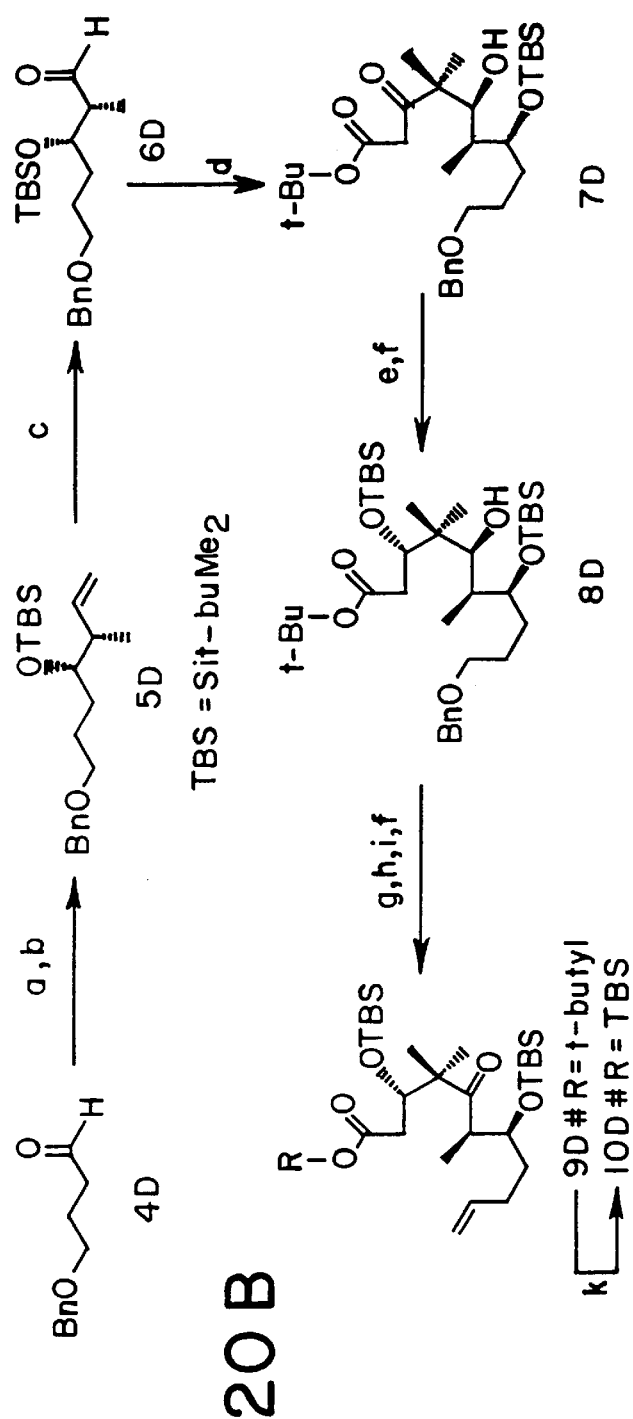
FIG. 20B

FIG. 22A
FIG. 22B
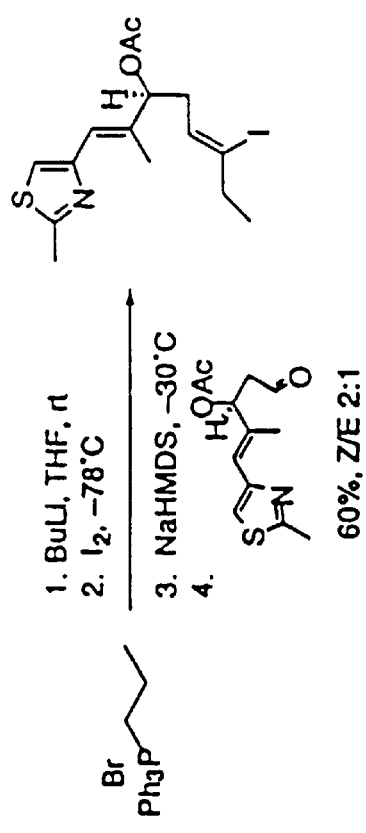
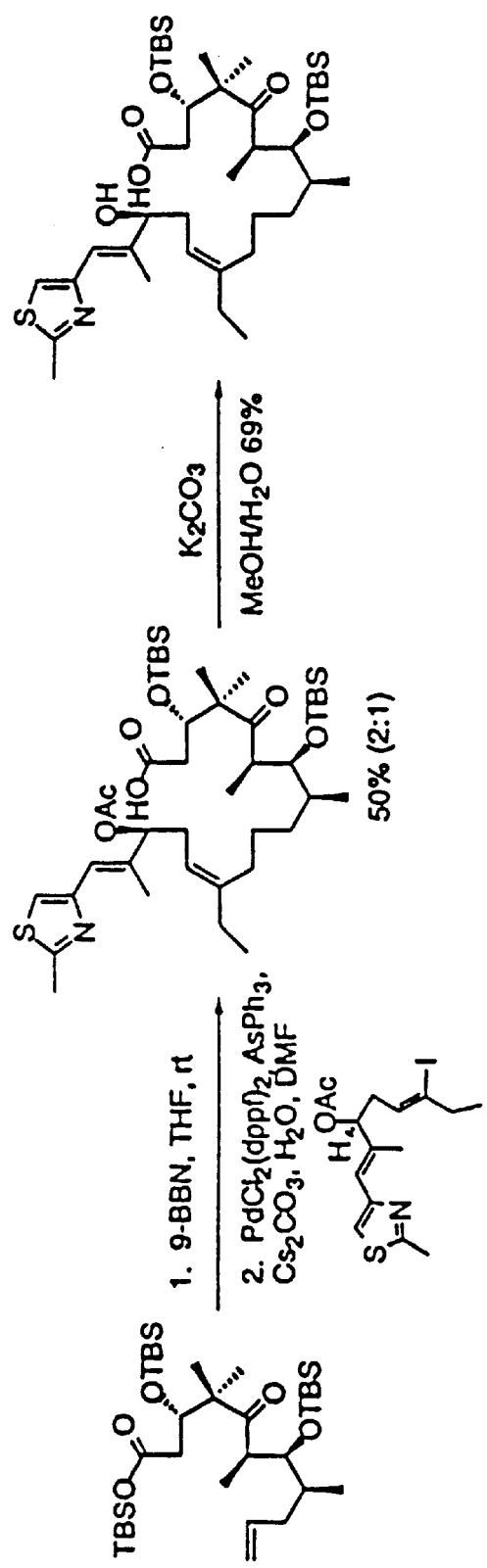

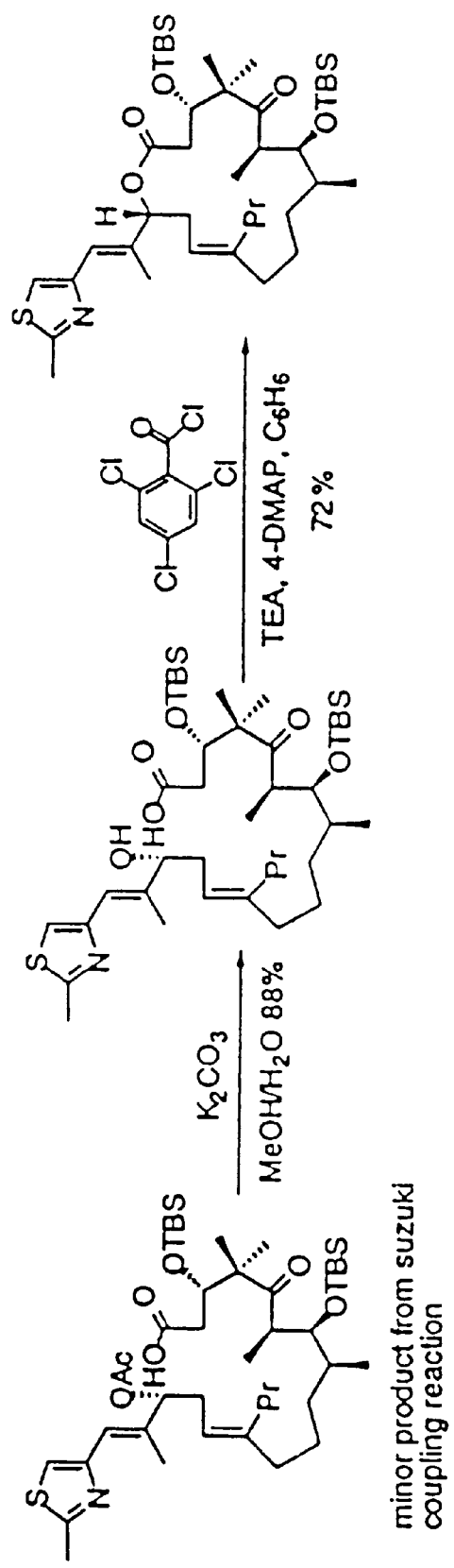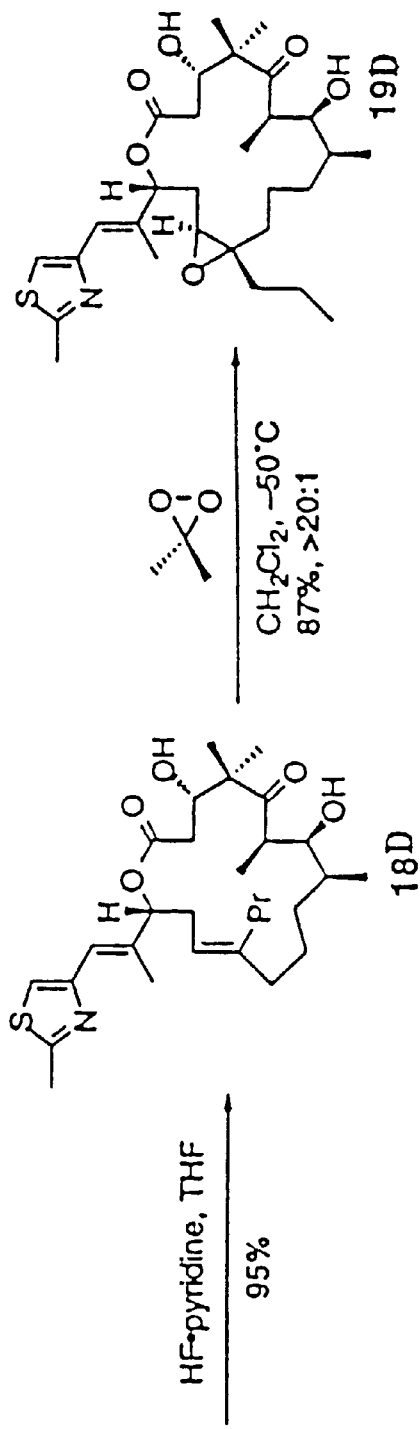
FIG. 24A
FIG. 24B

R = H, F, CF₃
R=H is the only compound completed, F and CF₃ are nearly completed

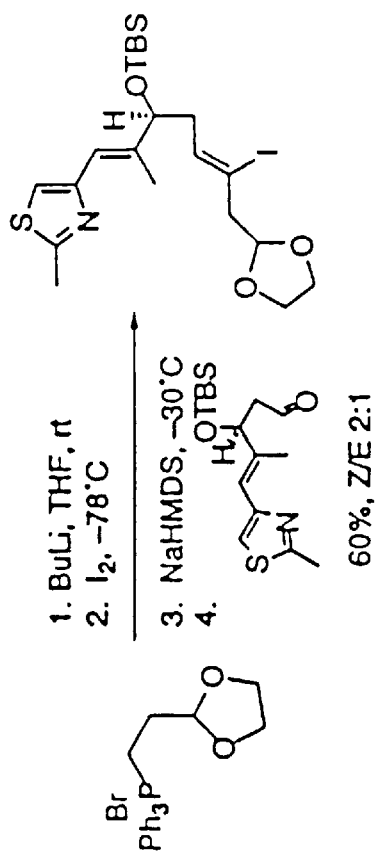
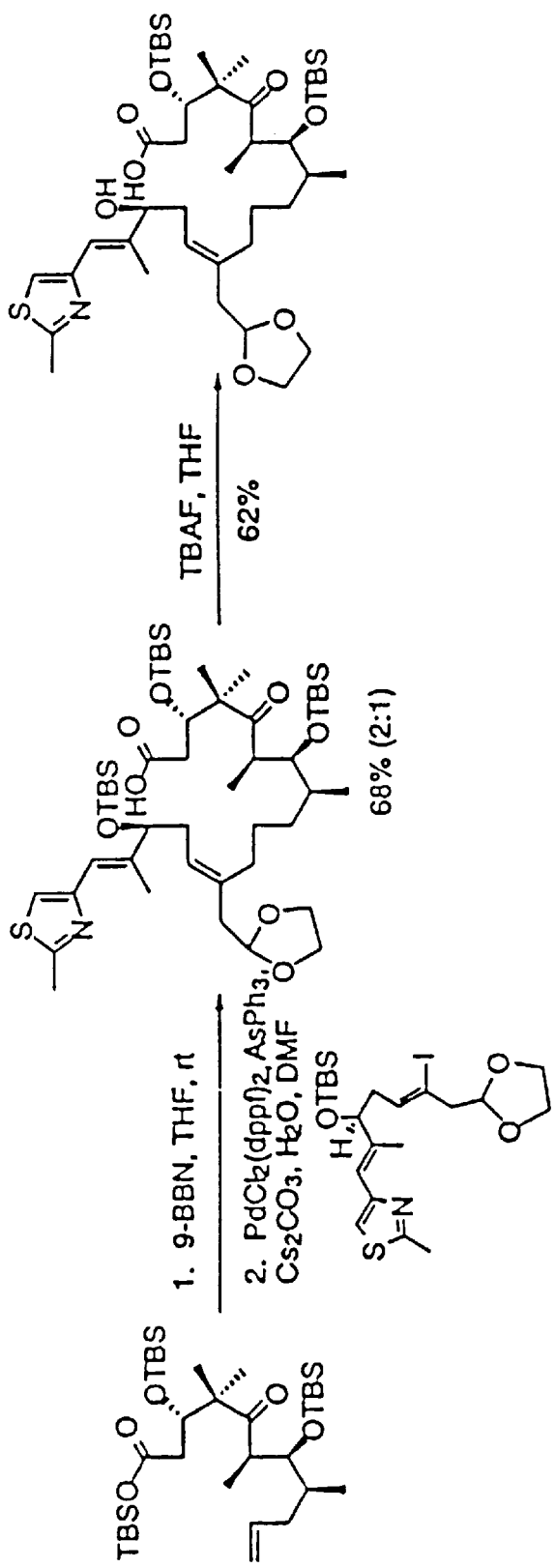
FIG. 27A
FIG. 27B

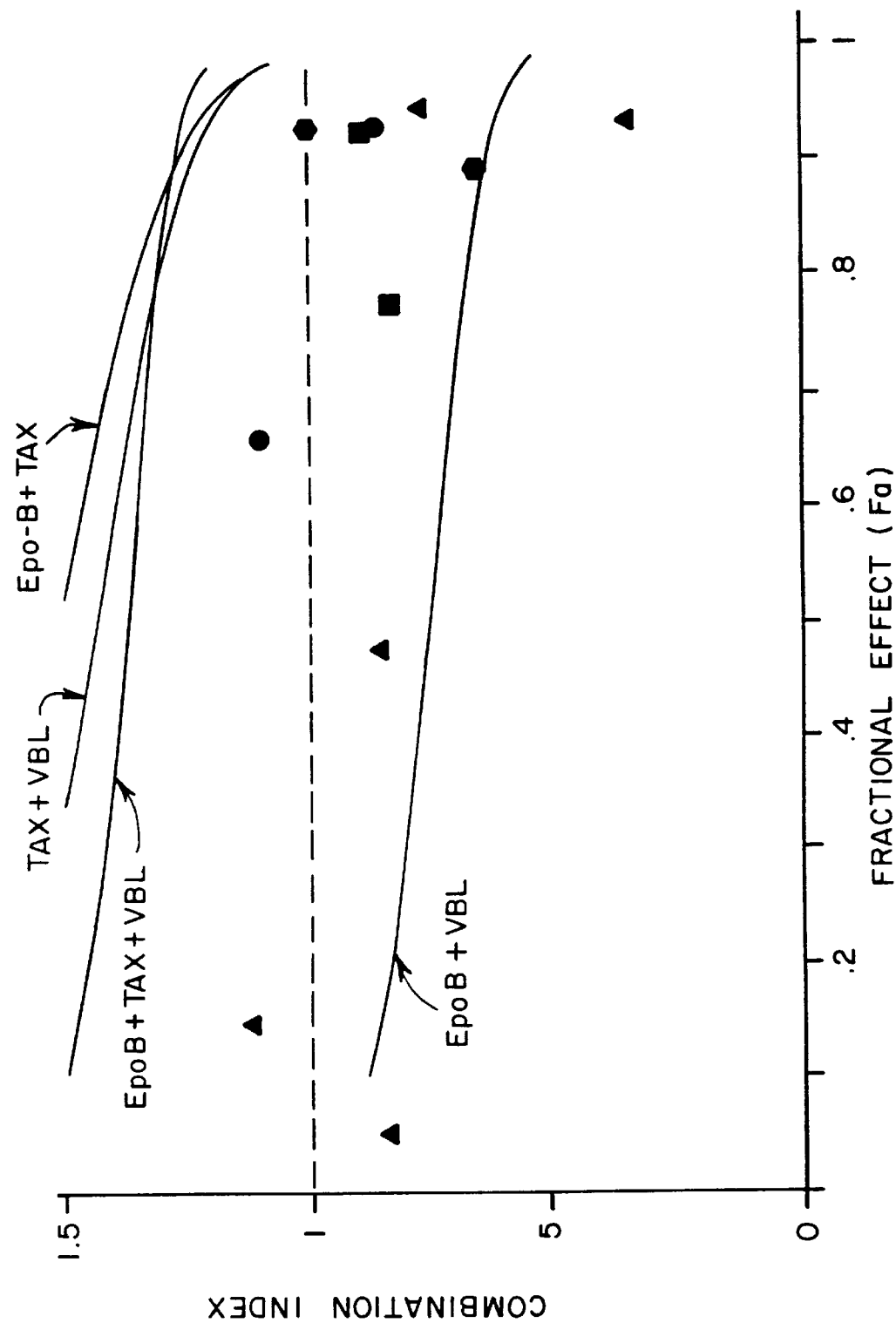

FIG. 40B
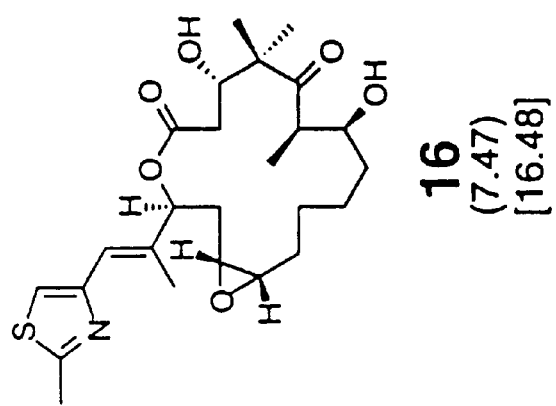
16
(7.47)
[16.48]
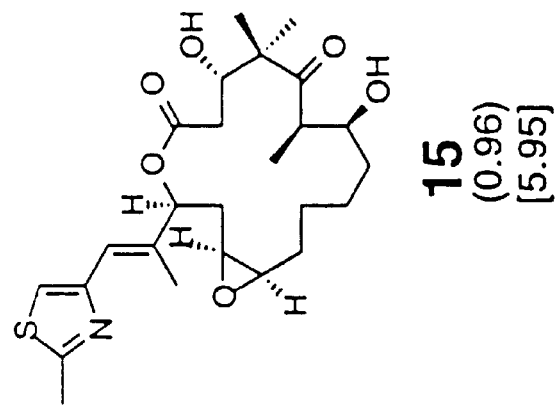
15
(0.96)
[5.95]
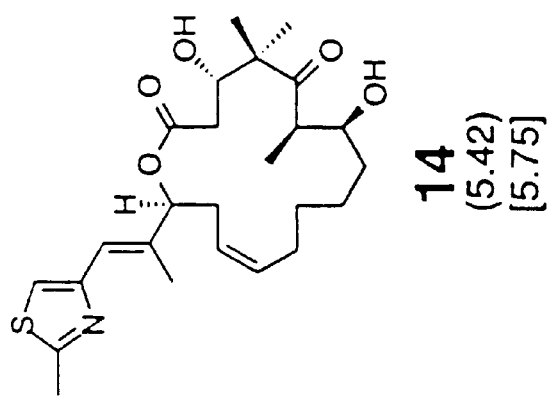
14
(5.42)
[5.75]

FIG. 41A
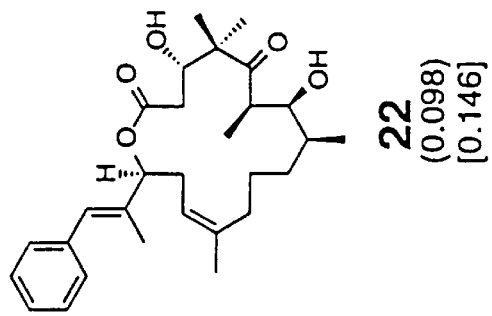
22
(0.098)
[0.146]
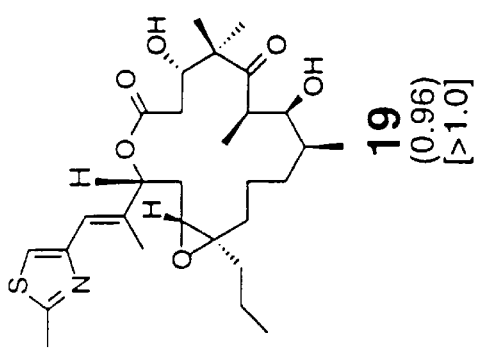
19
(0.96)
[>1.0]
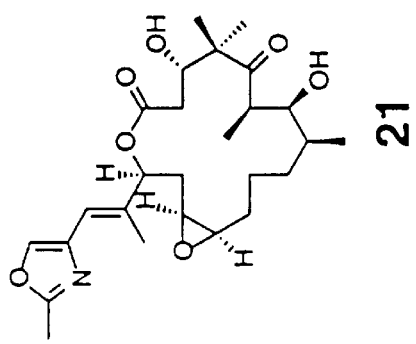
21
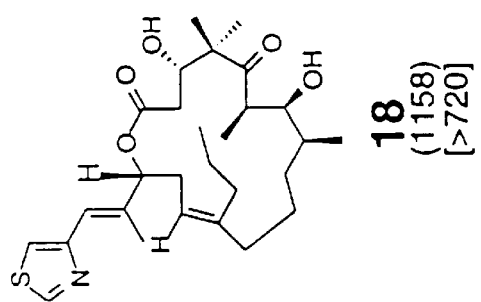
18
(1158)
[>720]
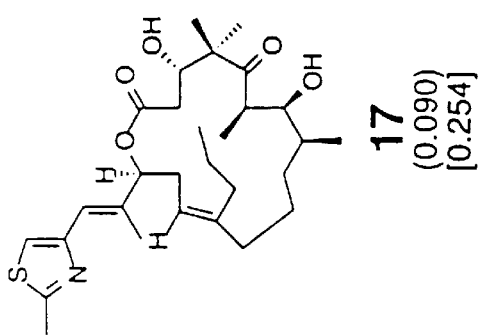
17
(0.090)
[0.254]
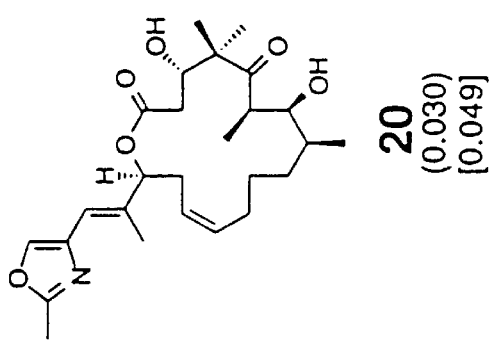
20
(0.030)
[0.049]

FIG. 41B
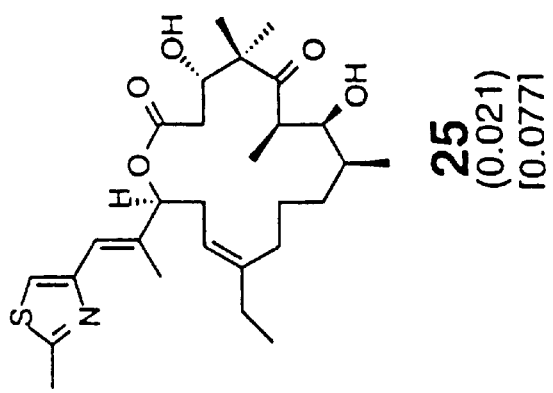
25
(0.021)
[0.077]
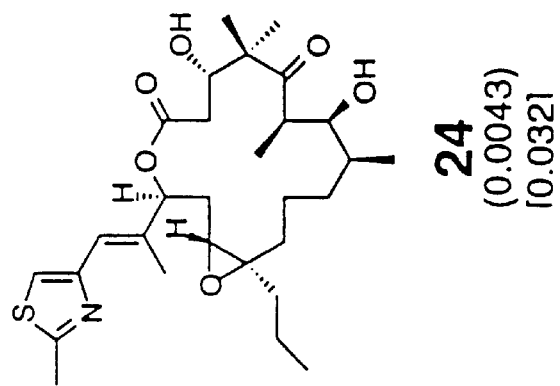
24
(0.0043)
[0.032]
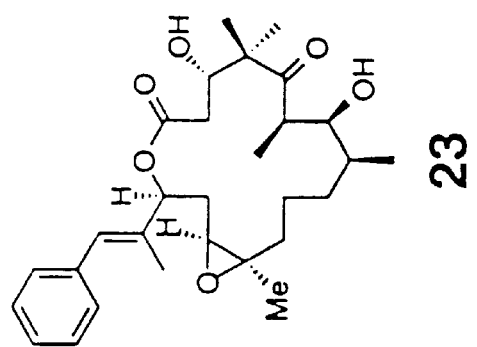
23

FIG. 42A
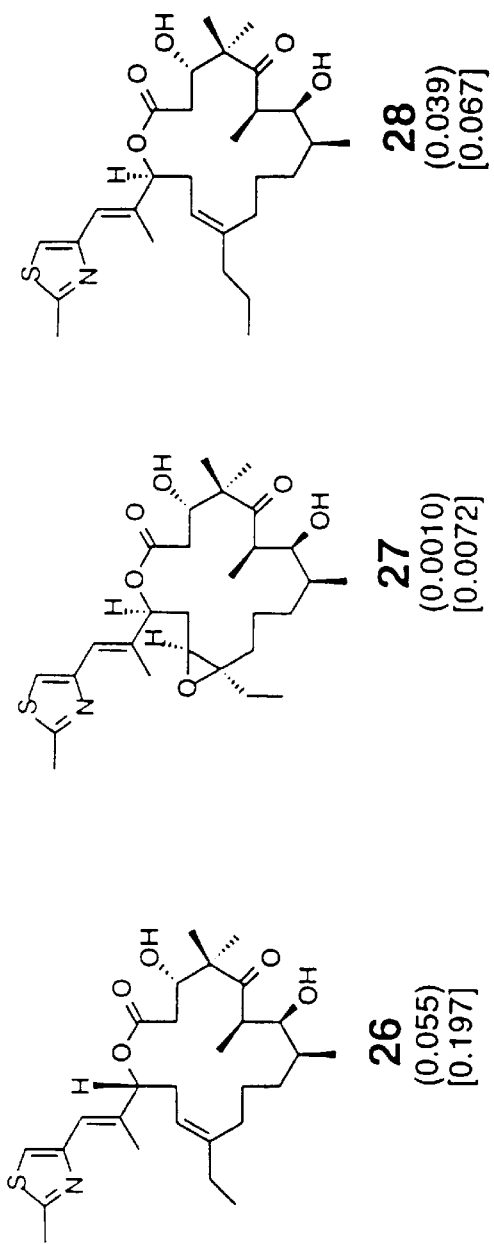
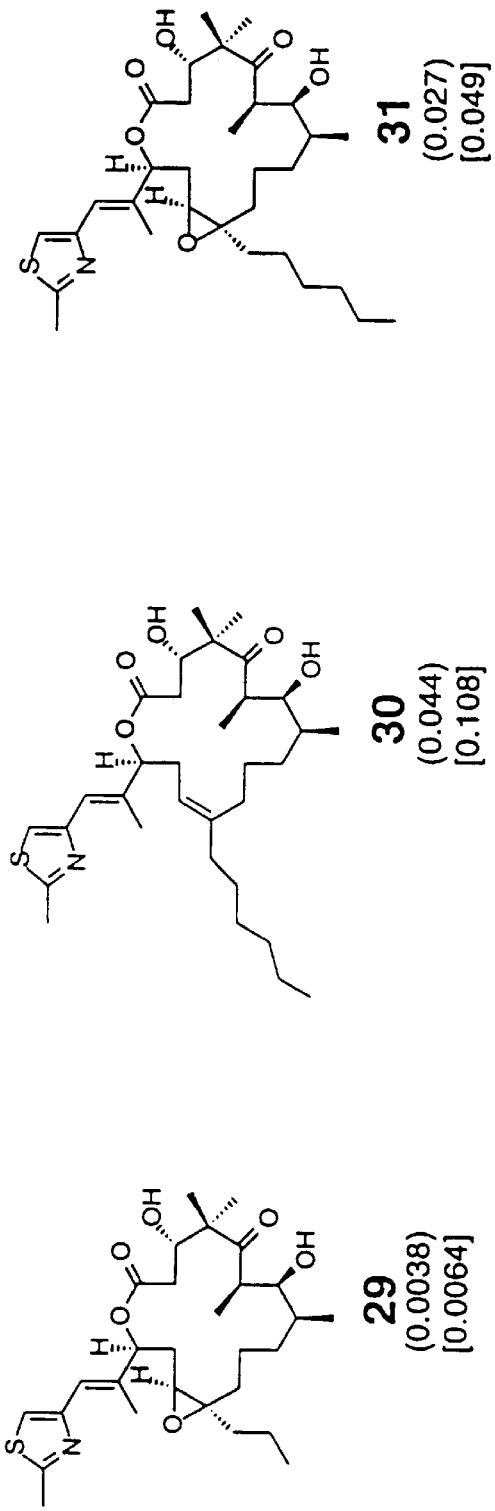

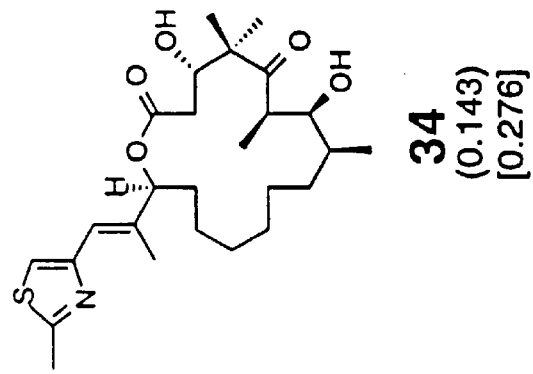
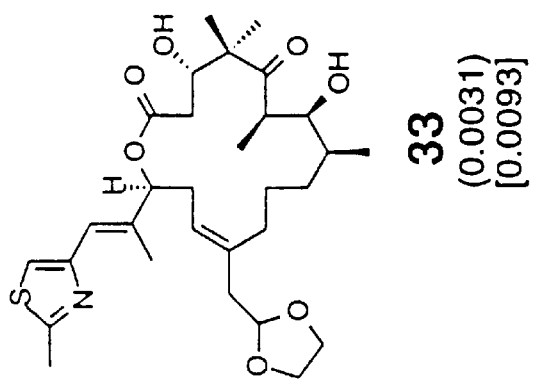
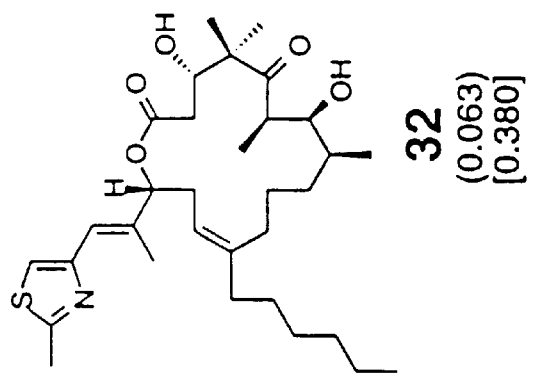
FIG. 42B

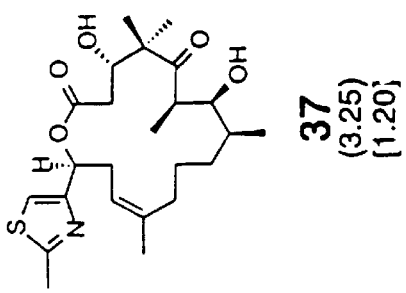
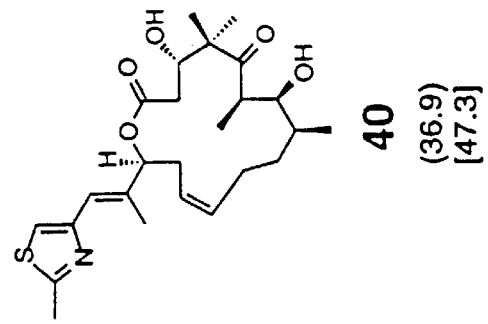
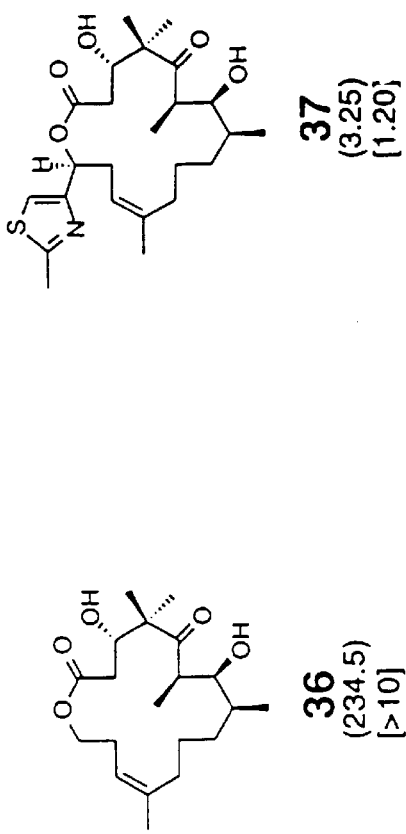
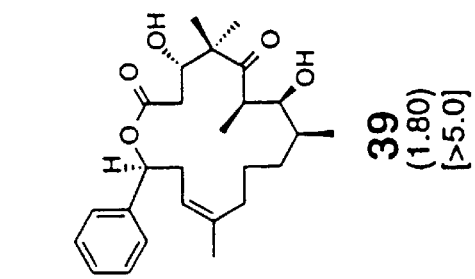
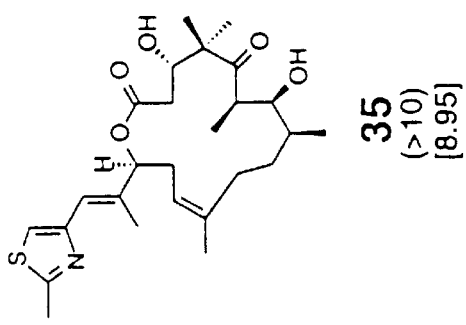
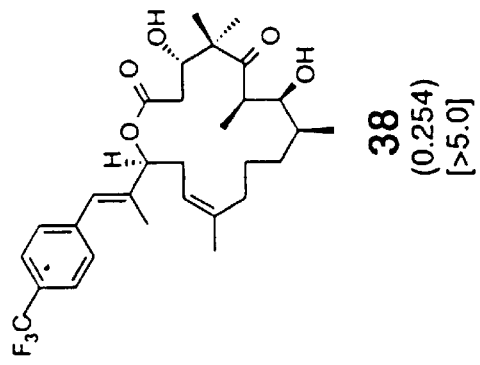
FIG. 42C

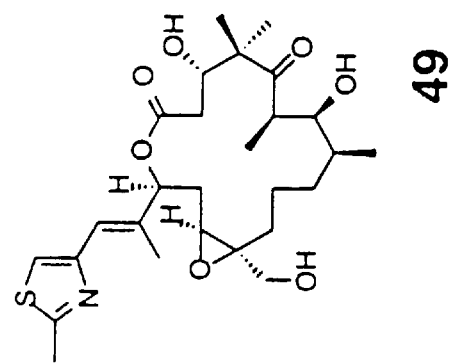
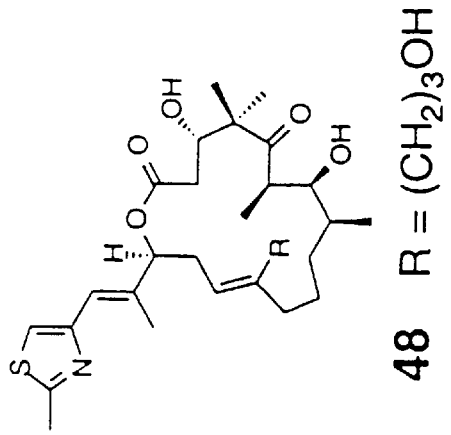
FIG. 42E
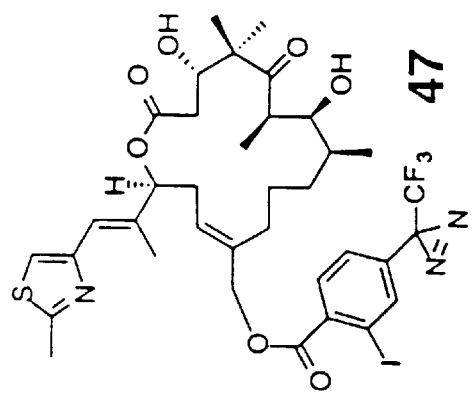

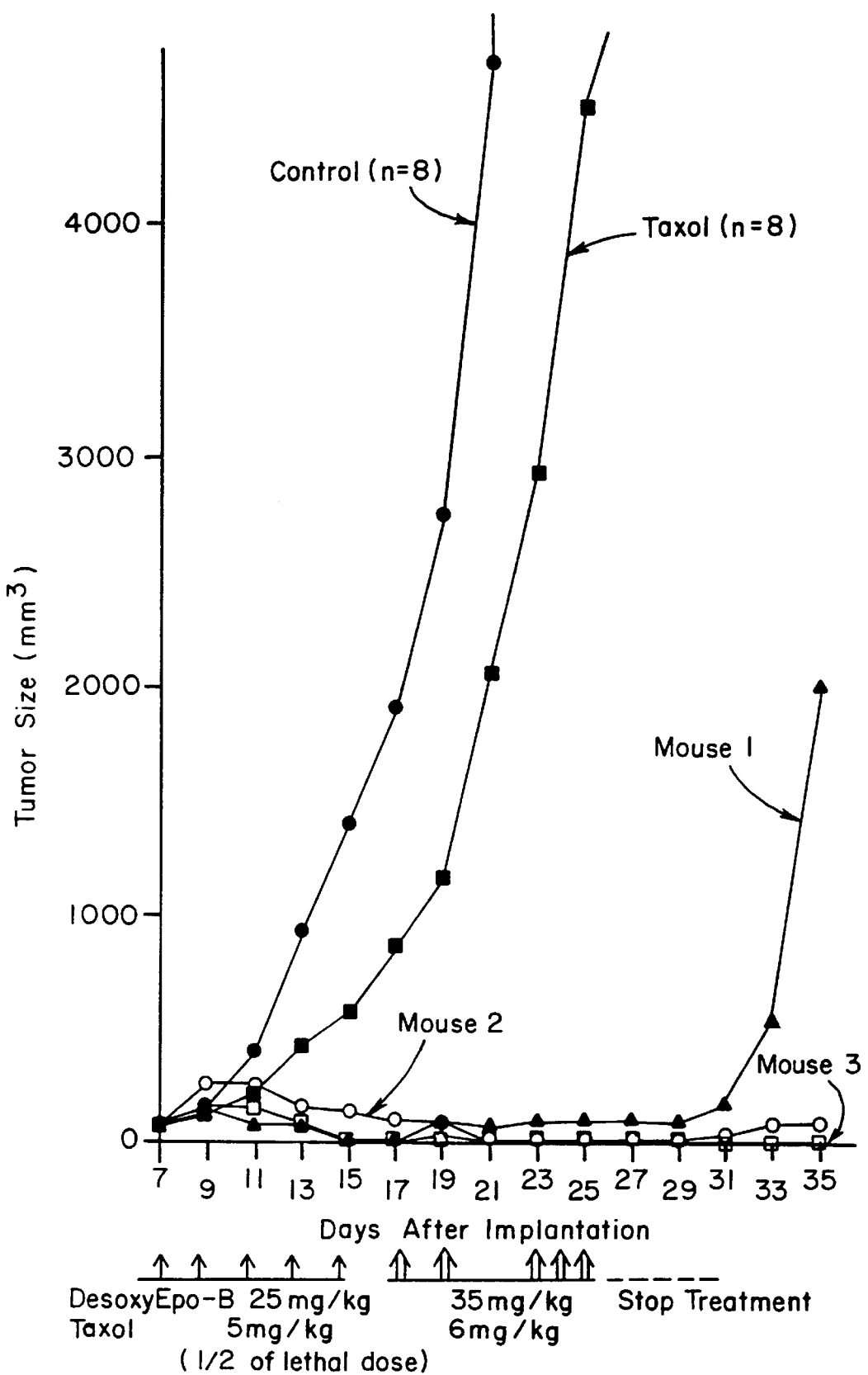

48  R = (CH$_2$)$_3$OH

SYNTHESIS OF EPOTHILONES, INTERMEDIATES THERETO AND ANALOGUES THEREOF

This application is based on U.S. Provisional Applications Serial Nos. 60/075,947, 60/092,319, and 60/097,733, filed Feb. 25, 1998, Jul. 9, 1998, and Aug. 24, 1998, respectively, the contents of which are hereby incorporated by reference into this application, and is a continuation-in-part of U.S. Ser. No. 08/986,025, filed Dec. 3, 1997, which was based on U.S. Provisional Applications Serial Nos. 60/032,282, 60/033,767, 60/047,566, 60/047,941, and 60/055,533, filed Dec. 3, 1996, Jan. 14, 1997, May 22, 1997, May 29, 1997, and Aug. 13, 1997, respectively, the contents of which are hereby incorporated by reference into this application.

This invention was made with government support under grants CA-28824, CA-39821, CA-GM 72231, GM-18248, CA-62948, and AIO-9355 from the National Institutes of Health, and grant CHE-9504805 from the National Science Foundation.

FIELD OF THE INVENTION

The present invention is in the field of epothilone macrolides. In particular, the present invention relates to processes for the preparation of epothilones A and B, desoxyepothilones A and B, and analogues thereof which are useful as highly specific, non-toxic anticancer therapeutics. In addition, the invention provides methods of inhibiting multidrug resistant cells. The present invention also provides novel compositions of matter which serve as intermediates for preparing the epothilones.

Throughout this application, various publications are referred to, each of which is hereby incorporated by reference in its entirety into this application to more fully describe the state of the art to which the invention pertains.

BACKGROUND OF THE INVENTION

Epothilones A and B are highly active anticancer compounds isolated from the Myxobacteria of the genus Sorangium. The full structures of these compounds, arising from an x-ray crystallographic analysis were determined by Höfle. G. Höfle et al., *Angew. Chem. Int. Ed. Engl.*, 1996, 35, 1567. The total synthesis of the epothilones is an important goal for several reasons. Taxol® is already a useful resource in chemotherapy against ovarian and breast cancer and its range of clinical applicability is expanding. G. I. Georg et al., *Taxane Anticancer Agents;* American Cancer Society: San Diego, 1995. The mechanism of the cytotoxic action of Taxol®, at least at the in vitro level, involves stabilization of microtubule assemblies. P. B. Schiff et al., *Nature* (London), 1979, 277, 665. A series of complementary in vitro investigations with the epothilones indicated that they share the mechanistic theme of the taxoids, possibly down to the binding sites to their protein target. D. M. Bollag et al., *Cancer Res.*, 1995, 55, 2325. Moreover, the epothilones surpass Taxol® in terms of cytotoxicity and far surpass it in terms of in vitro efficacy against drug resistant cells. Since multiple drug resistance (MDR) is one of the serious limitations of Taxol® (L. M. Landino and T. L. MacDonald in *The Chemistry and Pharmacology of Taxol® and its Derivatives,* V. Farin, Ed., Elsevier: New York, 1995, ch. 7, p. 301), any agent which promises relief from this problem merits serious attention. Furthermore, formulating the epothilones for clinical use is more straightforward than Taxol®.

Accordingly, the present inventors undertook the total synthesis of the epothilones, and as a result, have developed efficient processes for synthesizing epothilones A and B, the corresponding desoxyepothilones, as well as analogues thereof. The present invention also provides novel intermediates useful in the synthesis of epothilones A and B and analogues thereof, compositions derived from such epothilones and analogues, purified compounds of epothilones A and B, and desoxyepothilones A and B, in addition to methods of use of the epothilone analogues in the treatment of cancer. Unexpectedly, certain epothilones have been found to be effective not only in reversing multi-drug resistance in cancer cells, both in vitro and in vivo, but have been determined to be active as collateral sensitive agents, which are more cytotoxic towards MDR cells than normal cells, and as synergistic agents, which are more active in combination with other cytotoxic agents, such as vinblastin, than the individual drugs would be alone at the same concentrations. Remarkably, the desoxyepothilones of the invention have exceptionally high specificity as tumor cytotoxic agents in vivo, more effective and less toxic to normal cells than the principal chemotherapeutics currently in use, including Taxol®, vinblastin, adriamycin and camptothecin.

SUMMARY OF THE INVENTION

One object of the present invention is to provide processes for the preparation of epothilones A and B, and desoxyepothilones A and B, and related compounds useful as anticancer therapeutics. Another object of the present invention is to provide various compounds useful as intermediates in the preparation of epothilones A and B as well as analogues thereof.

A further object of the present invention is to provide synthetic methods for preparing such intermediates. An additional object of the invention is to provide compositions useful in the treatment of subjects suffering from cancer comprising any of the analogues of the epothilones available through the preparative methods of the invention optionally in combination with pharmaceutical carriers.

A further object of the invention is to provide methods of treating subjects suffering from cancer using any of the analogues of the epothilones available through the preparative methods of the invention optionally in combination with pharmaceutical carriers.

BRIEF DESCRIPTION OF THE DRAWING

FIGS. 19(A), 19(B) and 19(C) provide a synthetic pathway to 8-desmethyl deoxyepothilone A, and structures of trans-8-desmethyl-desoxyepothiolone A and a trans-iodoolefin intermediate thereto.

FIG. 20(A) shows structures of epothilones A and B and 8-desmethylepothilone and FIG. 20(B) shows a synthetic pathway to intermediate TBS ester 10 used in the preparation of desmethylepothilone A. (a) (Z)-Crotyl-B[(−)-Ipc]$_2$, −78° C., $Et_2O$, then 3N NaOH, 30% $H_2O_2$; (b) TBSOTf, 2,6-lutidine, $CH_2Cl_2$ (74% for two steps, 87% ee); (c) $O_3$, $CH_2Cl_2$/MeOH, −78° C., then DMS, (82%); (d) t-butyl isobutyrylacetate, NaH, BuLi, 0° C., then 6 (60%, 10:1); (e) $Me_4NBH(OAc)_3$, −10° C. (50%, 10:1 α/β) or $NaBH_4$, MeOH, THF, 0° C., (88%, 1:1 α/β; (f) TBSOTf, 2,6-lutidine, −40° C., (88%); (g) Dess-Martin periodinane, (90%); (h) $Pd(OH)_2$, $H_2$, EtOH (96%); (1) DMSO, oxalyl chloride, $CH_2Cl_2$, −78° C. (78%); (j) Methyl triphenylphosphonium bromide, NaHMDS, THF, 0° C. (85%); (k) TBSOTf, 2,6-lutidine, $CH_2Cl_2$, rt (87%).

FIGS. 22(A), 22(B) and 22(C) show a synthetic pathway to prepare epothilone analogue 27D.

FIGS. 24(A) and 24(B) show a synthetic pathway to prepare epothilone analogue 19D.

FIGS. 27(A), 27(B) and 27(C) show a synthetic pathway to prepare epothilone analogue 12-hydroxy ethylepothilone.

FIG. 38 provides a graphical representation of the effect of fractional combinations of cytotoxic agents.

FIGS. 40(A) and 40(B) show epothilone B and epothilone analogues #8–16. Potencies against human leukemia CCRF-CEM (sensitive) and CCRF-CEM/VBL MDR (resistant) sublines are shown in round and square brackets, respectively.

FIGS. 41(A) and 41(B) show epothilone analogues #17–25. Potencies against human leukemia CCRF-CEM (sensitive) and CCRF-CEM/VBL MDR (resistant) sublines are shown in round and square brackets, respectively.

FIGS. 42(A) and 42(B) show epothilone analogues #26–34. Potencies against human leukemia CCRF-CEM (sensitive) and CCRF-CEM/VBL MDR (resistant) sublines are shown in round and square brackets, respectively.

FIGS. 42(C) and 42(D) show epothilone analogues #35–46.Potencies against human leukemia CCRF-CEM (sensitive) and CCRF-CEM/VBL MDR (resistant) sublines are shown in round and square brackets, respectively.

FIG. 42(E) shows epothilone analogues #47–49.

DETAILED DESCRIPTION OF THE INVENTION

Figure 1A:
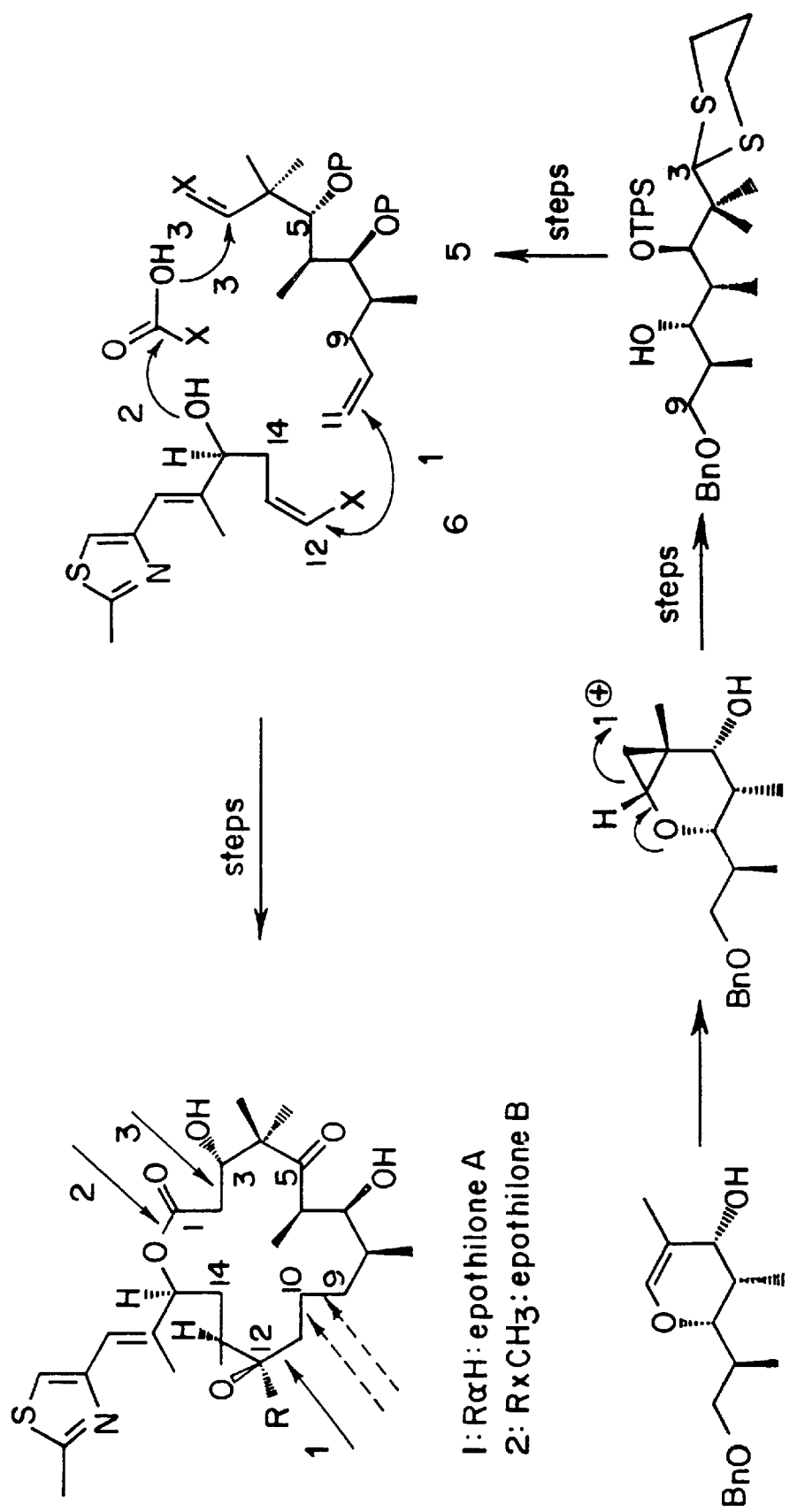
FIG. 1(A) shows a retrosynthetic analysis for epothilone A and B.

As used herein, the term "linear or branched chain alkyl" encompasses, but is not limited to, methyl, ethyl, propyl, isopropyl, t-butyl, sec-butyl, cyclopentyl or cyclohexyl. The alkyl group may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido and/or N-acylamino moieties.

As used herein, the terms "alkoxycarbonyl", "acyl" and "alkoxy" encompass, but are not limited to, methoxycarbonyl, ethoxycarbonyl, propoxycarbonyl, n-butoxycarbonyl, benzyloxycarbonyl, hydroxypropylcarbonyl, aminoethoxycarbonyl, sec-butoxycarbonyl and cyclopentyloxycarbonyl. Examples of acyl groups include, but are not limited to, formyl, acetyl, propionyl, butyryl and penanoyl. Examples of alkoxy groups include, but are not limited to, methoxy, ethoxy, propoxy, n-butoxy, sec-butoxy and cyclopentyloxy.

As used herein, an "aryl" encompasses, but is not limited to, a phenyl, pyridyl, pyrryl, indolyl, naphthyl, thiophenyl or furyl group, each of which may be substituted by various groups, which include, but are not limited, acyl, aryl alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthoxy. Examples of acyloxy groups include, but are not limited to, acetoxy, propanoyloxy, butyryloxy, pentanoyloxy and hexanoyloxy.

The subject invention provides chemotherapeutic analogues of epothilone A and B, including a compound having the structure:

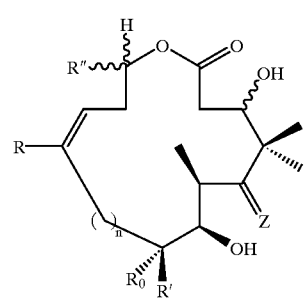

wherein R, R$_0$, and R' are independently H, linear or branched chain alkyl, optionally substituted by hydroxy, alkoxy, fluorine, $NR_1R_2$, N-hydroximino, or N-alkoxyimino, wherein $R_1$ and $R_2$ are independently H, phenyl, benzyl, linear or branched chain alkyl; wherein R″ is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, $N(OR_3)$ or N—$NR_4R_5$, wherein $R_3$, $R_4$ and $R_5$ are independently H or a linear or branched alkyl; and wherein n is 0, 1, 2, or 3. In one embodiment, the invention provides the compound having the structure:

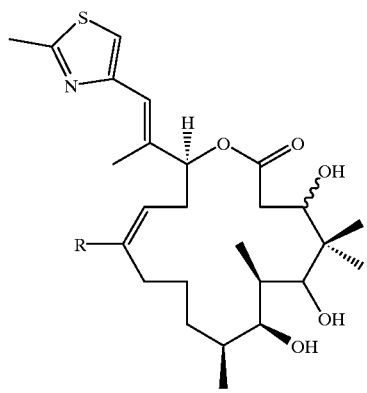

wherein R is H, methyl, ethyl, n-propyl, n-butyl, n-hexyl, $CH_2OH$, or $(CH_2)_3OH$.

The invention also provides a compound having the structure:

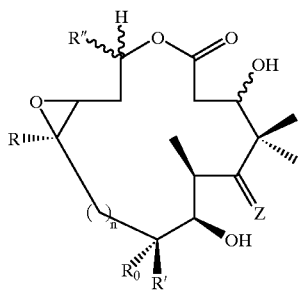

wherein R, $R_0$, and R' are independently H, linear or branched chain alkyl, optionally substituted by hydroxy, alkoxy, fluorine, $NR_1R_2$, N-hydroximino, or N-alkoxyimino, wherein $R_1$ and $R_2$ are independently H, phenyl, benzyl, linear or branched chain alkyl; wherein R″ is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, $N(OR_3)$ or N—$NR_4R_5$, wherein $R_3$, $R_4$ and $R_5$ are independently H or a linear or branched chain alkyl; and wherein n is 0, 1, 2, or 3. In a certain embodiment, the invention provides a compound having the structure:

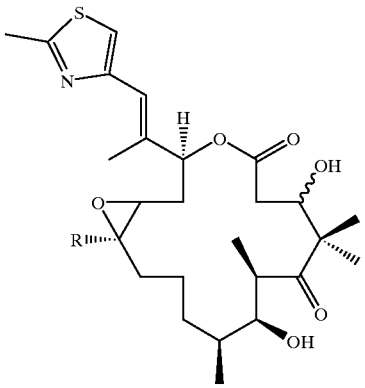

wherein R is H, methyl, ethyl, n-propyl, n-butyl, n-hexyl or $CH_2OH$.

In addition, the invention provides a compound having the structure:

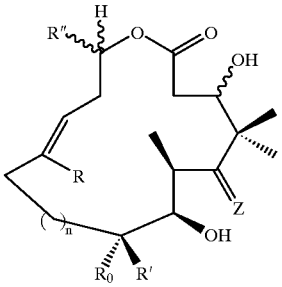

wherein R, $R_0$, and R' are independently H, linear or branched chain alkyl, optionally substituted by hydroxy, alkoxy, fluorine, $NR_1R_2$, N-hydroximino, or N-alkoxyimino, wherein $R_1$ and $R_2$ are independently H, phenyl, benzyl, linear or branched chain alkyl; wherein R″ is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, $N(OR_3)$ or N—$NR_4R_5$, wherein $R_3$, $R_4$ and $R_5$ are independently H or a linear or branched chain alkyl; and wherein n is 0, 1, 2, or 3. In particular, the invention provides a compound having the structure:

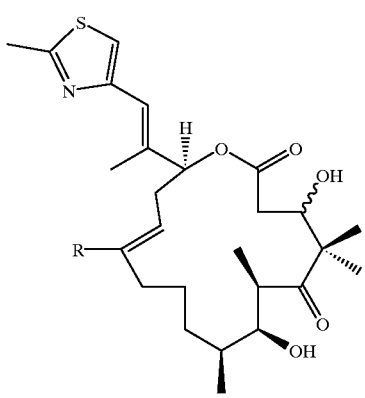

wherein R is H, methyl, ethyl, n-propyl, n-butyl, CH$_2$OH or (CH$_2$)$_3$OH.

The invention further provides a compound having the structure:

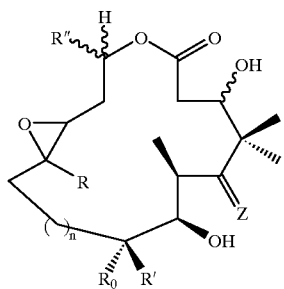

wherein R, R$_0$ and R' are independently H, linear or branched chain alkyl, optionally substituted by hydroxy, alkoxy, fluorine, NR$_1$R$_2$, N-hydroximino or N-alkoxyimino, wherein R$_1$ and R$_2$ are independently H, phenyl, benzyl, linear or branched chain alkyl; wherein R" is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, N(OR$_3$) or N—NR$_4$R$_5$, wherein R$_3$, R$_4$ and R$_5$ are independently H or a linear or branched chain alkyl; and wherein n is 0, 1, 2 or 3.

The invention also provides a compound having the structure:

The subject invention also provides various intermediates useful for the preparation of the chemotherapeutic compounds epithilone A and B, as well as analogues thereof. Accordingly, the invention provides a key intermediate to epothilone A and its analogues having the structure:

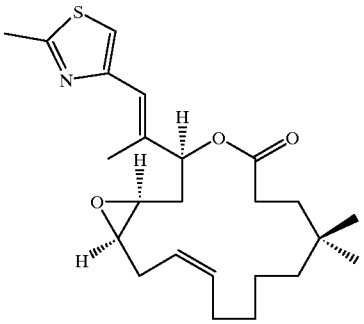

The subject invention also provides an intermediate to epothilone A and its analogues having the structure:

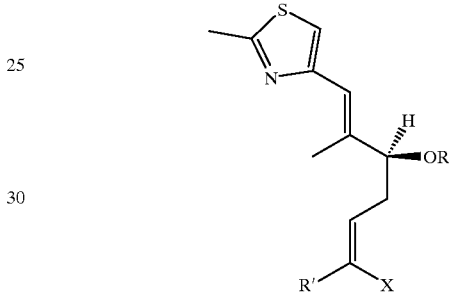

wherein R is hydrogen, a linear or branched acyl, substituted or unsubstituted aroyl or benzoyl; wherein R' is hydrogen, methyl, ethyl, n-propyl, n-hexyl,

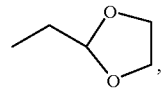

CH$_2$OTBS or (CH$_2$)$_3$-OTBDPS; and X is a halide. In one embodiment, the subject invention provides a compound of the above structure wherein R is acetyl and X is iodo.

The subject invention also provides an intermediate having the structure:

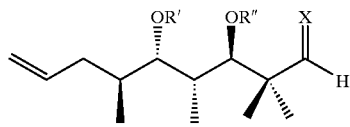

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, (OR)$_2$, (SR)$_2$, —(O—(CH$_2$)$_n$—O)—, —(O—(CH$_2$)$_n$—S)— or —(S—(CH$_2$)$_n$—S)—; and wherein n is 2, 3 or 4.

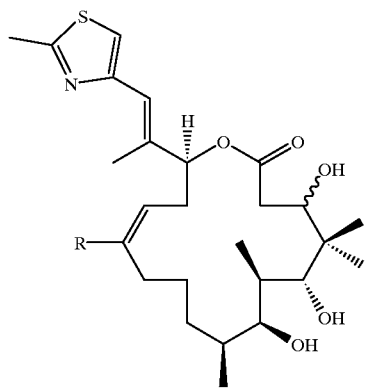

wherein R is H or methyl.

Another analogue provided by the invention has the structure:

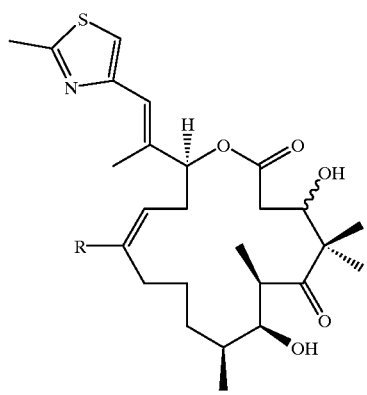

wherein R is H, methyl, ethyl, n-propyl, n-butyl, n-hexyl, $CH_2OH$, or $(CH_2)_3OH$.

Additionally, the subject invention provides an analogue having the structure:

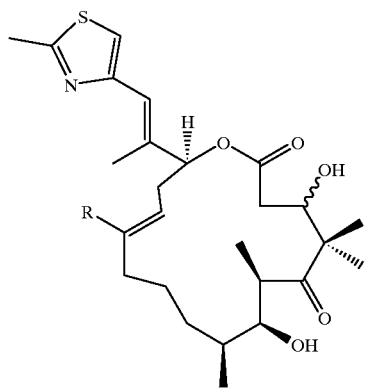

wherein R is H or methyl. The scope of the present invention includes compounds wherein the $C_3$ carbon therein possesses either an R or S absolute configuration, as well as mixtures thereof.

The subject invention further provides an analogue of epothilone A having the structure:

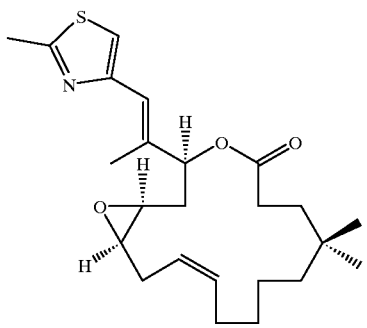

The subject invention also provides synthetic routes to prepare the intermediates for preparing epothilones. Accordingly, the invention provides a method of preparing a Z-iodoalkene ester having the structure:

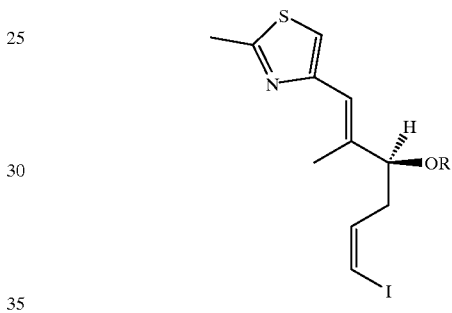

wherein R is hydrogen, a linear or branched alkyl, alkoxyalkyl, substituted or unsubstituted aryloxyalkyl, linear or branched acyl, substituted or unsubstituted aroyl or benzoyl, which comprises (a) coupling a compound having the structure:

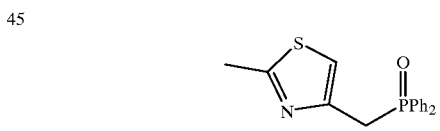

with a methyl ketone having the structure:

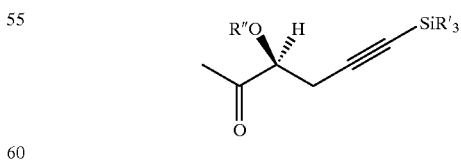

wherein R' and R" are independently a linear or branched alkyl, alkoxyalkyl, substituted or unsubstituted aryl or benzyl, under suitable conditions to form a compound having the structure:

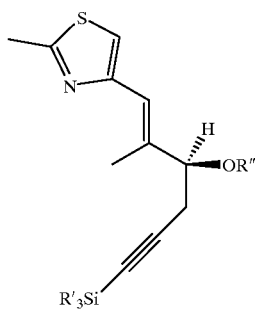

(b) treating the compound formed in step (a) under suitable conditions to form a Z-iodoalkene having the structure:

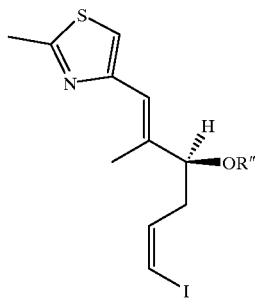

and (c) deprotecting and acylating the Z-iodoalkene formed in step (b) under suitable conditions to form the Z-iodoalkene ester. The coupling in step (a) may be effected using a strong base such as n-BuLi in an inert polar solvent such as tetrahydrofuran (THF) at low temperatures, typically below −50° C., and preferably at −78° C. The treatment in step (b) may comprise sequential reaction with N-iodosuccinimide in the presence of Ag(I), such as silver nitrate, in a polar organic solvent such as acetone, followed by reduction conditions, typically using a hydroborating reagent, preferably using $Cy_2BH$. Deprotecting step (c) involves contact with a thiol such as thiophenol in the presence of a Lewis acid catalyst, such as boron trifluoride-etherate in an inert organic solvent such as dichloromethane, followed by acylation with an acyl halide, such as acetyl chloride, or an acyl anhydride, such as acetic anhydride in the presence of a mild base such as pyridine and/or 4-dimethyaminopyridine (DMAP) in an inert organic solvent such as dichloromethane.

The subject invention also provides a method of preparing a Z-haloalkene ester having the structure:

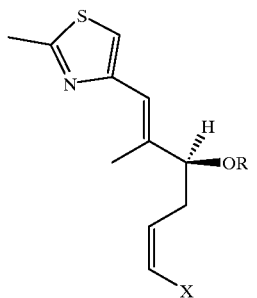

wherein R is hydrogen, a linear or branched alkyl, alkoxyalkyl, substituted or unsubstituted aryloxyalkyl, linear or branched acyl, substituted or unsubstituted aroyl or benzoyl; and wherein X is a halogen, which comprises (a) oxidatively cleaving a compound having the structure:

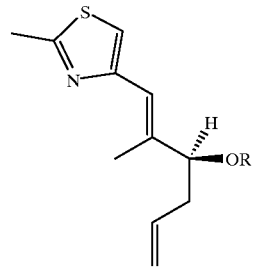

under suitable conditions to form an aldehyde intermediate; and (b) condensing the aldehyde intermediate with a halomethylene transfer agent under suitable conditions to form the Z-haloalkene ester. In one embodiment of the method, X is iodine. In another embodiment, the method is practiced wherein the halomethylene transfer agent is $Ph_3P=CHI$ or $(Ph_3P^+CH_2I)I^-$. Disubstituted olefins may be prepared using the haloalkylidene transfer agent $Ph_3P=CR'I$, wherein R' is hydrogen, methyl, ethyl, n-prop-yl, n-hexyl,

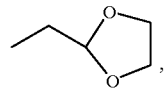

$CO_2Et$ or $(CH_2)_3OTBDPS$. The oxidative step (a) can beperformed using a mild oxidant as osmium tetraoxide at temperatures of about 0° C., followed by treatment with sodium periodate, or with lead tetraacetate/sodium carbonate, to complete the cleavage of the terminal olefin, and provide a terminal aldehyde. Condensing step (b) occurs effectively with a variety of halomethylenating reagents, such as Wittig reagents.

The subject invention further provides a method of preparing an optically pure compound having the structure:

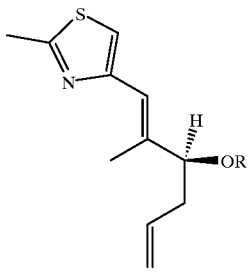

wherein R is hydrogen, a linear or branched alkyl, alkoxyalkyl, substituted or unsubstituted aryloxyalkyl, linear or branched acyl, substituted or unsubstituted aroyl or benzoyl, which comprises: (a) condensing an allylic organometallic reagent with an unsaturated aldehyde having the structure:

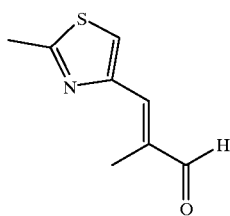

under suitable conditions to form an alcohol, and, optionally concurrently therewith, optically resolving the alcohol to form an optically pure alcohol having the structure:

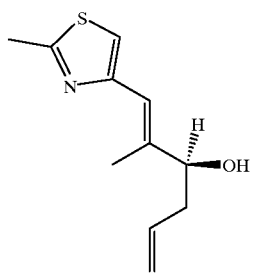

(b) alkylating or acylating the optically pure alcohol formed in step (a) under suitable conditions to form the optically pure compound. In one embodiment of the method, the allylic organometallic reagent is an allyl(trialkyl)stannane. In another embodiment, the condensing step is effected using a reagent comprising a titanium tetraalkoxide and an optically active catalyst. In step (a) the 1,2-addition to the unsaturated aldehyde may be performed using a variety of allylic organometallic reagents, typically with an allyltrialkylstannane, and preferably with allyltri-n-butylstannane, in the presence of chiral catalyst and molecular sieves in an inert organic solvent such as dichloromethane. Preferably, the method may be practiced using titanium tetraalkoxides, such as titanium tetra-n-propoxide, and S-(−)BINOL as the optically active catalyst. Alkylating or acylating step (b) is effected using any typical alkylating agent, such as alkylhalide or alkyl tosylate, alkyl triflate or alkyl mesylate, any typical acylating agent, such as acetyl chloride, acetic anhydride, benzoyl chloride or benzoyl anhydride, in the presence of a mild base catalyst in an inert organic solvent, such as dichloromethane.

The subject invention also provides a method of preparing an open-chain aldehyde having the structure:

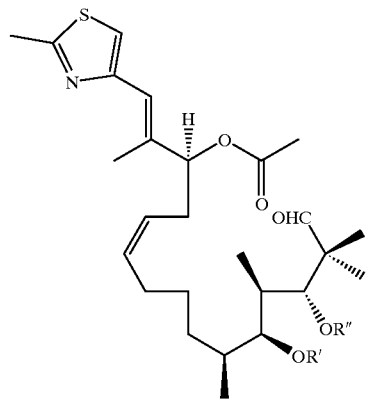

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises: (a) cross-coupling a haloolefin having the structure:

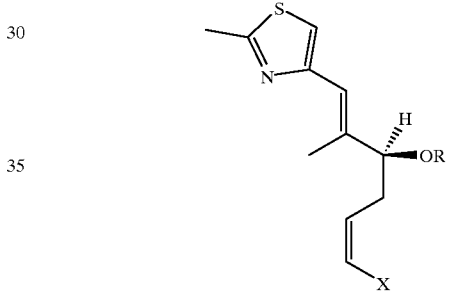

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl, and X is a halogen, with a terminal olefin having the structure:

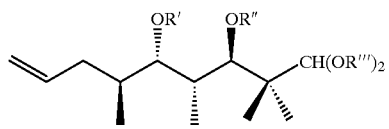

wherein $(OR''')_2$ is $(OR_0)_2$, $(SR_0)_2$, $-(O-(CH_2)_n-O)-$, $-(O-(CH_2)_n-S)-$ or $-(S-(CH_2)_n-S)-$ where $R_0$ is a linear or branched alkyl, substituted or unsubstituted aryl or benzyl; and wherein n is 2, 3 or 4, under suitable conditions to form a cross-coupled compound having the structure:

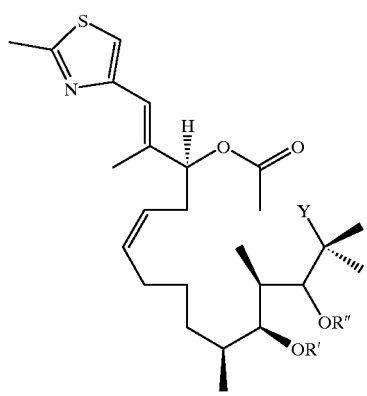

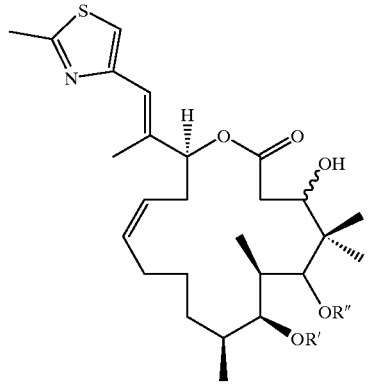

wherein Y is CH(OR*)$_2$ where R* is a linear or branched alkyl, alkoxyalkyl, substituted or unsubstituted aryloxyalkyl; and (b) deprotecting the cross-coupled compound formed in step (a) under suitable conditions to form the open-chain compound. Cross-coupling step (a) is effected using reagents known in the art which are suited to the purpose. For example, the process may be carried out by hydroborating the pre-acyl component with 9-BBN. The resulting mixed borane may then be cross-coupled with an organometallic catalyst such as PdCl$_2$(dppf)$_2$, or any known equivalent thereof, in the presence of such ancillary reagents as cesium carbonate and triphenylarsine. Deprotecting step (b) can be carried out with a mild acid catalyst such as p-tosic acid, and typically in a mixed aqueous organic solvent system, such as dioxane-water. The open-chain compound can be cyclized using any of a variety of non-nucleophilic bases, such as potassium hexamethyldisilazide or lithium diethyamide.

The subject invention also provides a method of preparing an epothilone having the structure:

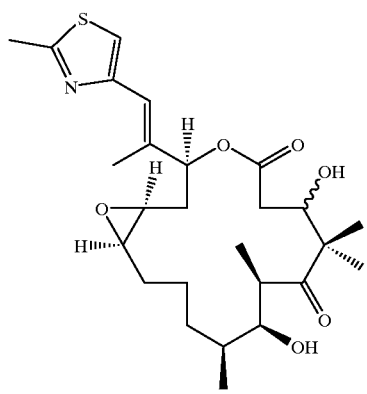

which comprises: (a) deprotecting a cyclized compound having the structure:

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, under suitable conditions to form a deprotected cyclized compound and oxidizing the deprotected cyclized compound under suitable conditions to form a desoxyepothilone having the structure:

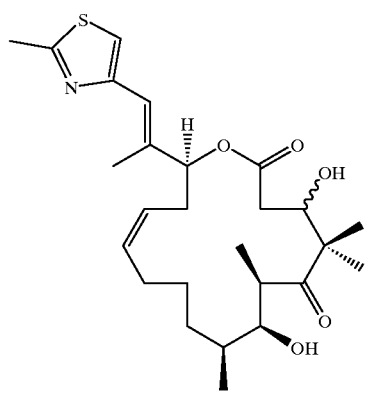

and (b) epoxidizing the desoxyepothilone formed in step (a) under suitable conditions to form the epothilone. Deprotecting step (a) is effected using a sequence of treatments comprising a catalyst such as HF-pyridine, followed by t-butyldimethylsilyl triflate in the presence of a base such as lutidine. Dess-Martin oxidation and further deprotection with a catalyst such as HF-pyridine provides the desoxyepothilone. The latter compound can then be epoxidized in step (b) using any of a variety of epoxidizing agents, such acetic peracid, hydrogen peroxide, perbenzoic acid, m-chloroperbenzoic acid, but preferably with dimethyldioxirane, in an inert organic solvent such as dichloromethane.

The subject invention further provides a method of preparing an epothilone precursor having the structure:

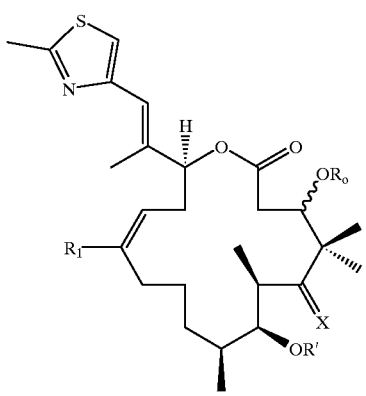

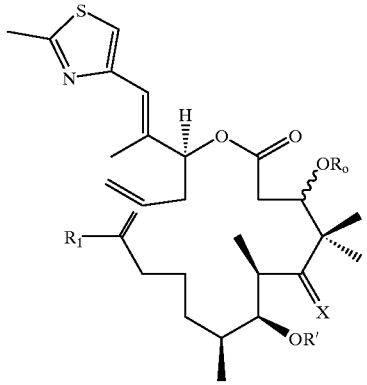

wherein $R_1$ is hydrogen or methyl; wherein X is O, or a hydrogen and OR", each singly bonded to carbon; and wherein $R_0$, R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises (a) coupling a compound having the structure:

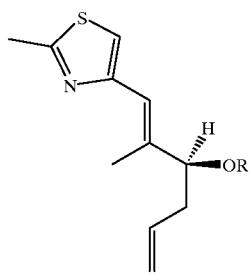

wherein R is an acetyl, with an aldehyde having the structure:

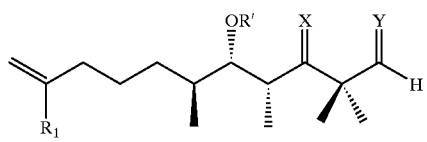

wherein Y is oxygen, under suitable conditions to form an aldol intermediate and optionally protecting the aldol intermediate under suitable conditions to form an acyclic epthilone precursor having the structure:

(b) subjecting the acylic epothilone precursor to conditions leading to intramolecular olefin metathesis to form the epothilone precursor. In one embodiment of the method, the conditions leading to intramolecular olefin metathesis require the presence of an organometallic catalyst. In a certain specific embodiment of the method, the catalyst contains Ru or Mo. The coupling step (a) may be effected using a nonnucleophilic base such as lithium diethylamide or lithium diisopropylamide at subambient temperatures, but preferably at about −78° C. The olefin metathesis in step (b) may be carried out using any catalyst known in the art suited for the purpose, though preferably using one of Grubbs's catalysts.

In addition, the present invention provides a compound useful as an intermediate for preparing epothilones having the structure:

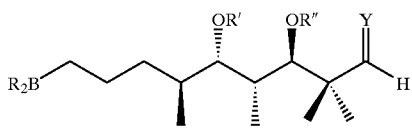

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, $(OR^*)_2$, $(SR^*)_2$, $-(O-(CH_2)_n-O)-$, $-(O-(CH_2)_n-S)-$ or $-(S-(CH_2)_n-S)-$; wherein $R^*$ is a linear or branched alkyl, substituted or unsubstituted aryl or benzyl; wherein $R_2B$ is a linear, branched or cyclic boranyl moiety; and wherein n is 2, 3 or 4. In certain embodiments, the invention provides the compound wherein R' is TBS, R" is TPS and X is $(OMe)_2$. A preferred example of $R_2B$ is derived from 9-BBN.

The invention also provides the compound having the structure:

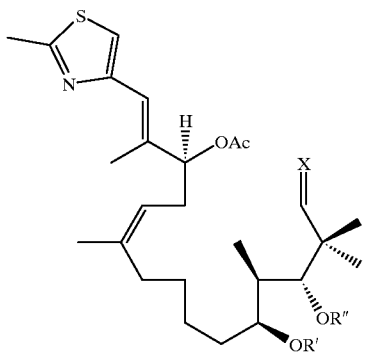

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, $(OR)_2$, $(SR)_2$, $—(O—(CH_2)_n—O)—$, $—(O—(CH_2)_n—S)—$ or $—(S—(CH_2)_n—S)—$; and wherein n is 2, 3 or 4. In certain embodiments, the invention provides the compound wherein R' is TBS, R" is TPS and X is $(OMe)_2$.

The invention further provides a desmethylepothilone analogoue having the structure:

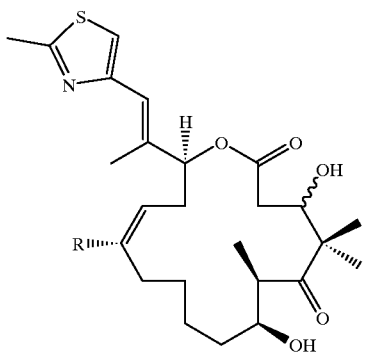

wherein R is H or methyl.

The invention provides a compound having the structure:

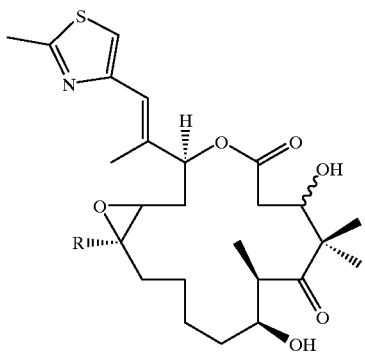

wherein R is H or methyl.

The invention also provides a trans-desmethyldeoxyepothilone analogue having the structure:

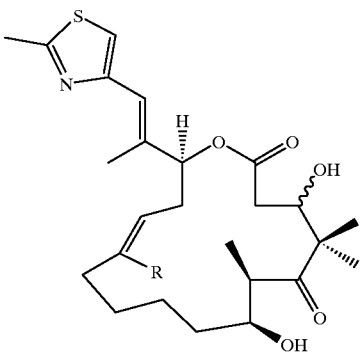

wherein R is H or methyl.

The invention also provides a trans-epothilone having the structure:

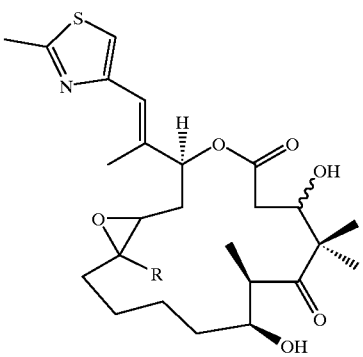

wherein R is H or methyl.

The invention also provides a compound having the structure:

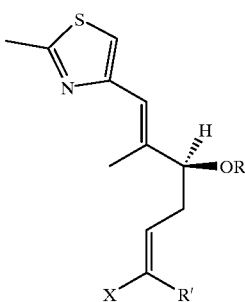

wherein R is hydrogen, a linear or branched alkyl, alkoxyalkyl, substituted or unsubstituted aryloxyalkyl, linear or branched acyl, substituted or unsubstituted aroyl or benzoyl; wherein R' is hydrogen, methyl, ethyl, n-propyl, n-hexyl,

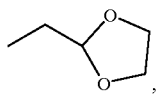

$CO_2Et$ or $(CH_2)_3OTBDPS$, and X is a halogen. In certain embodiments, the invention provides the compound wherein R is acetyl and X is iodine.

The invention additionally provides a method of preparing an open-chain aldehyde having the structure:

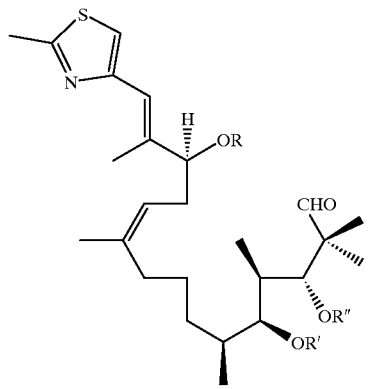

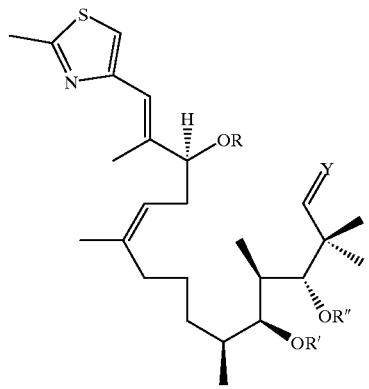

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises:

(a) cross-coupling a haloolefin having the structure:

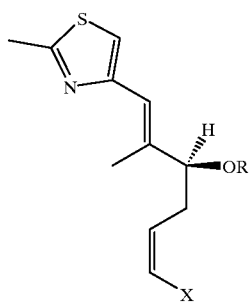

wherein X is a halogen, with a terminal borane having the structure:

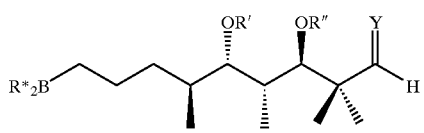

wherein $R^*_2B$ is a linear, branched or cyclic alkyl or substituted or unsubstituted aryl or benzyl boranyl moiety; and wherein Y is $(OR_0)_2$, $(SR_0)_2$, —(O—$(CH_2)_n$—O)—, —(O—$(CH_2)_n$—S)— or —(S—$(CH_2)_n$—S)— where $R_0$ is a linear or branched alkyl, substituted or unsubstituted aryl or benzyl; and wherein n is 2, 3 or 4, under suitable conditions to form a cross-coupled compound having the structure:

and (b) deprotecting the cross-coupled compound formed in step (a) under suitable conditions to form the open-chain aldehyde. In certain embodiments, the invention provides the method wherein R is acetyl; R' is TBS; R" is TPS; $R^*_2B$ is derived from 9-BBN; and Y is $(OMe)_2$. Cross-coupling step (a) is effected using reagents known in the art which are suited to the purpose. For example, the mixed borane may be cross-coupled with an organometallic catalyst such as $PdCl_2(dppf)_2$, or any known equivalent thereof, in the presence of such reagents as cesium carbonate and triphenylarsine. Deprotecting step (b) can be carried out using a mild acid catalyst such as p-tosic acid, typically in a mixed aqueous organic solvent system, such as dioxane-water.

The invention also provides a method of preparing a protected epothilone having the structure:

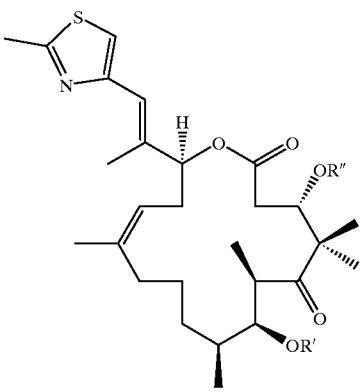

wherein R' and R" are independently hydrogen, a linear or branched alkyl, substituted or unsubstituted aryl or benzyl, trialkylsilyl, dialkyl-arylsilyl, alkyldiarylsilyl, a linear or branched acyl, substituted or unsubstituted aroyl or benzoyl, which comprises:

(a) monoprotecting a cyclic diol having the structure:

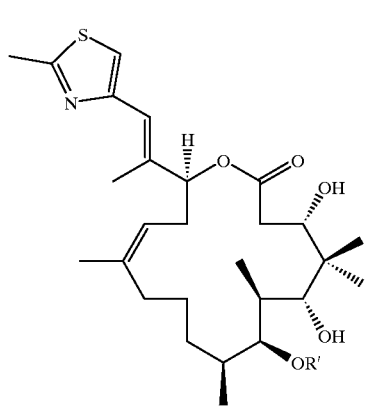

under suitable conditions to form a cyclic alcohol having the structure:

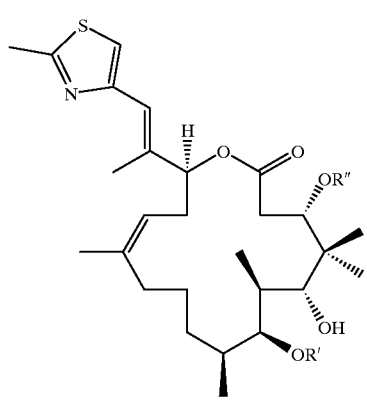

and (b) oxidizing the cyclic alcohol formed in step (a) under suitable conditions to form the protected epothilone. In certain embodiments, the invention provides the method wherein R' and R" are TBS. The monoprotecting step (a) may be effected using any of a variety of suitable reagents, including TBSOTf in the presence of a base in an inert organic solvent. The base may be a non-nucleophilic base such as 2,6-lutidine, and the solvent may be dichloromethane. The reaction is conducted at subambient temperatures, preferably in the range of −30° C. The oxidizing step (b) utilizes a selective oxidant such as Dess-Martin periodinane in an inert organic solvent such as dichloromethane. The oxidation is carried out at ambient temperatures, preferably at 20–25° C.

The invention further provides a method of preparing an epothilone having the structure:

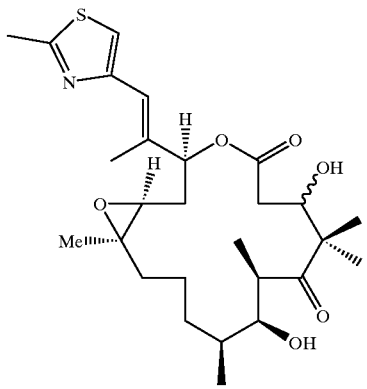

which comprises:

(a) deprotecting a protected cyclic ketone having the structure:

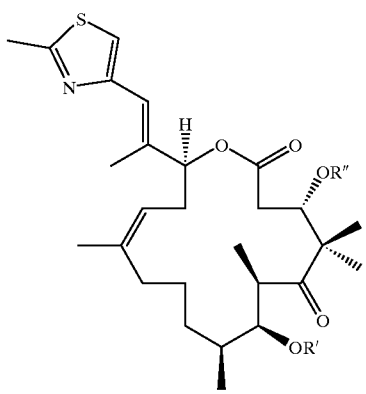

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, under suitable conditions to form a desoxyepothilone having the structure:

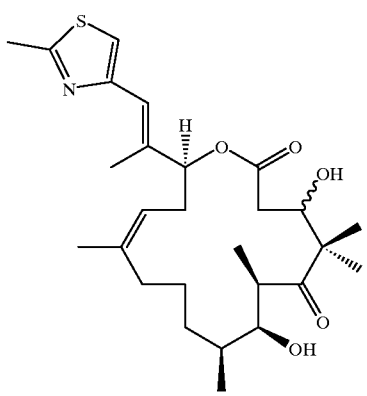

and (b) epoxidizing the desoxyepothilone formed in step (a) under suitable conditions to form the epothilone. In certain embodiments, the invention provides the method wherein R' and R" are TBS. Deprotecting step (a) is carried out by means of a treatment comprising a reagent such as HF.pyridine. The deprotected compound can be epoxidized in step (b) using an epoxidizing agent such acetic peracid, hydrogen peroxide, perbenzoic acid, m-chloroperbenzoic acid, but preferably with dimethyldioxirane, in an inert organic solvent such as dichloromethane.

The invention also provides a method of preparing a cyclic diol having the structure:

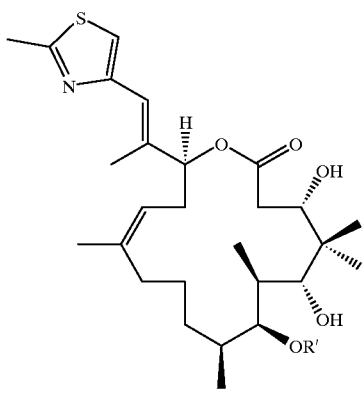

wherein R' is a hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises:

(a) cyclizing an open-chain aldehyde having the structure:

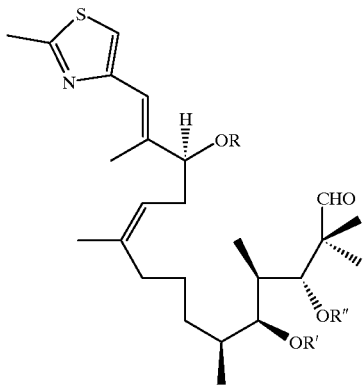

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein R" is a hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl under suitable conditions to form an enantiomeric mixture of a protected cyclic alcohol having the structure:

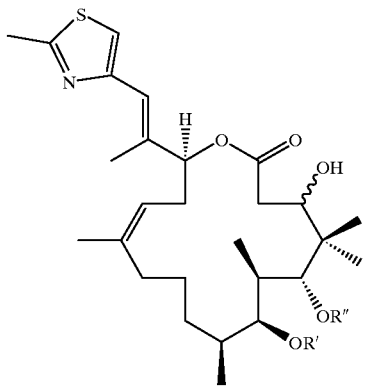

said mixture comprising an α- and a β-alcohol component;

(b) optionally isolating and oxidizing the α-alcohol formed in step (a) under suitable conditions to form a ketone and thereafter reducing the ketone under suitable conditions to form an enantiomeric mixture of the protected cyclic alcohol comprising substantially the β-alcohol; and (c) treating the protected cyclic alcohol formed in step (a) or (b) with a deprotecting agent under suitable conditions to form the cyclic diol. In certain embodiments, the invention provides the method wherein R' is TBS and R" is TPS. Cyclizing step (a) is performed using any of a variety of mild nonnucleophilic bases such as KHMDS in an inert solvent such as THF. The reaction is carried out at subambient temperatures, preferably between –90° C. and –50° C., more preferably at –78° C. Isolation of the unnatural alpha-OH diastereomer is effected by any usual purification method, including any suitable type of chromatography or by crystallization. Chromatographic techniques useful for the purpose include high pressure liquid chromatography, countercurrent chromatography or flash chromatography. Various column media are suited, including, inter alia, silica or reverse phase support. The beta-OH derivative is then oxidized using a selective oxidant, such as Dess-Martin periodinane. The resulting ketone is the reduced using a selective reductant. Various hydridoborane and aluminum hydride reagents are effective. A preferred reducing agent is sodium borohydride. Treating step (c) may be effected using a variety of deprotecting agents, including HF-pyridine.

The present invention provides a method of preparing a desoxyepothilone having the structure:

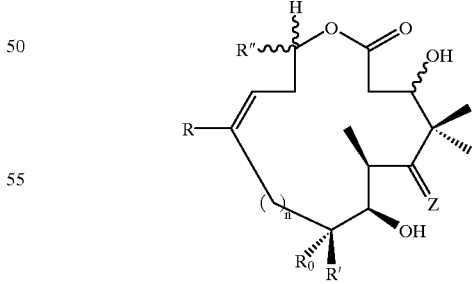

wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CX—, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, N(OR$_3$) or N—NR$_4$R$_5$, wherein R$_3$, R$_4$ and R$_5$ are independently H or a linear or branched alkyl; and wherein n is 0, 1, 2, or 3; which comprises treating an epothilone having a structure:

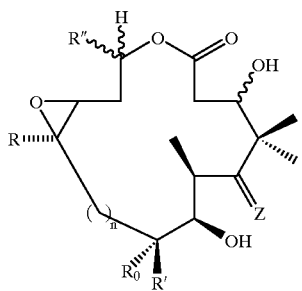

wherein R, R$_0$, R$_1$, R$_2$, R$_3$, R$_4$, R$_5$, R', R", X, Y, Z and n are defined as for the desoxyepothilone, under suitable conditions so as to deoxygenate the epothilone, and thereby to provide the desoxyepothilone. In one embodiment, the method is effected wherein the desoxyepothilone has the structure:

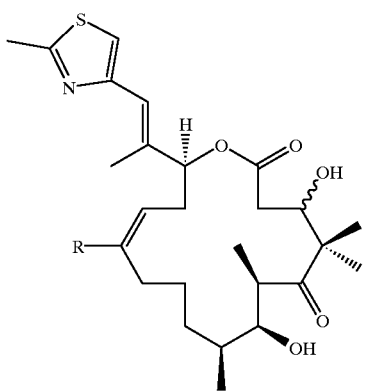

wherein R is H, methyl, ethyl, n-propyl, n-butyl, n-hexyl,

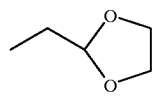

or (CH$_2$)$_3$—OH.

In another embodiment, the method is effected wherein the epothilone is deoxygenated using a zinc/copper couple. Preferably, the method is carried out wherein the epothilone is deoxygenated in the presence of a polar solvent comprising isopropanol and water.

The present invention further provides a method of preparing a desoxyepothilone having the structure:

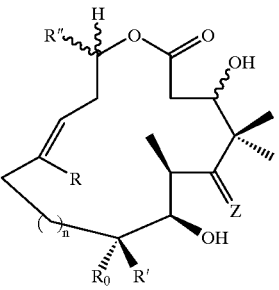

wherein R, R$_0$, and R' are independently H, linear or branched chain alkyl, optionally substituted by hydroxy, alkoxy, carboxy, carboxaldedyde, linear or branched alkyl or cyclic acetal, fluorine, NR$_1$R$_2$, N-hydroximino, or N-alkoxyimino, wherein R$_1$ and R$_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, N(OR$_3$) or N—NR$_4$R$_5$, wherein R$_3$, R$_4$ and R$_5$ are independently H or a linear or branched chain alkyl; and wherein n is 0, 1, 2, or 3; which comprises treating an epothilone having a structure:

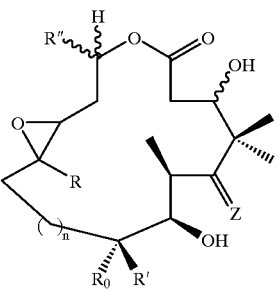

wherein R, R$_0$, R$_1$, R$_2$, R$_3$, R$_4$, R$_5$, R', R", X, Y, Z and n are defined as for the desoxyepothilone, under suitable conditions so as to deoxygenate the epothilone, and thereby to provide the desoxyepothilone. In one embodiment, the method is performed wherein the desoxyepothilone has the structure:

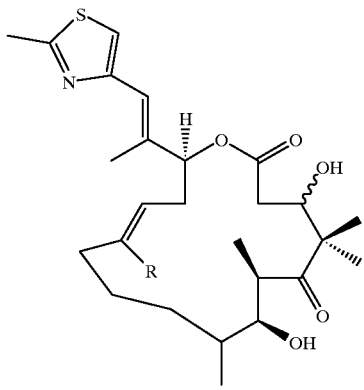

wherein R is H, methyl, ethyl, n-propyl, n-butyl, n-hexyl or hydroxypropyl. Preferably, the method is effected wherein the epothilone is deoxygenated using a zinc/copper couple. Favorably, the epothilone is deoxygenated in the presence of a polar solvent comprising isopropanol and water.

The present invention also provides a method of preparing a desoxyepothilone having the structure:

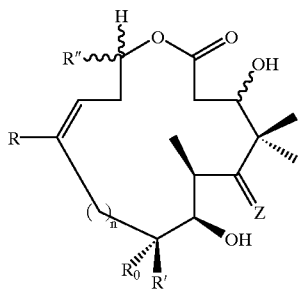

wherein R, $R_0$, and R' are independently H, linear or branched chain alkyl, optionally substituted by hydroxy, alkoxy, carboxy, carboxaldedyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; and wherein Z is O, $N(OR_3)$ or $N—NR_4R_5$ where $R_3$, $R_4$ and $R_5$ are independently H or a linear or branched alkyl; and wherein n is 0, 1, 2, or 3; which comprises treating a protected desoxyepothilone having the structure:

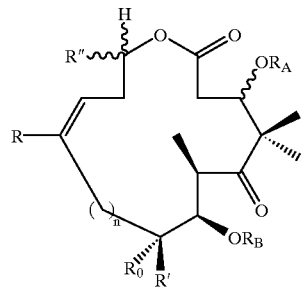

wherein $R_A$ is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein $R_B$ is hydrogen, t-butyloxycarbonyl, amyloxycarbonyl, (trialkylsilyl)alkyloxycarbonyl, (dialkylarylsilyl) alkyloxycarbonyl, benzyl, trialkylsilyl, dialkylarylsilyl, alkyldiarylsilyl, triarysilyl, a linear or branched acyl, substituted or unsubstituted aroyl or benzoyl; under suitable conditions to form the desoxyepothilone. In a certain embodiment, the invention provides a method wherein n is 3 and R" is 2-methyl-1,3-thiazolinyl. Preferably, the method is effected wherein $R_A$ is TES and $R_B$ is Troc. In a certain other embodiment, the invention provides a method wherein the treating step comprises contacting the protected desoxyepothilone (i) with $SmX_2$, where X is Cl, Br or I, in the presence of a polar nonaqueous solvent selected from the group consisting of tetrahydrofuran, p-dioxane, diethyl ether, acetonitrile and N,N-dimethylformamide, and optionally in the presence of N,N-dimethyl-N'-propylurea or hexamethylphosphoramide and (ii) with a source of fluoride ion selected from the group consisting of tetra-n-methylammonium fluoride, tetra-n-butylammonium fluoride and HF.pyridine.

The present invention also provides a method of preparing a protected desoxyepothilone having the structure:

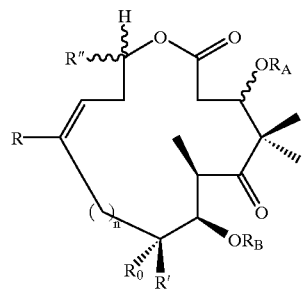

wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_A$ is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein $R_B$ is hydrogen, t-butyloxycarbonyl, amyloxycarbonyl, (trialkylsilyl)alkyloxycarbonyl, (dialkylarylsilyl)alkyloxycarbonyl, benzyl, trialkylsilyl, dialkylarylsilyl, alkyldiarylsilyl, triarysilyl, a linear or branched acyl, substituted or unsubstituted aroyl or benzoyl; which comprises cyclocondensing a hydroxy acid desoxyepothilone precursor having the structure:

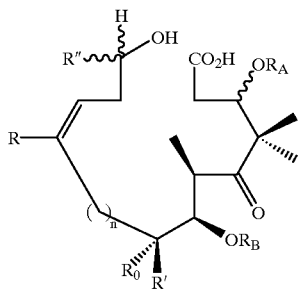

wherein R, $R_0$, $R_A$, $R_B$, R', R" and n are defined as above; under suitable conditions to form the protected desoxyepothilone. In particular, the method is carried out wherein n is 3 and R" is 2-methyl-1,3-thiazolinyl. Preferably, $R_A$ is a trialkylsilyl, and is more preferably, TES. $R_B$ is favorably trichloroethyloxycarbonyl (Troc). According to the method, the hydroxy acid desoxyepothilone precursor is cyclocondensed using a cyclocondensing reagent selected from the group consisting of acetic anhydride, pentafluorophenol, 2,4-dichlorobenzoyl chloride and, preferably, 2,4,6-trichlorobenzoyl chloride. In addition, the hydroxyacid is favorably cyclocondensed using 2,4,6-trichlorobenzoyl chloride in the presence of a tertiary amine selected from the group consisting of triethyl amine, tri-n-propylamine, diisopropylethylamine and diethyliso-propylamine, and optionally in the presence of pyridine or N,N-dimethylaminopyridine.

The present invention further provides a method of preparing a hydroxy acid desoxyepothilone precursor having the structure:

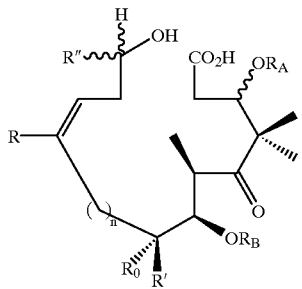

wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_A$ is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; wherein $R_B$ is hydrogen, t-butyloxycarbonyl, amyloxycarbonyl, (trialkylsilyl)alkyloxycarbonyl, (dialkylarylsilyl)alkyloxycarbonyl, benzyl, trialkylsilyl, dialkylarylsilyl, alkyldiarylsilyl, triarysilyl, linear or branched acyl, substituted or unsubstituted aroyl or benzoyl; which comprises selectively etherifying and hydrolyzing a hydroxy ester desoxyepothilone precursor having the structure:

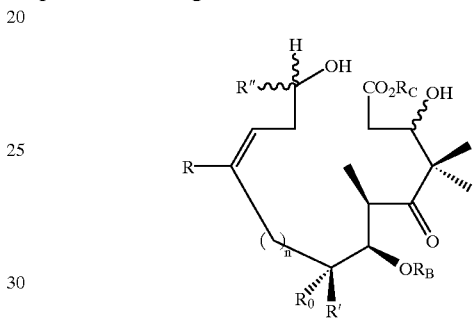

wherein R, $R_0$, $R_B$, $R_C$, R', R" and n are defined as above; and wherein $R_C$ is tertiary-alkyl; under suitable conditions to form the hydroxy acid desoxyepothilone precursor. In one embodiment, the invention is practiced wherein n is 3 and R" is 2-methyl-1,3-thiazolinyl. Preferably, $R_A$ is TES and $R_B$ is Troc. In accord with invention, the method is performed wherein the selective etherifying step comprises contacting the hydroxy ester desoxyepothilone precursor with a silylating reagent to form an ether intermediate, and the hydrolyzing step comprises contacting the ether intermediate with a protic acid or tetra-n-butylammonium fluoride. Favorably, the silylating reagent is TESOTf in the presence of 2,6-lutidine. The protic acid is typically HCl in the presence of an alkyl alcohol, preferably, methyl alcohol or ethyl alcohol.

The present invention also provides a method of preparing a hydroxy ester desoxyepothilone precursor having the structure:

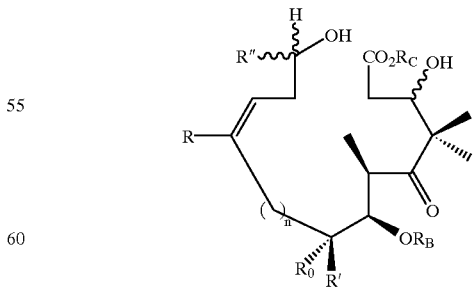

wherein R, $R_0$, and R' are independently H, linear or branched chain alkyl, optionally substituted by hydroxy, alkoxy, carboxy, carboxaldehyde, linear or branched alkyl or cyclic: acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyloxycarbonyl, (dialkylarylsilyl)alkyloxycarbonyl, benzyl, trialkylsilyl, dialkylarylsilyl, alkyldiarylsilyl, triarysilyl, linear or branched acyl, substituted or unsubstituted aroyl or benzoyl; and wherein $R_C$ is tertiary-alkyl; which comprises reducing a hydroxy ketoester desoxyepothilone precursor having the structure:

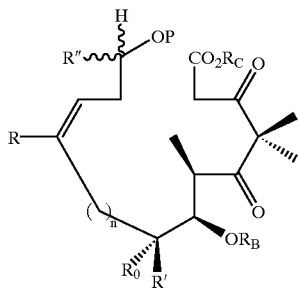

wherein P, R, $R_0$, $R_B$, $R_C$, R', R" and n are defined as above; under suitable conditions to form the hydroxy ester desoxyepothilone precursor. In one embodiment, the invention provides the method wherein n is 3 and R" is 2-methyl-1,3-thiazolinyl. In particular, $R_A$ is a trialkylsily group, and is, preferably, TES. $R_B$ is Troc. In accord with the invention, the reducing step comprises contacting the hydroxy ketoester desoxyepothilone precursor with a stereospecific reducing reagent. The stereospecific reducing reagent favorably comprises hydrogen gas at from about 900 pounds per square inch to about 2200 pounds per square inch in the presence of (R)-(BINAP)RuCl$_2$ and optionally in the presence of HCl and an alcohol selected from the group consisting of MeOH, EtOH, and I—PrOH. More preferably, the hydrogen gas pressure is 1200 psi.

The present invention further provides a method of preparing a hydroxy ketoester desoxyepothilone precursor having the structure:

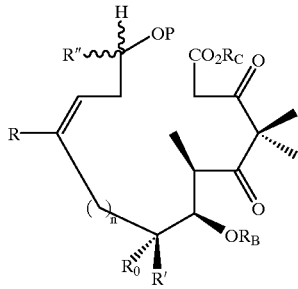

wherein P is H; wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyloxycarbonyl, (dialkylarylsilyl)alkyloxycarbonyl, benzyl, trialkylsilyl, dialkylarylsilyl, alkyldiarylsilyl, triarysilyl, a linear or branched acyl, substituted or unsubstituted aroyl or benzoyl; and wherein $R_C$ is tertiary-alkyl; which comprises deprotecting a protected ketoester desoxyepothilone precursor having the structure:

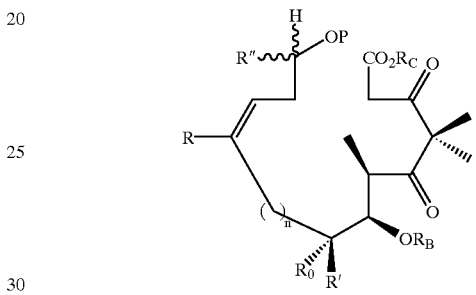

wherein R, $R_0$, $R_A$, $R_B$, $R_C$, R', R" and n are defined as above; and wherein P is a linear or branched alkyl, alkoxyalkyl, substituted or unsubstituted aryloxyalkyl, trialkylsilyl, aryldialkylsilyl, diarylalkylsilyl or triarylsilyl; under suitable conditions to form the hydroxy ketoester desoxyepothilone precursor. In one embodiment, n is 3 and R" is 2-methyl-1,3-thiazolinyl. $R_A$ is typically trialkylsilyl, and, preferably, is TES. $R_B$ is favorably Troc. The method is effectively practiced wherein P is TBS. In accord with the invention, the deprotecting step comprises contacting the protected ketoester desoxyepothilone precursor with a protic acid. Preferably, the protic acid is HCl in methyl alcohol or ethyl alcohol.

The present invention also provides a method of preparing a protected ketoester desoxyepothilone precursor having the structure:

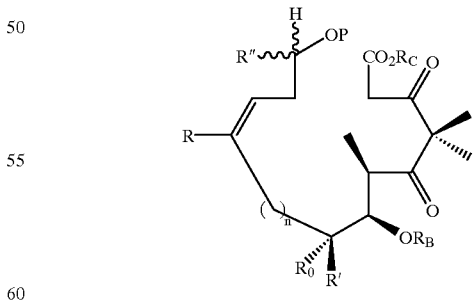

wherein P is a linear or branched alkyl, alkoxyalkyl, substituted or unsubstituted aryloxyalkyl, trialkylsilyl, aryldialkylsilyl, diarylalkylsilyl or triarylsilyl; wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyl-oxycarbonyl, (dialkylarylsilyl)alkyloxycarbonyl, benzyl, trialkylsilyl, dialkylarylsilyl, alkyldiarylsilyl, triarysilyl, a linear or branched acyl, substituted or unsubstituted aroyl or benzoyl; and wherein $R_C$ is tertiary-alkyl; which comprises coupling a terminal vinyl enol ether ester having the structure:

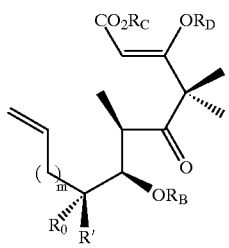

wherein R, $R_0$, $R_B$, $R_C$, and R' are defined as above; wherein m is 0, 1 or 2; and wherein $R_D$ is linear or branched alkyl, benzyl, trialkylsilyl, dialkylarylsilyl, alkyldiarylsilyl, linear or branched acyl, substituted or unsubstituted aroyl or benzoyl; with a protected halovinyl or metalvinyl compound having the structure:

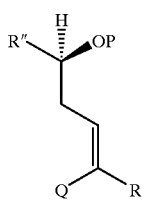

wherein R, P and R are defined as above; and wherein Q is a halide or a metal; under suitable conditions to form the protected ketoester desoxyepothilone precursor. In one embodiment, the invention provides the method wherein n is 3 and R" is 2-methyl-1,3-thiazolinyl. In another embodiment, the method is effectively performed wherein $R_A$ is a trialkylsilyl group, and is, preferably, TES, and $R_B$ is Troc. P is favorably TBS or TES, and Q is iodine or bromine. $R_D$ is typically methyl or TES. In accord with the invention, the coupling step comprises contacting the terminal vinyl enol ether ester and the protected halovinyl compound with noble metal complex capable of effecting a Suzuki coupling. For this step, the noble metal complex is effectively chosen as $Pd(dppf)_2Cl_2$ in the presence of $Ph_3As$ and $Cs_2CO_3$.

The present invention also provides a method of preparing a terminal vinyl enol ether ester having the structure:

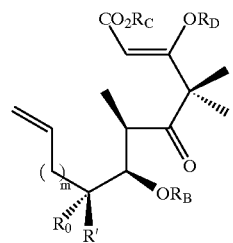

wherein $R_0$ and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein m is 0, 1 or 2; wherein $R_B$ is hydrogen, t-butyloxycarbonyl, amyloxycarbonyl, (trialkylsilyl)alkyl-oxycarbonyl, (dialkylarylsilyl)alky-loxycarbonyl, benzyl, trialkylsilyl, dialkylarylsilyl, alkyldiarylsilyl, triarysilyl, linear or branched acyl, substituted or unsubstituted aroyl or benzoyl; wherein $R_C$ is tertiary-alkyl; and wherein $R_D$ is linear or branched alkyl, benzyl, trialkylsilyl, dialkylarylsilyl, alkyldiarylsilyl, triarysilyl, linear or branched acyl, substituted or unsubstituted aroyl or benzoyl; which comprises:

(a) treating a keto enol ester having the structure:

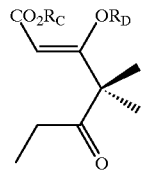

under suitable conditions to form an enolate enol ester having the structure:

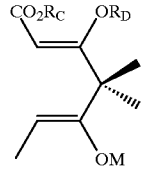

wherein M is Li, Na or K; and (b) coupling the enolate enol ester with a vinyl aldehyde having the structure:

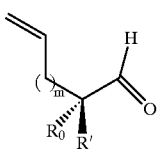

wherein m, and $R_0$ and R' are as defined above; under suitable conditions to form the terminal vinyl enol ether ester. In accord with the invention, the treating step comprises contacting the keto enol ester with a strong nonnucleophilic base selected from the group consisting of lithium diethylamide, lithium diethylamide, lithium diisopropylamide, lithium hydride, sodium hydride, potassium hydride and potassium t-butoxide. Preferably, the treating step is effected in a polar nonaqueous solvent selected from the group consisting of tetrahydrofuran, diethyl ether, di-n-propyl ether and dimethylformamide at a temperature from about −100° C. to about +10° C. More preferably, the temperature is from about −20° C. to 40° C. The coupling step as practiced in the invention comprises contacting the enolate enol ester with the vinyl aldehyde at a temperature from about −130° C. to about −78° C.

In addition, the invention provides a method of treating cancer in a subject suffering therefrom comprising administering to the subject a therapeutically effective amount of any of the analogues related to epothilone B disclosed herein optionally in combination with an additional chemotherapeutic agent and/or with a pharmaceutically suitable carrier. The method may be applied where the cancer is a solid tumor or leukemia. In particular, the method is applicable where the cancer is breast cancer or melanoma.

The subject invention also provides a pharmaceutical composition for treating cancer comprising any of the analogues of epothilone disclosed hereinabove, as an active ingredient, optionally though typically in combination with an additional chemotherapeutic agent and/or a pharmaceutically suitable carrier. The pharmaceutical compositions of the present invention may further comprise other therapeutically active ingredients.

The subject invention further provides a method of treating cancer in a subject suffering therefrom comprising administering to the subject a therapeutically effective amount of any of the analogues of epothilone disclosed hereinabove and a pharmaceutically suitable carrier. The method is especially useful where the cancer is a solid tumor or leukemia.

The compounds taught above which are related to epothilones A and B are useful in the treatment of cancer, and particularly, in cases where multidrug resistance is present, both in vivo and in vitro. The ability of these compounds as non-substrates of MDR in cells, as demonstrated in the Tables below, shows that the compounds are useful to treat, prevent or ameliorate cancer in subjects suffering therefrom.

The magnitude of the therapeutic dose of the compounds of the invention will vary with the nature and severity of the condition to be treated and with the particular compound and its route of administration. In general, the daily dose range for anticancer activity lies in the range of 0.001 to 25 mg/kg of body weight in a mammal, preferably 0.001 to 10 mg/kg, and most preferably 0.001 to 1.0 mg/kg, in single or multiple doses. In unusual cases, it may be necessary to administer doses above 25 mg/kg.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

Methods of preparation of intermediates are disclosed in U.S. Patent Application Serial Nos. 60/032,282, 60/033,767, 60/047,566, 60/047,941, and 60/055,533, filed Dec. 3, 1996, Jan. 14, 1997, May 22, 1997, May 29, 1997, and Aug. 13, 1997, respectively, the contents of which are hereby incorporated by reference into this application.

The present invention will be better understood from the Experimental Details which follow. However, one skilled in the art will readily appreciate that the specific methods and results discussed are merely illustrative of the invention as described in the claims which follow thereafter. It will be understood that the processes of the present invention for preparing epothilones A and B, analogues thereof and intermediates thereto encompass the use of various alternate protecting groups known in the art. Those protecting groups used in the disclosure including the Examples below are merely illustrative.

EXAMPLE 1

THP glycidol; 13: A solution of (R)-(+)-glycidol 12 (20 g; 270 mmol) and freshly distilled 3,4-dihydro-2H-pyran (68.1 g; 810 mmol) in $CH_2Cl_2$ (900 ml) was treated with pyridinium p-toluenesulfonate (2.1 g; 8.36 mmol) at rt and the resulting solution was stirred for 16 h. Approximately 50% of the solvent was then removed in vacuo and the remaining solution was diluted with ether (1 L). The organic layer was then washed with two portions of saturated aqueous sodium bicarbonate (500 ml), dried ($Na_2SO_4$), filtered, and concentrated. Purification of the residue by flash chromatography (silica, 25→50% ether:hexanes) afforded THP glycidol 13 (31.2 g; 73%) as a colorless liquid: IR (film): 2941, 1122, 1034 $cm^{-1}$; $^1H$ NMR ($CDCl_3$, 500 MHz)δ4.66(t, J=3.5 Hz, 1H), 4.64 (t, J=3.5 Hz, 1H), 3.93 (dd, J=11.7, 3.1 Hz, 1H), 3.86 (m, 2H), 3.73 (dd, J=11.8, 5.03 Hz, 1H), 3.67 (dd, J=11.8, 3.4 Hz, 1H), 3.51 (m, 2H), 3.40 (dd, J=11.7, 6.4, 1H), 3.18 (m, 2H), 2.80 (m, 2H), 2.67 (dd, J=5.2, 2.7 Hz, 1H), 2.58 (dd, J=5.0, 2.7 Hz,1H), 1.82 (m, 2H), 1.73 (m, 2H), 1.52 (m, 4H); $^{13}$C NMR (CDCl$_3$, 125MHz)δ98.9, 98.8, 68.5, 67.3, 62.4, 62.2, 50.9, 50.6,44.6, 44.5, 30.5, 30.4, 25.4, 19.3, 19.2; [a]$_D$=+4.98 (c=2.15, CHCl$_3$).

EXAMPLE 2

Alcohol 13a: Trimethylsilylacetylene (32.3 g; 329 mmol) was added via syringe to THF (290 ml), and the resulting solution was cooled to −78° C. and treated with n-butyllithium (154 ml of a 1.6 M solution in hexanes; 246.4 mmol). After 15 min, boron trifluoride diethyl etherate (34.9 g; 246 mmol) was added, and the resulting mixture was stirred for 10 min. A solution of epoxide 13 (26 g; 164.3 mmol) in THF (130 ml) was then added via a cannula and the resulting solution was stirred for 5.5 h at −78° C. The reaction was quenched by the addition of saturated aqueous sodium bicarbonate solution (250 ml) and the solution was allowed to warm to rt. The mixture was then diluted with ether (600 ml) and washed successively with saturated aqueous sodium bicarbonate solution (250 ml), water (250 ml), and brine (250 ml). The organic layer was then dried (Na$_2$SO$_4$), filtered, and concentrated in vacuo. Purification of the residue by flash chromatography (silica, 20% ether:hexanes) provided alcohol 13a (34 g; 76%).

EXAMPLE 3

MOM ether 13b: A solution of alcohol 13a (24 g; 88.9 mmol) and N,N-diisopropylethylamine (108 ml; 622 mmol) in anhydrous 1,2-dichloroethane (600 ml) was treated with chloromethyl methyl ether (17 ml; 196 mmol), and the resulting mixture was heated to 55° C. for 28 h. The dark mixture was then cooled to rt and treated with saturated aqueous sodium bicarbonate solution (300 ml). The layers were separated, and the organic layer was washed successively with saturated aqueous sodium bicarbonate solution (200 ml) and brine (200 ml). The organic layer was then dried (MgSO$_4$) and filtered through a pad of silica gel (ether rinse). Purification of the residue by flash chromatography (silica, 20→30% ether:hexanes) afforded MOM ether 13b (23.7 g; 85%) as a pale yellow oil.

EXAMPLE 4

Alcohol 14: A solution of THP ether 13b (20 g; 63.7 mmol) in methanol (90 ml) was treated with pyridinium p-toluenesulfonate (4.0 g; 15.9 mmol) and the resulting mixture was stirred at rt for 16 h. The reaction was then quenched by the addition of saturated aqueous sodium bicarbonate solution (100 ml), and the excess methanol was removed in vacuo. The residue was diluted with ether (300 ml), and the organic layer was washed successively with saturated aqueous sodium bicarbonate solution (200 ml) and brine (200 ml). The organic layer was dried (MgSO$_4$), filtered, and concentrated. Purification of the residue by flash chromatography (silica, 40→50% ether:hexanes) provided alcohol 14 (13.1 g; 95%) as a colorless oil.

EXAMPLE 5

Alcohol 14a: To a cooled (−78° C.) solution of oxalyl chloride (24.04 ml of a 2.0 M solution in CH$_2$Cl$_2$; 48.08 mmol) in CH$_2$Cl$_2$ (165 ml) was added anhydrous DMSO (4.6 ml; 64.1 mmol) in dropwise fashion. After 30 min, a solution of alcohol 14 (6.93 g; 32.05 mmol) in CH$_2$Cl$_2$ (65 ml+10 ml rinse) was added and the resulting solution was stirred at −78° C. for 40 min. Freshly distilled triethylamine (13.4 ml; 96.15 mmol) was then added, the cooling bath was removed, and the mixture was allowed to warm to 0° C. The reaction mixture was then diluted with ether (500 ml), and washed successively with two portions of water (250 ml) and one portion of brine (250 ml). The organic layer was then dried (MgSO$_4$), filtered, and concentrated.

The crude aldehyde (6.9 g) prepared in the above reaction was dissolved in ether (160 ml) and cooled to 0° C. Methylmagnesium bromide (32.1 ml of a 3.0 M solution in butyl ether; 96.15 mmol) was then added, and the solution was allowed to warm slowly to rt. After 10 h, the reaction mixture was cooled to 0° C. and the reaction was quenched by the addition of saturated aqueous ammonium chloride solution. The mixture was diluted with ether (200 ml) and washed successively with water (150 ml) and brine (150 ml). The organic layer was dried (MgSO$_4$), filtered, and concentrated. Purification of the residue by flash chromatography (silica, 40→50% ether:hexanes) provided alcohol 14a (6.3 g; 85% from 14).

EXAMPLE 6

Ketone 15: A solution of alcohol 14 (1.0 g; 4.35 mmol), 4 Å mol. sieves, and N-methylmorpholine-N-oxide (1.0 g; 8.7 mmol) in CH$_2$Cl$_2$ (20 ml) at rt was treated with a catalytic amount of tetra-n-propylammonium perruthenate, and the resulting black suspension was stirred for 3 h. The reaction mixture was then filtered through a pad of silica gel (ether rinse), and the filtrate was concentrated in vacuo. Purification of the residue by flash chromatography (silica, 10% ether:hexanes) afforded ketone 15 (924 mg; 93%) as a light yellow oil.

EXAMPLE 7

Alkene 17: A cooled (−78° C.) solution of phosphine oxide 16 (1.53 g; 4.88 mmol) in THF (15.2 ml) was treated with n-butyllithium (1.79 ml of a 2.45 M solution in hexanes). After 15 min, the orange solution was treated with a solution of ketone 15 (557 mg; 2.44 mmol) in THF (4.6 ml). After 10 min, the cooling bath was removed, and the solution was allowed to warm to rt. The formation of a precipitate was observed as the solution warmed. The reaction was quenched by the addition of saturated aqueous ammonium chloride solution (20 ml). The mixture was then poured into ether (150 ml) and washed successively with water (50 ml) and brine (50 ml). The organic layer was dried (Na$_2$SO$_4$), filtered, and concentrated. Purification of the residue by flash chromatography (silica, 10% ether:hexanes) afforded alkene 17 (767 mg; 97%) as a colorless oil: IR (film): 2956, 2177, 1506, 1249, 1149, 1032, 842, cm$^{-1}$; $^1$H NMR (CDCl$_3$, 500MHz)δ6.95(s, 1H), 6.53(s, 1H), 4.67(d, J=6.7 Hz, 1H), 4.57 (d, J=6.8 Hz, 1H), 4.29 (dd, J=8.1, 5.4 Hz, $_1$ H), 3.43 (s, 3H), 2.70 (s, 3H), 2.62 (dd, J=16.9, 8.2 Hz, 1H), 2.51 (dd, J=17.0,5.4 Hz, 1H), 2.02(s, 3H); $^{13}$C NMR (CDCl$_3$, 125 MHz)δ164.4, 152.5, 137.1, 121.8, 116.2, 103.7, 93.6, 86.1, 79.6, 55.4, 25.9, 19.1, 13.5; [α]$_D$=−27.3 (c=2.2, CHCl$_3$).

EXAMPLE 8

Alkynyl iodide formation: To a solution of the alkyne 17 (3.00 g, 9.29 mmol) in acetone (100 mL) at 0° C. was added NIS (2.51 g; 11.2 mmol) and AgNO$_3$ (0.160 g; 0.929 mmol). The mixture was then slowly warmed to rt. After 1.5 h, the reaction was poured into Et$_2$O (250 mL) and washed once with sat bisulfite (40 mL), once with sat NaHCO$_3$ (40 mL), once with brine (40 mL) and dried over anhydrous MgSO$_4$.

Purification by flash chromatography on silica gel using gradient elution with hexanes/ethyl acetate (10:1–7:1) gave 2.22 g (64%) of the iodide 17a as an amber oil.

EXAMPLE 9

Reduction of the alkynyl iodide: $BH_3 \cdot DMS$ (0.846 mL, 8.92 mmol) was added to a solution of cyclohexene (1.47 mL, 17.9 mmol) in $Et_2O$ (60 mL) at 0° C. The reaction was then warmed to rt. After 1 h, the iodide x (2.22 g, 5.95 mmol) was added to $Et_2O$. After 3 h, AcOH (1.0 mL) was added. After 30 additional min, the solution was poured into sat $NaHCO_3$ and extracted with $Et_2O$ (3×100 mL). The combined organics were then washed once with brine (50 mL) and dried over anhydrous $MgSO_4$. Purification by flash chromatography on silica gel eluting with hexanes/ethyl acetate (6:1) gave 1.45 g (65%) of the vinyl iodide 18 as a yellow oil.

EXAMPLE 10

MOM removal: To a solution of iodide 18 (1.45 g, 3.86 mmol) in $CH_2Cl_2$ (40 mL) at rt was added thiophenol (1.98 mL, 19.3 mmol) and $BF_3 \cdot Et_2O$ (1.90 mL, 15.43 mmol). After 22 h, the reaction was poured into EtOAc (150 mL) and washed with 1 N NaOH (2×50 mL) and dried over anhydrous $MgSO_4$. Purification by flash chromatography on silica gel using gradient elution with hexanes/ethyl acetate (4:1–2:1–1:1) gave 1.075 g (86%) of the alcohol 18a as a pale yellow oil.

EXAMPLE 11

Acetate formation: To a solution of alcohol 18a (1.04 g, 3.15 mmol) in $CH_2Cl_2$ (30 mL) was added pyridine (2.52 mL, 25.4 mmol), acetic anhydride (1.19 mL, 12.61 mmol) and DMAP (0.005 g). After 1 h, the volatiles were removed in vacuo. Purification of the resulting residue by flash chromatography on silica gel eluting with hexanes/ethyl acetate (7:1) gave 1.16 g (99%) of the acetate 19 as a pale yellow oil. IR (film):1737, 1368, 1232, 1018 cm$^{-1}$; $^1$H NMR ($CDCl_3$, 500MHz)δ6.97 (s, 1H), 6.53 (s,1H), 6.34 (dd, J=17.5, 1.0 Hz, 1H), 6.18 (dd, J=13.7, 6.9 Hz, 1 h), 5.40 (t, J=6.4 Hz, 1H), 2.70 (s, 3 h), 2.61 (m, 2H), 2.08 (2s, 6H). $^{13}$C NMR ($CDCl_3$, 125 MHz)δ169.8, 164.4, 152.2, 136.4, 136.1, 120.6, 116.4, 85.1, 38.3, 21.0, 19.1, 14.7; $[\alpha]_D$=−28.8 (c=1.47, $CHCl_3$).

EXAMPLE 12

To a solution of alcohol 4 (2.34 g, 3.62 mmol) and 2,6-lutidine (1.26 mL, 10.86 mmol) in $CH_2Cl_2$ (23 mL) at 0° C. was treated with TBSOTf (1.0 mL, 4.34 mmol). After stirrring for 1.5 h at 0° C. the reaction mixture was quenched with MeOH (200 uL) and the mixture stirred an additional 5 min. The reaction mixture was diluted with $Et_2O$ (100 mL) and washed successively with 1 N HCl (25 mL), water (25 mL), and brine (25 mL). The solution was dried over $MgSO_4$, filtered, and concentrated. The residue was purified by flash chromatography on silica gel eluting with 5% $Et_2O$ in hexanes to provide compund 7 (2.70 g, 98%) as a colorless foam.

EXAMPLE 13

A solution of compound 7 (2.93 g, 3.85 mmol) in $CH_2Cl_2$/$H_2O$ (20:1, 80 mL) was treated with DDQ (5.23 g, 23.07 mmol) and the resulting suspension was stirred at room temperature for 24 h. The reaction mixture was diluted with $Et_2O$ (200 mL) and washed with aqueous $NaHCO_3$ (2×40 mL). The aqueous layer was extracted with $Et_2O$ (3×40 mL) and the combined organic fractions were washed with brine (50 mL), dried over $MgSO_4$, filtered, and concentrated. Purification of the crude oil by flash chromatography on silica gel eluting with 30% ether in hexanes afforded alcohol 7A (2.30 g, 89%) as a colorless oil: IR (film) 3488, 1471, 1428, 1115, 1054 cm$^{-1}$; $^1$H NMR ($CDCl_3$, 500 MHz)δ7.70 (6H, dd, J=8.0, 1.5 Hz), 7.44 (9 H, s), 4.57 (1H, d, J=3.5 Hz), 4.19 (1H, s), 3.67 (1H, d, J=8.5 Hz), 3.06 (1H, dd, J=11.5, 5.0 Hz), 2.89 (1H, dd, J=11.5, 5.0 Hz), 2.68 (1H, d, J=13.5 Hz), 2.59 (1H, d, J=13.5 Hz), 2.34 (1H, dt, J=12.0, 2.5 Hz), 2.11 (1H, m), 1.84 (1H, dt, J=12.0, 2.5 Hz), 1.76 (2H, m), 1.59 (2H, m), 1.34 (3H, 5), 1.13 (3H, d, J=7.5 Hz), 1.10 (3H, s), 0.87 (9 H, s), 0.84 (3H, d, J=12.0 Hz), 0.02 (3H, s), 0.01 (3H, s); $^{13}$C NMR ($CDCl_3$, 125 MHz)δ136.18, 134.66, 130.16, 127.84, 78.41, 75.91, 63.65, 59.69, 45.43, 45.09, 37.72, 30.84, 30.50, 26.23, 25.89, 22.42, 21.05, 18.40, 15.60, 14.41, −3.23, −3.51; $[\alpha]_D$=−0.95 (c=0.173, $CHCl_3$).

EXAMPLE 14

To a solution of oxalyl chloride (414 μL, 4.74 mmol) in $CH_2Cl_2$ (40 mL) at −78° C. was added dropwise DMSO (448 uL, 6.32 mmol) and the resulting solution was stirred at −78° C. for 30 min. Alcohol 7a (2.12 g, 3.16 mmol) in $CH_2Cl_2$ (20 mL) was added and the resulting white suspension was stirred at −78° C. for 45 min. The reaction mixture was quenched with $Et_3N$ (2.2 mL, 15.8 mmol) and the solution was allowed to warm to 0° C. and stirred at this temperature for 30 min. The reaction mixture was diluted with $Et_2O$ (100 mL) and washed successively with aqueous $NH_4Cl$ (20 mL), water (20 mL), and brine (20 mL). The crude aldehyde was purified by flash chromatography on silica gel eluting with 5% $Et_2O$ in hexanes to provide aldehyde 8 (1.90 g, 90%) as a colorless oil.

EXAMPLE 15

A solution of (methoxymethyl)triphenylphosphonium chloride (2.97 g, 8.55 mmol) in THF (25 mL) at 0° C. was treated with KO$^t$Bu (8.21 mL, 1M in THF, 8.1 mmol). The mixture was stirred at 0° C. for 30 min. Aldehyde 8 (3.1 g, 4.07 mmol) in THF (10 mL) was added and the resulting solution was allowed to warm to room temperature and stirred at this temperature for 2 h. The reaction mixture was quenched with aqueous $NH_4Cl$ (40 mL) and the resulting solution extracted with $Et_2O$ (3×30 mL). The combined $Et_2O$ fractions were washed with brine (20 ml), dried over $MgSO_4$, filtered, and concentrated. The residue was purified by flash chromatography on silica gel eluting with 5% $Et_2O$ in hexanes to yield compound 9 (2.83 g, 86%) as a colorless foam.

EXAMPLE 16

To a solution of compound 9 (2.83 g, 3.50 mmol) in dioxane/$H_2O$ (9:1, 28 mL) was added pTSA.$H_2O$ (1.0 g, 5.30 mmol) and the resulting mixture was heated to 50° C. for 2 h. After cooling to room temperature the mixture was diluted with $Et_2O$ (50 mL) and washed with aqueous $NaHCO_3$ (15 mL), brine (20 ml), dried over $MgSO_4$, filtered, and concentrated to provide aldehyde 9a (2.75 g, 99%) as a colorless foam.

EXAMPLE 17

Methyltriphenylphosphonium bromide (1.98 g, 5.54 mmol) in THF (50 mL) at 0° C. was treated with lithium bis(trimethylsilyl)amide (5.04 mL, 1M in THF, 5.04 mmol)

and the resulting solution was stirred at 0° C. for 30 min. Aldehyde 9a (2.0 g, 2.52 mmol) in THF (5.0 mL) was added and the mixture was allowed to warm to room temperature and stirred at this temperature for 1 h. The reaction mixture was quenched with aqueous $NH_4Cl$ (15 mL) and extracted with $Et_2O$ (3×20 mL). The combined $Et_2O$ fractions were washed with brine (15 mL), dried over $MgSO_4$, filtered, and concentrated. The residue was purified by flash chromatography on silica gel eluting with 5% $Et_2O$ in hexanes to afford compound 10 (1.42 g, 76%) as a colorless foam.

EXAMPLE 18

A solution of compound 10 (1.0 g, 1.34 mmol) in MeOH/THF (2:1, 13 mL) was treated with [bis(trifluoroacetoxy) iodobenzene] (865 mg, 2.01 mmol) at room temperature. After 15 min the reaction mixture was quenched with aqueous $NaHCO_3$ (25 mL). The mixture was extracted with $Et_2O$ (3×25 mL) and the combined $Et_2O$ fractions were washed with brine, dried over $MgSO_4$, filtered, and concentrated. Purification of the residue by flash chromatography on silica gel eluting with 5% $Et_2O$ in hexanes provided compound 11 (865; mg, 92%) as a colorless foam: IR (film) 1428, 1252, 1114, 1075, 1046$cm^{-1}$; $^1H$ NMR ($CDCl_3$, 500 MHz)δ7.61 (6H, dd, J=7.9, 1.4 Hz), 7.38 (9 H, s), 5.47 (1H, m), 4.87 (1H, d, J=10.0 Hz), 4.76 (1H, d, J=15.9 Hz), 4.30 (1H, d, J=3.7 Hz), 3.95 (1H, s), 3.56 (1H, dd, J=7.5, 1.4 Hz), 3.39 (3H, s), 2.84 (3H, 5), 2.02 (1H, m), 1.64 (2H, m), 1.34 (1H, m), 1.11 (3 H, s), 1.02 (3H, d, J=7.4 Hz), 0.90 (3H, s), 0.85 (9 H, s), 0.62 (3H, d, J=6.8 Hz), −0.04 (3H, s), −0.05 (3H, s); $^{13}C$ NMR ($CDCl_3$, 125 MHz)δ138.29, 135.79, 135.04, 129.86, 127.78, 114.98, 110.49, 60.11, 55.57, 46.47, 43.91, 36.82, 34.21, 26.26, 19.60, 18.60, 17.08, 16.16, 13.92, −2.96, −3.84; $[\alpha]_D$=+1.74 (c=0.77, $CHCl_3$).

EXAMPLE 19

Suzuki Coupling: To a solution of olefin 11 (0.680 g, 1.07 mmol) in THF (8.0 mL) was added 9-BBN (0.5 M soln in THF, 2.99 mL, 1.50 mmol). In a separate flask, the iodide 19 (0.478 g, 1.284 mmol) was dissolved in DMF (10.0 mL). $CsCO_3$ (0.696 g, 2.14 mmol) was then added with vigorous stirring followed by sequential addition of $Ph_3As$ (0.034 g, 0.111 mmol), $PdCl_2(dppf)_2$ (0.091 g, 0.111 mmol) and $H_2O$ (0.693 mL, 38.5 mmol). After 4 h, then borane solution was added to the iodide mixture in DMF. The reaction quickly turned dark brown in color and slowly became pale yellow after 2 h. The reaction was then poured into $H_2O$ (100 mL) and extracted with $Et_2O$ (3×50 mL). The combined organics were washed with $H_2O$ (2×50 mL), once with brine (50 mL) and dried over anhydrous $MgSO_4$. Purification by flash chromatography on silica gel eluting with hexanes/ethyl acetate (7:1) gave 0.630 g (75%) of the coupled product 20 as a pale yellow oil.

EXAMPLE 20

Hydrolysis of dimethyl acetal 21: The acetate 20 (0.610 g, 0.770 mmol) was dissolved in dioxane/$H_2O$ (9:1, 15 mL) and p-TSA.$H_2O$ (0.442 g, 2.32 mmol) was added. The mixture was then heated to 55° C. After 3 h, the mixture was cooled to rt and poured into $Et_2O$. This solution was washed once with sat $NaHCO_3$ (30 mL), once with brine (30 mL) and dried over anhydrous $MgSO_4$. Purification by flash chromatography on silica gel eluting with hexanes/ethyl acetate (7:1) gave 0.486 g (85%) of the aldehyde 21 as a pale yellow oil. IR (film) 1737, 1429, 1237, 1115, 1053 $cm^{-1}$; $^1H$ NMR ($CDCl_3$, 500 MHz)δ9.74 (1H, s), 7.61 (6 H, dd, J=7.8, 1.2 Hz), 7.38 (9 H, m), 6.94 (1H, s), 6.53 (1H, s), 5.39 (1H, m), 5.31 (1H, m), 5.29 (1H, t, J=6.9 Hz), 4.61 (1H, d, J=4.3 Hz), 3.50 (1H, dd, J=5.2, 2.6 Hz), 2.70 (3H, s), 2.48 (2H, m), 2.14 (1H, m), 2.09 (3H, s), 2.07 (3H, s), 1.83 (2H, m), 1.41 (1H, m), 1.18 (1H, m), 1.01 (3H, s), 0.99 (3H, s), 0.91 (3H, d, J=7.4 Hz), 0.85 (9 H, s), 0.69 (1H, m), 0.58 (3H, d, J=6.8 Hz), −0.05 (3H, s), −0.06 (3H, s); $^{13}C$ NMR ($CDCl_3$, 125 MHz)δ205.46, 170.01, 164.49, 152.46, 137.10, 135.60, 134.22, 132.55, 130.65, 127.84, 123.82, 120.66, 116.19, 81.09, 78.47, 76.73, 51.66, 43.14, 38.98, 30.99, 30.42, 27.63, 26.10, 21.15, 20.92, 20.05, 19.15, 18.49, 15.12, 14.70, 12.75, −3.25, −4.08; $[\alpha]_D$=−18.7 (c=0.53, $CHCl_3$).

EXAMPLE 21

Aldol: To a solution of the acetate-aldehyde 21 (84 mg,0.099 mmol) in THF at −78° C. was added KHMDS (0.5M in toluene, 1.0 ml, 0.5 mmol)) dropwise. The resulting solution was stirred at −78° C. for 30 min. Then the reaction mixture was cannulated to a short pad of silica gel and washed with ether. The residue was purified by flash chromatography (silica, 12% EtOAc in hexane) to give the lactone 22 (37 mg of 3-S and 6 mg of 3-R, 51%) as white foam.

EXAMPLE 22

Monodeprotection: Lactone 22 (32 mg, 0.0376 mmol) was treated with 1 ml of pyridine buffered HF.pyridine—THF solution at room temperture for 2 h. The reaction mixture was poured into saturated aqueous $NaHCO_3$ and extracted with ether . The organic layer was washed in sequence with saturated $CuSO_4$ (10 ml×3) and saturated $NaHCO_3$ (10 ml), then dried over $Na_2SO_4$ and concentrated under vacuum. The residue was purified by flash chromatography (silica, 25% EtOAc in hexane) and to give diol 22a (22 mg, 99%) as white foam.

EXAMPLE 23

TBS-protection: To a cooled (−30° C.) solution of diol 22a (29 mg, 0.0489 mmol) and 2,6-lutidine (0.017 ml, 0.147 mmol) in anhydrous $CH_2Cl_2$ (1 ml) was added TBSOTf (0.015 ml, 0.0646 mmol). The resulting solution was then stirred at −30° C. for 30 min. The reaction was quenched with 0.5M HCl (10 ml) and extracted with ether (15 ml). Ether layer was washed with saturated $NaHCO_3$, dried ($Na_2SO_4$) and concentrated in vacuo. Purifiction of the residue by flash chromatogrphy (silica, 8% EtOAc in hexane) afforded TBS ether 22B (32 mg, 93%) as white foam.

EXAMPLE 24

Ketone Formation: To a solution of alcohol 22B (30 mg, 0.0424 mmol) in $CH_2Cl_2$ (2.0 mL) at 25° C. was added Dess-Martin periodinane (36 mg, 0.0848 mmol) in one portion. The resulting solution was then allowed to stir at 25° C. for 1.5 h. The reaction was quenched by the addition of 1:1 saturated aqueous sodium bicarbonate: sodium thiosulfate (10 ml) and stirred for 5 min. The mixture was then extracted with ether (3×15ml). The organic layer was dried ($Na_2SO_4$), filtered, and concentrated in vacuo . Purification of the residue by flash chromatography (silica, 8% EtOAc in hexane) provided ketone 22C (25 mg, 84%) as white foam. IR (film): 2928, 1745, 1692, 1254, 1175, 836 $cm^{-1}$; $^1H$ NMR ($CDCl_3$, 500 MHz)δ6.97 (s, 1H), 6.57 (s, 1H), 5.53 (dt, J=3.4, 11.1 Hz, 1H), 5.37 (dd, J=16.4, 9.9 Hz, 1H), 5.00 (d, J=10.3 Hz, 1H), 4.02 (d, J=9.7 Hz, 1H), 3.89 (d, J=8.7 Hz, 1H), 3.00 (m, 1H), 2.82 (d, J=6.5 Hz, 1H), 2.71 (m, 5H), 2.36 (q, J=10.7 Hz, 1H), 2.12 (, 3H), 2.07 (dd, J=8.2, 1H), 1.87 (bs, 1H), 1.49 (m, 3H), 1.19 (m, 5H), 1.14 (s, 3H), 1.08 (d, J=6.8 Hz, 3H), 0.94 (m, 12H), 0.84 (s, 9H), 0.12 (s, 3H), 0.10 (s, 3H), 0.07 (s, 3H), −0.098 (s, 3H); $^{13}$C NMR (CDCl$_3$, 125 MHz)δ218.7, 170.1, 164.5, 152.6, 137.9, 133.9, 124.8, 119.6, 115.9, 72.7, 53.2, 43.9, 41.0, 40.3, 32.9, 32.3, 28.4, 27.1, 26.3, 26.1, 26.0, 19.2, 19.1, 18.3, 18.2, 17.1, 16.0, 15.2, 14.3, −4.2, −4.4, −4.6, −4.8 $[\alpha]_D$=−21.93 (c=1.4, CHCl$_3$).

EXAMPLE 25

Desoxy compound: To a solution of TBS ether 22C (27 mg, 0.038 mmol) in THF(1 ml) at 25° C. in a plastic vial was added dropwise HF.pyridine (0.5 ml). The resulting solution was allowed to stir at 25° C. for 2 h. The reaction mixture was diluted with chloroform (2 ml) and very slowly added to satured sodium bicarbonate (20 ml). The mixture was extracted with CHCl$_3$ (20 ml×3). The organic layer was dried (Na$_2$SO$_4$), filtered, and concentrated in vacuo. Purification of the residue by flash chromatography (silica, 30% EtOAc in hexane) provided diol 23 (18 mg, 99%) as white foam: IR (film): 3493, 2925, 1728, 1689, 1249 cm$^{-1}$; $^1$H NMR (CDCl$_3$, 500 MHz)δ6.96 (s, 1H), 6.59 (s, 1H), 5.44 (dt, J=4.3, 10.4 Hz, 1H), 5.36 (dt, J=5.1, 10.2 Hz, 1H), 5.28 (dd, J=1.7, 9.8 Hz, 1H), 4.11 (d, J=7.2 Hz, 1H), 3.74 (s, 1H), 3.20 (d, J=4.5 Hz, 1H), 3.14 (dd, J=2.2, 6.8 Hz, 1H), 3.00 (s, 1H), 2.69 (m, 4H), 2.49 (dd, J=11.3, 15.1 Hz, 1H), 2.35 (dd, J=2.5, 15.1 Hz, 1H), 2.27 (m, 1H), 2.05 (m, 1H), 2.04 (s, 3H), 2.01 (m, 1H) 1.75 (m, 1H), 1.67 (m, 1H), 1.33 (m, 4H), 1.21 (s, 1H), 1.19 (m, 2H), 1.08 (d, J=7.0 Hz, 3H), 1.00 (s, 3H), 0.93 (d, J=7.1 Hz, 3H); $^{13}$C NMR (CDCl$_3$, 125 MHz) δ226.5, 176.5, 171.1, 158.2, 144.7, 139.6, 131.1, 125.7, 122.0, 84.6, 80.2, 78.6, 59.4, 47.9, 45.4, 44.6, 38.5, 37.9, 33.7, 33.6, 28.7, 25.1, 25.0, 21.9, 21.7, 19.6; $[\alpha]_D$=−84.7 (c=0.85, CHCl$_3$).

EXAMPLE 26

Epothilone: To a cooled (−50° C.) solution of desoyepothilone (9 mg, 0.0189 mmol) in dry CH$_2$Cl$_2$ (1 ml) was added freshly prepared dimethyldioxirane (0.95 ml, 0.1 M in acetone). The resulting solution was allowed to warm up to −30° C. for 2 h. A stream of nitrogen was then bubbled through the solution to remove excess DMDO. The residue was purified by flash chromatography (silica, 40% EtOAc in hexane) and afforded epothilone A (4.6 mg, 49%) as colorless solid and 0.1 mg of cis-epoxide diastereomer. This material was identical with the natural epothilone A in all respects.

EXAMPLE 27

Procedure for Ring-closing Olefin Metathesis:

To a stirred solution of diene 24 (5 mg, 0.0068 mmol) in dry benzene (1.5 mL) was added Grubbs's catalyst (2.8 mg, 0.0034 mmol). After 12 h, an additional portion of catalyst was added (2.8 mg). After an additional 5 h, the reaction was concentrated. Purification by silica gel chromatography eluting with hexanes/ethyl acetate (11:1) gave the lactone 23 (3.5 mg, 94%, 2:1 E/Z).

EXAMPLE 28

Preparation of Compound 19:

Alcohol 2A: A mixture of (S)-(−)-1,1$^1$-bi-2-naphthol (259 mg. 0.91 mmoL), Ti(O-i-Pr)$_4$ (261 µL;0.90 mmol), and 4 Å sieves (3.23g) in CH$_2$Cl$_2$ (16 mL) was heated at reflux for 1 h. The mixture was cooled to rt and aldehyde 1 was added. After 10 min. the suspension was cooled to −78° C., and allyl tributyltin (3.6 mL; 11.60 mmol) was added. The reaction mixture was stirred for 10 min at −78° C. and then placed in a −20° C. freezer for 70 h. Saturated NaHCO$_3$ (2mL) was added, and the mixture was stirred for 1 h, poured over Na$_2$SO$_4$, and then filtered through a pad of MgSO$_4$ and celite. The crude material was purified by flash chromatography (hexanes/ethyl acetate, 1:1) to give alcohol 2A as a yellow oil (1.11 g; 60%).

EXAMPLE 29

Acetate 3A: To a solution of alcohol 2A (264 mg; 1.26 mmol) in CH$_2$Cl$_2$ (12 mL) was added DMAP (15mg: 0.098 mmol), Et$_3$N (0.45 mL; 3.22 mmol), and Ac$_2$O (0.18 mL; 1.90 mmol). After 2 h, the reaction mixture was quenched by 20 mL of H$_2$O, and extracted with EtOAC (4×20 mL). The combined organic layer was dried with MgSO$_4$, filtered, and concentrated. Flash chromatrography (EtOAC/hexanes, 1:3) afforded acetate 3A as a yellow oil (302 mg; 96%).

EXAMPLE 30

Vinyl Iodide 19: To a solution of acetate 3A (99 mg; 0.39 mmol) in acetone at 0° C. was added H$_2$O (4 drops), OsO$_4$ (2.5% wt. in butyl alcohol; 175 µL; 0.018 mmol), and N-methyl-morpholine-N-oxide (69 mg; 0.59 mmol). The mixture was stirred at 0° C. for 2 h and 45 min and then quenched with Na$_2$SO$_3$. The solution was poured to 10 mL of H$_2$O and extracted with EtOAc (5×10 mL). The combined organic layer was dried over MgSO4, filtered, and concentrated.

To a solution of this crude product in THF/H$_2$O (4 mL, 3: 1) was added NaIO$_4$ (260 mg; 1.22 mmol). After 1.25 h, the reaction mixture was then quenched with 10 mL of H$_2$O and concentrated. The residue was extracted with EtOAc (5×10 mL). The organic layer was dried over MgSO$_4$, filtered, and concentrated. Flash chromatography (EtOAc/hexanes, 1:1) gave a yellow oil (80 mg) which contained unidentified by-product(s). This mixture was used without further purification.

To a solution of (Ph$_3$P$^+$CH$_2$I)I$^-$ (100 mg; 0.19 mmol) in 0.25 mL of THF at rt was added 0.15 mL (0.15 mmol) of NaHMDS (1 M in THF). To the resulting solution at −78° C. was added HMPA (22 µL; 0.13 mmol) and the product from previous step (16 mg) in THF (0.25 mL). The reaction mixture was then stirred at rt for 30 min. After the addition of hexanes (10 mL), the solution was extracted with EtOAc (4×10 mL). The combined EtOAC layer was dried (MgSO$_4$), filtered, and concentrated. Preparative TLC (EtOAc/hexanes, 2.3) afforded vinyl iodide 19 as a yellow oil (14 mg; 50% for three steps).

EXAMPLE 31

Iodoolefin acetate 8C: To a suspension of ethyltriphenylphosphonium iodide (1.125 g, 2.69 mmol) in THF (10 mL) was added nBuLi (2.5 M soln in hexanes, 1.05 mL, 2.62 mmol) at rt. After disappearance of the solid material, the solution was added to a mixture of iodine (0.613 g, 2.41 mmol) in THF (20 mL) at −78° C. The resulting suspension was vigorously stirred for 5 min at −78° C., then warmed up −20° C., and treated with sodium hexamethyldisilazane (1 M soln in THF, 2.4 mL, 2.4 mmol). The resulting red solution was stirred for 5 min followed by the slow addition of aldehyde 9C (0.339 g, 1.34 mmol). The mixture was stirred at −20° C. for 40 min, diluted with pentane (50 mL), filtered through a pad of celite, and concentrated. Purification of the residue by flash column chromatography (hexanes/ethyl acetate, 85:15) gave 0.202 g (25% overall from vinyl acetate 10C) of the vinyl iodide 8C as a yellow oil. IR (film): 2920, 1738, 1234 cm$^{-1}$; $^1$H NMR (CDCl$_3$): δ6.98 (s, 1H), 6.56 (s, 1H), 5.42 (dd, J=5.43, 6.57 Hz, 1H), 5.35 (t, J=6.6 Hz, 1H), 2.71 (s, 3H), 2.54 (q, J=6.33, 2H), 2.50 (s, 3H), 2.09 (s, 6H); $^{13}$C NMR (CDCl$_3$): δ170.1, 164.6, 152.4, 136.9, 130.2, 120.6, 116.4, 103.6, 40.3, 33.7, 21.2, 19.2, 14.9; $[\alpha]_D$=−20.7 (c=2.45, CHCl$_3$).

EXAMPLE 32

Acetal 13C: To a solution of olefin "7C" (0.082 g, 0.13 mmol) in THF (0.5 mL) was added 9-BBN (0.5 M soln in THF, 0.4 mL, 0.2 mmol). After stirring at rt. for 3.5 h, an additional portion of 9-BBN (0.5 M soln in THF, 0.26 mL, 0.13 mmol) was added. In a separate flask, iodide 8C (0.063 g, 0.16 mmol) was dissolved in DMF (0.5 mL). Cs$_2$CO$_3$ (0.097 g, 0.30 mmol) was then added with vigorous stirring followed by sequential addition of PdCl$_2$(dppf)$_2$ (0.018 g, 0.022 mmol), Ph$_3$As (0.0059 g, 0.019 mmol), and H$_2$O (0.035 mL, 1.94 mmol). After 6 h, then borane solution was added to the iodide mixture in DMF. The reaction quickly turned dark brown in color and slowly became pale yellow after 3 h. The reaction was then poured into H$_2$O (10 mL) and extracted with Et$_2$O (3×15 mL). The combined organic layers were washed with H$_2$O (3×15 mL), brine (1×20 mL), dried over MgSO$_4$, filtered, and concentrated. Flash column chromatography (hexanes/ethyl acetate, 9:1) gave 0.089 g (77%) of the coupled product 13C as a yellow oil.

EXAMPLE 33

Aldehyde 14C: Acetal 13C (0.069 g, 0.077 mmol) was dissolved in dioxane/H$_2$O (9:1, 1 mL) and pTSA.H$_2$O (0.045 g, 0.237 mmol) was added. The mixture was then heated to 55° C. After 3 h, the mixture was cooled to rt, poured into Et$_2$O, and extracted with Et$_2$O (4×15 mL). The combined ether solutions were washed with sat NaHCO$_3$ (1×30 mL), brine (1×30 mL), dried over MgSO$_4$, filtered, and concentrated. Flash column chromatography (hexanes/ethyl acetate, 3:1) gave 0.046 g (71%) of the aldehyde 14C as a pale yellow oil.

EXAMPLE 34

Macrocycle 15C-(SR): To a solution of aldehyde 14C (0.021 g, 0.024 mmol) in THF (5 mL) at −78° C. was added KHMDS (0.5 M soln in toluene, 0.145 mL, 0.073 mmol). The solution was stirred at −78° C. for 1 h, then quenched with sat'd NH$_4$Cl, and extracted with ether (3×15 mL). The combined organic layers were dried with MgSO$_4$, filtered, and concentrated. Flash column chromatography (hexanes/ ethyl acetate, 7:1) gave 0.008 g of the desired α-alcohol 15C-(S) and 0.006 g of β-alcohol 15C-(R) (67% total ) as pale yellow oils.

EXAMPLE 35

Macrocycle 15C-(S): To a solution of β-alcohol 15C-(R) (0.006 g, 0.0070 mmol) in 0.5 mL of CH$_2$Cl$_2$ at rt. was added Dess-Martin periodinane (0.028 g, 0.066 mmol). After 0.5 h, an additional portion of Dess-Martin periodinane (0.025 mg, 0.059 mmol) was added. The resulting solution was stirred at rt for additional 1 h, then treated with ether (2 mL) and sat'd Na$_2$S$_2$O$_3$/sat'd NaHCO$_3$ (3 mL, 1:1), poured into H$_2$O (20 mL), and extracted with ether (4×10 mL). The combined ether solutions were washed with H$_2$O (1×30 mL), brine (1×30 mL), dried with MgSO$_4$, filtered, and concentrated. To a solution of crude ketone 15C' in MeOH/THF (2 mL, 1:1) at −78° C. was added NaBH$_4$ (0.015 g, 0.395 mmol). The resulting solution was stirred at rt for 1 h, quenched with sat NH$_4$Cl, and extracted with ether (3×15 mL). The organic layers were dried with MgSO$_4$, filtered, and concentrated. Flash column chromatography (hexanes/ethyl acetate, 9:1) gave 0.0040 g (67%) of the α-alcohol 15C-(S) as a pale yellow oil and 0.0006 g of β-alcohol 15C-(R).

EXAMPLE 36

Diol 15C": The silyl ether 15C-(S) (0.010 g, 0.012 mmol) was dissolved in HF.pyridine/pyridine/THF (1 mL). The solution was stirred at rt. for 2 h, then diluted with Et$_2$O (1 mL), poured into a mixture of Et$_2$O/sat. NaHCO$_3$ (20 mL, 1:1), and extracted with Et$_2$O (4×10 mL). The Et$_2$O solutions were washed with sat CuSO$_4$ (3×30 mL), sat NaHCO$_3$ (1×30 mL), brine (1×30 mL), dried with MgSO$_4$, filtered, and concentrated. Flash column chromatography (hexanes/ ethyl acetate, 9:1) gave 0.0066 g (93%) of the diol 15C" as a pale yellow oil.

EXAMPLE 37

Alcohol 15C''': To a solution of diol 15C" (0.0066 g, 0.011 mmol) in 0.5 mL of CH$_2$Cl$_2$ at −78° C. was added 2,6-lutidine (7 μL, 0.060 mmol) and TBSOTf (5 μL, 0.022 mmol). The resulting solution was stirred at −30° C. for 0.5 h, then quenched with H$_2$O (5 mL), and extracted with Et$_2$O (4×10 mL). The ether solutions were washed with 0.5 M HCl (1×10 mL), sat'd NaHCO$_3$ (1×10 mL), dried over MgSO$_4$, filtered, and concentrated. Flash column chromatography (hexanes/ethyl acetate, 93:7) gave 0.0070 g (89%) of the alcohol 15C''' as a pale yellow oil.

EXAMPLE 38

Ketone 16C: To a solution of alcohol 15C''' (0.006 g, 0.0083 mmol) in 0.5 mL of CH$_2$Cl$_2$ at rt. was added Dess-Martin periodinane (0.030 g, 0.071 mmol). After 1.25 h, another portion of Dess-Martin periodinane (0.025 mg, 0.059 mmol) was added. The resulting solution was stirred at rt for additional 0.75 h, treated with ether (1 mL) and sat'd Na$_2$S$_2$O$_3$/sat'd NaHCO$_3$ (2 mL, 1:1), poured into H$_2$O (20 mL), and extracted with ether (4×10 mL). The ether solution was washed with sat NaHCO$_3$ (1×20 mL), dried with MgSO$_4$, filtered, and concentrated. Flash column chromatography (hexanes/ethyl acetate, 9:1) gave 0.0040 g (67%) of the ketone 16C as a pale yellow oil.

EXAMPLE 39

Desoxyepothiolone B 2C: To a solution of ketone 16C (0.004 g, 0.0056 mmol) in THF (0.35 mL) was added HF.pyridine (0.25 mL) dropwise over 20 min. The solution was stirred at rt for 1.5 h, diluted with CHCl$_3$ (2 mL), poured into sat'd NaHCO$_3$/CHCl$_3$ (20 mL, 1:1) slowly, and extracted with CHCl$_3$ (4×10 mL). The combined CHCl$_3$ layers were dried with MgSO$_4$, filtered, and concentrated. Flash column chromatography (hexanes/ethyl acetate, 3:1) gave 0.0022 g (80%) of the desoxyepothilone B 2C as a pale yellow oil.

EXAMPLE 40

Epothilone B 2: To a solution of desoxyepothiolone B (0.0022 g, 0.0041 mmol) in CH$_2$Cl$_2$ (0.25 mL) at −50° C. was added dimethyldioxirane (0.1 mL, 0.0095 mmol) dropwise. The resulting solution was stirred at −50° C. for 1 h. The dimethyldioxirane and solvent were removed by a stream of N$_2$. The residue was purified by flash column chromatography (hexanes/ethyl acetate, 1:1) gave 0.0015 g (70%) of epothiolone B (2) as a pale yellow oil which was identical with an authentic sample in $^1$H NMR, IR, mass spectrum, and $[\alpha]_D$.

EXAMPLE 41

8-Desmethylepothilone A

Crotylation product: To a stirred mixture of potassium tert-butoxide (1.0 M soln in THF, 50.4 mL, 50.4 mmol), THF (14 mL), and cis-2-butene (9.0 mL, 101 mmol) at −78° C. was added n-BuLi (1.6 M, in hexanes, 31.5 mL, 50.4 mmol). After complete addition of n-BuLi, the mixture was stirred at −45° C. for 10 min and then cooled to −78° C. (+)-B-Methoxydiisopinocampheylborane (19.21 g, 60.74 mmol) was then added dropwise in $Et_2O$ (10 mL). After 30 min, $BF_3.Et_2O$ (7.47 mL, 60.74 mmol) was added followed by aldehyde 4D (9.84 g, 60.74 mmol) in THF (15 mL) generating a viscous solution which could not be stirred. The mixture was shaken vigorously every 10 min to ensure homogeneity. After 3 h at −78° C., the reaction was treated with 3N NaOH (36.6 mL, 110 mmol) and 30% $H_2O_2$ (15 mL) and the solution brought to reflux for 1 h. The reaction was poured into $Et_2O$ (300 mL) and washed with $H_2O$ (100 mL), brine (30 mL) and dried over anhydrous $MgSO_4$. The crude material was placed in a bulb-to-bulb distillation apparatus to remove the ligand from the desired product. Heating at 80° C. at 2 mm Hg removed 90% of the lower boiling ligand. Further purification of the alcohol 4D was achieved by flash chromatography on silica gel eluting with $Et_2O$ in $CH_2Cl_2$ (2%→4%) to give pure alcohol 4D as a clear oil. The erythro selectivty was >50:1 as judged by $^1H$ NMR spectroscopy. The product was determined to be 87% ee by formation of the Mosher ester: IR (film): 3435, 2861, 1454, 1363, 1099 $cm^{-1}$; $^1H$ NMR ($CDCl_3$, 400 MHz) δ7.34 (5H, m), 5.80 (1H, m), 5.09 (1H, dd, J=1.6, 8.3 Hz), 5.04 (1H, d, J=1.6 Hz), 4.52 (2H, s), 3.51 (2H, t, J=5.8 Hz), 3.47 (1H, m), 2.27 (2H, m), 1.73 (3H, m), 1.42 (1H, m), 1.04 (3H, d, J=6.9 Hz); $^{13}C$ NMR ($CDCl_3$, 100 MHz) δ141.1, 138.2, 128.3, 127.6, 127.5, 115.0, 74.5, 72.9, 70.4, 43.7, 31.3, 26.5, 14.6.

EXAMPLE 42

TBS ether 5D: Alcohol 4D (5.00 g, 21.4 mmol) was dissolved in $CH_2Cl_2$ (150 mL) and 2,6-lutidine (9.97 mL, 85.6 mmol) was added. The mixture was cooled to 0° C. and TBSOTf (9.83 mL, 42.8 mmol) was slowly added. The reaction was then warmed to rt. After 1 h, the reaction was poured into $Et_2O$ (300 mL) and washed once with 1 N HCl (50 mL), once with sat $NaHCO_3$ (50 mL), once with brine (30 mL) and dried over anhydrous $MgSO_4$. Purification by flash chromatography on silica gel eluting with hexanes/ diethyl ether (97:3) gave 6.33 g (85%) of pure olefin 5D as a clear oil: IR (film): 1472, 1361, 1255, 1097, 1068$cm^{-1}$; $^1H$ NMR ($CDCl_3$, 400 MHz) δ7.30 (5H, m), 5.81 (1H, m), 4.97 (1H, dd, J=1.4, 4.8 Hz), 4.94 (1 H, d, J=1.1 Hz), 3.51 (1H, q, J=5.1 Hz), 3.41 (2H, dt, J=2.1, 6.6 Hz), 2.27 (1H, q, J=5.5 Hz), 1.68 (1 h, m), 1.55 (1H, m), 1.41 (2H, m), 0.93 (3H, d, J=6.9 Hz), 0.85 (9 H, s), −0.01 (6H, s); $^{13}C$ NMR ($CDCl_3$, 100MHz) δ141.2, 138.6, 128.3, 127.6, 127.4, 113.9, 75.6, 72.7, 70.6, 42.7, 30.1, 25.9, 25.4, 18.1, 15.1, −4.3, −4.4.

EXAMPLE 43

Aldehyde 6D: The olefin 5 (4.00 g, 11.49 mmol) was dissolved in 1:1 $MeOH/CH_2Cl_2$ (100 mL). Pyridine (4.0 mL) was then added and the mixture cooled to −78° C. Ozone was then bubbled through the reaction for 10 minutes before the color turned light blue in color. Oxygen was then bubbled through the reaction for 10 min. Dimethyl sulfide (4.0 mL) was then added and the reaction slowly warmed to rt. The reaction was stirred overnight and then the volatiles were removed in vacuo. Purification by flash chromatography on silica gel eluting with hexanes/ethyl acetate (9:1) gave 3.31 g (82%) of the aldehyde 6D as a clear oil: IR (film): 2856, 1727, 1475, 1361, 1253, 1102 $cm^{-1}$; $^1H$ NMR ($CDCl_3$, 400 MHz) δ9.76 (1 H, s), 7.33 (5H, m), 4.50 (2H, s), 4.11 (1H, m), 3.47 (2H, m), 2.46 (1H, m), 1.50–1.70 (4 H, band), 1.05 (3H, d, J=7.0 Hz), 0.86 (9 H, s), 0.06 (3H, s), 0.03 (3H, s); $^{13}C$ NMR ($CDCl_3$, 100 MHz) δ204.8, 138.3, 128.2, 127.4, 127.3, 72.7, 71.7, 69.9, 51.1, 31.1, 25.9, 25.6, 17.8, 7.5, −4.4, −4.8.

EXAMPLE 44

Dianion addition product 7D: The tert-butyl isobutyrylacetate (0.653 g, 3.51 mmol) was added to a suspension of NaH (60% in mineral oil, 0.188 g, 4.69 mmol) in THF (50 mL) at rt. After 10 min, the mixture was cooled to 0° C. After an additional 10 min, n-BuLi (1.6 M in hexanes, 2.20 mL, 3.52 mmol) was slowly added. After 30 min, the aldehyde 6D (1.03 g, 2.93 mmol) was added neat. After 10 min, the reaction was quenched with $H_2O$ (10 mL) and extracted with $Et_2O$ (2×75 mL). The combined organics were washed once with brine (30 mL) and dried over anhydrous $MgSO_4$. The crude reaction mixture contained a 15:1 ratio of diastereomers at C5. Purification by flash chromatography on silica gel eluting with hexanes/ethyl acetate (9:1→7:1) gave 0.723 g (47%) of the desired alcohol 7D as a clear oil: IR (film): 3531, 2953, 1739, 1702, 1367, 1255, 1153 $cm^{-1}$; $^1H$ NMR ($CDCl_3$, 400 MHz) δ7.33 (5H, m), 4.49 (2H, s), 3.75 (1H, d, J=2.6 Hz), 3.71 (1H, m), 3.62 (1H, d, J=16.0 Hz), 3.53 (1H, d, J=16.0 Hz), 3.44 (2H, t, J=5.1 Hz), 2.70 (1H, d, J=2.6 Hz), 1.83 (1 H, m), 1.55 (4H, m), 1.46 (9 H, s), 1.17 (3H, s), 1.11 (3H, s), 0.89 (9 H, s), 0.82 (3H, d, J=7.0 Hz), 0.09 (6H, s); $^{13}C$ NMR ($CDCl_3$, 100 MHz) δ208.9, 167.3, 138.4, 128.3, 127.6, 127.5, 81.3, 79.5, 78.7, 72.8, 70.1, 52.4, 47.6, 35.8, 30.6, 28.2, 25.9, 25.8, 22.6, 20.5, 17.9, 7.05, −4.0, −4.5.

EXAMPLE 45

Directed reduction: To a solution of tetramethylammonium triacetoxyborohydride (1.54 g, 5.88 mmol) in acetonitrile (4.0 mL) was added anhydrous AcOH (4.0 mL). The mixture was stirred at rt for 30 min before cooling to −10° C. A solution of the ester 7D (0.200 g, 0.39 mmol) in acetonitrile (1.0 mL) was added to the reaction and it was stirred at −10° C. for 20 h. The reaction was quenched with 1N sodium-potassium tartrate (10 mL) and stirred at rt for 10 min. The solution was then poured into sat $NaHCO_3$ (25 mL) and neutralized by the addition of solid $Na_2CO_3$. The mixture was then extracted with EtOAc (3×30 mL) and the organics were washed with brine (20 mL) and dried over anydrous $MgSO_4$. Purification by flash chromatography on silica gel eluting with hexanes/ethyl acetate (4:1) gave 0.100 g (50%) of the diol as 10:1 ratio of diastereomeric alcohols.

EXAMPLE 46

Monoprotection of the diol: The diol (1.76 g, 3.31 mmol) was dissolved in $CH_2Cl_2$ (100 mL) and cooled to 0° C. 2,6-lutidine (12.2 mL, 9.92 mmol) was added followed by TBSOTf (1.14 mL, 4.96 mmol) and the reaction slowly warmed to rt. After 1 h, the reaction was poured into $Et_2O$ (300 mL) and washed once with 1N HCl (50 mL), once with sat $NaHCO_3$ (50 mL), once with brine (30 mL) and dried over anhydrous $MgSO_4$. Purification by flash chromatography on silica gel eluting with hexanes/ethyl acetate (20:1→15:1) gave 2.03 g (95%) of the alcohol 8D as a clear oil, which was used as a mixture of diastereomers.

EXAMPLE 47

C5 Ketone formation: The alcohol 8D (2.03 g, 3.14 mmol) was dissolved in $CH_2Cl_2$ (50 mL) and Dess-Martin periodinane (2.66 g, 6.28 mmol) was added. After 2 h, a 1:1 mixture of sat'd NaHCO$_3$/sat Na$_2$S$_2$O$_3$ (20 mL) was added. After 10 min, the mixture was poured into Et$_2$O (300 mL) and the organic layer was washed with brine (30 mL) and dried over anhydrous MgSO$_4$. Purification by flash chromatography on silica gel eluting with hexanes/ethyl acetate (15:1) gave 1.85 g (91%) of the ketone (benzyl ether) as a clear oil, which was used as a mixture of diastereomers.

EXAMPLE 48

Debenzylation: The ketone (benzyl ether) (1.85 g, 2.87 mmol) was dissolved in EtOH (50 mL), and Pd(OH)$_2$ (0.5 g) was added. The mixture was then stirred under an atmosphere of H$_2$. After 3 h, the reaction was purged with N$_2$ and then filtered through a pad of celite rinsing with CHCl$_3$ (100 mL). Purification by flash chromatography on silica gel eluting with ethyl acetate in hexanes (12%→15%) gave 1.43 g (90%) of the diastereomeric alcohols as a clear oil. The C3 diastereomers were separated by flash chromatography on TLC-grade SiO$_2$ eluting with ethyl acetate in hexanes (15%):

Alpha isomer: IR (film): 3447, 1732, 1695, 1254, 1156 cm$^{-1}$; $^1$H NMR (CDCl$_3$, 400 MHz) δ4.24 (1H, dd, J=3.6, 5.8 Hz), 3.83 (1H, m), 3.53 (1H, m), 3.06 (1H, t, J=7.1 Hz), 2.36 (1H, dd, J=3.6, 17.2 Hz), 2.12 (1H, dd, J=3.9, 17.2 Hz), 1.68 (1H, t, J=5.4 Hz), 1.54 (2H, m), 1.41 (1H, m), 1.37 (9 H, s), 1.31 (1 H, m), 1.16 (3 H, s), 1.02 (3 H, s), 0.99 (3 H, d, J=6.8 Hz), 0.84 (9 H, s), 0.81 (9 H, s), 0.05 (3 H, s), 0.01 (6 H, s), −0.01 (3 H, s); $^{13}$C NMR (CDCl$_3$, 100 MHz) δ217.7, 171.3, 80.57, 73.5, 73.1, 63.0, 53.4, 26.8, 41.2, 32.1, 28.1, 28.0, 26.0, 25.9, 23.1, 19.8, 18.1 (overlapping), 15.3, −4.0, −4.3 (overlapping), −4.8.

Beta isomer: IR (film): 3442, 2857, 1732, 1700, 1472, 1368, 1255cm$^{-1}$; $^1$H NMR (CDCl$_3$, 400 MHz) δ4.45 (1 H, t, J=5.3 Hz), 3.86 (1 H, m), 3.52 (2 H, q, J=5.9 Hz), 3.01 (1 H, m), 2.28 (1 H, dd, J=4.3, 17.1 Hz), 2.16 (1 H, dd, J=5.5, 17.1 Hz), 1.67 (1 H, t, J=5.6 Hz), 1.56 (2 H, m), 1.44 (1 H, m), 1.37 (9 H, s), 1.34 (1 H, m), 1.13 (3 H, s), 0.97 (3 H, d, J=7.4 Hz), 0.96 (3 H, s), 0.83 (9 H, s), 0.79 (9 H, s), 0.01 (3 H, s), 0.00 (6 H, s), −0.07 (3 H, s); $^{13}$C NMR (CDCl$_3$, 100 MHz) δ217.1, 171.2, 80.6, 73.5, 72.1, 62.9, 63.9, 46.4, 41.2, 32.0, 28.1, 28.0, 26.0, 25.9, 21.5, 19.5, 18.2, 18.1, 15.8, −4.0, −4.3, −4.4, −4.7.

EXAMPLE 49

Aldehyde formation: DMSO (0.177 mL, 2.50 mmol) was added to a mixture of oxalyl chloride (0.11 mL, 1.25 mmol) in CH$_2$Cl$_2$ (15 mL) at −78° C. After 10 min, the alcohol (0.531 g, 0.96 mmol) was added in CH$_2$Cl$_2$ (4 mL). After 20 min, TEA (0.697 mL, 5.00 mmol) was added to the reaction followed by warming to rt. The reaction was then poured into H$_2$O (50 mL) and extracted with Et$_2$O (3×50 mL). The organics were washed once with H$_2$O (30 mL), once with brine (30 mL) and dried over anhydrous MgSO$_4$. The aldehyde was used in crude form.

EXAMPLE 50

Wittig olefination to give 9D: NaHMDS (1.0 M soln in THF, 1.54 mL, 1.54 mmol) was added to a suspension of methyl triphenylphosphonium bromide (0.690 g, 1.92 mmol) in THF (20 mL) at 0° C. After 1 h, the crude aldehyde (0.96 mmol) was added in THF (5 mL). After 15 min at 0° C., H$_2$O (0.1 mL) was added and the reaction poured into hexanes (50 mL). This was filtered through a plug of silica gel eluting with hexanes/Et$_2$O (9:1, 150 mL). The crude olefin 9D was further purified by flash chromatography on silica gel eluting with ethyl acetate in hexanes (5%) to give 0.437 g (83% for two steps) of the olefin 9D as a clear oil: IR (film): 2857, 1732, 1695, 1472, 1368, 1255, 1156 cm$^{-1}$; $^1$H NMR (CDCl$_3$, 400 MHz) δ5.72 (1 H, m), 4.91 (2 H, m), 4.25 (1 H, dd, J=3.9, 5.4 Hz), 3.81 (1 H, m), 3.05 (1 H, m), 2.38 (1 H, dd, J=7.9, 17.2 Hz), 2.12 (1 H, dd, J=6.6, 17.2 Hz), 2.04 (2 H, q, J=7.5 Hz), 1.47 (1 H, m), 1.39 (9 H, s), 1.34 (1 H, m), 1.20 (3 H, s), 1.00 (3 H, s), 3.00 (3 H, d, J=6.7 Hz), 0.85 (9 H, s), 0.83 (9 H, s), 0.07 (3 H, s), 0.00 (6 H, s), −0.05 (3 H, s); 13C NMR (CDCl$_3$, 100 MHz) δ217.5, 172.1, 137.9, 114.0, 80.4, 74.0, 73.0, 53.0, 46.9, 41.3, 35.1, 29.0, 28.1, 26.0, 25.9, 22.8, 20.2, 18.2 (overlapping), 14.9, −4.1, −4.2, −4.3, −4.8.

EXAMPLE 51

TBS ester 10D: The olefin 9D (0.420 g, 0.76 mmol) was dissolved in CH$_2$Cl$_2$ (15 mL) and treated successively with 2,6-lutidine (1.33 mL, 11.4 mmol) and TBSOTf (1.32 mL, 5.73 mmol). After 7 h, the reaction was poured into Et$_2$O (100 mL) and washed successively with 0.2N HCl (25 mL), brine (20 mL) and dried over anhydrous MgSO$_4$. The residue was purified by flash chromatography on a short pad of silica gel with fast elution with hexanes/ethyl acetate (20:1) to give the TBS ester 10D as a clear oil. The purification must be done quickly to avoid hydrolysis of the silyl ester: IR (film): 2930, 1721, 1695, 1472, 1254, 1091 cm$^{-1}$; $^1$H NMR (CDCl$_3$, 400 MHz) δ5.73 (1H, m), 4.91 (2H, m), 4.25 (1H, dd, J=3.8, 5.4 Hz) 3.80 (1H, q, J=6.8 Hz), 3.06 (1H, m), 2.50 (1H, dd, J=3.7, 17.3 Hz), 2.19 (1H, dd, J=5.7, 17.3 Hz), 2.04 (2H, dd, J=7.6, 15.3 Hz), 1.49 (1H, m), 1.36 (1H, m), 1.21 (3H, s), 1.00 (3H, d, J=6.8 Hz), 0.88 (9 H, s), 0.85 (9 H, s), 0.83 (9 H, s), 0.22 (3H, s), 0.22 (3H, s), 0.21 (3H, s), 0.06 (3H, s), 0.01 (6H, s), −0.05 (3H, s); $^{13}$C NMR (CDCl$_3$, 100 MHz) δ217.3, 172.3, 138.5, 114.4, 74.5, 73.0, 53.2, 46.9, 41.8, 35.1, 29.0, 26.0, 25.7, 25.5, 22.8, 20.4, 18.2, 18.1, 17.5, 14.9, −2.9, −4.0, −4.2, −4.3, −4.8, −4.9.

EXAMPLE 52

Suzuki coupling: The acetate acid 13D was purified by flash chromatography on silica gel eluting with hexanes/ethyl acetate (7:1→4:1). This was further purified by preparative-TLC eluting with hexanes/ethyl acetate (2:1) to remove unreacted vinyl iodide 12D from the acetate acid 13D. Isolated yield of the acid was 0.297 g (62% based on 90% purity with borane residues).

EXAMPLE 53

Hydrolysis of acetate acid 13D: The acetate 13D (0.220 g, 0.297 mmol) was dissolved in MeOH/H$_2$O (2:1, 15 mL) and K$_2$CO$_3$ (0.300 g) was added. After 3 h, the reaction was diluted with sat NH$_4$Cl (20 mL) and extracted with CHCl$_3$ (5×20 mL). The hydroxy-acid 14D was purified by flash chromatography on silica gel eluting with hexanes/ethyl acetate (4:1→2:1) to give 0.146 g (70%) of the pure hydroxy acid 14D. IR (film): 3510–2400, 1712, 1694, 1471, 1254, 1093 cm$^{-1}$; $^1$H NMR (CDCl$_3$, 400 MHz) δ6.96 (1H, s), 6.66 (1H, s), 5.55 (1H, m), 5.38 (1H, m), 4.38 (1H, dd, J=3.4, 6.1 Hz), 4.19 (1H, t, J=7.5 Hz), 3.84 (1H, m), 3.05 (1H, t, J=7.0 Hz), 2.72 (3H, s), 2.49 (1H, dd, J=3.2, 16.4 Hz), 2.42 (2H, m), 2.33 (1H, dd, J=6.2, 16.4 Hz), 2.07 (2H, m), 2.02 (3H, s), 1.33 (4H, m), 1.19 (3H, s), 1.14 (3H, s), 1.06 (3H, d, J=6.7 Hz), 0.89 (9 H, s), 0.88 (9 H, s), 0.11 (3H, s), 0.07 (3H, s), 0.04 (6 H, s); $^{13}$C NMR (CDCl$_3$, 100 MHz) δ217.8, 176.6, 164.9, 152.5, 141.7, 132.9, 125.0, 119.0, 115.31 73.5, 73.3, 53.4, 47.0, 40.1, 35.8, 33.2, 29.8, 27.4, 26.0, 25.9, 24.5, 19.0, 18.1, 15.2, 14.3, −4.0, −4.2, −4.2, −4.7.

EXAMPLE 54

Macrolactonization: DCC (0.150 g, 0.725 mmol), 4-DMAP (0.078 g, 0.64 mmol) and 4-DMAP.HCl (0.110 g, 0.696 mmol) were dissolved in $CHCl_3$ (80 mL) at 80° C. To this refluxing solution was added by syringe pump the hydroxy acid 14D (0.020 g, 0.029 mmol) and DMAP (0.010 g) in $CHCl_3$ (10 mL) over 20 h. The syringe needle was placed at the base of the condenser to ensure proper addition. After 20 h, the reaction was cooled to 50° C. and AcOH (0.046 mL, 0.812 mmol) was added. After 2 h, the reaction was cooled to rt and washed with sat $NaHCO_3$ (30 mL), brine (30 mL) and dried over anhydrous $Na_2SO_4$. The lactone 15D was purified by flash chromatography on silica gel eluting with hexanes/ethyl acetate (20:1→15:1) to give 0.014 g (75%): IR (film): 2929, 1741, 1696, 1254, 1097 $cm^{-1}$; $^1H$ NMR ($CDCl_3$, 400 MHz) δ6.95 (1H, s), 6.55 (1H, s), 5.48 (1H, m), 5.37 (1H, m), 5.16 (1H, d, J=9.8 Hz), 4.17 (1H, d, J=8.3 Hz), 4.07 (1H, t, J=7.2 Hz), 3.02 (1H, t, J=7.2 Hz), 2.77 (1H, m), 2.70 (3H, s), 2.64 (2H, m), 2.29 (1H, m), 2.15 (1H, m), 2.12 (3H, s), 1.92 (1H, m), 1.71 (1H, m), 1.44 (2H, m), 1.26 (1H, m), 1.17 (3H, s), 1.12 (3H, s), 1.11 (3H, d, J=7.0 Hz), 0.91 (9 H, s), 0.85 (9 H, s), 0.09 (3H, s), 0.06 (6H, s), −0.04 (3H, s); $^{13}C$ NMR ($CDCl_3$, 100 MHz) δ215.2, 171.9, 164.5, 152.5, 138.0, 133.5, 123.8, 120.0, 116.7, 79.4, 76.2, 72.5, 53.5, 47.4, 39.9, 34.5, 31.9, 31.5, 30.2, 27.7, 26.1, 25.9, 24.1, 23.8, 23.1, 22.6, 19.2, 18.5, 18.2, 16.3, 14.9, 14.1, −3.7, −4.2, −4.7, −5.2.

EXAMPLE 55

Desmethyldeoxyepothilone A (16D): To the lactone 15D (0.038 g, 0.056 mmol) in THF (2.0 mL) was added HF.pyridine (1.0 mL). After 2 h, the reaction was poured into sat $NaHCO_3$ (30 mL) and extracted with $CHCl_3$ (5×20 mL). The organics were dried over $Na_2SO_4$. The crude diol 16D was purified by flash chromatography on silica gel eluting with hexanes/ethyl acetate (3:1→2:1) to give 0.023 g (89%): IR (film): 3501, 2933, 1734, 1684, 1290, 1248, 1045 $cm^{-1}$; $^1H$ NMR ($CDCl_3$, 400 MHz) δ6.95 (1H, s), 6.59 (1H, s), 5.40 (2H, m), 5.23 (1 H, dd, J=1.4, 9.5 Hz), 4.38 (1H, bd, J=11.1 Hz), 3.78 (1H, t, J=6.9 Hz), 3.59 (1H, bs), 3.47 (1H, s), 2.99 (1H, q, J=7.0 Hz), 2.68 (3H, s), 2.66 (1H, m), 2.46 (1H, dd, J=11.4, 14.4 Hz), 2.26 (1H, dd, J=2.2, 14.4 Hz), 2.22 (1H, m), 2.06 (3H, s), 1.96 (1H, m), 1.49 (3H, m), 1.35 (3H, m), 1.30 (3H, s), 1.15 (3H, d, J=6.9 Hz), 1.06 (3H, s); $^{13}C$ NMR ($CDCl_3$, 100MHz) δ221.5, 170.3, 165.1, 151.8, 139.1, 132.8, 125.2, 119.1, 115.5, 78.4, 72.5, 70.8, 53.8, 42.7, 39.6, 32.3, 31.8, 28.3, 26.8, 24.8, 23.1, 19.0, 17.2, 16.0, 11.1.

EXAMPLE 56

Epoxide formation: Diol 16D (0.008 g, 0.017 mmol) was dissolved in $CH_2Cl_2$ (1.0 mL) and cooled to −60° C. Dimethyldioxirane (0.06 M, 0.570 mL, 0.0034 mmol) was then slowly added. The reaction temperature was slowly warmed to −25° C. After 2 h at −25° C., the volatiles were removed from the reaction at −25° C. under vacuum. The resulting residue was purified by flash chromatography on silica gel eluting with MeOH in $CH_2Cl_2$ (1%→2%) to give a 1.6:1 mixture of cis -epoxides 3D and the diastereomeric cis-epoxide (0.0058 g, 74%). The diastereomeric epoxides were separated by preparative-TLC eluting with hexanes/ethyl acetate (1:1) after 3 elutions to give pure diastereomers:

Beta epoxide3D: IR (film): 3458, 2928, 1737, 1685, 1456, 1261, 1150, 1043, 1014$cm^{-1}$; $^1H$ NMR ($CD_2Cl_2$, 500 MHz) δ7.01 (1H, s), 6.56 (1H, s), 5.35 (1H, dd, J=2.3, 9.6 Hz), 4.30 (1H, dd, J=3.0, 5.7 Hz), 3.85 (1H, m), 3.81 (1H, d, J=5.7 Hz), 3.42 (1H, d, J=2.0 Hz), 3.03 (1H, q, J=6.8 Hz), 2.97 (1H, m), 2.88 (1H, m), 2.67 (3H, s), 2.46 (1H, dd, J=9.0, 14.5 Hz),2.33(1H,dd, J=2.6, 14.5 Hz),2.13(1H,dt, J=3.0, 15.0 Hz),2.08(3H, s), 1.82 (1H, m), 1.52 (6H, m), 1.41 (1H, m), 1.33 (3H, s), 1.21 (4H, m), 1.12 (3H, d, J=7.0 Hz), 1.06 (3H, s); $^{13}C$ NMR ($CD_2Cl_2$, 125 MHz) δ221.9, 170.6, 165.6, 152.2, 138.3, 120.2, 116.6, 77.3, 73.4, 69.9, 57.7, 55.3, 43.7, 39.7, 32.6, 32.0, 29.8, 27.2, 25.7, 24.7, 22.5, 19.2, 19.0, 15.6, 15.6, 11.5;

Alpha epoxide: IR (film): 3439, 2918, 1735, 1684, 1455, 1262, 1048, 1014 $cm^{-1}$; $^1H$ NMR ($CD_2Cl_2$, 500 MHz) δ7.02 (1H, s), 6.56 (1H, s), 5.62 (1H, d, J=8.1 Hz), 4.33 (1H, dd, J=2.7, 11.0 Hz), 3.85 (1H, t, J=5.9 Hz), 3.27 (1H, d, J=5.3 Hz), 3.11 (1H, m), 3.07 (1 H, d, J=7.0 Hz), 3.04 (1H, s), 2.87 (1H, m), 2.68 (3H, s), 2.46 (1H, dd, J=11.1, 14.1 Hz), 2.35 (1H, dd, J=2.3, 14.1 Hz), 2.11 (3H, s), 2.06 (1H, ddd, J=1.9, 4.5, 15.1 Hz), 1.87 (1H, m), 1.52 (6H, m), 1.38 (2H, m), 1.29 (3H, s), 1.08 (3H, d, J=6.9 Hz), 1.03 (3 H, s); $^{13}C$ NMR ($CD_2Cl_2$, 125MHz) δ222.1, 170.2, 165.3, 152.5, 137.6, 119.7, 116.7, 76.7, 72.9, 70.6, 57.1, 55.1, 44.7, 40.0, 32.1, 31.4, 30.0, 26.6, 25.5, 24.7, 21.3, 19.3, 18.7, 15.7, 11.5.

EXAMPLE 57

Experimental Data for C-12 Hydroxy Epothilone Analogs

Propyl hydroxy compound 43: $^1H$ NMR ($CDCl_3$, 400 MHz) δ6.96 (1H, s), 6.59 (1H, s), 5.16–5.23 (2H, band), 4.28 (1H, m), 3.72 (1H, m), 3.63 (2H, t, J=6.3 Hz), 3.17 (1H, dd, J=2.2, 0.5 Hz), 3.02 (1H, s), 2.70 (3H, s), 2.65 (2H, m), 2.46 (1H, dd, J=10.9, 14.6 Hz), 2.29 (2H, m), 1.98–2.09 (6H, band), 1.60–1.91 (6H, band), 1.35 (3H, s), 1.33 (3H, s), 1.18 (3H, d, J=6.8 Hz), 1.07 (3H, s), 1.01 (3H, d, J=7.1 Hz); $^{13}C$ NMR ($CDCl_3$, 100 MHz) δ220.69, 170.29, 165.00, 151.81, 141.63, 138.93, 120.64, 118.81, 115.52, 78.53, 77.23, 73.93, 71.85, 62.26, 53.63, 41.57, 39.54, 37.98, 32.33, 32.14, 31.54, 30.75, 29.67, 25.27, 22.89, 18.92, 17.67, 15.98, 15.74, 13.28; MS e/m 536.2, calc 535.29.

Hydroxy methyl compound 46: $^1H$ NMR ($CDCl_3$, 400 MHz) δ6.97 (1H, s), 6.63 (1H, s), 5.43 (1H, dd, J=5.7, 9.1 Hz), 5.24 (1H, d, J=7.4 Hz), 4.31 (1H, d, J=9.7 Hz), 4.05 (2H, dd, J=7.3, 31.0 Hz), 3.87 (1H, bs), 3.69 (1H, bs), 3.17 (1H, dd, J=2.0, 6.9 Hz), 3.03 (1H, s), 2.69 (3H, s), 2.63 (1H, m), 2.45 (1H, dd, J=11.2, 14.6 Hz), 2.37 (1H, m), 2.25 (2H, m), 2.11 (1H, m), 2.05 (3H, s), 1.78 (1H, m), 1.70 (1H, m), 1.35 (3H, s), 1.34 (2H, m), 1.29 (1H, m), 1.18 (3H, d, J=6.8 Hz), 1.06 (3H, s), 1.00 (3H, d, J=7.0 Hz); $^{13}C$ NMR ($CDCl_3$, 100MHz)δ220.70, 170.16, 165.02, 151.63, 141.56, 138.41, 121.33, 118.65, 115.33, 77.74, 77.25, 74.11, 71.37, 65.75, 53.86, 41.52, 39.52, 37.98, 31.46, 27.70, 25.10, 22.86, 18.74, 17.20, 16.17, 15.63, 13.41.

EXAMPLE 58

4,4-Dimethyl-3,5-dioxoheptanoate, tert-butyl ester 47. t-Butyl 4-methyl-3-oxo-4-methyl pentanoate (22.5 g, 121 mmol) was added dropwise in 20 mL of dry THF to a slurry of NaH (6.29 g, 60% dispersion in mineral oil, 157.2 mmol) in 500 mL of dry THF. The reaction mixture was stirred at 0° C. for 30 min and then the cold bath was cooled to −50° C. Freshly distilled propionyl chloride (12.3 g, 133.0 mmol) was added rapidly (neat) via syringe to the cold solution. The reaction was monitored by TLC and the cold bath was maintained below −30° C. until the reaction was complete. After 1 hr, the reaction was quenched by pouring into a solution of saturated aqueous $NH_4Cl$ and subjected to an aqueous workup. Flash column chromatography with 2% EtOAc/hexanes afforded the desired tricarbonyl 42 (16.4 g, 67.8 mmol) in 56% yield; $^1H$ NMR (400 MHz, $CDCl_3$):

δ12.43 (s, 0.20H), 5.07 (s, 0.20H), 3.36 (s, 1.6H), 2.47 (q, J=7.13 Hz, 2H), 1.44 (s, 9H), 1.35 (s, 6H), 1.03 (t, J=7.18 Hz, 3H); $^{13}$C NMR (100 MHz, CDCl$_3$): δ209.7, 202.9, 166.1, 81.91, 62.53, 43.34, 31.67, 27.82 (3),21.03 (2), 7.82; IR (neat) 3411.8, 1742.6, 1718.5, 1702.0, 1644.2, 1460.6, 1156.1 cm$^{-1}$.

4,4-Dimethyl-5-oxo-3-triethylsilyloxy-2-heptenoate, tert-butyl ester 48. The ester 47 (5.79 g, 23.9 mmol) in THF was added to a suspension of NaH (60% in mineral oil, 1.24 g, 31.1 mmol) in THF (200 mL) at 0° C. After 20 min, the reaction was cooled to −50° C. and TESOTf (5.95 mL, 26.32 mmol) was added. After an additional 20 min, the reaction was poured into saturated aqueous NaHCO$_3$ (300 mL). This mixture was extracted with Et$_2$O (2×200 mL) and the combined organic layers were dried over anhydrous MgSO$_4$O. The resulting oil was purified by flash column chromatography on SiO2 eluting with Et$_2$O/hexanes (1:20 to 1:5) to give 6.65 g (78%) of the desired enol ether 48 as a clear oil; $^1$H NMR (400 MHz, CDCl$_3$): δ5.16 (s, 1H), 2.48 (q, J=7.2 Hz, 2H), 1.45 (s, 9H), 1.24 (s, 6H), 1.02 (t, J=7.2 Hz, 3H), 0.95 (t, J=8.1 Hz, 9H), 0.74 (q, J=8.1 Hz, 6H); $^{13}$C NMR (100 MHz, CDCl$_3$): δ211.2, 169.4, 165.1, 97.77, 78.93, 55.54, 30.33, 28.21, 22.94, 8.15, 6.78, 6.02; IR (neat) 1712, 1619, 1384, 1243, 1150 cm$^{-1}$.

EXAMPLE 59

(6R,7R,8S)-7-Hydroxy-5-oxo-4,4,6,8-tetramethyl-3-triethylsilyloxy-2,10-undecadienoate, tert-butyl ester 49. The keto enol ether 48 (7.80 g, 22.0 mmol) in 175 mL of dry THF was cooled to −30° C. in a cold bath (CO$_2$(s)/CH$_3$CN) and then, a cooled solution of LDA (27.2 mmol, 0.90 M in THF) was added dropwise via syringe over 5 min. Immediately after the addition of the keto enol ether, the reaction vessel was placed in a −120° C. cold bath (N2(liq)/pentane) and the reaction mixture was stirred for 10 min. Then, the aldehyde (2.0 g, 20.0 mmol) was added via syringe in 1 mL of dry THF. The reaction was complete after 30 min and was quenched by pouring into a solution of saturated aqueous NaHCO$_3$. The desired aldol product 49 (6.0 g, 13.2 mmol) was isolated in 60% yield (yield of the major product of a 5.5:1 mixture of diastereomers, epimeric at C-8) after flash column chromatography with 6–8% Et$_2$O/hexanes; (major diastereomer, higher Rf); $^1$H NMR (400 MHz, CDCl$_3$): δ5.78 (m, 1H), 5.22 (m, 1H), 5.05 (m, 2H), 3.37 (m, 2H), 3.18 (q, J=7.08 Hz, 1H), 2.52 (m, 1H), 1.85 (dt, J=14.0, 8.37 Hz, 1H), 1.62 (m, 1H), 1.55 (s, 3H), 1.46 (s, 9H), 1.22 (s, 3H), 1.25 (s, 3H), 1.04 (d, J=6.90 Hz, 3H), 0.95 (t, J=7.94 Hz, 6H), 0.76 (q, J=8.26 Hz, 9H); $^{13}$C NMR (100 MHz, CDCl$_3$): δ217.8, 168.1, 164.6, 137.1, 116.2, 99.03, 79.21, 74.82, 56.74, 40.65, 37.39, 35.06, 28.24, 22.53, 22.29, 14.77, 10.54, 6.95, 6.04; (minor diastereomer, lower Rf) $^1$H NMR (400 MHz, CDCl$_3$): δ5.73 (m, 1H), 5.23 (s, 1H), 5.02 (m, 2H), 3.43 (d, J=8.74 Hz, 1H), 3.21 (m, 2H), 2.06 (m, 1H), 1.84 (m, 1H), 1.62 (m, 1H), 1.55 (s, 3H), 1.46 (s, 9H), 1.27 (s, 3H), 1.24 (s, 3H), 1.06 (d, J=6.91 Hz, 3H), 0.96 (t, J=8.06 Hz, 9H), 0.77 (q, J=7.53 Hz, 6H); $^{13}$C NMR (100 MHz, CDCl$_3$): δ217.8, 168.5, 165.0, 136.8, 116.8, 99.46, 79.62, 75.47, 57.17, 41.43, 37.86, 35.58, 30.70, 28.66, 28.31, 22.90, 22.74, 16.53, 11.77, 7.37, 6.44.

EXAMPLE 60

(6R,7R,8S)-7-Trichloroethoxyethylcarbonate-3 5-dioxo-4,4,6,8-tetramethyl-10-und ecenoate, tert-butyl ester 50. The alcohol 49 (1.61 g, 3.55 mmol) was dissolved in 20 mL of dry CH$_2$Cl$_2$ and cooled to 0° C. in an ice bath. Then, pyridine (1.12 g, 14.2 mmol) and trichloroethoxyethylcarbonoyl chloride (TrocCl) (1.50 g, 7.10 mmol) were added via syringe in that order. The reaction was stirred at 0° C. for 5 min and then the ice bath was removed and the reaction was allowed to come to rt and stir for 30 minutes. After this period of time, TLC analysis showed the complete consumption of the starting material. The reaction mixture was cooled to 0° C. and the TES enol ether was hydrolyzed by the addition of 20 mL of 0.5 M methanolic HCl. The reaction mixture was stirred for 5 min at 0° C. and then quenched by pouring into a solution of saturated aqueous NaHCO$_3$. The desired tricarbonyl 50 (1.54 g, 3.01 mmol) was isolated after an aqueous workup and flash column chromatography with 7–9% Et$_2$O/hexanes; $^1$H NMR (400 MHz, CDCl$_3$): δ12.63 (s, 0.25H), 5.70 (m, 1H), 5.15 (s, 0.25H), 5.08–4.88 (m, 2H), 4.91 (dd, J=6.60, 5.01 Hz, 0.30H), 4.78 (m, 1H), 4.77 (dd, J=7.86, 3.58 Hz, 0.70H), 4.72 (dd, J=11.8, 9.66 Hz, 1H), 3.48 (d, J=16.2 Hz, 0.75H), 3.42 (d, J=16.2 Hz, 0.75H), 3.36 (m, 0.30H), 3.30 (m, 0.70H), 1.88 (m, 2H), 1.50 (s, 3H), 1.46 (s, 9H), 1.39 (s, 3H), 1.12 (d, J=6.88 Hz, 0.70H), 1.10 (d, J=6.88 Hz, 1.3H), 0.93 (d, J=6.63 Hz, 1.3H), 0.88 (d, J=6.86 Hz, 0.70H); $^{13}$C NMR (100 MHz, CDCl$_3$): δ210.5, 209.5, 203.16, 178.3, 172.6, 166.2, 154.1, 135.9, 135.6, 117.2, 116.9, 94.69, 94.56, 90.69, 82.68, 81.98, 81.65, 81.53, 63.58, 54.34, 46.56, 41.99, 41.62, 36.41, 35.84, 34.49, 34.44, 31.56, 28.23(3),27.94(3),22.62, 22.08, 21.56, 20.80, 15.95, 15.58, 14.09, 13.02, 12.98, 11.35; IR (neat) 1757.9, 1718.9, 1700.2, 1642.2, 1620.7, 1250.6, 1156.3 cm$^{-1}$.

EXAMPLE 61

TBS vinyl iodide 51. n-BuLi (1.6 M in hexanes, 7.69 mL, 12.3 mmol) was added to a suspension of ethyl triphenylphosphonium iodide (5.15 g, 12.3 mmol) in THF (50 mL) at 25° C. After 20 min, the clear red solution was transferred dropwise via syringe to a vigorously stirred solution of I$_2$ (3.12 g, 12.3 mmol) in THF (100 mL) at −78° C. The resulting pale yellow suspension was stirred rapidly and warmed to 20° C. Then, NaHMDS (1.0 M soln in THF, 12.3 mL, 12.3 mmol) was added dropwise via syringe. During the addition of the NaHMDS, the reaction mixture changed from a yellow-orange slurry and to bright red solution. The TBS aldehyde (D.-S. Su et al., Angew.Chem.Int.Ed.Engl., 1997, 36, 757; 2.00 g, 6.15 mmol) was then added in THF. After 30 min, the reaction mixture was poured into hexanes (100 mL) and H$_2$O (0.5 mL) was added. The solution was then passed through a plug of SiO2 eluting with 2:1 hexanes/Et$_2$O. The iodide was purified by flash chromatography on SiO2 eluting with hexanes/ethyl acetate (20:1 to 15:1) to give the vinyl iodide 51 (1.46 g, 55%) as a yellow oil: $^1$H NMR (400 MHz, CDCl$_3$): δ6.95 (s, 1H), 6.50 (s, 1H), 5.45 (dt, J=1.5, 6.8 Hz, 1H), 4.22 (t, J=6.4 Hz,1H), 2.73 (s, 3H), 2.48 (s, 3H), 2.39 (m, 2H), 2.02 (s, 3H), 0.90 (s, 9H), 0.06 (3, s),0.02 (3, s); $^{13}$C NMR (100 MHz, CDCl$_3$): δ164.86, 153.46, 142.17, 132.54, 119.23, 115.68, 102.79, 77.70, 44.40, 39.09, 26.35, 19.65, 18.63, 14.54, 4.59, −4.84; IR (neat) 2928, 1470, 1252, 1068 cm$^{-1}$.

Post-Suzuki, C-15 Hydroxy Tricarbonyl 52. 9-BBN (0.5 M soln in THF, 6.68 mL, 3.34 mmol) was added over a 45 min period to a solution of the olefin 50 (1.43 g, 2.78 mmol) in THF (15 mL) at 25° C. After 2 h, TLC analysis revealed the complete consumption of the starting olefin. In a separate flask, containing the vinyl iodide 51 (1.20 g, 2.80 mmol) and DMF (20 mL), were added successively and with vigorous stirring: Cs$_2$CO$_3$ (1.82 g, 5.60 mmol), Pd(dppf)$_2$Cl$_2$ (0.454 g, 0.56 mmol), AsPh$_3$ (0.171 g, 0.56 mmol) and H$_2$O (1.82 mL, 0.1 mmol). Then the borane solution, prepared above, was added rapidly to the vigorously stirred solution containing the vinyl iodide. After 2 h, the reaction was complete and the reaction mixture was poured into Et$_2$O (300 mL) and washed with H$_2$O (3×200 mL), brine (1×50 mL) and dried over anhydrous MgSO$_4$. This crude product was purified by flash column chromatography on SiO$_2$ eluting with hexanes/ ethyl acetate (18:1 to 13:1 to 10:1) to afford the TBS protected coupled product as an impure mixture which was taken on to the next step.

The crude TBS protected coupled product (~2.78 mmol) was dissolved in 0.36 N HCl in MeOH (30 mL) at 25° C. After 3.5 h, the mixture was poured into a solution of saturated aqueous NaHCO$_3$ and extracted with CHCl$_3$ (4×60 mL). The combined organic layers were washed once with brine (50 mL) and dried over anhydrous Na$_2$SO$_4$. The diol was purified by flash column chromatography on SiO$_2$ eluting with hexanes/ethyl acetate (4:1 to 3:1 to 2:1) to give the pure product 52 as a clear oil (0.910 g, 46% for two steps): $^1$H NMR (400 MHz, CDCl$_3$): δ6.96 (s, 1H), 6.56 (s, 1H), 5.16 (t, J=6.9 Hz, 1H), 4.83 (d, J=11.9 Hz, 1H), 4.75 (dd, J=3.4, 8.0 Hz, 1H), 4.70 (d, J=11.9 Hz, 1H), 4.14 (t, J=6.4 Hz, 1H), 3.45 (q, J=13.2 Hz, 2H), 3.32 (m, 1H), 2.72 (s, 3H), 2.32 (t, J=6.5 Hz, 2H), 2.04 (s, 3H), 2.01 (m, 2H), 1.74 (m, 2H), 1.69 (s, 3H), 1.45 (s, 9H), 1.38 (s, 6H), 1.09 (d, J=6.9 Hz, 3H), 0.93 (d, J=6.9 Hz, 3H); $^{13}$C NMR (100 MHz, CDCl$_3$): δ209.51, 203.04, 166.15, 164.39, 154.14, 152.72, 141.71, 138.24, 120.70, 118.76, 115.28, 94.54, 81.85, 77.31, 76.57, 63.41, 54.16, 46.47, 41.48, 34.56, 33.95, 31.98, 31.53, 27.85, 24.85, 23.45, 21.47, 20.75, 19.04, 15.60, 14.33, 11.35; IR (neat) 3546, 3395, 1756, 1717, 1699, 1644, 1621, 1506, 1456, 1251 cm$^{-1}$.

EXAMPLE 62

Noyori C-3/C-15 Diol Product 53. The diketone 52 (0.900 g, 1.27 mmol) was dissolved in 0.12 N HCl in MeOH (10 mL) at 25° C. The RuBINAP catalyst (0.018 M in THF, 1.0 mL, 0.018 mmol) was then added and the mixture transferred to a Parr apparatus. The vessel was purged with H$_2$ for 5 min and then pressurized to 1200 psi. After 12 h at 25° C., the reaction was returned to atmospheric pressure and poured into a saturated solution of NaHCO$_3$. This mixture was extracted with CHCl$_3$ (4×50 mL) and the combined organic layers were dried over anhydrous Na$_2$SO$_4$. The product was purified by flash column chromatography on silica gel eluting with hexanes/ethyl acetate (4:1 to 2:1) to give 0.75 g (81%) of the hydroxy ester 53 as a white foam; $^1$H NMR (400 MHz, CDCl$_3$): δ6.94 (s, 1H), 6.55 (s, 1H), 5.15 (t, J=6.9 Hz, 1H), 4.85 (t, J=5.3 Hz, 1H), 4.81 (d, J=12.0 Hz, 1H), 4.71 (d, J=12.0 Hz, 1H), 4.12 (m, 2H), 3.43 (m, 2H), 2.70 (s, 3H), 2.37 (dd, J=2.2, 6.2 Hz, 1H), 2.30 (t, J=6.7 Hz, 2H), 2.24 (dd, J=10.6, 16.2 Hz, 1H), 2.03 (s, 3H), 1.99 (m, 2H), 1.68 (s, 3H), 1.44 (s, 9H), 1.18 (s, 3H), 1.16 (s, 3H), 1.09 (d, J=6.8 Hz, 3H), 0.94 (d, J=6.8 Hz, 3H); $^{13}$C NMR (100 MHz, CDCl$_3$): δ215.95, 172.39, 164.39, 154.21, 152.74, 141.70, 138.33, 120.59, 118.77, 115.27, 94.64, 82.98, 81.26, 76.51, 72.78, 51.82, 41.40, 37.36, 34.66, 33.96, 32.08, 31.10, 30.20, 27.96, 25.06, 23.45, 21.73, 21.07, 19.17, 19.01, 16.12, 15.16, 14.33, 12.17; IR (neat) 3434.0, 1757.5, 1704.5, 1249.9, 1152.8 cm$^{-1}$.

EXAMPLE 63

C-3/C-15Bis(TES) Carboxylic Acid 54. 2,6-Lutidine (0.48 g, 4.5 mmol) and TESOTf (0.59 g, 2.25 mmol) were added successively to a cooled solution of the diol 53 (164 mg, 0.225 mmol) in CH$_2$Cl$_2$ (2.5 mL) at −78° C. The reaction mixture was stirred at −78° C. for 5 min and then warmed to rt. The reaction was stirred at rt for 6 hr and then quenched with saturated aqueous NH$_4$Cl and subjected to an aqueous workup. The crude product was concentrated in vacuo and subjected directly to the next set of reaction conditions; $^1$H NMR (400 MHz, CDCl$_3$): δ6.96 (s, 1H), 6.66 (s, 1H), 5.04 (t, J=6.93 Hz, 1H), 4.90 (d, J=12.0 Hz, 1H), 4.77 (dd, J=7.99, 3.21 Hz, 1H),4.66(d, J=12.0 Hz, 1H),4.46 (m, 1H),4.10(dq, J=12.3, 7.11 Hz, 2H), 3.42 (m, 1H), 2.70 (s, 3H), 2.60 (dd, J=16.7, 2.34 Hz, 1H), 2.34 (dd, J=16.7, 7.94 Hz, 1H), 2.27(dd, J=14.0, 6.97 Hz, 1H), 2.18 (m, 1H),2.09(m, 1H), 2.04(s, 1H), 1.95(5, 3H), 1.82 (m, 2H), 1.61 (s, 3H), 1.44 (m, 2H), 1.27–1.22 (m, 4H), 1.14 (d, J=8.45 Hz, 3H), 1.11 (d, J=6.81 Hz, 2H), 1.04 (d, J=6.88 Hz, 2H), 1.15–1.01 (m, 2H), 0.94 (t, J=7.92 Hz, 18H), 0.65–0.57 (m, 12H); $^{13}$C NMR (100 MHz, CDCl$_3$): δ215.11, 175.34, 165.00, 154.14, 152.80, 142.60, 136.84, 121.31, 118.79, 114.60, 94.77, 81.60, 79.06, 76.64, 73.87, 54.19, 41.18, 39.56, 35.09, 34.52, 32.29, 31.95, 24.76, 23.62, 22.55, 18.95, 18.64, 15.87, 13.69, 11.33, 6.94, 6.83, 5.07, 4.76; IR (neat) 3100–2390, 1756.8, 1708.8, 1459.3, 1250.6, 816.1 cm$^{-1}$.

EXAMPLE 64

C-15 Hydroxy Acid for Macrolactonization 55. The crude bis(triethylsilyl)ether 54, prepared above, was dissolved in 5 mL of dry THF and then cooled to 0° C. Then, 1 mL of 0.12 M HCl/MeOH was added. The reaction mixture was stirred at 0° C. for 20 min and then checked for completion. TLC analysis at this time revealed the complete consumption of starting material. The reaction was quenched by pouring into a solution of saturated aqueous NaHCO$_3$ and subjected to an aqueous workup. Flash column chromatography with 25 to 30:1 CHCl$_3$/MeOH afforded the desired carboxylic acid 55 in 77% yield; $^1$H NMR (400 MHz, CDCl$_3$): δ6.96 (s, 1H), 6.69 (1, s), 5.11 (t, J=6.9 Hz, 1H), 4.91 (d, J=12.0 Hz, 1H), 4.71 (dd, J=3.1, 8.2 Hz, 1H), 4.64 (d, J=12.0 Hz, 1H), 4.42 (d, J=5.9 Hz, 1H), 4.10 (m, 1H), 3.43 (m, 1H), 2.71 (s, 3H), 2.57 (dd, J=2.1, 10.5 Hz, 1H), 2.25 (m, 3H), 2.11 (m, 1H), 1.98 (s, 3H), 1.95 (m, 2H), 1.72 (m 1), 1.67 (s, 3H), 1.45 (m, 2H), 1.16 (s, 3H), 1.13 (s, 3H), 1.09 (d, J=6.7 Hz, 3H), 0.99 (d, J=6.7 Hz, 3H), 0.95 (t, J=7.9 Hz, 9H), 0.64 (dq, J=2.3, 7.9 Hz, 6H); $^{13}$C NMR (100 MHz, CDCl$_3$): δ215.11, 176.00 (165.10, 154.18, 152.35, 142.24, 138.55, 120.74, 118.21, 115.02, 94.76, 81.91, 76.86, 76.63, 73.95, 54.08, 41.28, 39.64, 34.73, 34.16, 32.02, 31.67, 24.71, 23.41, 22.49, 19.17, 18.62, 15.71, 14.86, 11.20, 6.93, 5.05); IR (neat) 3400–2390, 1755.9, 1703.8, 1250.4, 735.4 cm$^{-1}$.

EXAMPLE 65

C-3 Triethylsilyl/C-7 Trichloroethoxyethylcarbonate Macrolactonization Product 56. Triethylamine (155 mg, 1.53 mmol) and 2,4,6-trichlorobenzoyl chloride (312 mg, 1.28 mmol) were added to a solution of the hydroxy acid 55 (198 mg, 0.256 mmol) in 3.6 mL of dry THF. The reaction mixture was stirred for 0.25 h at rt and then diluted with 45 mL of dry toluene. The resultant solution was added slowly dropwise, via syringe pump, over 3 hr to a stirred solution of DMAP (328 mg, 2.68 mmol) in 145 mL of dry toluene. After the addition of the substrate was complete, the reaction was stirred for an additional 0.5 h and then taken up in an equal volume of Et$_2$O and washed with 1N HCl (1×), saturated aqueous NaHCO$_3$ (1×), and brine (1×). The organic layer was dried over MgSO$_4$ and concentrated in vacuo. Flash column chromatography of the crude product with 10% EtOAc/hexanes afforded the desired macrolactone (153 mg,0.20 mmol) in 78% yield; $^1$H NMR (400 MHz, CDCl$_3$): δ6.96 (s, 1H), 6.53 (s, 1H), 5.20 (m, 2H), 5.04 (d, J=10.2 Hz, 1H), 4.84 (d, J=12.0 Hz, 1H), 4.78 (d, J=12.0 Hz, 1H), 4.07 (m, 1H), 3.32 (m, 1H), 2.86–2.63 (m, 3H), 2.70 (s, 3H), 2.48 (m, 1H), 2.11 (s, 3H), 2.04 (dd, J=6.17, 14.7 Hz, 1H), 1.73 (m, 4H), 1.66 (s, 3H), 1.25 (m, 2H), 1.19 (s, 3H), 1.15 (s, 3H), 1.12 (d, J=6.68 Hz, 3H), 1.01 (d, J=6.83 Hz, 3H), 0.89 (t, J=8.00 Hz, 9H), 0.58 (q, J=7.83 Hz, 6H); $^{13}$C NMR (100 MHz, CDCl$_3$): δ212.75, 170.66, 164.62, 154.60, 152.52, 140.29, 138.44, 119.81, 119.38, 116.28, 94.84, 86.44, 80.14, 76.59, 76.10, 53.55, 45.89, 39.23, 35.47, 32.39, 31.69, 31.57, 31.16, 29.68, 27.41, 25.00, 23.44, 22.94, 19.23, 18.66, 16.28, 14.83, 6.89, 5.22; IR (neat) 1760.5, 1742.6, 1698.0, 1378.8, 1246.2, 1106.0, 729.8 cm$^{-1}$.

EXAMPLE 66

SmI$_2$ Mediated Deprotection of Troc Group 57. Samarium metal (0.334 g, 2.22 mmol) and iodine (0.51 g, 2.0 mmol) in 25 mL of dry, deoxygenated THF were stirred together vigorously for 2.5 hr at ambient temperature. During this period of time, the reaction mixture progressed from a dark orange to an olive green to deep blue color. The resultant deep blue solution of SmI2 was used directly in the following reaction. SmI2 (25 mL of a 0.08 M stock solution, 2.0 mmol) was added rapidly via syringe to a stirred solution of the macrolactone 57 (200 mg, 0.26 mmol) and a catalytic amount of NiI$_2$ (10 mg) in 10 mL of dry THF at −78° C. The resultant deep blue solution was maintained at −78° C. with continued vigorous stirring for 2.5 hr. TLC analysis at this time revealed the complete consumption of the starting material and formation of a single, lower Rf product. The reaction mixture was quenched with saturated aqueous NaHCO$_3$ and subjected to an aqueous workup. Flash column chromatography with 25% EtOAc/hexanes afforded the desired alcohol 57 (143 mg, 0.24 mmol) in 91% yield; $^1$H NMR (400 MHz, CDCl$_3$): δ6.95 (s, 1H), 6.54 (s, 1H), 5.15 (m, 1H), 5.05(d, J=10.15 Hz, 1H),4.08(dd, J=10.1, 2.66 Hz, 1H),3.87(m, 1H),3.01 (s, 1H),3.06 (m, 1H), 2.83–2.65 (m, 3H), 2.70 (s, 3H), 2.44 (m, 1H), 2.10 (s, 3H), 2.07 (m, 1H), 1.83 (m, 1H), 1.77 (m, 1H), 1.71 (m, 1H), 1.64 (s, 3H), 1.60 (s, 1H), 1.37 (m, 1H), 1.31 (m, 1H), 1.20 (m, 1H), 1.15 (s, 3H), 1.14 (m, 5H), 1.02 (d, J=7.02 Hz, 3H), 0.89 (t, J=7.97 Hz, 9H), 0.64–0.52 (m, 6H); $^{13}$C NMR (100 MHz, CDCl$_3$): δ218.34, 170.73, 164.59, 152.46, 139.07, 138.49, 120.48, 119.54, 116.00, 79.31, 75.81, 73.48, 53.62, 42.98, 39.48, 39.01, 32.85, 32.41, 31.20, 26.12, 24.26, 22.01, 22.46, 19.18, 16.44, 15.30, 13.99, 6.98 (3), 5.27 (3); IR (neat) 3524.0, 1740.3, 1693.4, 1457.2, 1378.4, 733.2 cm$^{-1}$.

EXAMPLE 67

Desoxyepothilone B 2C. The TES protected alcohol 57 (143 mg, 0.24 mmol) was dissolved in 2 mL of dry THF in a plastic reaction vessel and cooled to 0° C. in an ice bath. The resultant solution was treated with 1 mL of HF-pyridine. The reaction mixture was stirred for 80 min at 0° C. and then quenched by pouring into a saturated aqueous solution of NaHCO$_3$. An aqueous workup followed by flash column chromatography with 10% EtOAc/hexanes afforded desoxyepothilone B (112 mg, 0.23 mmol) in 95% yield. The resultant product exhibited a $^1$H NMR spectrum identical to that of authentic desoxyepothilone B.

Total Synthesis of Desoxyepothilone B

EXAMPLE 68 tert-Butyl 4methyl-3-oxopentanoate (1E). Meldrum's acid (80 g, 555 mmol) was dissolved in 600 mL of CH$_2$Cl$_2$ and cooled to 0° C. Freshly distilled pyridine (87.8 g, 1.11 mol) was added to the CH$_2$Cl$_2$ solution and then isobutyryl chloride (65.0 g, 610.5 mmol) was added to the mixture via a pressure equalizing addition funnel. The reaction was stirred at 0° C. for 1 hr and then warmed to rt and stirred for 2 hr. Then, the reaction was quenched with water (200 mL) and washed with 0.5 M HCl (×2), water (×1), and brine (×1). The organize layer was dried over MgSO$_4$ and concentrated in vacuo. The crude product was azeotropically dried with benzene (250 mL), and then dissolved in 200 mL of benzene and 200 mL of tert-butanol was added. The resultant reaction was heated at reflux for 4 hr. After this period, the volatiles were removed in vacuo and the product then distilled on the high vacuum pump (bp 62–63° C., 0.1 mm Hg). The desired β-keto ester 1E was obtained (58.6 g, 315.5 mmol) in 57% yield as a clear, colorless, light oil.

EXAMPLE 69 tert-Butyl 4,4-dimethy-3,5-dioxoheptanoate (2E). β-Keto ester 1E (55.0 g, 295.3 mmol) was added dropwise in 50 mL of dry THF to a slurry of NaH (9.7 g, 60% dispersion in mineral oil, 383.9 mmol) in 1.15 L of dry THF. The reaction mixture was stirred at 0° C. for 30 min and then the cold bath was cooled to −50° C. Propionyl chloride (27.3 g, 295.3 mmol) was added rapidly (neat) by syringe to the cold solution. The reaction was monitored by TLC and the cold bath was maintained below −30° C. until the reaction was complete. After 1 hr, the reaction was quenched by pouring into a solution of saturated aqueous NH$_4$Cl and subjected to an aqueous workup. The aqueous layer was extracted with Et$_2$O (×2, 200 mL). Flash column chromatography with 2% EtOAc/hexanes afforded the desired tricarbonyl 2E (50.7 g, 209.6 mmol) in 71% yield; $^1$H NMR (400 MHz, CDCl$_3$); δ12.43 (s, 0.20H), 5.07 (s, 0.20H), 3.36 (s, 1.6H), 2.47 (q, J=7.13 Hz, 2H), 1.44 (s, 9H), 1.35 (s, 6H), 1.03 (t, J=7.18 Hz, 3H); $^{13}$C NMR (100 MHz, CDCl$_3$): δ209.7, 202.9, 166.1, 81.91, 62.53, 43.34, 31.67, 27.82 (3), 21.03 (2), 7.82; IR (neat) 3411.8, 1742.6, 1718.5, 1702.0, 1644.2, 1460.6, 1156.1 cm$^{-1}$.

EXAMPLE 70 tert-Butyl-4,4-dimethyl-3-methoxy-5-oxo-2-heptenoate (3E). Trimethylsilyldiazomethane (TMSCHN$_2$, 46.2 mL of a 2.0 M solution in THF, 92.4 mmol) was added by syringe to a stirred solution of the tricarbonyl (16.0 g, 66.0 mmol) and diisopropylethylamine (Hunig's base, 16.1 mL, 92.4 mmol) in 330 mL of a 9:1 solution of acetonitrile:methanol at rt. The resultant reaction mixture was stirred at rt for 18–20 hr. The reaction mixture was then quenched with saturated aqueous NaHCO$_3$ and the enol ether extracted with Et$_2$O (×3, 50 mL). The combined organic layers were washed with brine and then dried of MgSO$_4$, filtered and concentrated in vacuo. Flash column chromatography of the crude product (2% EtOAc/hexanes) afforded the desired enol ether 3E (12.5 g, 48.4 mmol) in 74% yield; $^1$H NMR (400 MHz, CDCl$_3$): δ5.18 (s,1H), 3.88 (s, 3H), 2.45 (q, J=7.33 Hz, 2H), 1.48 (s, 9H), 1.25 (s, 6H), 1.02 (t, J=7.21 Hz, 3H).

EXAMPLE 71

(67R,7R,8S)-7-Hydroxy-5-oxo-4,4,6,8-tetramethy-3-triethysilyloxy-2,10-undecadienoate, tert-butyl ester (6E). The keto enol ether 3E (8.0 g, 31.3 mmol) in 750 mL of dry THF was cooled to −30° C. in a cold bath (CO$_2$(s)/CH$_3$CN) and then a solution of LDA(37.5 mmol, 0.90 M in THF) was added dropwise via syringe over 10 min. The reaction mixture was stirred at −30 to −33° C. for 20 min. Then the reaction vessel was placed in a −120° C. cold bath (N₂(liq)/ pentane) and the reaction mixture was stirred for 10 min. Finally the aldehyde 5 (3.6 g, 36.7 mmol; aldehyde 5E was readily prepared according to the procedure outlined in: Lin, N.-H., et al., *J. Am. Chem. Soc.* 1996, 118, 9062.) was added via syringe in 5 mL of CH₂Cl₂. The reaction was complete after 10 min and was quenched by pouring into a solution of saturated aqueous NH₄Cl. The desired aldol product 6E (5.2 g, 14.7 mmol) was isolated in 47% yield (yield of the major product of a 5.5:1 mixture of diastereomers, epimeric at C-8) after flash column chromatography with 6–5% EtOAc/ hexanes; (major diasteromer, high $R_f$); ¹H NMR (400 MHz, CDCl₃): δ5.78 (m, 1H), 5.18 (s, 1H), 4.98 (m, 2H), 3.90 (s, 3H), 3.37 (m, 1H), 3.35 (s, 1H), 3.35 (s, 1H), 3.12 (q, J=7.74 Hz, 1H), 2.53 (m, 1H), 1.87 (dt, J=13.8, 8.47 Hz, 1H), 1.61 (m, 1H), 1.55 (s, 1H), 1.48 (s, 9H), 1.28 (s, 3H), 1.27 (s, 3H), 1.05 (d, J=6.91 Hz, 3H), 0.079 (d, J=6.76 Hz, 3H); ¹³C NMR (100 MHz, CDCl₃): δ217.7, 171.2, 164.8, 137.0, 116.3, 97.29, 80.22, 74.67, 62.17, 56.05, 41.05, 37.31, 34.99, 28.13, 22.69, 22.67, 15.00, 10.44; (minor diastereomer, low $R_f$): ¹H NMR (400 MHz, CDCl₃): δ5.76 (m, 1H), 5.19 (s, 1H), 5.06 (m, 2H), 1.48 (s, 3H), 3.41 (m, 1H), 3.17 (m, 1H), 3.12 (m, 1H), 2.11 (m, 1H), 1.86 (m, 1H), 1.63 (m, 1H), 1.48 (s, 9H), 1.28 (s, 3H), 1.27 (s, 3H), 1.07 (s, J=6.91 Hz, 3H), 0.99 (d, J=6.64 Hz, 3H).

EXAMPLE 72

(6R,7R,8S)-7-(2,2,2-Trichloroethoxycarbonate)-5-oxo-4,4,6,8-tetramethyl-3-triethylsilyloxy-2,10-undecadienoate, tert-butyl ester. Alcohol 6E (5.2 g, 14.7 mmol) was dissolved in 70 mL of dry CH₂Cl₂ and cooled to 0° C. in an ice bath. Then, pyridine (4.65 g, 58.8 mmol) and trichloroethoxyethylcarbonoyl chloride (TrocCl) (6.23 g, 29.4 mmol) were added by syringe in that order. The reaction was stirred at 0° C. for 5 min and then the ice bath was removed and the reaction was allowed to come to rt and stir for 30 minutes. After this period of time, TLC analysis showed the complete consumption of the starting material. The reaction mixture was quenched by pouring it into a solution of saturated aqueous NaHCO₃. Flash column chromatography with 3% EtOAc/hexanes through a short plug of silica gel afforded the desired enol ether which was subjected immediately to hydrolysis; ¹H NMR (400 MHz, CDCl₃): δ5.71 (m, 1H), 5.21 (s, 1H), 5.02 (m, 2H), 4.86 (d, J=11.9 Hz, 1H), 4.85 (m, 1 H), 4.72 (d, J=11.9 Hz, 1H), 3.91 (s, 3H), 3.25 (m, 1H), 2.26 (m, 1H), 1.87 (m, 1H), 1.81 (m, 1H), 1.48 (s, 9H), 1.31 (s, 3H), 1.26 (2, 3H), 1.11 (d, J=6.85 Hz, 3H), 0.91 (d, J=6.64 Hz, 3H).

EXAMPLE 73

(6R,7R,8S)-7-Trichloroethoxyethylcarbonate-3,5-dioxo-4,4,6,8-tetramethyl-10-undecenoate, tert-butyl ester (7E). The Troc-protected enol ether (as above) was dissolved in acetone and treated with 300 mg (catalytic) of p-TsOH at rt for 5–6 hrs. The reaction was monitored by TLC and after complete consumption of the starting enol ether was apparent, the reaction mixture was quenched with saturated aqueous NaHCO₃. The desired tricarbonyl 7E (6.8 g, 12.8 mmol), 87% (2 steps) was isolated after an aqueous workup and flash column chromatography with 7–9% EtOAc/ hexanes; ¹H NMR (400 MHz, CDCl₃): δ12.63 (s, 0.25H), 5.70 (m, 1H), 5.15 (s, 0.25H), 5.08–4.88 (m, 2H), 4.91 (dd, J=6.60, 5.01 Hz, 0.30H), 4.78 (m, 1H), 4.77 (dd, J=7.86, 3.58 Hz, 0.70H), 4.72 (dd, J=11.8, 9.66 Hz, 1H), 3.48 (d, J=16.2 Hz, 0.75H), 3.42 (d, J=16.2 Hz, 0.75H), 3.36 (m, 0.30H), 3.30 (m, 0.70H), 1.88 (m, 2H), 1.50 (s, 3H), 1.46 (s, 9H), 1.39 (s, 3H), 1.12 (d, J=6.88 Hz, 0.70H), 1.10 (d, J=6.88 Hz, 1.3H), 0.93 (d, J=6.63 Hz, 1.3H), 0.88 (d, J=6.86 Hz, 0.70H); ¹³C NMR (100 MHz, CDCl₃): δ210.5, 209.5, 203.16, 178.3, 172.6, 166.2, 154.1, 135.9, 135.6, 117.2, 116.9, 94.69, 94.56, 90.69, 82.68, 81.98, 81.65, 81.53, 63.58, 54.34, 46.56, 41.99, 41.62, 36.41, 35.84, 34.49, 34.44, 31.56, 28.23 (3), 27.94 (3), 22.62, 22.08, 21.56, 20.80, 15.95, 15.58, 14.09, 13.02, 12.98, 11.35; IR (neat) 1757.98, 1718.9, 1700.2, 1642.2, 1620.7, 1250.6, 1156.3 cm⁻¹.

EXAMPLE 74

Allylic Alcohol (16E). A mixture of (S)-(−)-1,1'-bi-2-naphthol (1.37 g, 4.8 mmol), Ti(O-i-Pr)₄ (1.36 g, 4.8 mmol), and 4 Å sieves (11 g) in CH₂Cl₂ (300 mL) was heated at reflux for 1 h. The mixture was cooled to rt and aldehyde 15E (8.0 g, 47.9 mmol; prepared according to the procedure outlined in an earlier Danishefsky synthesis of the epothilones: Meng, D.; Sorensen., E. J.; Bertinato, P.; Danishefsky, S. J. *J. Org. Chem.* 1996, 61, 7998) was added. After 10 min, the suspension was cooled to −78° C., and allyl tri-n-butyltin (20.9 g, 67.1 mmol) was added. The reaction mixture was stirred for 10 min at −78° C. and then placed in a 20° C. freezer for 70 h. Saturated aqueous NaHCO solution (2 mL) was added, and the mixture was stirred for 1 h, poured over Na₂SO₄, and then filtered through a pad of MgSO₄ and celite. The crude material was purified by flash chromatography with EtOAc/hexanes (5%→10%→15%→20%→25%→30%, two column volumes each) to give alcohol 16E as a yellow oil (6.0 g, 88.0 mmol) in 60% yield; $[\alpha]_D$=−15.9 (c. 4.9, CHCl₃); IR (film) 3360, 1641, 1509, 1434, 1188, 1017, 914 cm⁻¹; ¹H NMR (500 MHz, CDCl₃, 25° C.) δ6.92 (s, 1 H), 6.55 (s, 1H), 5.82 (m, 1H), 5.13 (dd, J=17.1, 1.3 Hz, 1H), 5.09 (d, J=10.2 Hz, 1H), 4.21 (t, J=6.0 Hz, 1H), 2.76 (br s, 1H), 2.69 (s, 3H), 2.40 (m, 2H), 2.02 (s, 3H); ¹³C NMR (125 MHz, CDCl₃, 25° C.) δ164.5, 152.6, 141.5, 134.6, 119.2, 117.6, 115.3, 76.4, 39.9, 19.0, 14.2; HRMS calcd. for C₁₁H₁₅NOS: 209.0874 found: 209.0872 (M+H).

EXAMPLE 75

TBS allylic ether (17E). Alcohol 16E (5.70 g, 27.3 mmol) was dissolved in 50 mL of dry CH₂Cl₂ and cooled to −78° C. Then, 2,6-lutidine (7.6 g, 70.9 mmol) and TBSOTf (9.36 g, 35.4 mmol) were added via syringe successively and in that order. The reaction mixture was stirred at this temperature for 30 minutes and then quenched by pouring the reaction mixture into saturated aqueous NaHCO₃. An aqueous workup followed by flash column chromatography with 2% EtOAc/hexanes afforded the desired TBS ether (7.37 g, 22.8 mmol) in 84% yield. The allylic alcohol, 17E, could also be prepared according to the general procedure outlined in the following references: (a) Racherla, U. S.; Brown, H. C. *J. Org. Chem.* 1991, 56, 401. (b) Yang, Z.; He, Y.; Vourloumis, D.; Vallberg, H.; Nicolaou, K. C. *Angew. Chem., Int. Ed. Engl.*, 1997, 36, 166.

EXAMPLE 76

Aldehyde (18E). To a solution of TBS ether 17E (7.37 g, 22.8 mmol) in acetone (150 mL) at 0° C. was added 6.7 g of a 60% solution of N-methyl-morpholine-N-oxide (NMO) in water (34.2 mmol), OsO₄ (0.039 M in THF, 6 mL, 0.23 mmol). The resultant mixture was stirred at 0° C. for 2 h and then quenched with saturated aqueous Na₂SO₃ solution (100 mL). The solution was poured into H₂O (100 mL) and extracted with EtOAc (8×50 mL). The combined organic layer was dried over MgSO$_4$, filtered, concentrated, and flashed through a short plug of silica gel to afford (7.8 g, 21.8 mmol) the crude diol in 96% yield.

To a solution of the crude diol (7.8 g, 21.8 mmol; the oxidation procedure described here may also be acomplished with NaIO$_4$ as outlined in a previous Danishefsky synthesis of the epothilones: Meng, D., et al., *J. Ann. Chem. Soc.* 1997, 119, 10073.) in 400 mL benzene at 0° C. was added Pb(OAc)$_4$ (19.4 g, 43.7 mmol) and Na$_2$CO$_3$ (9.24 g, 87.2 mmol). The reaction mixture was stirred at 0° C. for 10 min and then rt for 1.5 hr. After this period of time, the reaction mixture was quenched by pouring into brine. The reaction was filtered through Celite™ and then the resultant aqueous layer was extracted with EtOAc (5×50 mL) dried over MgSO$_4$. Flash column chromatography on silica gel with 20% EtOAc/hexanes on a short pad of silica gave the aldehyde 18E as a yellow oil (5.02 g, 15.5 mmol) in 71% yield.

EXAMPLE 77

TBS vinyl iodide (19E). n-BuLi (2.5 M in hexanes, 22.6 mL, 55.4 mmol) was added to a suspension of ethyl triphenylphosonium iodide (23.2 g, 55.4 mmol) in THF (100 mL) at 25° C. After 30 min, the clear red solution was transferred dropwise by syringe to a vigorously stirred solution of 12 (14.1 g, 55.4 mmol) in THF (1100 mL) at −78° C. After addition of the Wittig reagent was completed, the resulting pale yellow suspension was stirred rapidly and warmed to 20° C. Then, NaHMDS (1.0 M soln in THF, 55.4 mL, 55.4 mmol) was added dropwise by syringe. During the addition of the NaHMDS, the reaction mixture changed from a yellow-orange slurry and to bright red solution. Aldehyde 18E (6.0 g, 18.5 mmol) was then added in THF. After 30 min, the reaction mixture was poured into hexanes (400 mL) and then 0.5 mL brine was added. The solution was then passed through a plug of SiO$_2$ eluting with 2:1 hexanes/Et$_2$O. The iodide was purified by flash chromatography on SiO$_2$ eluting with hexanes/ethyl acetate (20:1 to 15:1) to give the vinyl iodide 19E (5.0 g, 10.2 mmol, 50%) as a yellow oil: $^1$H NMR (400 MHz, CDCl$_3$): δ6.95 (s, 1H), 6.50 (s, 1H), 5.45 (dt, J=1.5, 6.8 Hz, 1H), 4.22 (t, J=6.4 Hz, 1H), 2.73 (s, 3H), 2.48 (s, 3H), 2.39 (m, 2H), 2.02 (s, 3H), 0.90 (s, 9H), 0.06 (3, s), 0.02 (3, s); $^{13}$C NMR (100 MHz, CDCl$_3$): δ164.86, 153.46, 142.17, 132.54, 119.23; 115.68, 102.79, 77.70, 44.40, 39.09, 26.35, 19.65, 18.63, 14.54, −4.59, −4.84; IR (neat) 2928, 1470, 1252, 1068 cm$^{-1}$.

EXAMPLE 78

Post-Suzuki, C-15 Hydroxy Tricarbonyl (10E). 9-BBN (0.5 M soln in THF, 14.1 mL, 7.03 mmol) was added over a 45 min period to a solution of the olefin 7E (2.78 g, 5.41 mmol) in THF (25 mL) at 25° C. After 2 h, TLC analysis revealed the complete consumption of the starting olefin.

In a separate flask, containing the vinyl iodide 18E (2.65 g, 5.41 mmol) and DMF (45 mL), were added successively and with vigorous stirring: Cs$_2$CO$_3$ (3.52 g, 10.82 mmol); Pd(dppf)$_2$Cl$_2$ (1.10 g, 1.35 mmol), AsPh$_3$ (0.41 g, 1.35 mmol) and H$_2$O (3.5 mL, 0.19 mol). Then the borane solution, prepared above, was added rapidly by syringe to the vigorously stirred solution containing the vinyl ioidide. After 2 h, the reaction TLC analysis revealed that the reaction was complete. The reaction mixture was poured into Et$_2$O (3×200 mL), brine (1×50 mL) dried over anhydrous MgSO$_4$. This crude product was purified by flash column chromatography on SiO$_2$ eluting with hexanes/ethyl acetate (18:1 to 13:1 to 10:1) to afford the TBS protected coupled product 9E as an impure mixture which was taken on to the next step without further purification.

The crude TBS protected coupled product 9E was dissolved in 0.5 M HCl in MeOH (30 mL) at 25° C. The reaction was monitored by TLC for corruption and after 3.5 h (disappearance of starting TBS ether), the mixture was poured into a solution of saturated aqueous NaHCO$_3$ and extracted with CHCl$_3$ (4×60 mL). The combined organic layers were washed once with brine (50 mL) and dried over with anhydrous MgSO$_4$. The diol was purified by flash column chromatography on SiO$_2$ eluting with hexanes/ethyl acetate (4:1 to 3:1 to 2:1) to give the pure product 10E as a clear oil (2.44 g, 3.35 mmol, 62% for two steps): $^1$H NMR (400 MHz, CDCl$_3$: δ6.96 (s, 1H), 6.56 (s, 1H), 5.16 (t, J=6.9 Hz, 1H), 4.83 (d, J=11.9 Hz, 1H), 4.75 (dd, J=3.4, 8.0 Hz, 1H), 4.70 (d, J=11.9 Hz, 1H), (t, J=6.4 Hz, 1H), 3.45 (q, J=13.2 Hz, 2H), 3.32 (m, 1H), 2.72 (s, 3H), 2.32 (t, J=6.5 Hz, 2H), 2.04 (s, 3H), 2.01 (m, 2H), 1.74 (m, 2H), 1.69 (s, 3H), 1.45 (s, 9H), 1.38 (s, 6H), 1.09 (d, J=6.9 Hz, 3H), 0.93 (d, J=6.9 Hz, 3H); $^{13}$C NMR (100 MHz CDCl$_3$: δ209.51, 203.04, 166.15, 164.39, 154.14, 152.72, 141.71, 138.24, 120.70, 118.76, 115.28, 94.54, 81.85, 77.31, 76.57, 63.41, 54.16, 46.47, 41.48, 34.56, 33.95, 31.98, 31.53, 27.85, 24.85, 23.45, 21.47, 20.75, 19.04, 15.60, 14.33, 11.35; IR (neat) 3546, 3395, 1756, 1717, 1699, 1644, 1621, 1506, 1456, 1251, cm$^{-1}$.

EXAMPLE 79

Noyori C-3/C-15 Diol Product (11E). The diketone 10E (1.77 g, 2.43 mmol) was dissolved in 0.12 N HCl in MeOH (21 mL, 1.3 eq) at 25° C. The (R)-RuBINAP catalyst (0.045) M in THF, 8.0 mL, 0.36 mmol) was then added and the mixture transferred to a Parr apparatus. The vessel was purged with H$_2$ for 5 min and then pressurized to 1200 psi. After 12–14 h at 25° C., the reaction was returned to atmospheric pressure and poured into a saturated solution of NaHCO$_3$. This mixture was extracted with CHCl$_3$ (4×50 mL) and the combined organic layers were dried over anhydrous MgSO$_4$. The product was purified by flash column chromatography on silica gel eluting with hexanes/ethyl acetate (4:1 to 2:1) to give 1.42 g (81%) of the hydroxy ester 11E as a green foam; $^1$H NMR (400 MHz, CDCl$_3$: δ6.96 (s, 1H), 6.55 (s, 1H), 5.15 (t, J=6.9 Hz, 1H), 4.85 (t, J=5.3 Hz, 1H), 4.81 (d, J=12.0 Hz, 1H), 4.71 (d, J=12.0 Hz, 1H), 4.12 (m, 2H), 3.43 (m, 2H), 2.70 (s, 3H), 2.37 (dd, J=2.2, 6.2 Hz, 1H), 2.30 (t, J=6.7 Hz, 2H), 2.24 (dd, J=10.6, 16.2 Hz, 1H), 2.03 (s, 3H), 1.99 (m, 2H), 1.68 (S, 3 h), 1.44 (s, 9 h), 1.18 (s, 3 h), 1.16 (s, 3H), 1.09 (d, J=6.8 Hz, 3H), 0.94 (d, J=6.8 Hz, 3H); $^{13}$C NMR (100 MHz CDCl$_3$): δ215.95, 172.39, 164.39, 154.21, 152.74, 141.70, 138.33, 120.59, 118.77, 115.27, 94.64, 82.98, 81.26, 76.51, 72.78, 51.82, 41.40, 37.36, 34.66, 33.96, 32.08, 31.10, 30.20, 27.96, 25.06, 23.45, 21.73, 21.07, 19.17, 19.01, 16.12, 15.16, 14.33, 12.17; IR (neat) 3434.0, 1757.5, 1704.5, 1249.9, 1152.8 cm$^{-1}$.

C-3/C-15 Bis(TES) Carboxylic Acid. 2,6-Lutidine (2.1 g, 19.6 mmol) and TESOTf (2.6 g, 9.8 mmol) were added successively to a cooled solution of the diol 11E (2.38, 3.26 mmol) in CH$_2$Cl$_2$ (30 mL) at −78° C. The reaction mixture was stirred at −78° C. for 5 min and then warmed to rt and stirred for 1 hr. Then 2,6-lutidine (4.9 g, 45.6 mmol) and TESOTF (6.0 g, 22.8 mmol) were added successively to a −78° C. cooled solution. The reaction was stirred at rt for 6 hr and then quenched with saturated aqueous NH$_4$Cl and subjected to an aqueous workup. The crude product was concentrated in vacuo and the 2,6-lutidine removed on high vacuum pump and then subjected directly to the next set of reaction conditions; $^1$H NMR (400 MHz, CDCl$_3$): δ6.96 (s, 1H), 6.66 (s, 1H), 5.04 (t, J=6.93 Hz, 1H), 4.90 (d, J=12.0 Hz, 1H), 4.77 (dd, J=7.99, 3.21 Hz, 1H), 4.66 (d, J=12.0 Hz, 1H), 4.46 (m, 1H), 4.10 (dq, J=12.3, 7.11 Hz, 2H), 3.42 (m, 1H), 2.70 (s, 3H), 2.60 (dd, J=16.7, 2.34 Hz, 1H), 2.34 (dd, J=16.7, 7.94 Hz, 1H), 2.27 (dd, J=14.0, 6.97 Hz, 1H), 2.18 (m, 1H), 2.09 (m, 1H), 2.04 (s, 1H), 1.95 (s, 3H), 1.82 (m, 2H), 1.61 (s, 3H), 1.44 (m, 2H), 1.27–1.22 (m, 4H), 1.14 (d, J=8.45 Hz, 3H), 1.11 (d, J=6.81 Hz, 2H), 1.04 (d, J=6.88 Hz, 2H), 1.15–1.01 (m, 2H), 0.94 (t, J=7.92 Hz, 18H), 0.65–0.57 (m, 12H); $^{13}$C NMR (100 MHz, CDCl$_3$): δ215.11, 175.34, 165.00, 154.14, 152.80, 142.60, 136.84, 121.31, 118.79, 114.60, 94.77, 81.60, 79.06, 76.64, 73.87, 54.19, 41.18, 39.56, 35.09, 34.52, 32.29, 31.95, 24.76, 23.62, 22.55, 18.95, 18.64, 15.87, 13.69, 11.33, 6.94, 6.83, 5.07, 4.76; IR (neat) 3100–2390, 1756.8, 1708.8, 1459.3, 1250.6, 816.1 cm$^{-1}$.

EXAMPLE 80

C-15 Hydroxy Acid for Macrolactonization (12E). The crude bis(triethylsilyl)ether, prepared above, was dissolved in 20 mL of dry THF and then cooled to 0° C. Then, 6 ml of 0.12 M HCl/MeOH was added. The reaction mixture was stirred at 0° C. for 3 min and maintained at 0° C. for the duration. The reaction was monitored closely by TLC analysis. Methanolic HCl (0.12 M) was added in small portions, and roughly 1.3 equivalents of 0.12 M HCl was required for the hydrolysis of the C-15TBS ether (approximately 30–40 mL). The reaction was complete in apoximately 30 min. The reaction was quenched by pouring into a solution of saturated aqueous NaHCO$_3$ and subjected to an aqueous workup. Flash column chromatography with 40% EtOAc/hexanes afforded the desired carboxylic acid 12E (1.71 g, 2.20 mmol) in 67% yield; $^1$H NMR (400 MHz, CDCl$_3$): δ6.96 (s, 1H), 6.69 (l, s), 5.11 (t, J=6.9 Hz, 1H), 4.91 (d, J=12.0 Hz, 1H), 4.71 (dd, J=3.1, 8.2 Hz, 1H), 4.64 (d, J=12.0 Hz, 1H), 4.42 (d, J=5.9 Hz, 1H), 4.10 (m, 1H), 3.43 (m, 1H), 2.71 (s, 3H), 2.57 (dd, J=2.1, 10.5 Hz, 1H),2.25(m,3H),2.11 (m, 1H), 1.98(s,3H), 1.95(m,2H), 1.72 (m, 1), 1.67(s,3H), 1.45 (m, 2H), 1.16 (s, 3H), 1.13 (s, 3H), 1.09 (d, J=6.7 Hz, 3H), 0.99 (d, J=6.7 Hz, 3H), 0.95 (t, J=7.9 Hz, 9H), 0.64 (dq, J=2.3, 7.9 Hz, 6H); $^{13}$C NMR (100 MHz, CDCl$_3$): δ215.11, 176.00 (165.10, 154.18, 152.35, 142.24, 138.55, 120.74, 118.21, 115.02, 94.76, 81.91, 76.86, 76.63, 73.95, 54.08, 41.28, 39.64, 34.73, 34.16, 32.02, 31.67, 24.71, 23.41, 22.49, 19.17, 18.62, 15.71, 14.86, 11.20, 6.93, 5.05); IR (neat) 3400–2390, 1755.9, 1703.8, 1250.4, 735.4 cm$^{-1}$.

EXAMPLE 81

C-3 Triethylsilyl/C-7 Trichloroethoxyethylcarbonate Macrolactonization Product (13E). Triethylamine (155 mg, 1.53 mmol) and 2,4,6-trichlorobenzoyl chloride (312 mg, 1.28 mmol) were added to a solution of the hydroxy acid 12E (198 mg, 0.256 mmol) in 3.6 ml of dry THF. The reaction mixture was stirred for 15 min (and NO LONGER) at rt and then diluted with 20 mL of dry toluene. The resultant solution was added slowly dropwise, via syringe pump, over 3 hr to a previously prepared, stirred solution of DMAP (328 mg, 2.68 mmol) in 300 mL of dry toluene. After the addition of the substrate was complete, the reaction was stirred for an additional 0.5 h and then concentrated in vacuo. Flash column chromatography of the crude product with 10% EtOAc/hexanes afforded the macrolactone 13E (153 mg, 0.20 mmol) in 78% yield; $^1$H NMR (400 MHz, CDCl$_3$): δ6.96 (s, 1H), 6.53 (s, 1H), 5.20 (m, 2H), 5.04 (d, J=10.2 Hz, 1H), 4.84 (d, J=12.0 Hz, 1H), 4.78 (d, J=12.0 Hz, 1H), 4.07 (m, 1H), 3.32 (m, 1H), 2.86–2.63 (m, 3H), 2.70 (s, 3H), 2.48 (m, 1H), 2.11 (s, 3H), 2.04 (dd, J=6.17, 14.7 Hz,1H), 1.73 (m, 4H), 1.66 (s, 3H), 1.25 (m, 2H), 1.19 (s, 3H), 1.15 (s, 3H), 1.12 (d, J=6.68 Hz, 3H), 1.01 (d, J=6.83 Hz, 3H), 0.89 (t, J=8.00 Hz, 9H), 0.58 (q, J=7.83 Hz, 6H); $^{13}$C NMR (100 MHz, CDCl$_3$): δ212.75, 170.66, 164.62, 154.60, 152.52, 140.29, 138.44, 119.81, 119.38, 116.28, 94.84, 86.44, 80.14, 76.59, 76.10, 53.55, 45.89, 39.23, 35.47, 32.39, 31.69, 31.57, 31.16, 29.68, 27.41, 25.00, 23.44, 22.94, 19.23, 18.66, 16.28, 14.83, 6.89, 5.22; IR (neat) 1760.5, 1742.6, 1698.0, 1378.8, 1246.2, 1106.0, 729.8 cm$^{-1}$.

EXAMPLE 82

SmI$_2$ Mediated Deprotection of Troc Group. Samarium metal (0.52 g, 3.43 mmol) and iodine (0.78 g, 3.09 mmol) in 40 mL of dry, deoxygenated THF were stirred together vigorously at reflux for 2.5 hr. During this period of time, the reaction mixture progressed from a dark orange to an olive green to deep blue color. The resultant deep blue solution of SmI$_2$ was used directly in the following reaction. A catalytic amount of NiI$_2$ (10 mg) was added in one portion to the vigorously stirted solution of SmI$_2$. The reaction mixture was stirred 5 min at rt and then cooled to –78° C. in a a dry ice/acetone bath. Then, the macrolactone 13E (297 mg, 0.386 mmol), in 10 mL of dry THF, was added over 1 min to the rapidly stirred, cold solution of SmI$_2$/NiI$_2$. The resultant deep blue solution was maintained at –78° C. with continued vigorous stirring for 1 hr. TLC analysis at this time revealed the complete consumption of the starting material and formation of a single, lower R$_f$product. The reaction mixture was quenched with saturated aqueous NaHCO$_3$ and subjected to an aqueous workup. Flash column chromatography with 25% EtOAc/hexanes afforded the C-7 alcohol (204 mg, 0.343 mmol) in 89% yield; $^1$H NMR (400 MHz, CDCl$_3$): δ6.95 (s, 1H), 6.54 (s, 1H), 5.15 (m, 1H),5.05 (d, J=10.15 Hz,1H),4.08 (dd, J=10.1, 2.66 Hz,1H),3.87 (m, 1H),3.01 (s, 1H), 3.06 (m, 1H), 2.83–2.65 (m, 3H), 2.70 (s, 3H), 2.44 (m, 1H), 2.10 (s, 3H), 2.07 (m, 1H), 1.83 (m, 1H), 1.77 (m, 1H), 1.71 (m, 1H), 1.64 (s, 3H), 1.60 (s,1H), 1.37 (m, 1H), 1.31 (m, 1H), 1.20 (m, 1H), 1.15 (s, 3H), 1.14 (m, 5H), 1.02 (d, J=7.02 Hz, 3H), 0.89 (t, J=7.97 Hz, 9H), 0.64–0.52 (m, 6H); $^{13}$C NMR (100 MHz, CDCl,): δ218.34, 170.73, 164.59, 152.46, 139.07, 138.49, 120.48, 119.54, 116.00, 79.31, 75.81, 73.48, 53.62, 42.98, 39.48, 39.01, 32.85, 32.41, 31.20, 26.12, 24.26, 22.01, 22.46, 19.18, 16.44, 15.30, 13.99, 6.98(3),5.27(3); IR (neat) 3524.0, 1740.3, 1693.4, 1457.2, 1378.4, 733.2 cm$^{-1}$.

EXAMPLE 83

Desoxyepothilone B (12E). The C-3 TES protected alcohol (204 mg, 0.343 mmol) was dissolved in 6 mL of dry THF in a plastic reaction vessel and cooled to 0° C. in an ice bath. The resultant solution was treated with 3 mL of HF-pyridine. The reaction mixture was stirred for 80 min at 0° C. and then quenched by pouring into a saturated aqueous solution of NaHCO$_3$. An aqueous workup followed by flash column chromatography with 10% EtOAc/hexanes afforded desoxyepothilone B 12E (160 mg, 0.32 mmol) in 95% yield. The resultant product exhibited a $^1$H NMR spectrum identical to desoxyepothilone B prepared as described hereinabove.

Discussion

Total Synthesis of (–)-Epothilone A.

The first known method for preparing epothilone A (1) is provided by this invention. Carbons 9through 11 insulate domains of chirality embracing carbons 3 through 8 on the acyl side of the macrolactone, and carbons 12 through 15 on the alkyl side. Transmitting stereochemical information from one of the segments to the other is unlikely. Thus, the approach taken deals with the stereochemistry of each segment individually. In the acyl segment, this strategy required knowledge of both the relative and absolute configurations of the "polypropionate-like" network. In the alkyl segment, two possibilities emerge. In one instance, the C12-C13 epoxide would be included in the construct undergoing merger with the acyl related substructure. In that case it would be necessary to secure the relative stereochemical relationship of carbons 15, 13 and 12. It was necessary to consider the the possibility that the epoxide would be deleted from the alkyl-side moiety undergoing coupling. This approach would only be feasible if the epoxide could be introduced with acceptable stereocontrol after closure of the macrocycle. The synthesis of compound 4, which contains most of the requisite stereochemical information required for the acyl fragment, is described above. This intermediate is prepared by a novel oxidatively induced solvolytic cleavage of the cyclopropanopyran 3. Also described above is a construct containing the alkyl side coupling partner embodying the absolute and relative stereochemistry at carbons 15, 13 and 12, which differs from the alternative approach set forth below.

In considering the union of the alkyl and acyl domains, several potential connection sites were available. At some point, an acylation would be required to establish an ester (or lactone) bond (see bold arrow 2). Furthermore, an aldol construction was required to fashion a C2-C3 connection. Determining the exact timing of this aldol step required study. It could be considered in the context of elongating the C3-C9 construct to prepare it for acylation of the C-15 hydroxyl. Unexpectedly, it was discovered that the macrolide could be closed by an unprecedented macroaldolization. (For a previous instance of a keto aldehyde macroaldolization, see: C. M. Hayward, et al., *J. Am. Chem. Soc.,* 1993, 115, 9345.) This option is implied by bold arrow 3 in FIG. 1(A).

Figure 1B:
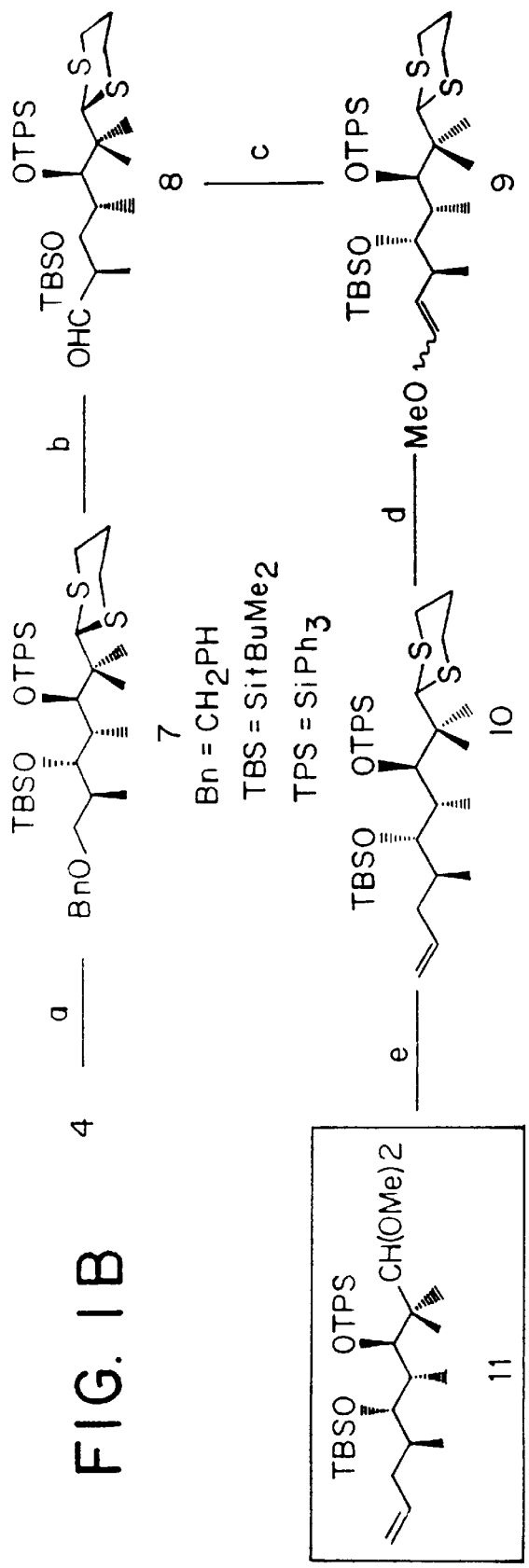
FIG. 1(B) provides synthesis of compound 11. (a) t-BuMe$_2$OTf, 2,6-lutidine, CH$_2$Cl$_2$, 98%; (b) (1) DDQ, CH$_2$Cl$_1$/H$_2$O, 89%; (2) (COCl)$_2$, DMSO, CH$_2$Cl$_2$, −78° C.; then Et$_3$N, −78° C.→rt, 90%; (c) MeOCH$_2$PPh$_3$Cl, t-BuOK, THF, 0° C.→rt, 86%; (d) (1) p-TsOH, dioxane/H$_2$O, 50° C., 99%; (2) CH$_3$PPh$_3$Br, NaHMDS, PhCH$_3$, 0° C.→rt, 76%; (e) PhI(OCOCF$_3$)$_2$, MeOH/THF, rt, 0.25 h, 92%.
Figure 12B:
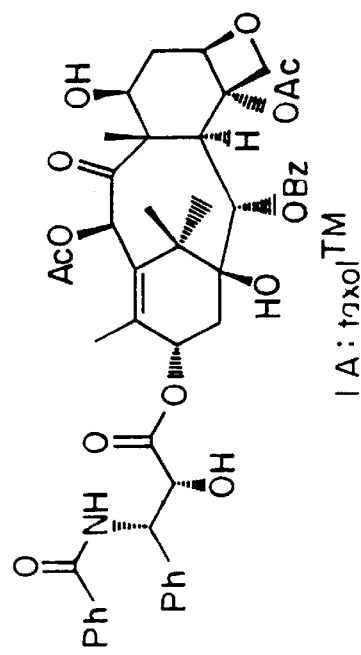
FIG. 12 illustrates (A) structures of epothilones A (1) and B (2) and (B) of Taxol® (1A).
Figure 12A:
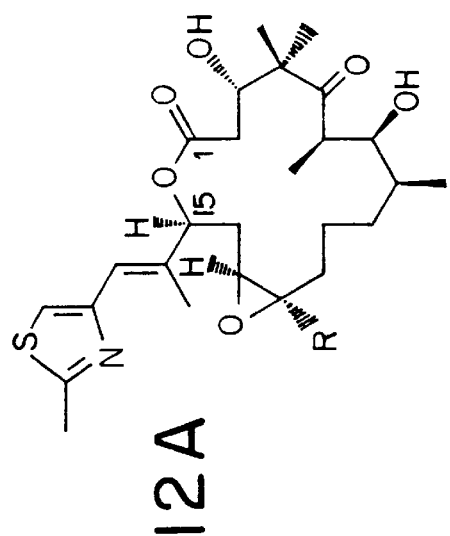
Figure 2:
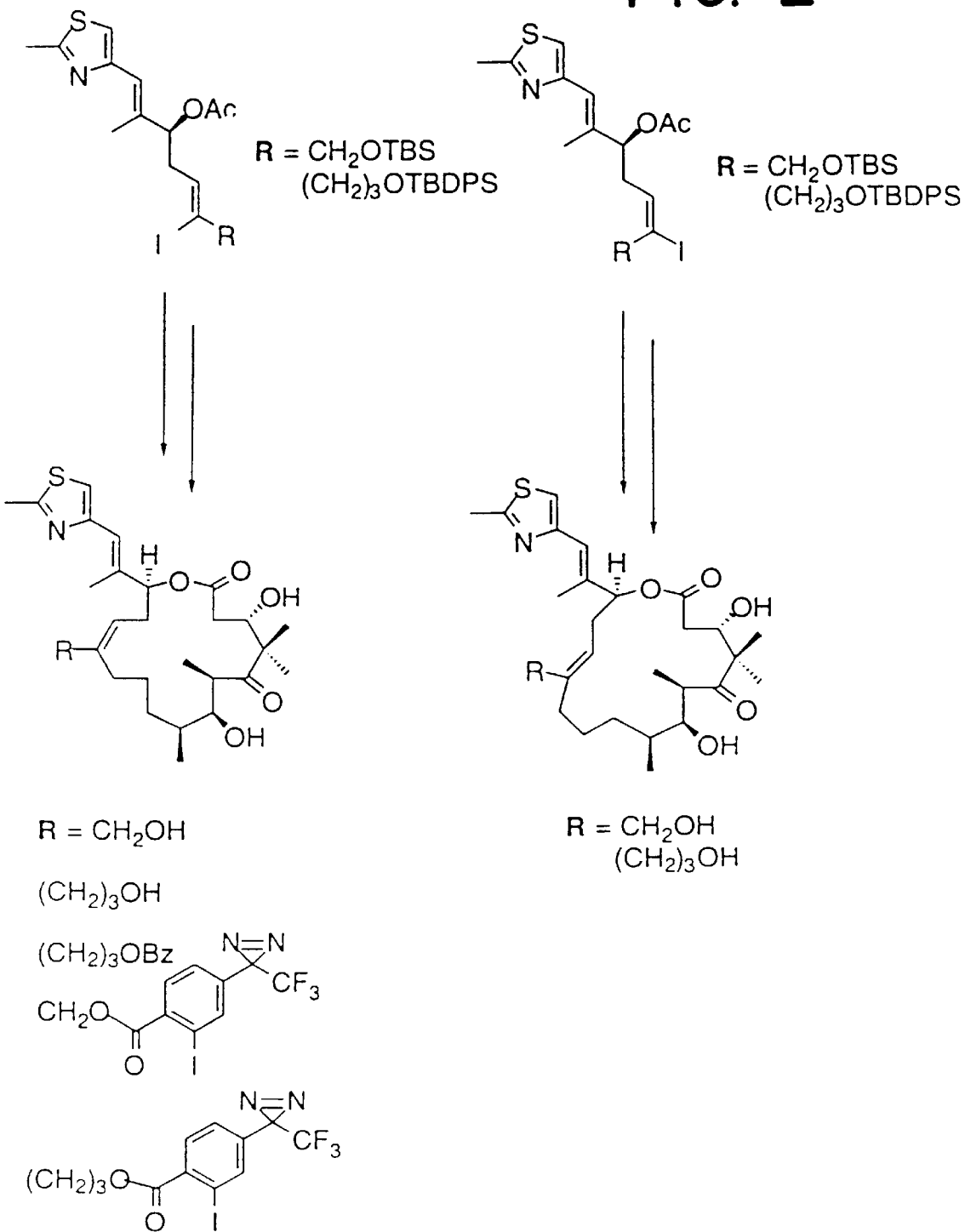
FIG. 2 provides key intermediates in the preparation of 12,13-E- and -Z-deoxyepothilones.
Figure 3A:
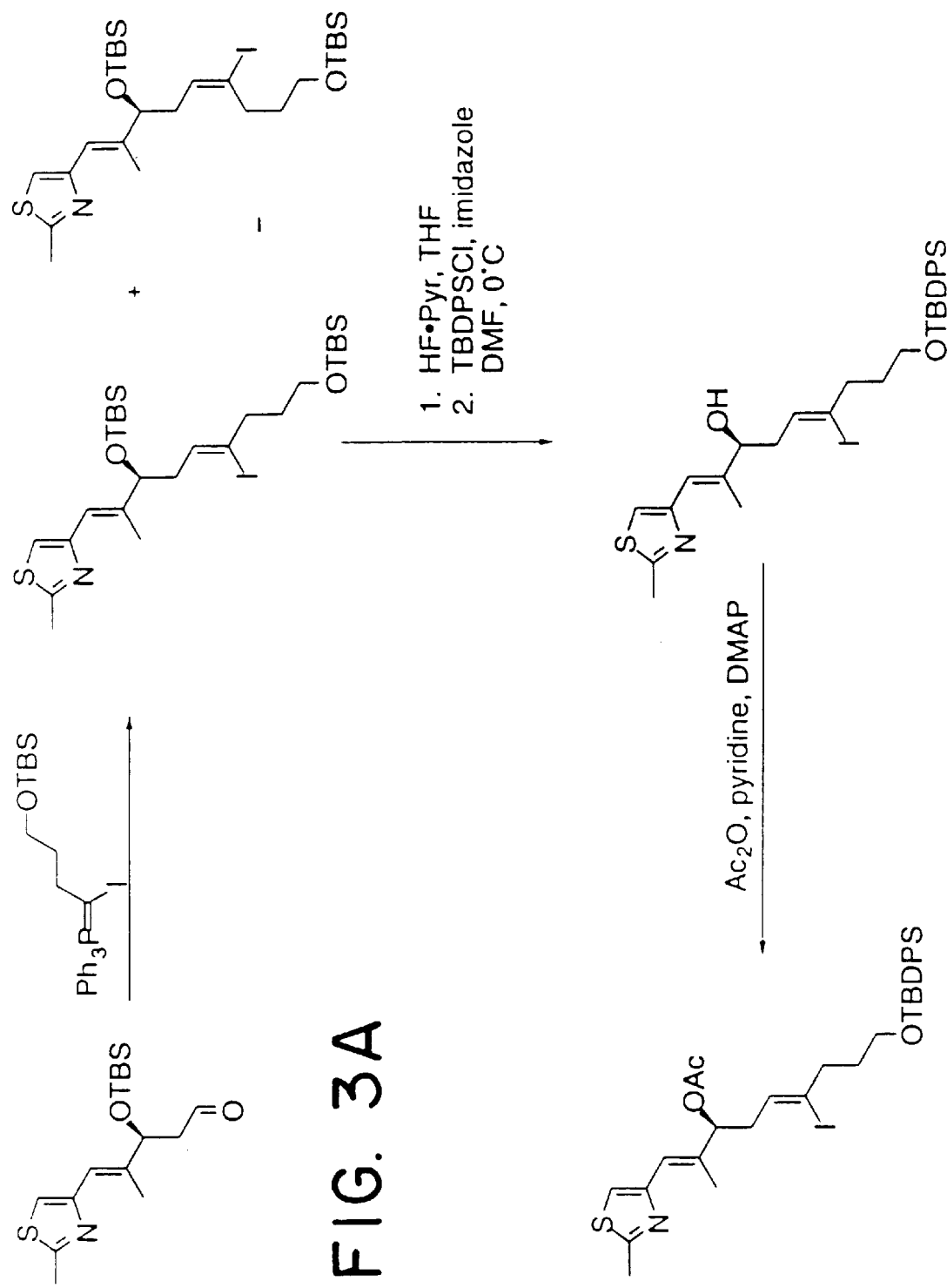
FIGS. 3(A) and 3(B) provide syntheses of key iodinated intermediates used to prepare hydroxymethylene and hydroxypropylene-substituted epothilone derivatives.
Figure 3B:
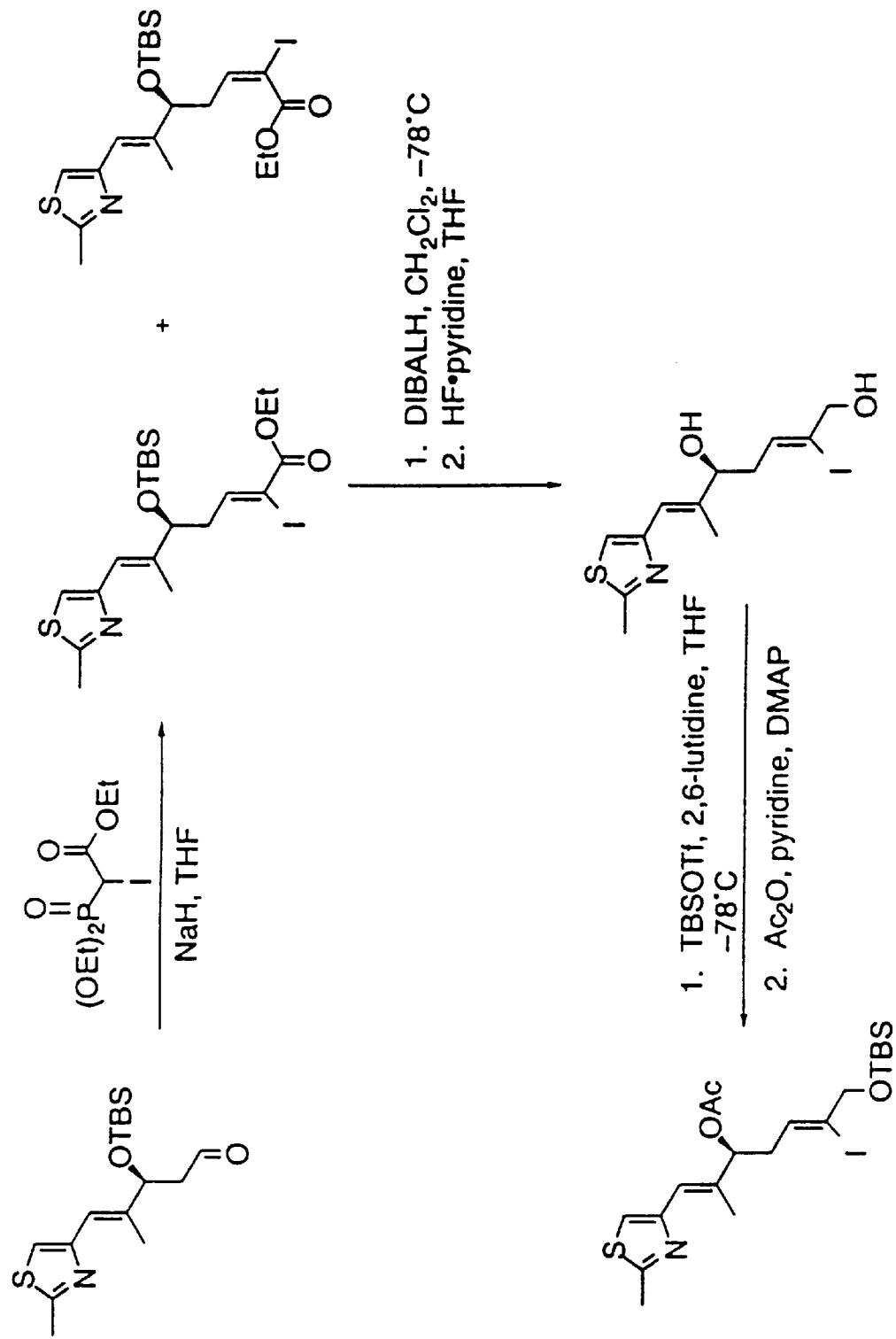
Figure 3C:
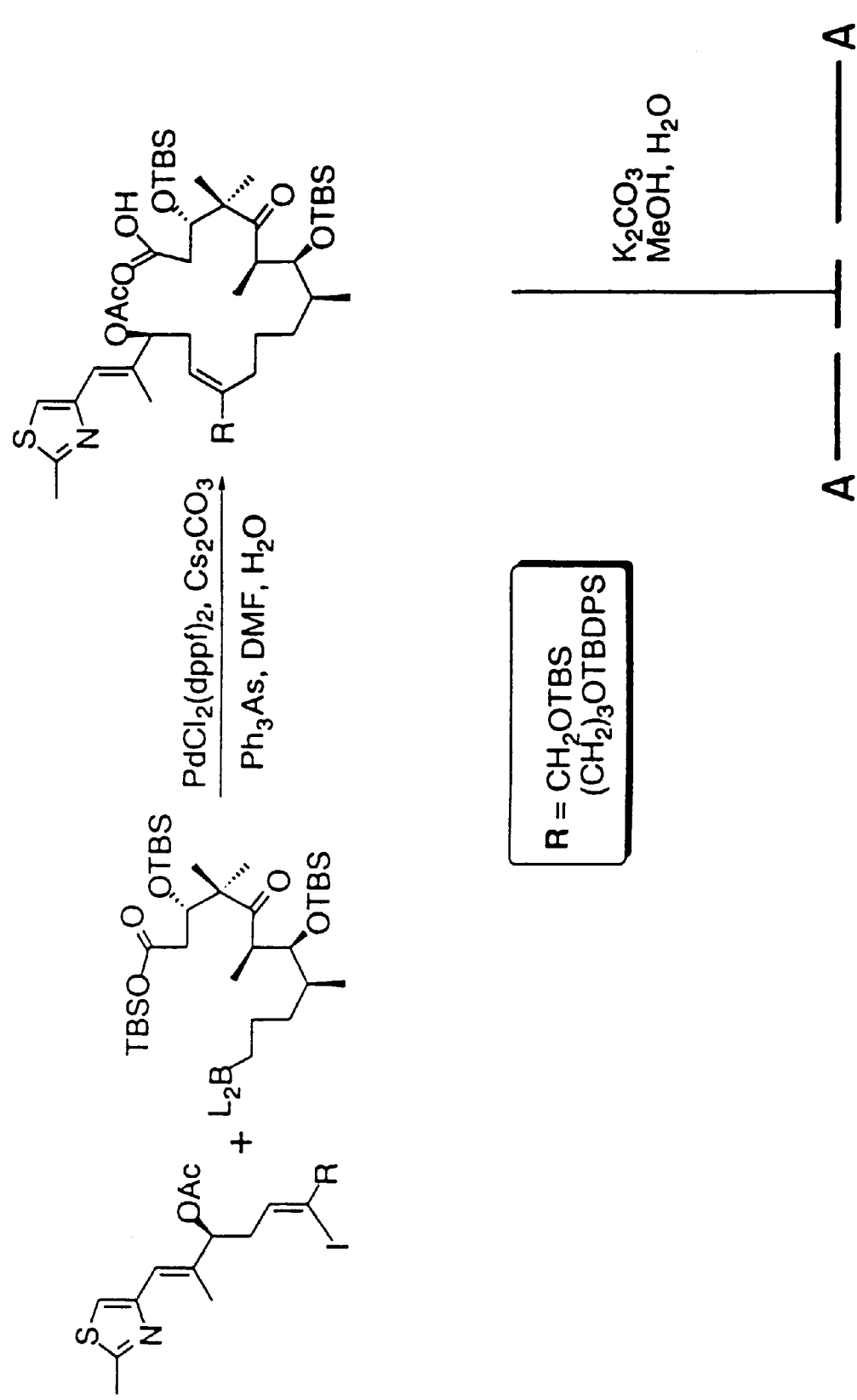
FIGS. 3(C) and 3(D) provide methods of preparing hydroxymethylene- and hydroxypropylene-substituted epothilone derivatives, said methods being useful generally to prepare 12,13-E epothilones wherein R is methyl, ethyl, n-propyl, and n-hexyl from the corresponding E-vinyl iodides.
Figure 3D:
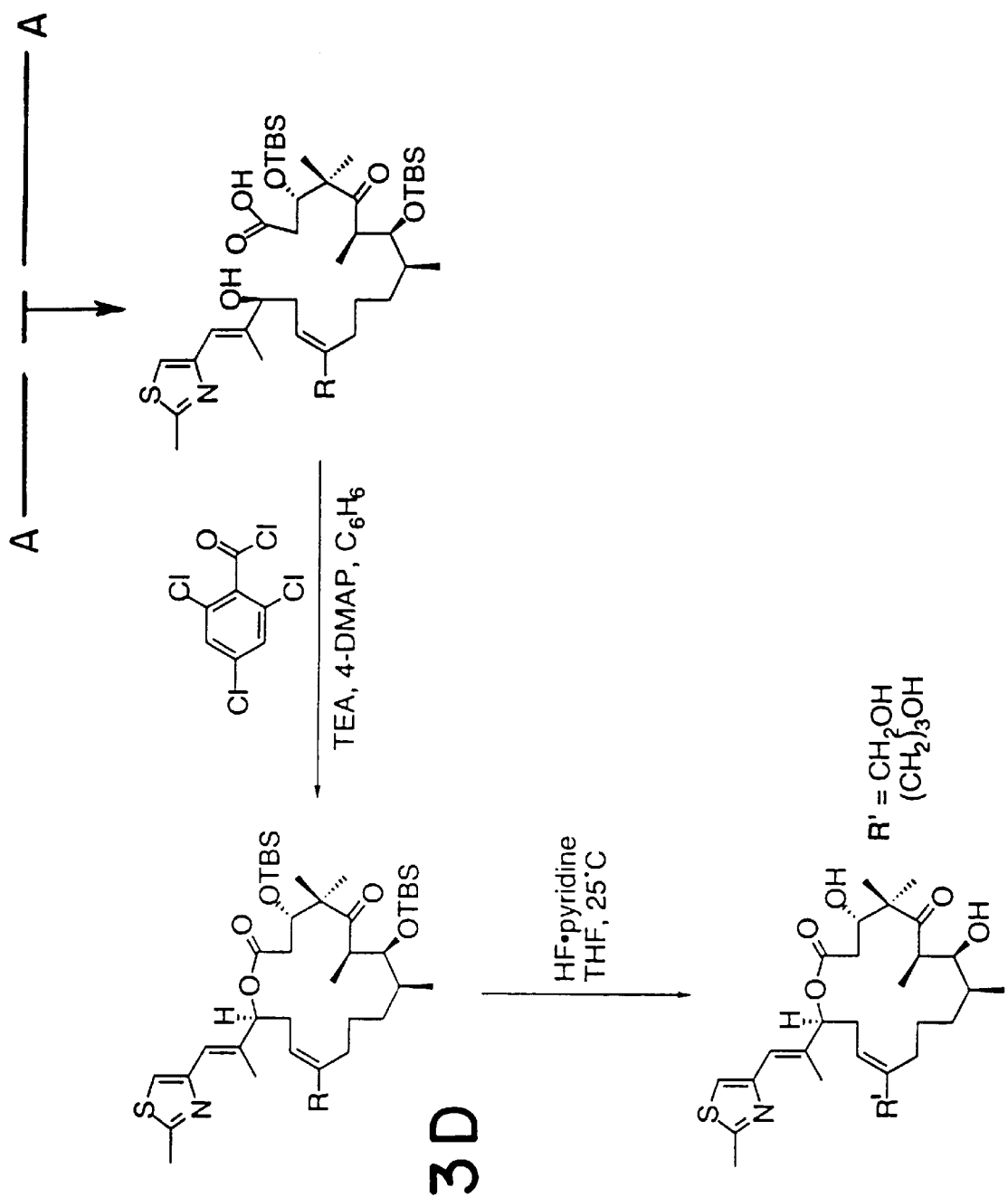
Figure 3E:
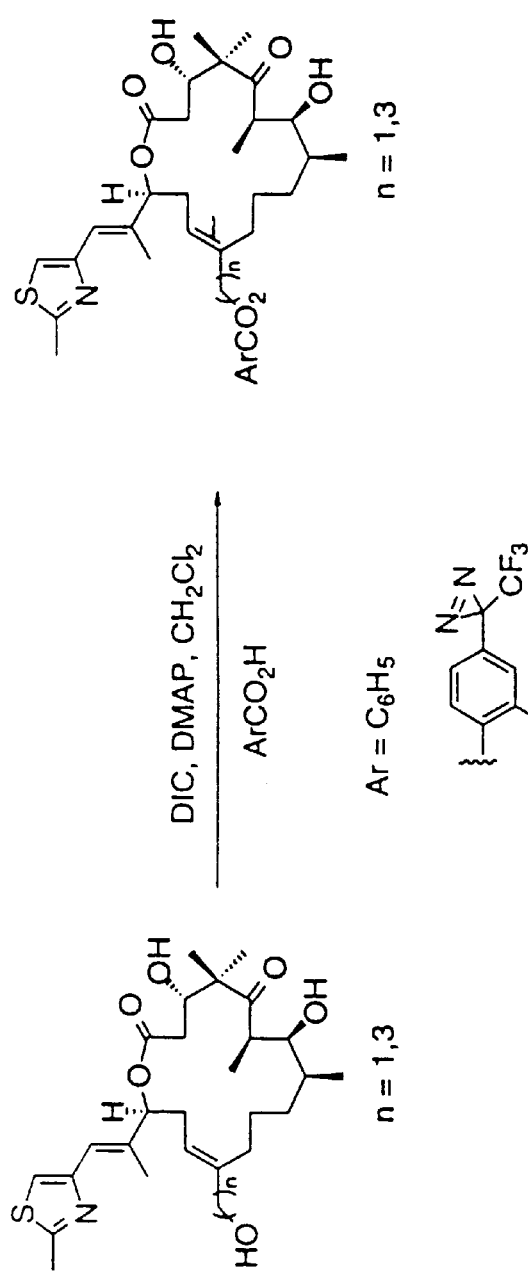
FIGS. 3(E) and 3(F) show reactions leading to benzoylated hydroxymethyl-substituted desoxyepothilone and hydroxymethylene-substituted epothilone (epoxide).
Figure 3F:
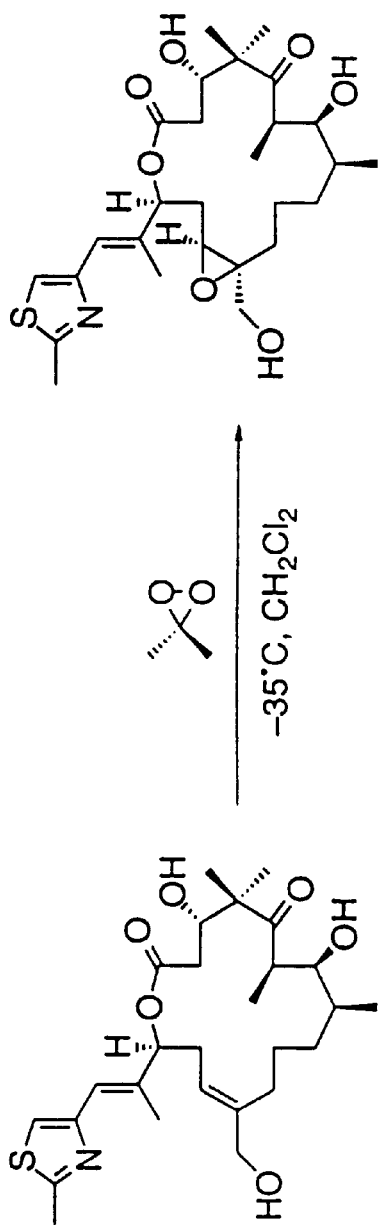

The first stage merger of the acyl and alkyl fragments (see bold arrow 1) posed a difficult synthetic hurdle. It is recognized in the art (P. Bertinato, et al., *J. Org. Chem.,* 1996, 61, 8000; vide infra) that significant resistance is encountered in attempting to accomplish bond formation between carbons 9 and 10 or between carbons 10 and 11, wherein the epoxide would be included in the alkyl coupling partner. These complications arose from unanticipated difficulties in fashioning acyl and alkyl reactants with the appropriate complementarity for merger across either of these bonds. An initial merger between carbons 11 and 12 was examined. This approach dictated deletion of the oxirane linkage from the O-alkyl coupling partner. After testing several permutations, generalized systems 5 and 6 were examined to enter the first stage coupling reaction. The former series was to be derived from intermediate 4. A de novo synthesis of a usable substrate corresponding to generalized system 5 would be necessary (FIG. 1(B)).

The steps leading from 4 to 11 are shown in Scheme 2. Protection of the future C-7 alcohol (see compound 7) was followed by cleavage of the benzyl ether and oxidation to aldehyde 8. Elongation of the aldehyde to the terminal allyl containing fragment 10 proceeded through end ether 9 (mixture of E and Z geometrical isomers). Finally, the dithiane linkage was oxidatively cleaved under solvolytic trapping conditions, giving rise to specific coupling component 11. G. Stork; K. Zhao, *Tetrahedron Lett.* 1989, 30, 287.

Figure 4A:
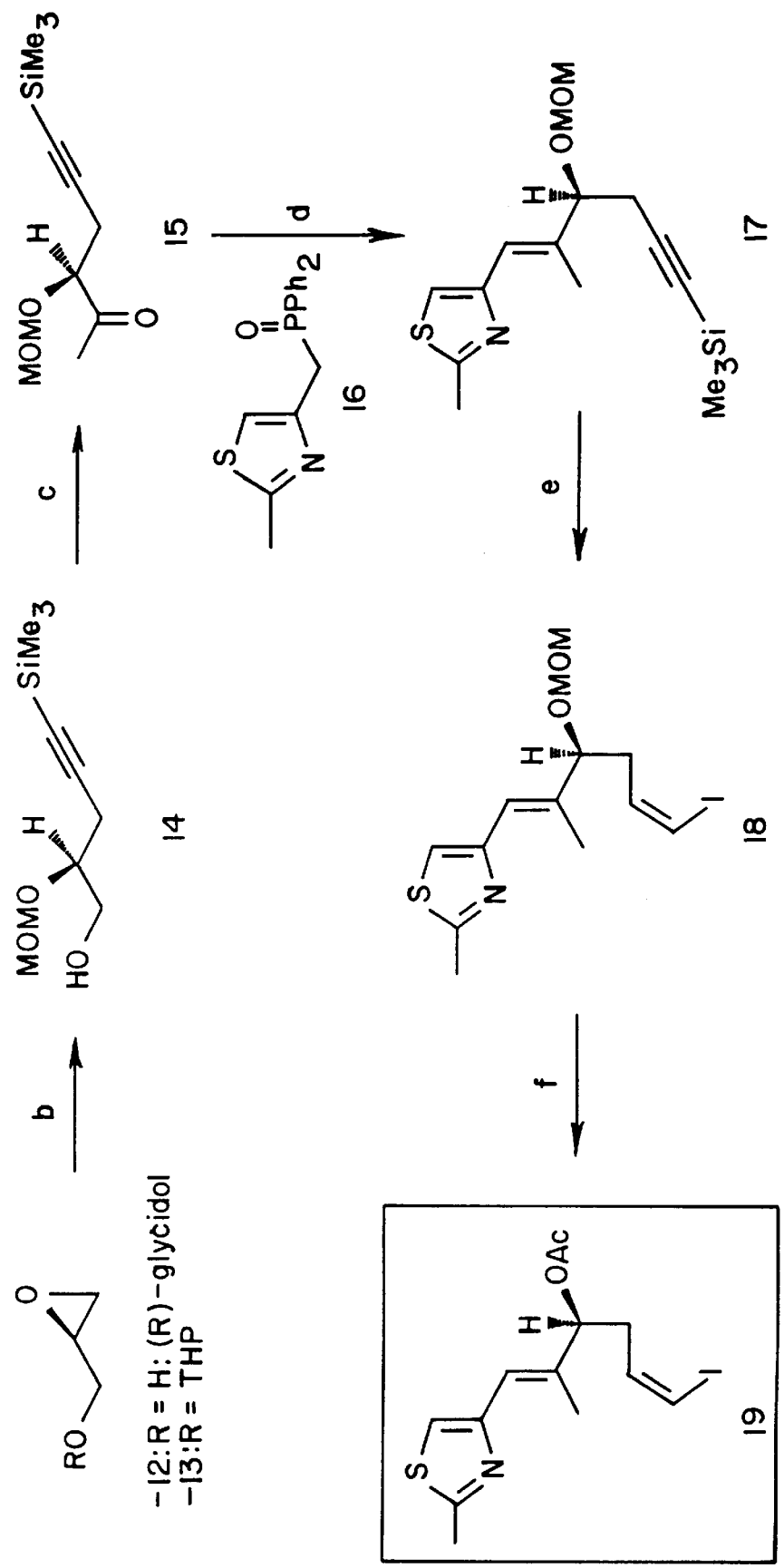
FIG. 4(A) provides synthesis of compound 19. (a) DHP, PPTS, $CH_2Cl_2$, rt: (b) (1) $Me_3SiCCLi$, $BF_3$—$OEt_2$, THF, −78° C.; (2) MOMCl, I—$Pr_2NEt$, $Cl(CH_2)_2Cl$, 55° C.; (3) PPTS, MeOH, rt; (c) (1) $(COCl)_2$, DMSO, $CH_2Cl_2$, −78° C.; then $Et_3N$, −78° C.→rt; (2) MeMgBr, $Et_2O$, 0° C.→rt, (3) TPAP, NMO, 4 Å mol. sieves, $CH_2Cl_2$, 0° C.→rt; (d) 16, n-BuLi, THF, −78° C.; then 15, THF, −78° C.→rt; (e) (1) N-iodosuccinimide, $AgNO_3$, $(CH_3)_2CO$; (2) $Cy_2BH$, $Et_2O$, AcOH; (f) (1) PhSH, $BF_3$—$OEt_2$, $CH_2Cl_2$, rt; (2) $Ac_2O$, pyridine, 4-DMAP, $CH_2Cl_2$, rt.

The synthesis of the alkyl fragment started with commercially available (R)-glycidol 12 which was converted, via its THP derivative 13, to alcohol 14. After cleavage of the tetrahydropyran blocking group, the resultant alcohol was smoothly converted to the methyl ketone 15, as shown. The latter underwent an Emmons-type homologation with phosphine oxide 16. D. Meng et al., *J. Org. Chem.,* 1996, 61, 7998. This Emmons coupling provided a ca. 8:1 mixture of olefin stereoismoers in favor of trans-17. The resultant alkyne 17 was then converted, via compound 18 to Z-iodoalkene 19 (see FIG. 4(A)). E. J. Corey et al., *J. Am. Chem. Soc.,* 1985, 107, 713.

Figure 4B:
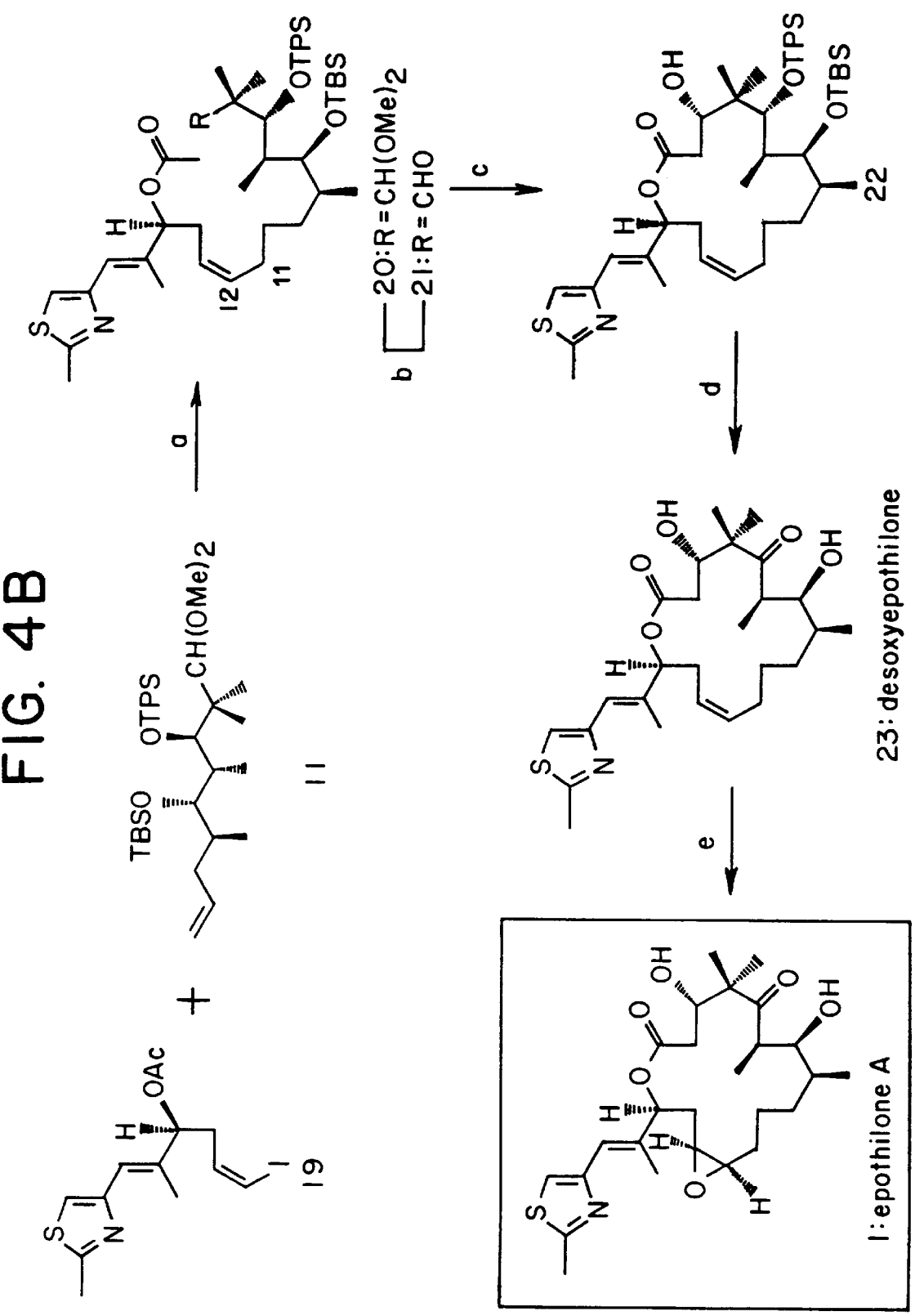
FIG. 4(B) presents synthesis of compound 1. (a) 11, 9-BBN, THF, rt; then $PdCl_2(dppf)_2$, $Cs_2CO_3$, $Ph_3As$, $H_2O$, DMF, 19, rt, 71%; (b) p-TsOH, dioxane/$H_2O$, 50° C.; (c) KHMDS, THF, −78° C., 51%; (d) (1) HF-pyridine, pyridine, THF, rt, 97%; (2) t-$BuMe_2$ SiOTf, 2,6-lutidine, $CH_2Cl_2$, −25° C., 93%; (3) Dess-Martin periodinane, $CH_2Cl_2$, 87%; (4) HF-pyridine, THF, rt, 99%; (e) dimethyldioxirane, $CH_2Cl_2$, 0.5 h, −50° C., 45% (≧20:1).
Figure 5:
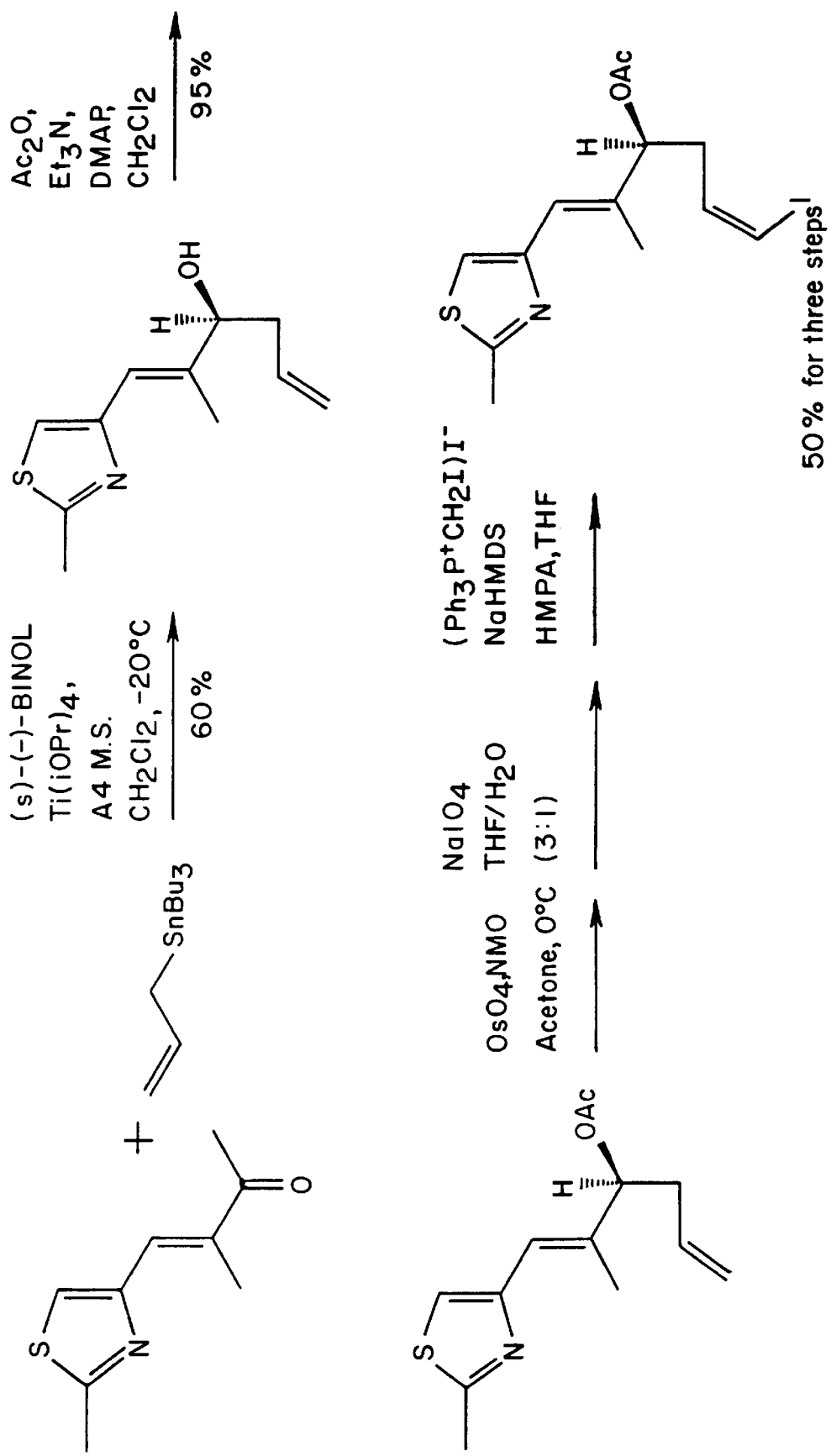
FIG. 5 shows a scheme of the synthesis of the "left wing" of epothilone A.
Figure 6A:
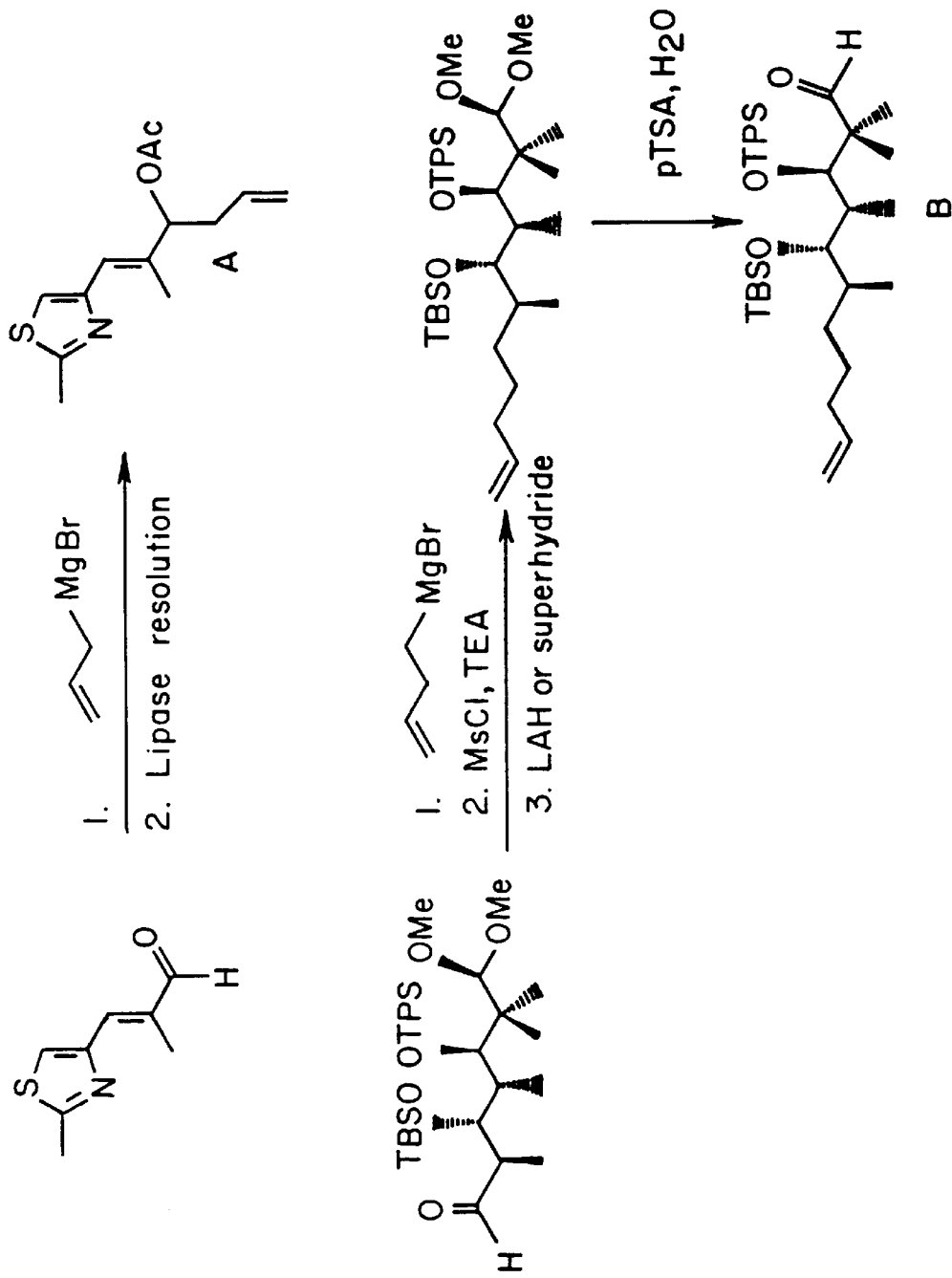
FIGS. 6(A) and 6(B) provide a scheme of an olefin metathesis route to epothilone A and other analogues.
Figure 6B:
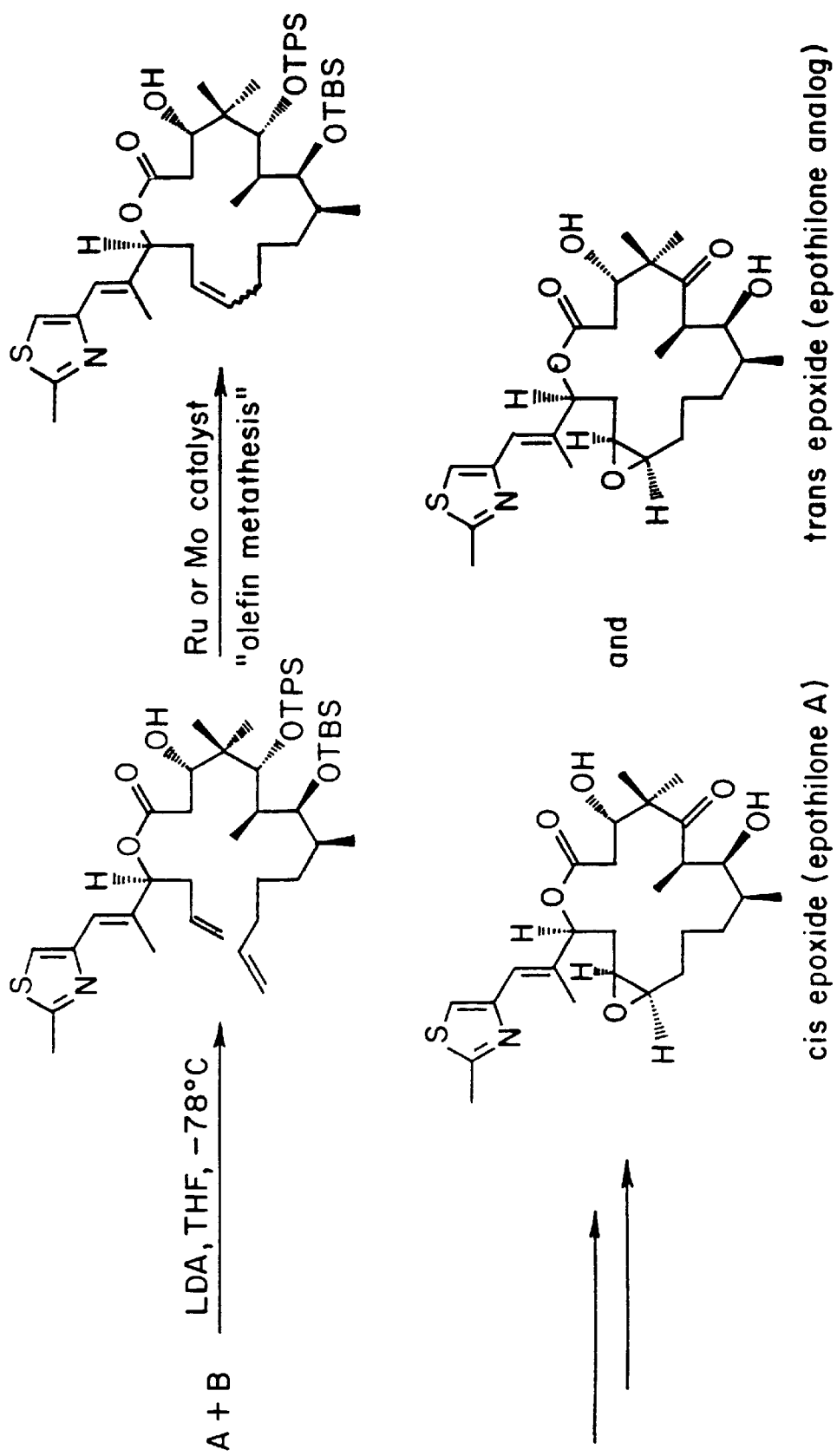

The critical first stage coupling of the two fragments was achieved by a B-alkyl Suzuki carbon-carbon bond construction. N. Miyaura et al., *J. Am. Chem. Soc.,* 1989, 111, 314; N. Miyaura and A. Suzuki, *Chem. Rev.,* 1995, 95, 2457. Thus, hydroboration of the pre-acyl fragment 11 was accomplished by its reaction with 9-BBN. The resultant mixed borane cross-coupled to iodoolefin 19, under the conditions indicated, to give 20 in 71% yield. (FIG. 4(B)) Upon cleavage of the acetal, aldehyde 21 was in hand.

The availability of 21 permitted exploration of the strategy in which the methyl group of the C-1 bound acetoxy function would serve as the nucleophilic component in a macroaldolization. Cf. C. M. Hayward et al., supra. Deprotonation was thereby accomplished with potassium hexamethyldisilazide in THF at -78° C. Unexpectedly, these conditions give rise to a highly stereoselective macroaldolization, resulting in the formation of the C-3 (S)-alcohol 22, as shown. The heavy preponderance of 22 was favored when its precursor potassium aldolate is quenched at ca. 0° C. When the aldolate was protonated at lower temperature, higher amounts of the C-3 (R) compound were detected. In fact, under some treatments, the C-3 (R) epimer predominates. It is therefore possible to generate highly favorable C-3(R):C-3(S) ratios in analytical scale quenches. In preparative scale experiments, the ratio of 22 to its C-3 epimer is 6:1.

With compound 22 in ready supply, the subgoal of obtaining desoxyepothilone (23) was feasible. This objective was accomplished by selective removal of the triphenylsilyl (TPS) group in 22, followed, sequentially, by selective silylation of the C-3 alcohol, oxidation of the C-5 alcohol, and, finally, fluoride-induced cleavage of the two silyl ethers.

Examination of a model made possible by the published crystal structure of epothilone (Höfle et al., supra), suggested that the oxirane is disposed on the convex periphery of the macrolide. Oxidation of 23 was carried out with dimethyl dioxirane under the conditions shown. The major product of this reaction was (-)epothilone A (1), the identity of which was established by nmr, infrared, mass spectral, optical rotation and chromotaraphic comparisons with authentic material. Höfle et al., supra. In addition to epothilone A (1), small amounts of a diepoxide mixture, as well as traces of the diastereomeric cis C12-C13 monoepoxide ($\geq$20:1) were detected.

The method of synthesis disclosed herein provides workable, practical amounts of epothilone A. More importantly, it provides routes to congeners, analogues and derivatives not available from the natural product itself. Studies Toward a Synthesis of Epothilone A: Use of Hydropyran Templates For the Management of Acyclic Stereochemical Relationships.

The synthesis of an enantiomerically pure equivalent of the alkoxy segment (carbons 9–15) was carried out in model studies. The key principle involves transference of stereochemical bias from an (S)-lactaldehyde derivative to an emerging dihydropyrone. The latter, on addition of the thiazole moiety and disassembly, provides the desired acyclic fragment in enantiomerically pure form.

Figure 14A:
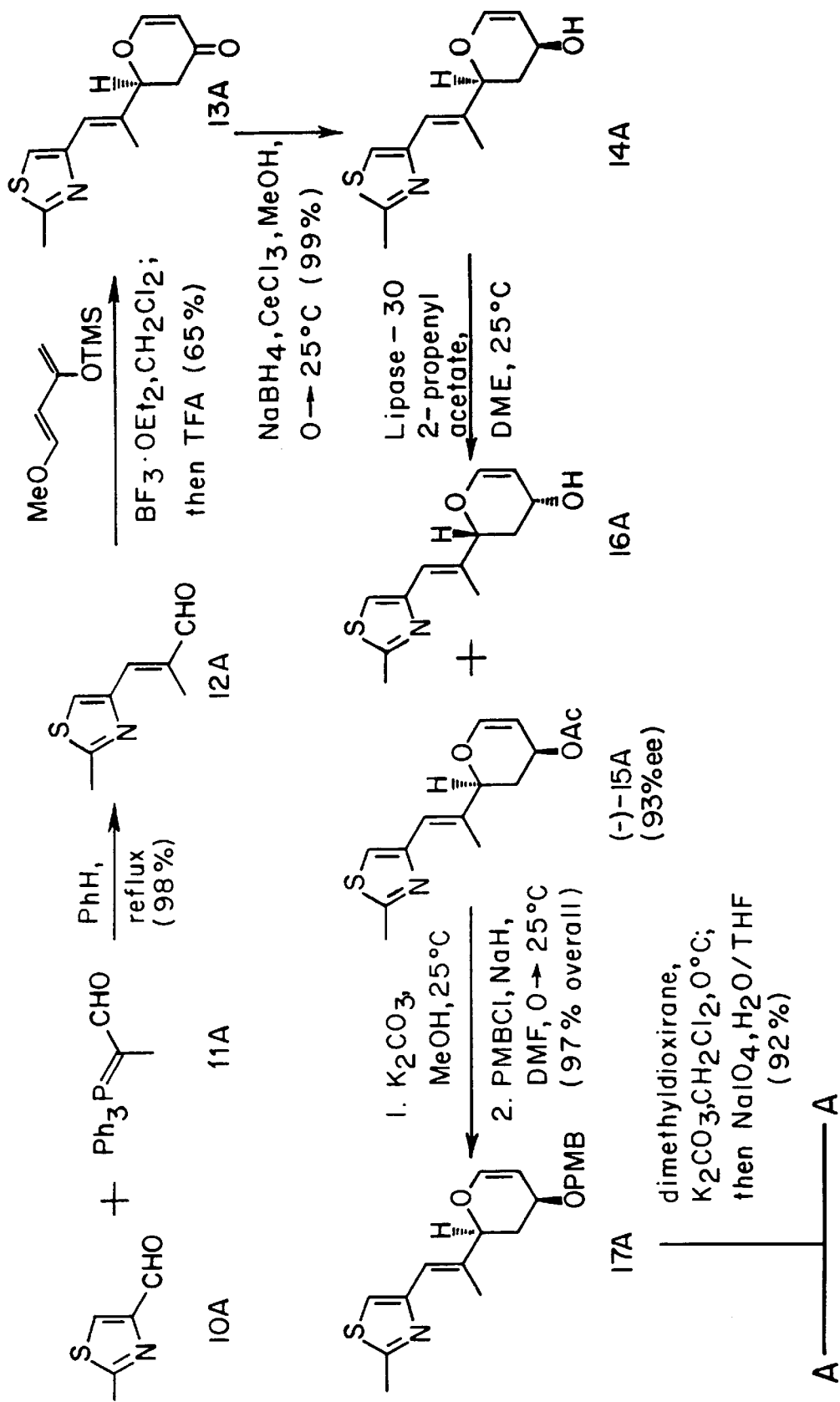
FIGS. 14(A) and 14(B) show the preparation of intermediate 4A.
Figure 14B:
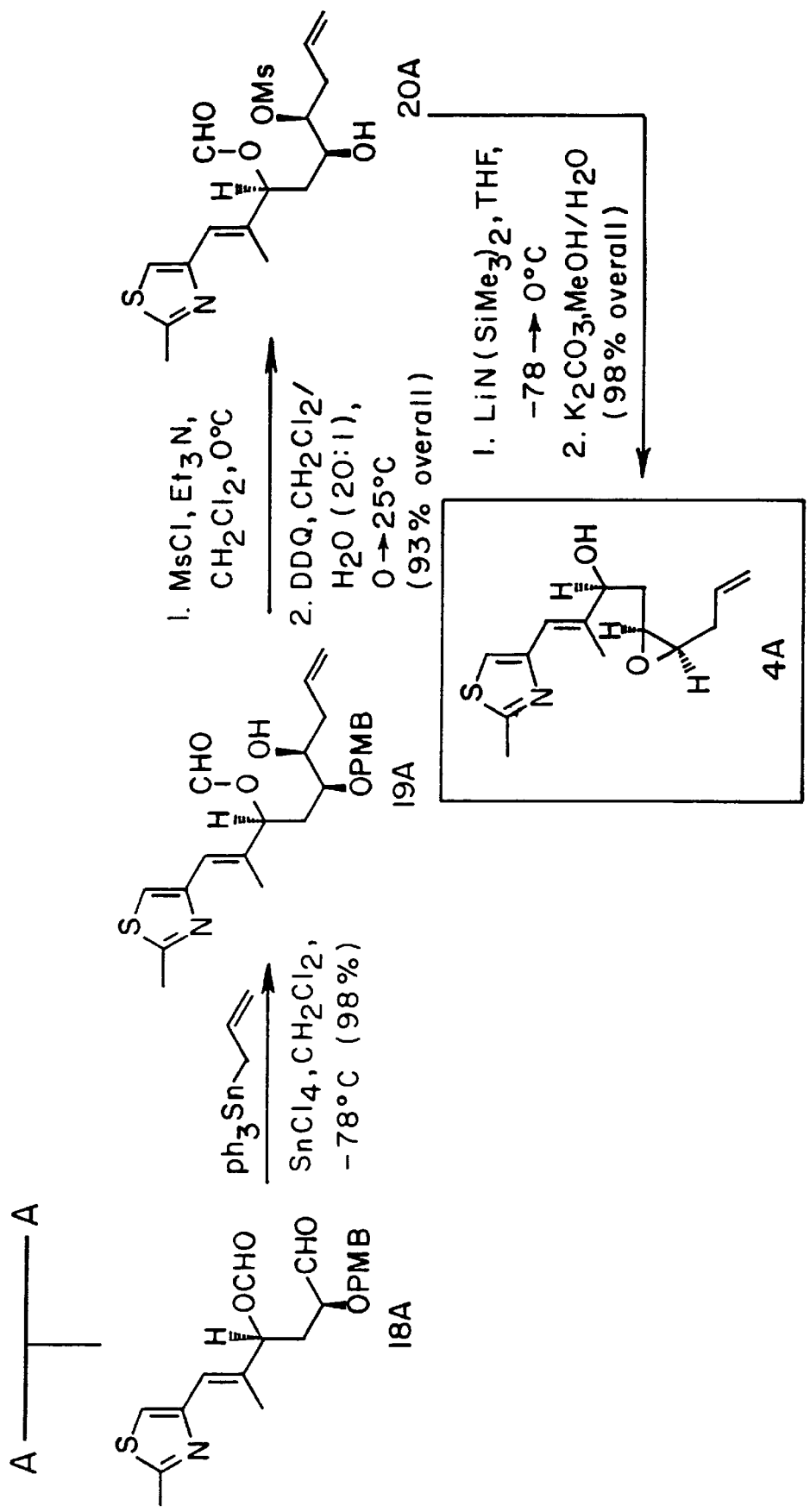

Various novel structural features of the epothilones make their synthesis challenging. The presence of a thiazole moiety, as well as a cis epoxide, and a geminal dimethyl grouping are key problems to be overcome. An intriguing feature is the array of three contiguous methylene groups which serves to insulate the two functional domains of the molecules. The need to encompass such an achiral "spacer element" actually complicates prospects for continuous chirality transfer and seems to call for a strategy of merging two stereochemically committed substructures. The present invention provides a synthesis of compound 4A (FIG. 14), expecting that, in principle, such a structure could be converted to the epothilones themselves, and to related screening candidates.

Figure 13:
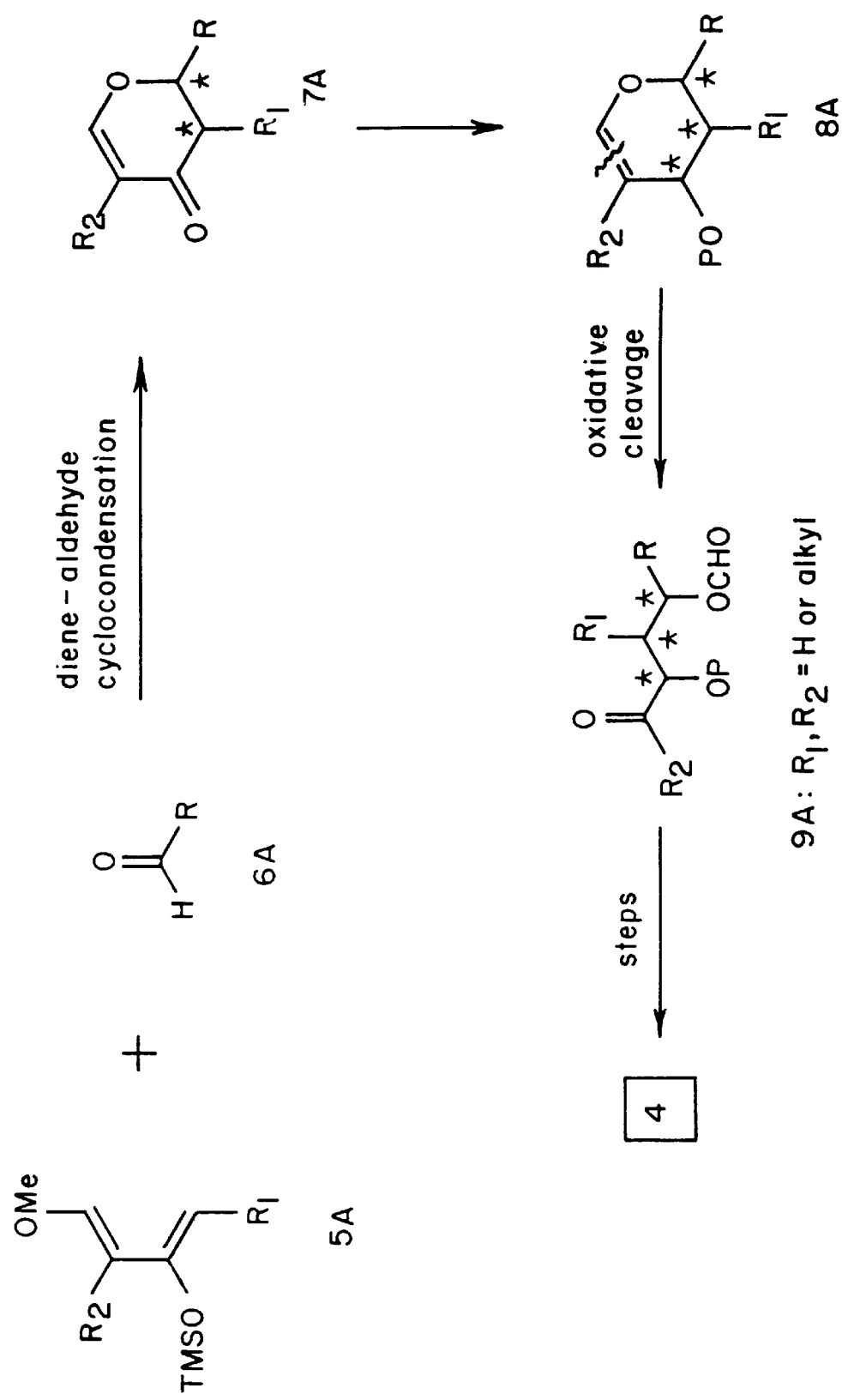
FIG. 13 shows a method of elaborating acyclic stereochemical relationships based on dihydropyrone matrices.

The identification of compound 4A as a synthetic intermediate served as an opportunity to illustrate the power of hydropyran matrices in addressing problems associated with the control of stereochemistry in acyclic intermediates. The synthesis of dihydropyrones was previously disclosed through what amounts to overall cyclocondensation of suitably active dienes and aldehydic heterodienophiles. Danishefsky, S. J. *Aldrichimica Acta,* 1986, 19, 59. High margins of steroselectivity can be realized in assembling (cf. 5A+6A→7A) such matrices (FIG. 13). Moreover, the hydropyran platforms service various stereospecific reactions (see formalism 7A→8A). Furthermore, the products of these reactions are amenable to ring opening schemes, resulting in the expression of acyciic fragments with defined stereochemical relationships (cf. 8A→9A). Danishefsky, S. J. *Chemtracts,* 1989, 2, 273.

The present invention provides the application of two such routes for the synthesis of compound 4A. Route 1, which does not per se involve control of the issue of absolute configuration, commences with the known aldehyde 10A. Shafiee, A., et al., *J. Heterocyclic Chem.,* 1979, 16, 1563; Schafiee, A.; Shahocini, S. *J. Heterocyclic Chem.,* 1989, 26, 1627. Homologation, as shown, provided enal 12A. Cyclocondensation of 12A with the known diene (Danishefsky, S. J.; Kitahara, T. *J. Am. Chem. Soc.,* 1974, 96, 7807), under $BF_3$ catalysis, led to racemic dihydropyrone 13A. Reduction of 13A under Luche conditions provided compound 14A. Luche, J.-L. *J. Am. Chem. Soc.,* 1978, 100, 2226. At this point it was feasible to take advantage of a previously introduced lipase methodology for resolution of glycal derivatives through enzymatically mediated kinetic resolution. Berkowitz, D. B. and Danishefsky, S. J. *Tetrahedron Lett.,* 1991, 32, 5497; Berkowitz, D. B.; Danishefsky, S. J.; Schulte, G. K. *J. Am. Chem. Soc.,* 1992, 114, 4518. Thus, carbinol 14A was subjected to lipase 30, in the presence of isopropenyl acetate, following the prescriptions of Wong (Hsu, S.-H., et al., *Tetrahedron Lett.,* 1990, 31, 6403) to provide acetate 15A in addition to the enantiomerically related free glycal 16A. Compound 15A was further advanced to the PMB protected system 17A. At this juncture, it was possible to use another reaction type previously demonstrated by the present inventors. Thus, reaction of 17A with dimethyldioxirane (Danishefsky, S. J.; Bilodeau, M. T. *Angew. Chem. Int. Ed. Engl.,* 1996, 35, 1381) generated an intermediate (presumably the corresponding glycal epoxide) which, upon treatment with sodium metaperiodate gave rise to aldehyde formate 18A. Allylation of 18A resulted in the formation of carbinol 19A in which the formate ester had nicely survived. (For a review of allylations, see: Yamamoto, Y.; Asao, N. *Chem. Rev.* 1993, 93, 2207.) However, 19A was accompanied by its anti stereoisomer (not shown here) [4:1]. Mesylation of the secondary alcohol, followed by deprotection (see 19A→20A) and cyclization, as indicated, gave compound 4A.

Figure 15:
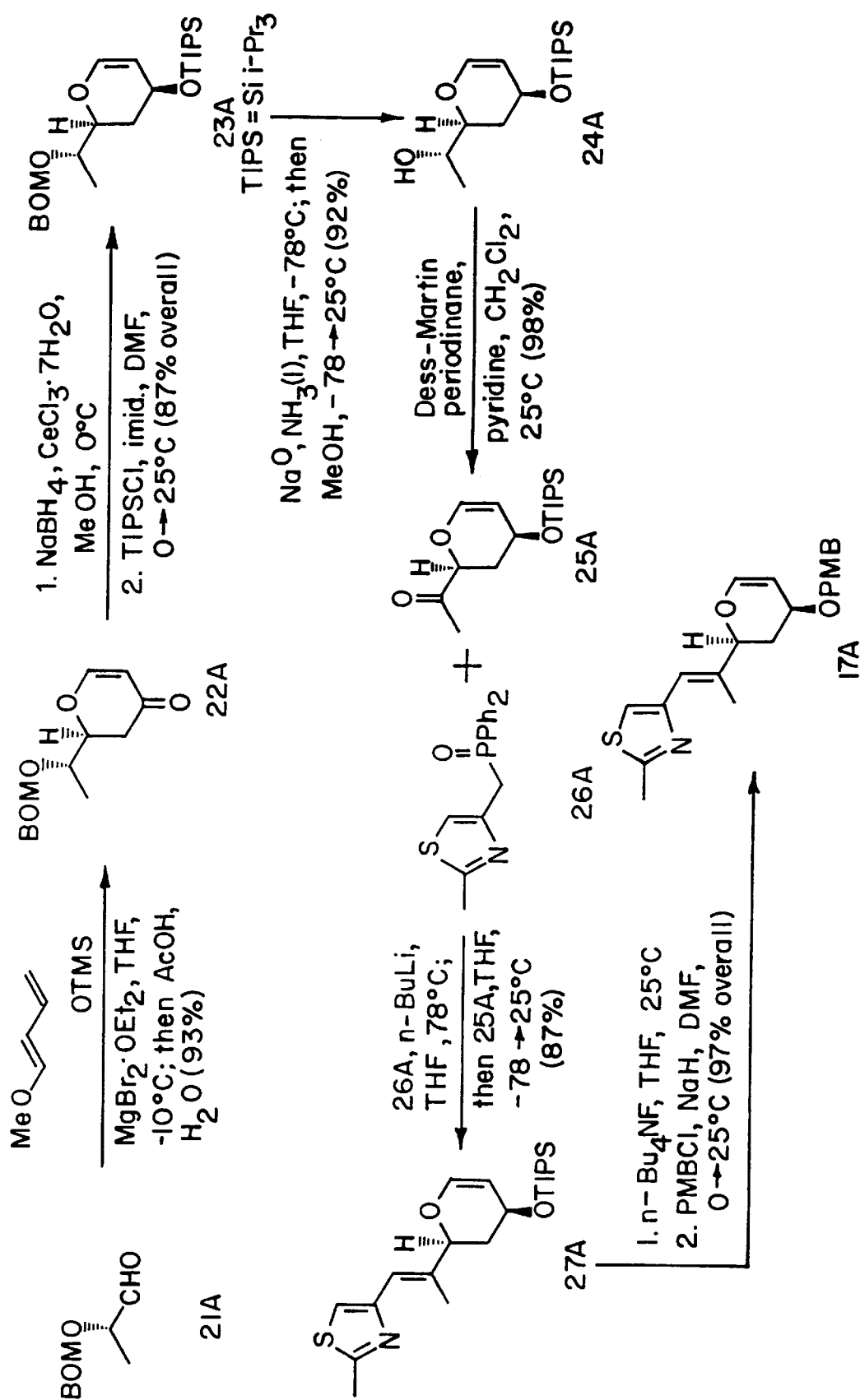
FIG. 15 shows an alternative enantioselective synthesis of compound 17A.

In this synthesis, only about half of the dihydropyrone was secured through the process of kinetic resolution. While, in theory, several of the synthetic stratagems considered contemplate use of each enantiomer of 15A to reach epothilone itself, another route was sought to allow for full enantiomeric convergence. The logic of this route is that the chirality of a "dummy" asymmetric center is communicated to the emerging pyran following previously established principles of tunable diastereoselection in the cyclocondensation reaction. (Danishefsky, supra) Cyclo-condensation of lactaldehyde derivative 21A (Heathcock, C. H., et al.,*J. Org. Chem.,* 1980, 45, 3846) with the indicated diene, under ostensible chelation control, afforded 22A. The side chain ether could then be converted to the methyl ketone 25A as shown (see 22A→23A→24A→25A). Finally, an Emmons condensations (for example, see: Lythgoe, B., et al., *Tetrahedron Lett.,* 1975, 3863; Toh, H. T.; Okamura, W. H. *J. Org. Chem.,* 1983, 48, 1414; Baggiolini, E. G., et al., *J. Org. Chem.,* 1986, 51, 3098) of 25A with the phoshphine oxide 26A was transformed to phosphine oxide 26A according to the procedure described in Toh, supra) as shown in FIG. 15 gave rise to 27A. (The known 2-methyl-4-chloromethylthiazole (see Marzoni, G. *J. Heterocyclic Chem.,* 1986, 23, 577.) A straightforward protecting group adjustment then afforded the previously encountered 17A. This route illustrates the concept of stereochemical imprinting through a carbon center which eventually emerges in planar form after conferring enantioselection to subsequently derived stereocenters. The use of the dihydropyrone based logic for securing the stereochemical elements of the epothilones, as well as the identification of a possible strategy for macrocyclization will be described in the following section.

Studies Toward a Synthesis of Epothilone A: Sterocontrolled Assembly of the Acyl Region and Models for Macrocyclization.

Ring-forming olefin metathesis has been employed to construct 16-membered ring congeners related to epothilone A. A stereospecific synthesis of the C3-C9 sector of the acyl fragment was achieved by exploiting a novel oxidative opening of a cyclopropanated glycal.

Figure 7:
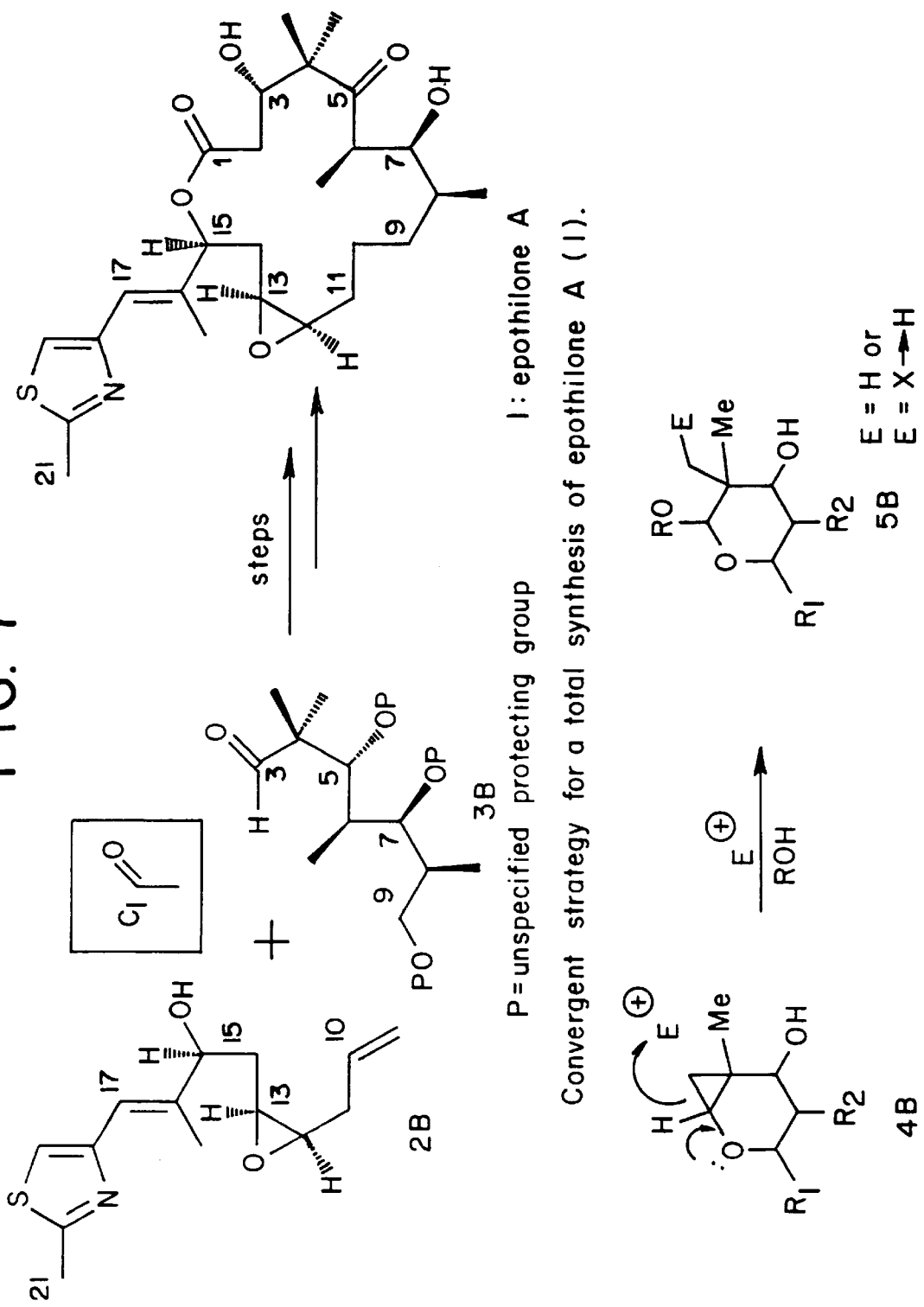
FIG. 7 illustrates a convergent strategy for a total synthesis of epothilone A (1) and the glycal cyclopropane solvolysis strategy for the introduction of geminal methyl groups.

Disclosed in the previous section is a synthesis of the "alkoxy" segment of epothilone (1) (see compound 2B, FIG. 7) encompassing carbons 10 to 21. In this section the synthesis of another fragment encoding the stereochemical information of acyl section carbons 3 to 9. It was envisioned that the aldehydo center ($C_3$) of the formal target 3B would serve as an attachment site to a nucleophilic construct derived from compound 2B (requiring placement of a 2 carbon insert, as suggested in FIG. 7), through either inter- or intramolecular means. In such a context, it would be necessary to deal independently with the stereochemistry of the secondary alcohol center eventually required at $C_3$. One of the interesting features of system 3B is the presence of geminal methyl groups at carbon 4 (epothilone numbering). Again, use is made of a dihydropyran strategy to assemble a cyclic matrix corresponding, after appropriate disassembly, to a viable equivalent of system 3B. The expectation was to enlarge upon the dihydropyran paradigm to include the synthesis of gem-dimethyl containing cyclic and acyclic fragments. The particular reaction type for this purpose is generalized under the heading of transformation of 4B→5B (see FIG. 7). Commitment as to the nature of the electrophile E is avoided. Accordingly, the question whether a reduction would or would not be necessary in going from structure type 5B to reach the intended generalized target 3B is not addressed.

Figure 8:
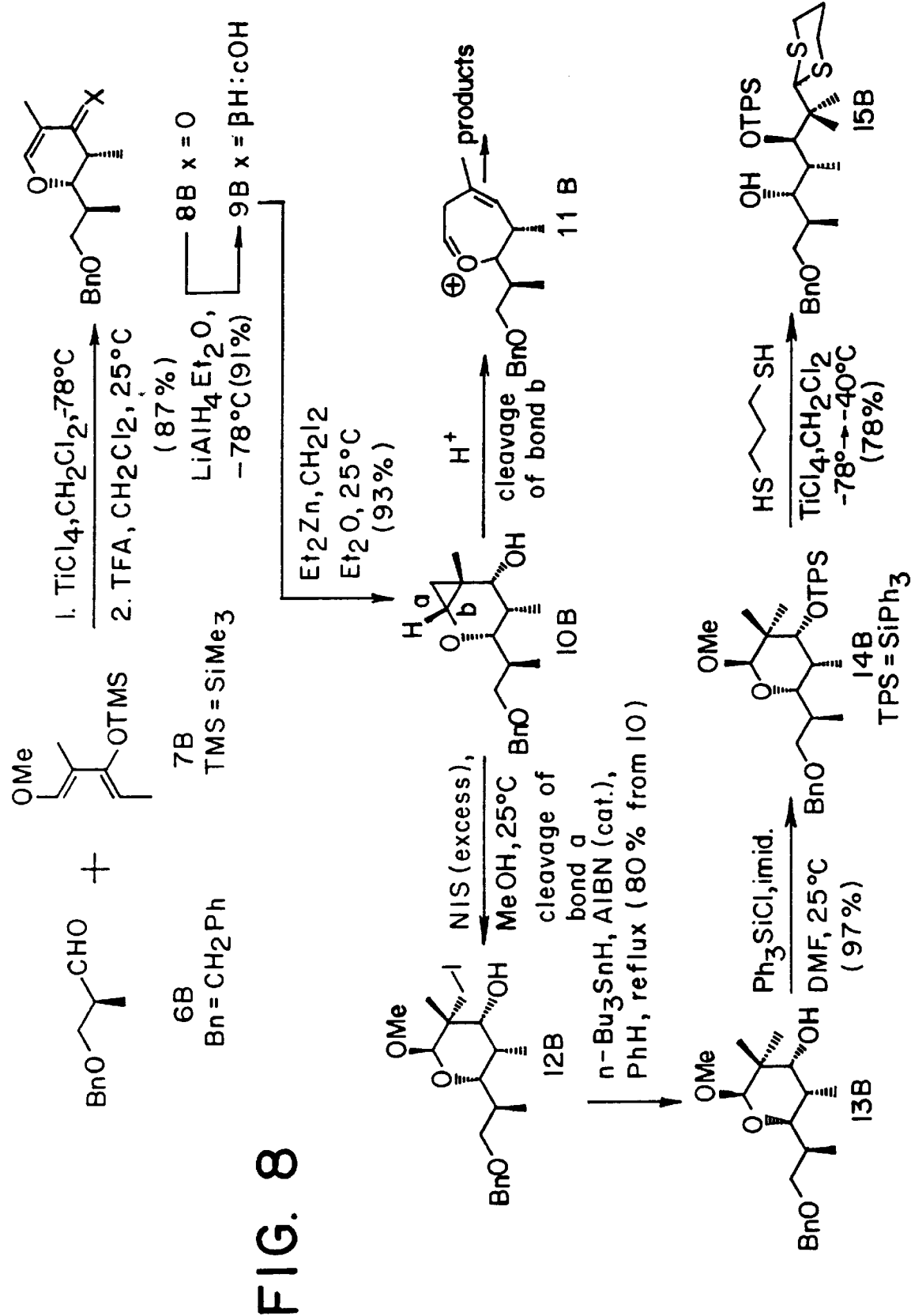
FIG. 8 provides an enantioselective synthesis of compound 15B.

The opening step consisted of a stereochemically tuneable version of the diene-aldehyde cyclocondensation reaction (FIG. 8; Danishefsky, S. J., *Aldrichimica Acta*, 1986, 19, 59), in this instance drawing upon chelation control in the merger of the readily available enantiomerically homogenous aldehyde 6B with the previously known diene 7B. Danishefsky, S. J., et al., *J. Am. Chem. Soc.* 1979, 101, 7001. Indeed, as precedent would have it, under the influence of titanium tetrachloride there was produced substantially a single isomer shown as compound 8B. In the usual and stereochemically reliable way (Danishefsky, S. J., *Chemtracts Org. Chem.* 1989, 2, 273), the dihydropyrone was reduced to the corresponding glycal, 9B. At this point, it was feasible to utilize a directed Simmons-Smith reaction for the conversion of glycal 9B to cyclopropane 10B. Winstein, S.; Sonnenberg, J. *J. Am. Chem. Soc.*, 1961, 83, 3235; Dauben, W. G.; Berezin, G. H. *J. Am. Chem. Soc.*, 1963, 85, 468; Furukawa, J., et al., *Tetrahedron*, 1968, 24, 53; For selected examples, see Soeckman, R. K. Jr.: Charette, A. B.; Asberom, T.; Johnston, B. H. *J. Am. Chem. Soc.*, 1991, 113, 5337; Timmers, C. M.; Leeuwenurgh, M. A.; Verheijen, J. C.; Van der Marel, G. A.; Van Boom, J. H. *Tetrahedron: Asymmetry*, 1996, 7, 49. This compound is indeed an interesting structure in that it corresponds in one sense to a cyclopropano version of a C-glycoside. At the same time, the cyclopropane is part of a cyclopropylcarbinyl alcohol system with attendant possibilities for rearrangement. Wenkert, E., et al., *J. Amer. Chem. Soc.*, 1970, 92, 7428. It was intended to cleave the C-glycosidic bond of the cyclopropane in a fashion which would elaborate the geminal methyl groups, resulting in a solvent-derived glycoside with the desired aidehyde oxidation state at C-3 (see hypothesized transformation 4B→5B, FIG. 7). In early efforts, the non-oxidative version of the projected reaction (i.e. $E^+=H^+$) could not be reduced to practice. Instead, products clearly attributable to the ring expanded system 11 were identified. For example, exposure of 10B to acidic methanol gave rise to an epimeric mixture of seven-membered mixed-acetals, presumably through the addition of methanol to oxocarbenium ion 11B.

However, the desired sense of cyclopropane opening, under the influence of the ring oxygen, was achieved by subjecting compound 10B to oxidative opening with N-iodosuccinimide. (For interesting Hg(II)-induced solvolyses of cyclopropanes that are conceptually similar to the conversion of 10B to 12B, see: Collum, D. B.; Still, W. C.; Mohamadi, F. *J. Amer. Chem. Soc.*, 1986, 108, 2094; Collum, D. B.; Mohamadi, F.; Hallock, J. S.; *J. Amer. Chem. Soc.*, 1983, 105, 6882. Following this precedent, a Hg(II)-induced solvolysis of cyclopropane 10B was achieved, although this transformation proved to be less efficient than the reaction shown in FIG. 8.) The intermediate iodomethyl compound, obtained as a methyl glycoside 12B, when exposed to the action of tri-n-butyltinhydride gave rise to pyran 13B containing the geminal methyl groups. Protection of this alcohol (see 13B→14B), followed by cleavage of the glycosidic bond, revealed the acyclic dithiane derivative 15B which can serve as a functional version of the hypothetical aldehyde 3B.

Possible ways of combining fragments relating to 2B and 3B in a fashion to reach epothilone and congeners thereof were examined. In view of the studies of Schrock (Schrock, R. R., et al., *J. Am. Chem. Soc.*, 1990, 112, 3875) and Grubbs (Schwab, P. et al., *Angew. Chem. Int. Ed. Engl.*, 1995, 34, 2039; Grubbs, R. H.; Miller, S. J. Fu, G. C. *Acc. Chem. Res.*, 1995, 28, 446; Schmalz, H.-G., *Angew. Chem. Int. Ed. Engl.*, 1995, 34, 1833) and the disclosure of Hoveyda (Houri, A. F., et al., *J. Am. Chem. Soc.*, 1995, 117, 2943), wherein a complex lactam was constructed in a key intramolecular olefin macrocyclization step through a molybdenum mediated intramolecuar olefin in metathesis reaction (Schrock, supra; Schwab, supra), the possibility of realizing such an approach was considered. (For other examples of ring-closing metathesis, see: Martin, S. F.; Chen, H.-J.; Courtney, A. K.; Lia, Y.; Pätzel, M.; Ramser, M N.; Wagman, A. S. *Tetrahedron*, 1996, 52, 7251; Furstner, A.; Langemann, K. J. *Org. Chem.*, 1996, 61, 3942.)

Figure 9:
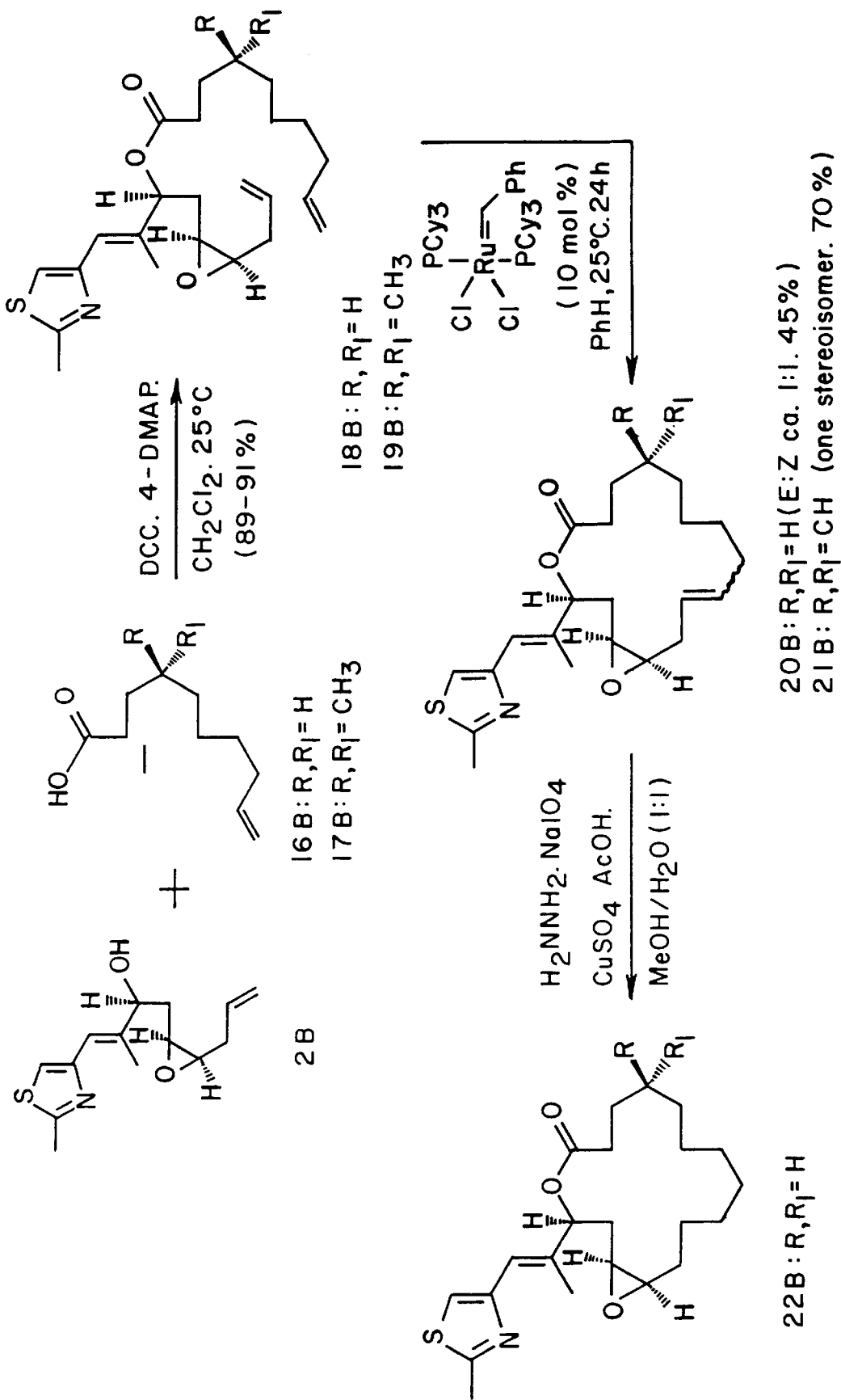
FIG. 9 shows the construction of epothilone model systems 20B, 21B, and 22B by ring-closing olefin metathesis.
Figure 10:
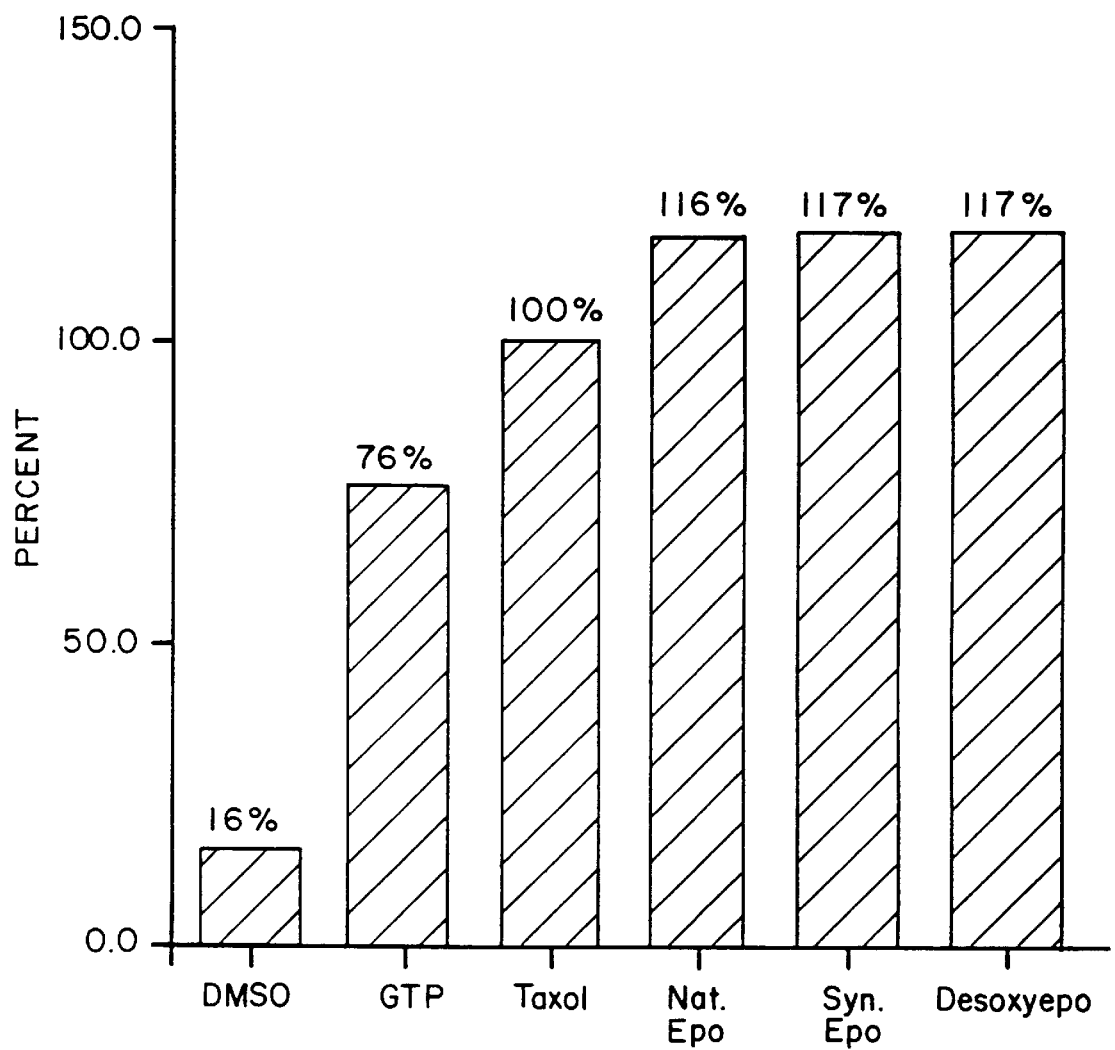
FIG. 10 illustrates a sedimentation test for natural, synthetic and desoxyepothilone A.
Figure 11:
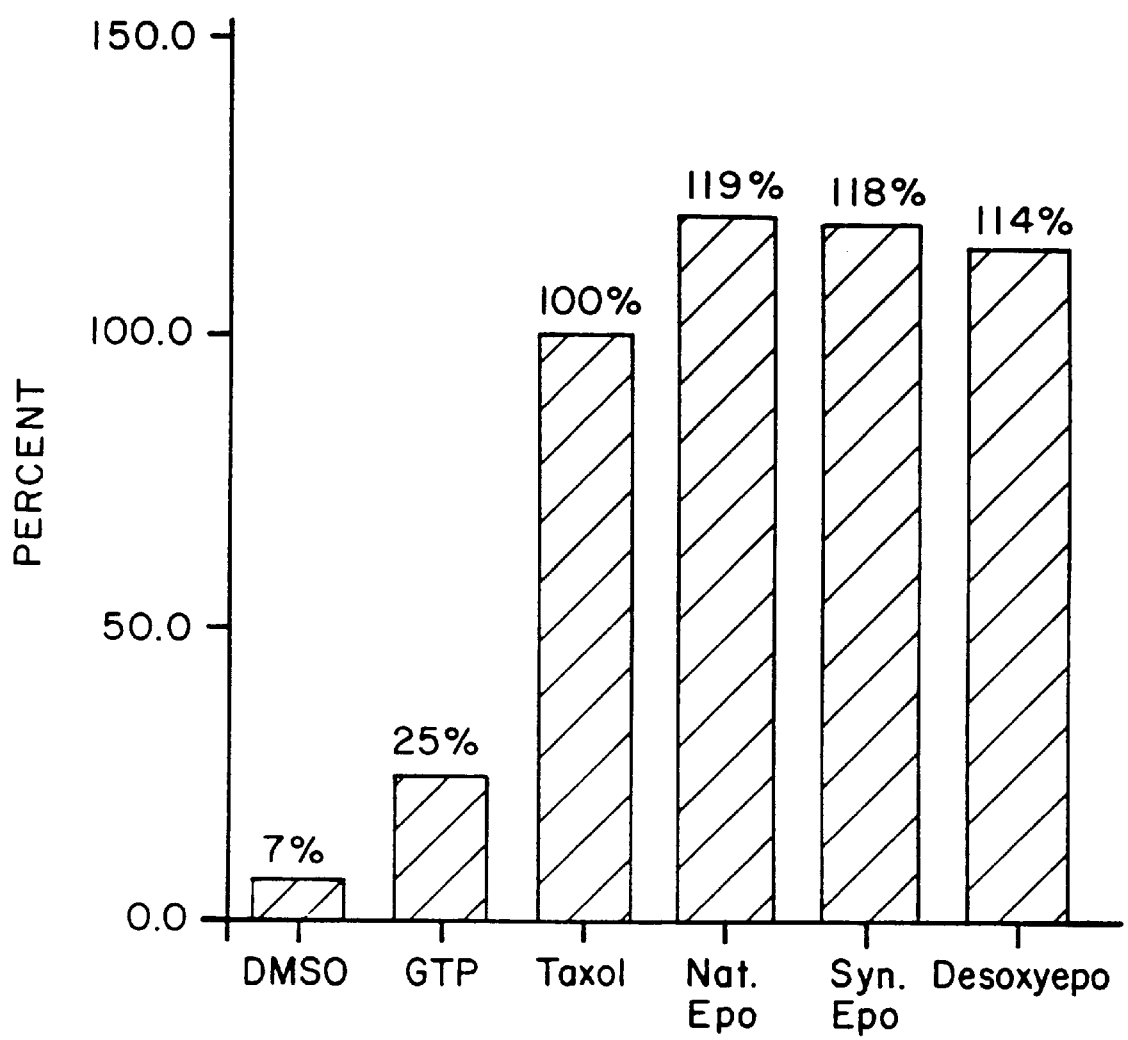
FIG. 11 illustrates a sedimentation test for natural, synthetic and desoxyepothilone A after cold treatment at 4° C.

The matter was first examined with two model ω-unsaturated acids 16B and 17B which were used to acylate alcohol 2B to provide esters 18B and 19B, respectively (see FIG. 9). These compounds did indeed undergo olefin metathesis macrocyclization in the desired manner under the conditions shown. In the case of substrate 18B, compound set 20B was obtained as a mixture of E- and Z-stereoisomers [ca. 1:1]. Diimide reduction of 20B was then conducted to provide homogeneous 22B. The olefin metathesis reaction was also extended to compound 19B bearing geminal methyl groups corresponding to their placement at C4 of epothilone A. Olefin metathesis occurred, this time curiously producing olefin 21B as a single entity in 70% yield (stereochemisty tentatively assigned as Z.) Substantially identical results were obtained through the use of Schrock's molybdenum alkylidene metathesis catalyst.

As described above, olefin metathesis is therefore amenable to the challenge of constructing the sixteen membered ring containing both the required epoxy and thiazolyl functions of the target system. It is pointed out that no successful olefin metathesis reaction has yet been realized from seco-systems bearing a full compliment of functionality required to reach epothilone. These negative outcomes may merely reflect a failure to identify a suitable functional group constraint pattern appropriate for macrocylization.

The Total Synthesis of Epothilone B: Extension of the Suzuki Coupling Method

The present invention provides the first total synthesis of epothilone A (1). D. Meng, et al., *J. Org. Chem*, 1996, 61, 7998 P. Bertinato, et al., *J. Org. Chem*, 1996, 61, 8000. A. Balog, et al., *Angew. Chem. Int. Ed. Engl.*, 1996, 35, 2801. D. Meng, et al., *J. Amer. Chem. Soc.*, 1997, 119, 10073. (For a subsequent total synthesis of epothilone A, see: Z. Yang, et al., *Angew. Chem. Int. Ed. Engl.*, 1997, 36, 166.) This synthesis proceeds through the Z-desoxy compound (23) which underwent highly stereoselective epoxidation with 2,2-dimethyldioxirane under carefully defined conditions to yield the desired β-epoxide. The same myxobacterium of the genus Sorangium which produces 23 also produces epothilone B (2). The latter is a more potent agent than 23, both in antifungal screens and in cytotoxicity/cell nucleus disintegration assays. G. Höfle, et al., *Angew. Chem. Int. Ed. Engl.* 1996, 35, 1567; D. M. Bollag, et al., *Cancer Res.* 1995, 55, 2325.

An initial goal structure was desoxyepothilone B (2C) or a suitable derivative thereof. Access to such a compound would enable the study of the regio- and stereoselectivity issues associated with epoxidation of the C12-C13 double bond. A key issue was the matter of synthesizing Z-trisubstituted olefinic precursors of 2C with high margins of stereoselection. A synthetic route to the disubstituted system (A. Balog, et al., *Agnew. Chem. Int. Ed. Engl.*, 1996, 35, 2801) employed a palladium-mediated B-alkyl Suzuki coupling (N. Miyaura, et al., *J. Am. Chem. Soc.* 1989, 111, 314. (For a review, see: N. Miyaura, A. Suzuki, *Chem. Rev.* 1995, 95, 2457) of the Z-vinyl iodide 19 (FIG. 4(A)) with borane 7C derived from hydroboration of compound 11 (FIG. 1(A)) with 9-BBN (FIG. 4(B)).)

A preliminary approach was to apply the same line of thinking to reach a Z-tri-substituted olefin (FIG. 17) en route to 2C. Two issues had to be addressed. First, it would be necessary to devise a method to prepare vinyl iodide 8C, the tri-substituted analog of 19. If this goal could be accomplished, a question remained as to the feasibility of conducting the required B-alkyl Suzuki coupling reaction to reach a Z-tri-substituted olefin. The realization of such a transformation with a "B-alkyl" (as opposed to a "B-alkenyl" system) at the intermolecular level, and where the vinyl iodide is not of the β-iodoenoate (or β-iodoenone) genre, was not precedented. (For some close analogies which differ in important details from the work shown here, see: N. Miyaura, et al., *Bull. Chem. Soc. Jpn.* 1982, 55, 2221; M. Ohba, et al., *Tetrahedron Lett.*, 1995, 36, 6101; C. R. Johnson, M. P. Braun, *J. Am. Chem. Soc.* 1993, 115, 11014.)

Figure 16:
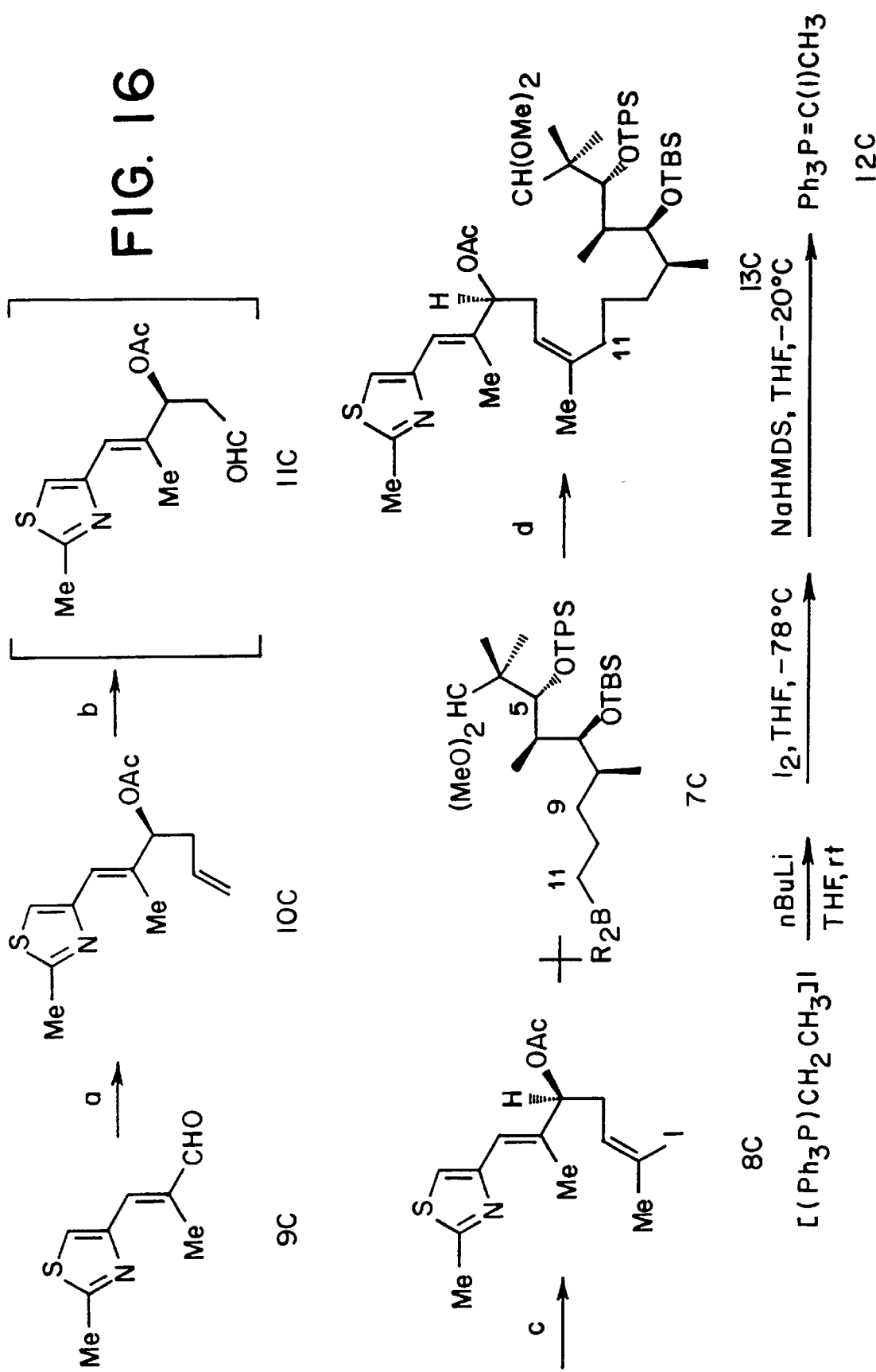
FIG. 16 provides a synthetic pathway to intermediate 13C. (a) 1. tributyl allyltin, (S)-(−)-BINOL, $Ti(Oi-Pr)_4$, $CH_2Cl_2$, −20° C., 60%, >95% e.e.; 2. $Ac_2O$, $Et_3N$, DMAP, $CH_2Cl_2$, 95%; (b) 1. $OsO_4$, NMO, acetone/$H_2O$, 0° C.; 2. $NaIO_4$, THF/$H_2O$; (c) 12, THF, −20° C., Z isomer only, 25% from 10; (d) $Pd(dppf)_2$, $Cs_2CO_3$, $Ph_3As$, $H_2O$, DMF, rt. 77%.

The synthesis of compound 8C is presented in FIG. 16. The route started with olefin 10C which was prepared by catalytic asymmetric allylation of 9C (G. E. Keck, et al., *J. Am. Chem. Soc.*, 1993, 115, 8467) followed by acetylation. Site-selective dihydroxylation of 10C followed by cleavage of the glycol generated the unstable aldehyde 11C. Surprisingly, the latter reacted with phosphorane 12C (J. Chen, et al., *Tetrahedron Lett.*, 1994, 35, 2827) to afford the Z-iodide 8C albeit in modest overall yield. Borane 7C was generated from 11 as described herein. The coupling of compound 7C and iodide 8C (FIG. 16) could be conducted to produce the pure Z-olefin 13C.

Figure 17:
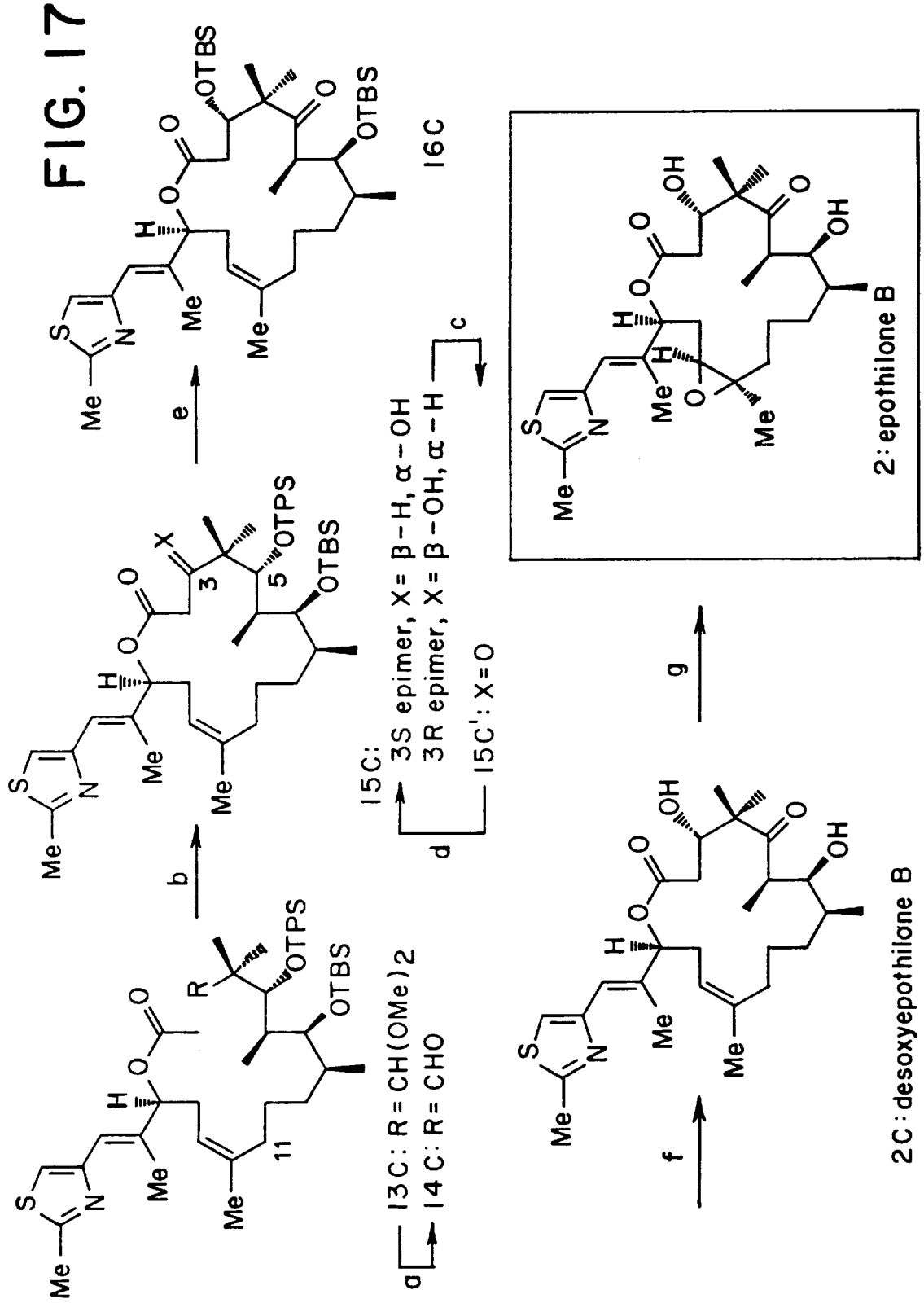
FIG. 17 provides a synthetic pathway to intermediate epothilone B (2). (a) p-TsOH, dioxane/$H_2O$, 55° C., 71%; (b) KHMDS, THF, −78° C., 67%, α/β: 1.5:1; (c) Dess-Martin periodinane, $CH_2Cl_2$; (d) $NaBH_4$, MeOH, 67% for two steps; (e) 1. HF-pyridine, pyridine, THF, rt, 93%; 2. TBSOTf, 2,6-lutidine, $CH_2Cl_2$, −30° C., 89%; 3. Dess-Martin periodinane, $CH_2Cl_2$, 67%; (f) HF-pyridine, THF, rt, 80%; (g) dimethyldioxirane, $CH_2Cl_2$, −50° C., 70%.
Figure 18A:
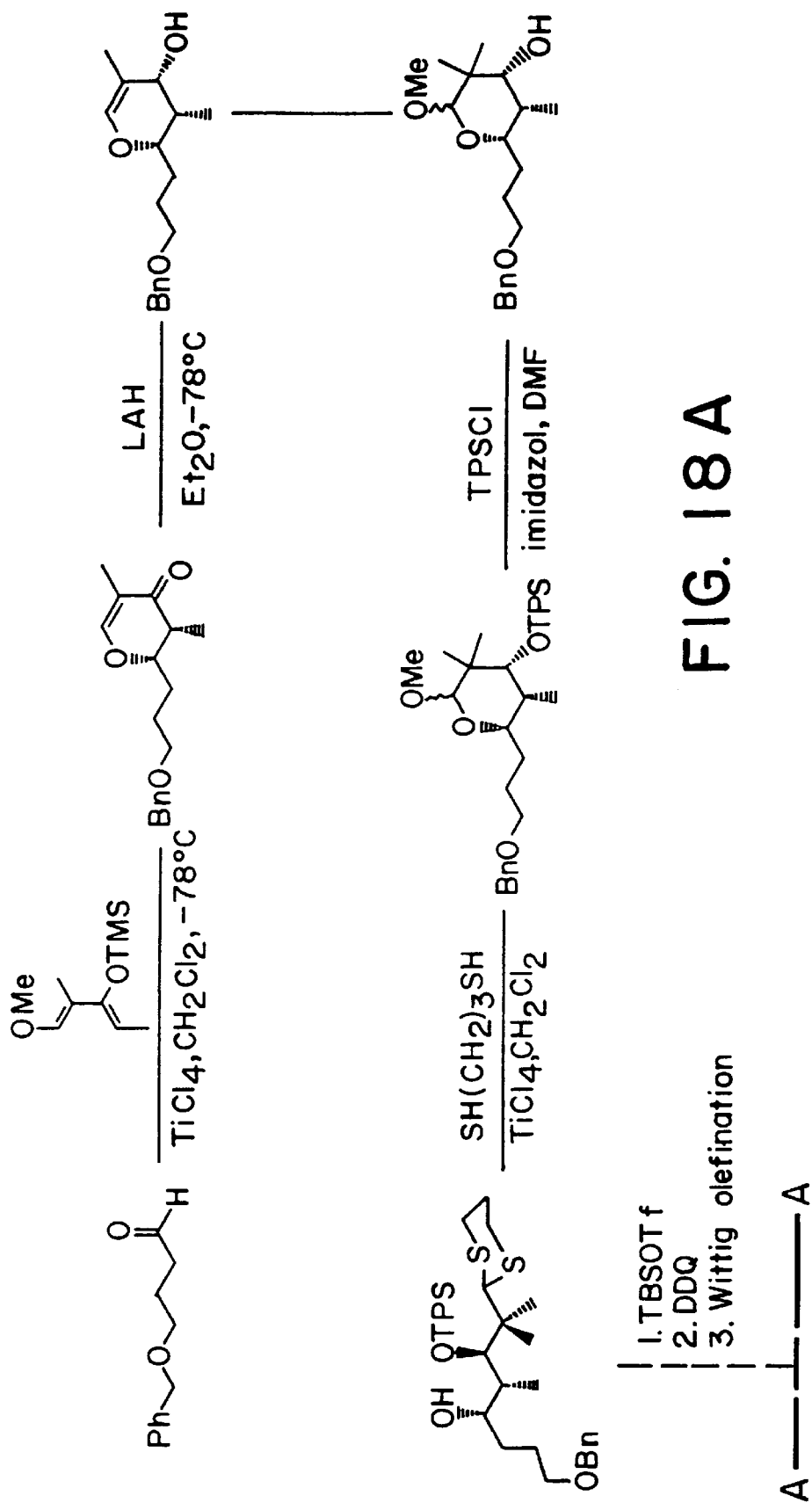
FIGS. 18(A) and 18(B) provide a synthetic pathway to a protected intermediate for 8-desmethyl deoxyepothilone A.
Figure 18B:
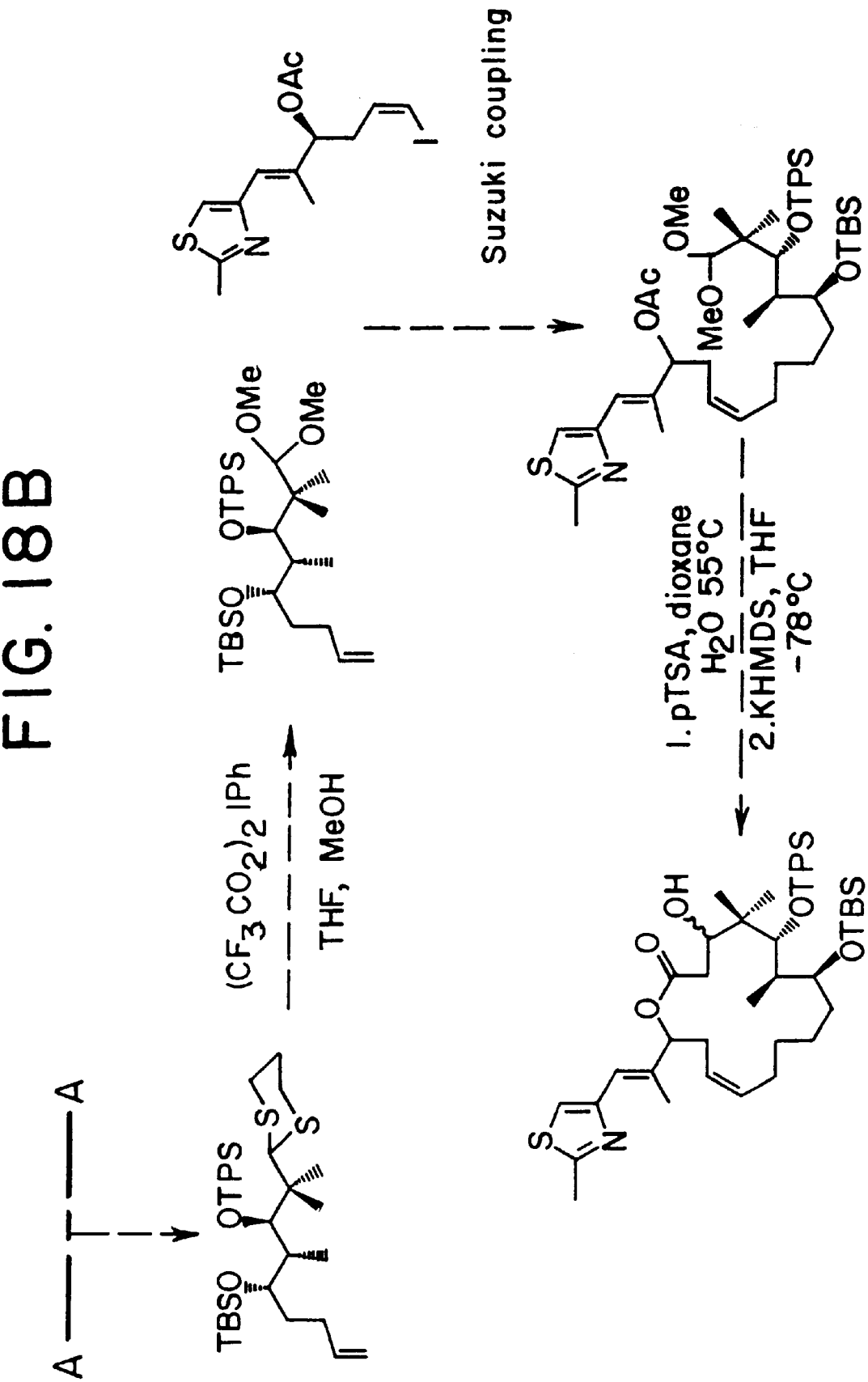
Figures 19A, 19B:
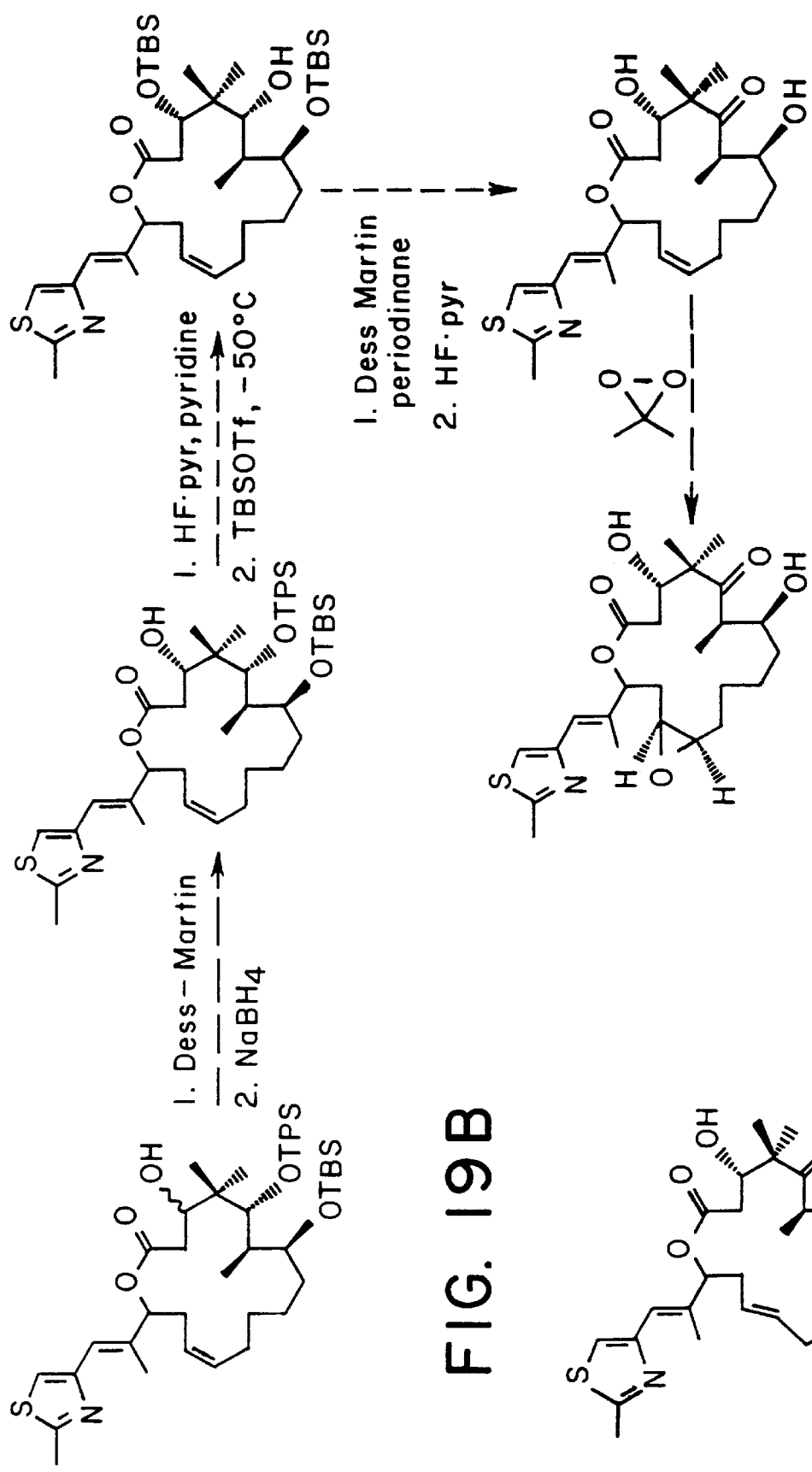

With compound 13C in hand, protocols similar to those employed in connection with the synthesis of 23 could be used. (A. Balog, et al., *Angew. Chem. Int. Ed. Engl.*, 1996, 35, 2801). Thus, cleavage of the acetal linkage led to aldehyde 14C which was now subjected to macroaldolization (FIG. 17). The highest yields were obtained by carrying out the reaction under conditions which apparently equilibrate the C3 hydroxyl group. The 3R isomer was converted to the required 3S epimer via reduction of its derived C3-ketone (see compound 15C). The kinetically controlled aldol condensation leading to the natural 3S configuration as discribed in the epothilone A series was accomplished. However, the overall yield for reaching the 3S epimer is better using this protocol. Cleavage of the C-5 triphenyisilyl ether was followed sequentially by monoprotection (t-butyldimethylsilyl) of the C3 hydroxyl, oxidation at C5 (see compound 16C), and, finally, cleavage of the silyl protecting groups to expose the C3 and C7 alcohols (see compound 2C).

It was found that Z-desoxyepothilone B (2C) undergoes very rapid and substantially regio- and stereoselective epoxidation under the conditions indicated (although precise comparisons are not available, the epoxidation of 2C appears to be more rapid and regioselective than is the case with 23) (A. Balog, et al., *Angew. Chem. Int. Ed. Engl.*, 1996, 35, 2801), to afford epothilone B (2) identical with an authentic sample ($^1$H NMR, mass spec, IR, $[\alpha]_D$). Accordingly, the present invention dislcoses the first total synthesis of epothilone B. Important preparative features of the present method include the enantioselective synthesis of the trisubstituted vinyl iodide 8C, the palladium-mediated stereospecific coupling of compounds 7C and 8C to produce compound 13C (a virtually unprecedented reaction in this form), and the amenability of Z-desoxyepothilone B (2C) to undergo regio- and stereoselective epoxidation under appropriate conditions.

Desmethylepothilone A

Total syntheses of epothilones A and B have not been previously disclosed. Balog, A., et al., *Angew. Chem., Int. Ed. Engl.* 1996, 35, 2801; Nicolaou, K. C., et al., *Angew. Chem., Int. Ed. Engl.* 1997, 36, 166. Nicolaou, K. C., et al., *Angew. Chem., Int. Ed. Engl.* 1997, 36, 525; Schinzer, D., et al., *Angew. Chem., Int. Ed. Engl.* 1997, 36, 523. Su, D. -S., et al., *Angew. Chem. Int. Ed. Engl.* 1997, 36, 757. The mode of antitumor action of the epothilones closely mimics that of Taxol® (paclitaxel). Höfle, G., et al., H. *Angew. Chem., Int. Ed. Engl.* 1996, 35, 1567. Although Taxol® is a clinically proven drug, its formulation continues to be difficult. In addition, Taxol® induces the multidrug resistance (MDR) phenotype. Hence, any novel agent that has the same mechanism of action as Taxol® and has the prospect of having superior therapeutic activity warrants serious study. Bollag, D. M., et al., *Cancer Res.* 1995, 55, 2325.

The present invention provides epothilone analogs that are more effective and more readily synthesized than epothilone A or B. The syntheses of the natural products provide ample material for preliminary biological evaluation, but not for producing adequate amounts for full development. One particular area where a structural change could bring significant relief from the complexities of the synthesis would be in the deletion of the C8 methyl group from the polypropionate domain (see target system 3D). The need to deal with this C8 chiral center complicates all of the syntheses of epothilone disclosed thus far. Deletion of the C8 methyl group prompts a major change in synthetic strategy related to an earlier diene-aldehyde cyclocondensation route. Danishefsky, S. J. *Chemtracts* 1989, 2, 273; Meng, D., et al., *J. Org. Chem.* 1996, 61, 7998; Bertinato, P., et al., *J. Org. Chem.* 1996, 61, 8000.

As shown in FIG. 20, asymmetric crotylation (87% ee) of 4D (Brown, H. C.; Bhat, K. S. *J. Am. Chem. Soc.* 1986, 108, 5919), followed by protection led to TBS ether 5D. The double bond was readily cleaved to give aldehyde 6D. The aldehyde was coupled to the dianion derived from t-butyl isobutyrylacetate to provide 7D. The ratio of the $C_{5S}$ (7D): $C_{5R}$ compound (not shown) is ca 10:1. That the Weiler-type β-ketoester dianion chemistry (Weiler, L. *J. Am. Chem. Soc.* 1970, 92, 6702.; Weiler, L.; Huckin, S. N. *J. Am. Chem. Soc.* 1974, 96, 1082) can be conducted in the context of the isobutyryl group suggested several alternate approaches for still more concise syntheses. Directed reduction of the $C_3$ ketone of 7D following literature precedents (Evans, D. A., et al., *J. Org. Chem.* 1991, 56, 741), followed by selective silylation of the $C_3$ hydroxyl gave a 50% yield of a 10:1 ratio of the required $C_{3S}$ (see compound 8D) to $C_{3R}$ isomer (not shown). Reduction with sodium borohydride afforded a ca. 1:1 mixture of $C_3$ epimers. The carbinol, produced upon debenzylation, was oxidized to an aldehyde which, following methylenation through a simple Wittig reaction, afforded olefin 9D. Treatment of this compound with TBSOTf provided ester 10D which was used directly in the Suzuki coupling with the vinyl iodide 12D.

Figure 21:
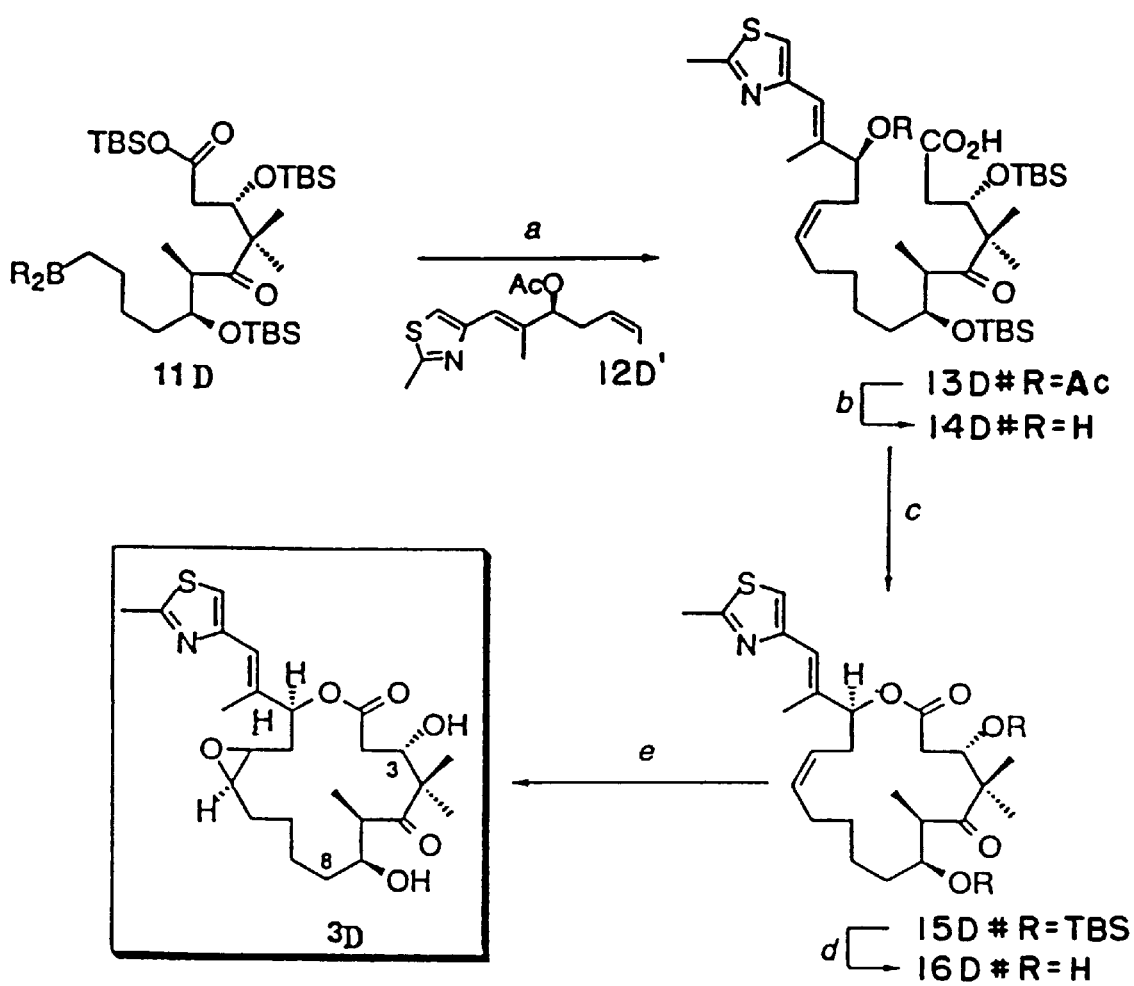
FIG. 21 shows a synthetic pathway to 8-desmethylepothilone A. (a) $Pd(dppf)_2Cl_2$, $Ph_3As$, $Cs_2CO_3$, $H_2O$, DMF, rt (62%); (b) $K_2CO_3$, MeOH, $H_2O$ (78%); (c) DCC, 4-DMAP, 4-DMAP.HCl, $CHCl_3$ (78%); (d) HF.pyr, THF, rt (82%), (e) 3,3-dimethyl dioxirane, $CH_2Cl_2$, −35° C. (72%, 1.5:1).
Figure 22C:
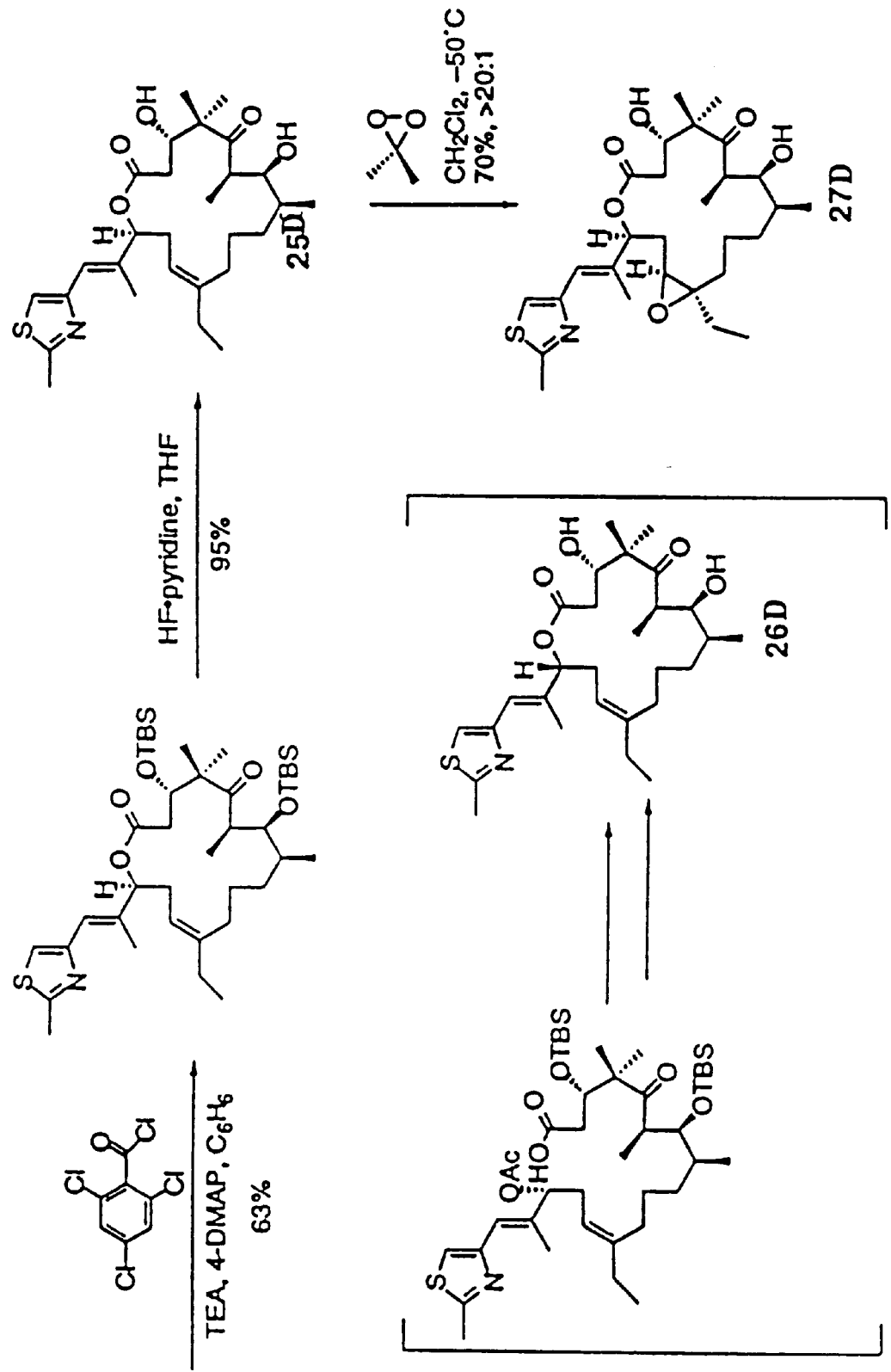
Figure 23A:
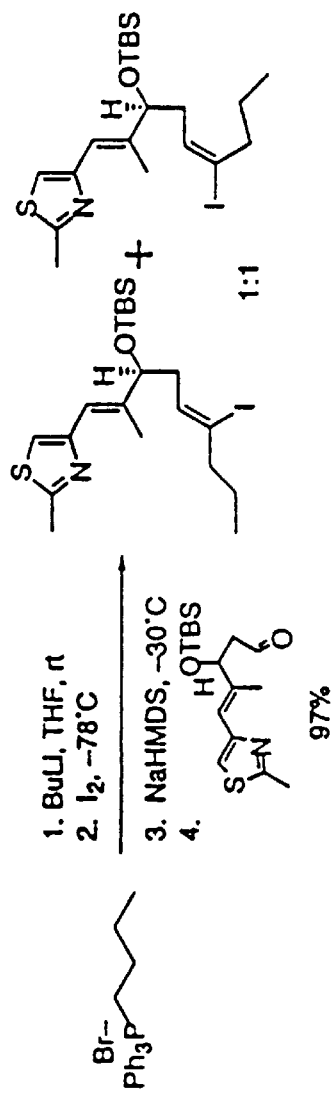
FIGS. 23(A), 23(B) and 23(C) show a synthetic pathway to prepare epothilone analogue 24D.
Figure 23B:
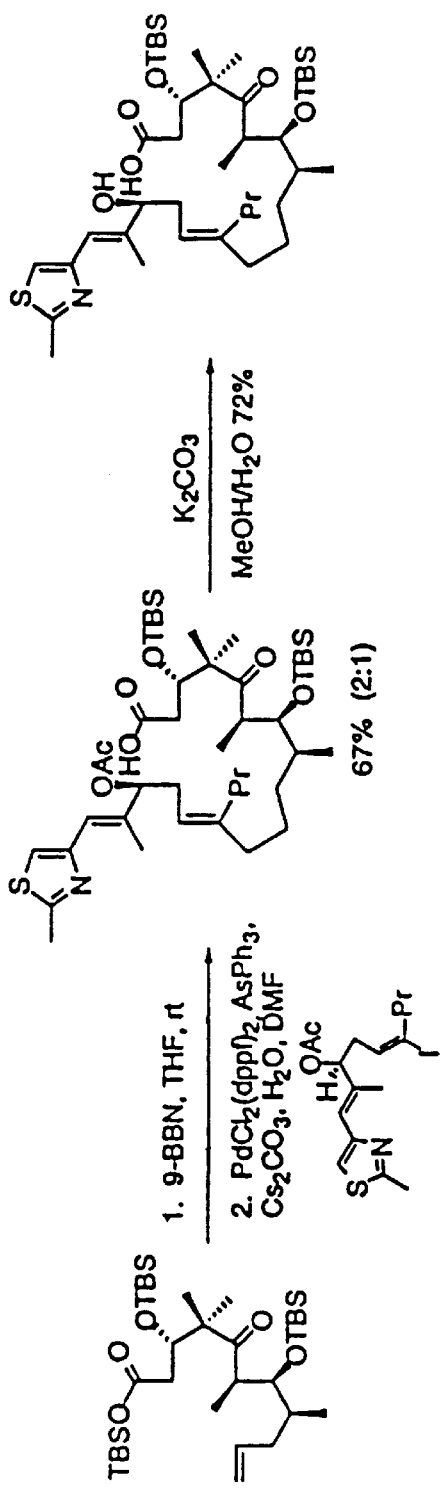
Figure 23C:
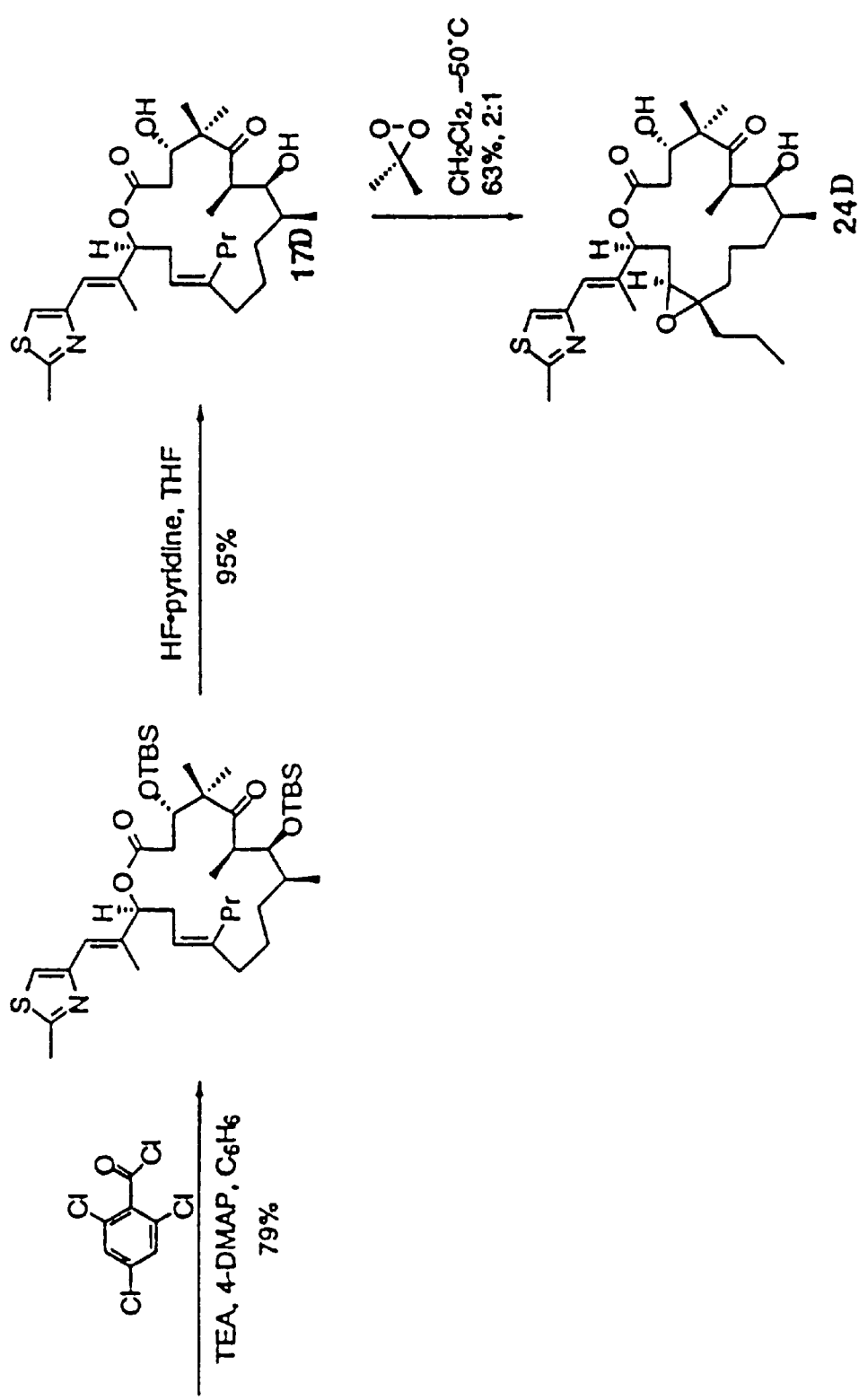
Figure 25A:
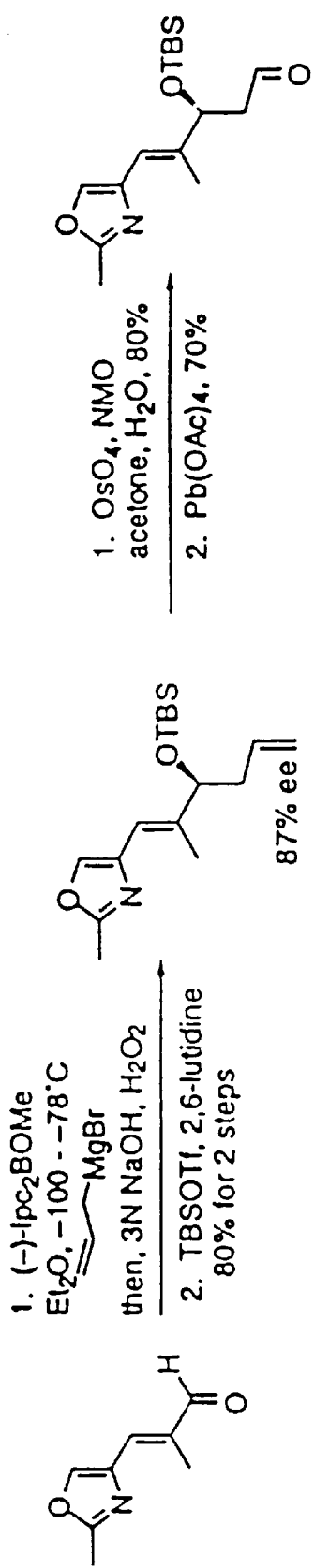
FIGS. 25(A), 25(B), 25(C) and 25(D) show a synthetic pathway to prepare epothilone analogue 20D.
Figure 25B:
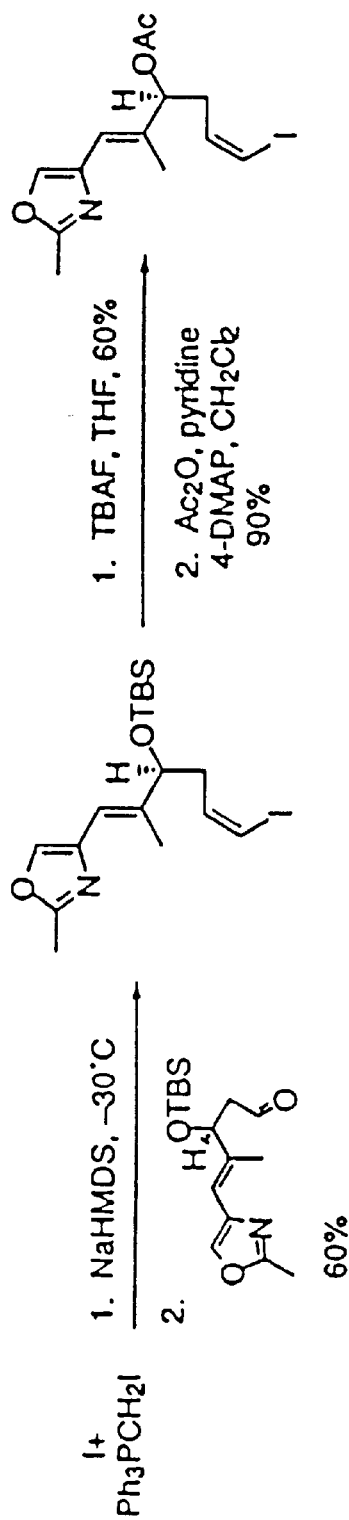
Figure 25C:
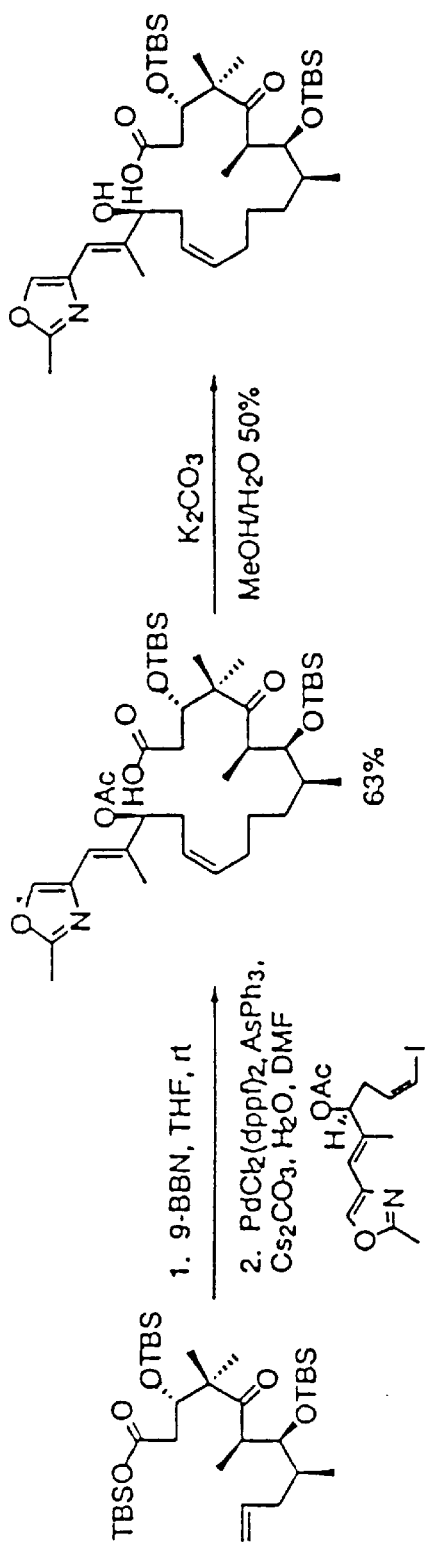
Figure 25D:
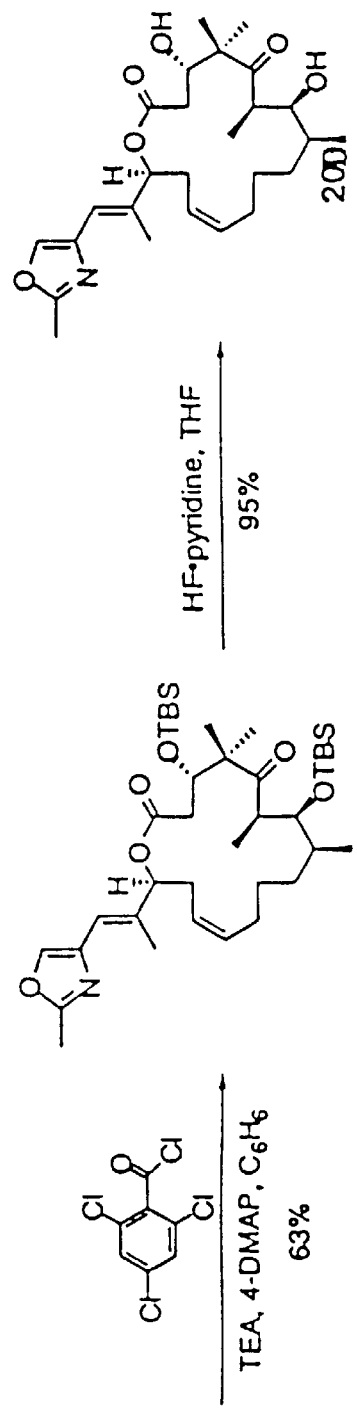
Figure 26A:
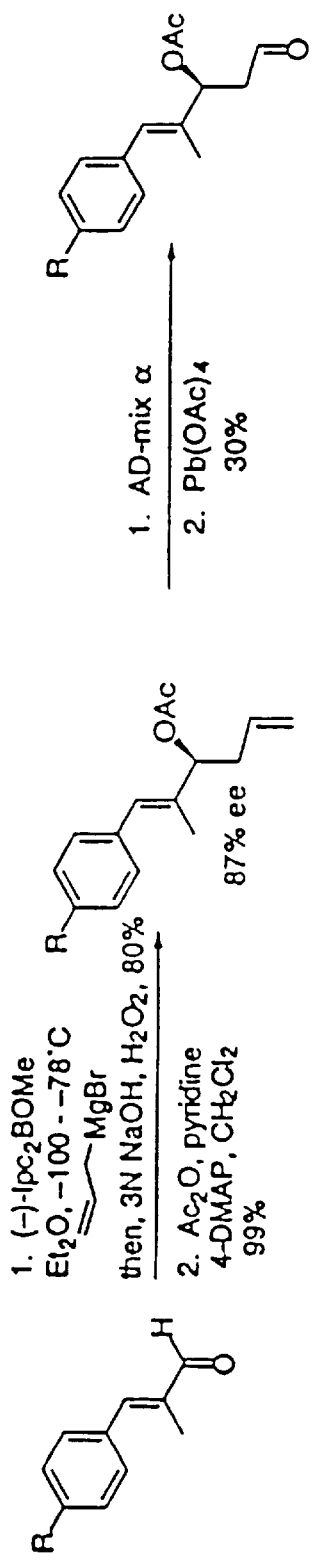
FIGS. 26(A), 26(B), 26(C) and 26(D) show a synthetic pathway to prepare epothilone analogue 22D.
Figure 26B:
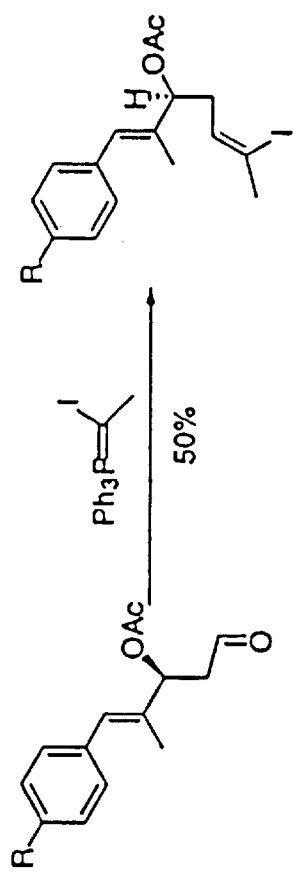
Figure 26C:
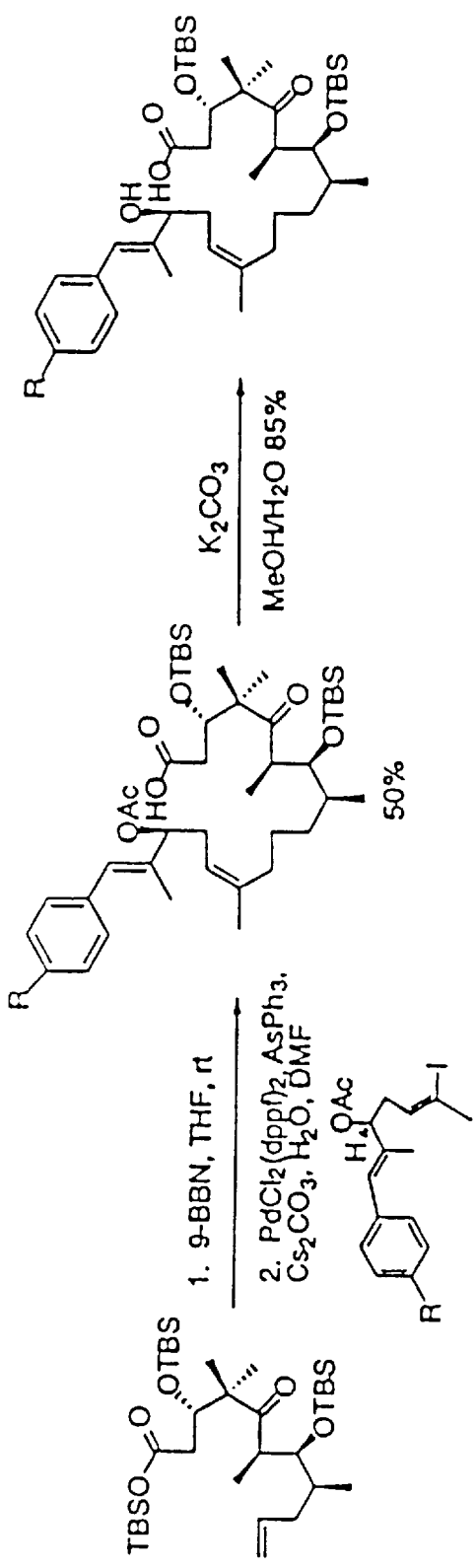
Figure 26D:
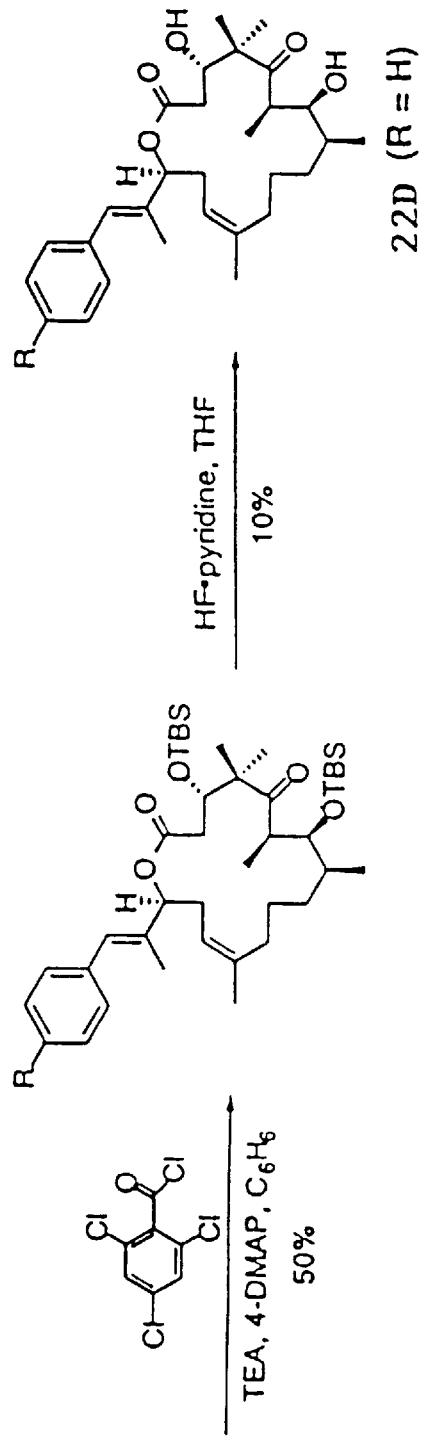
Figure 27C:
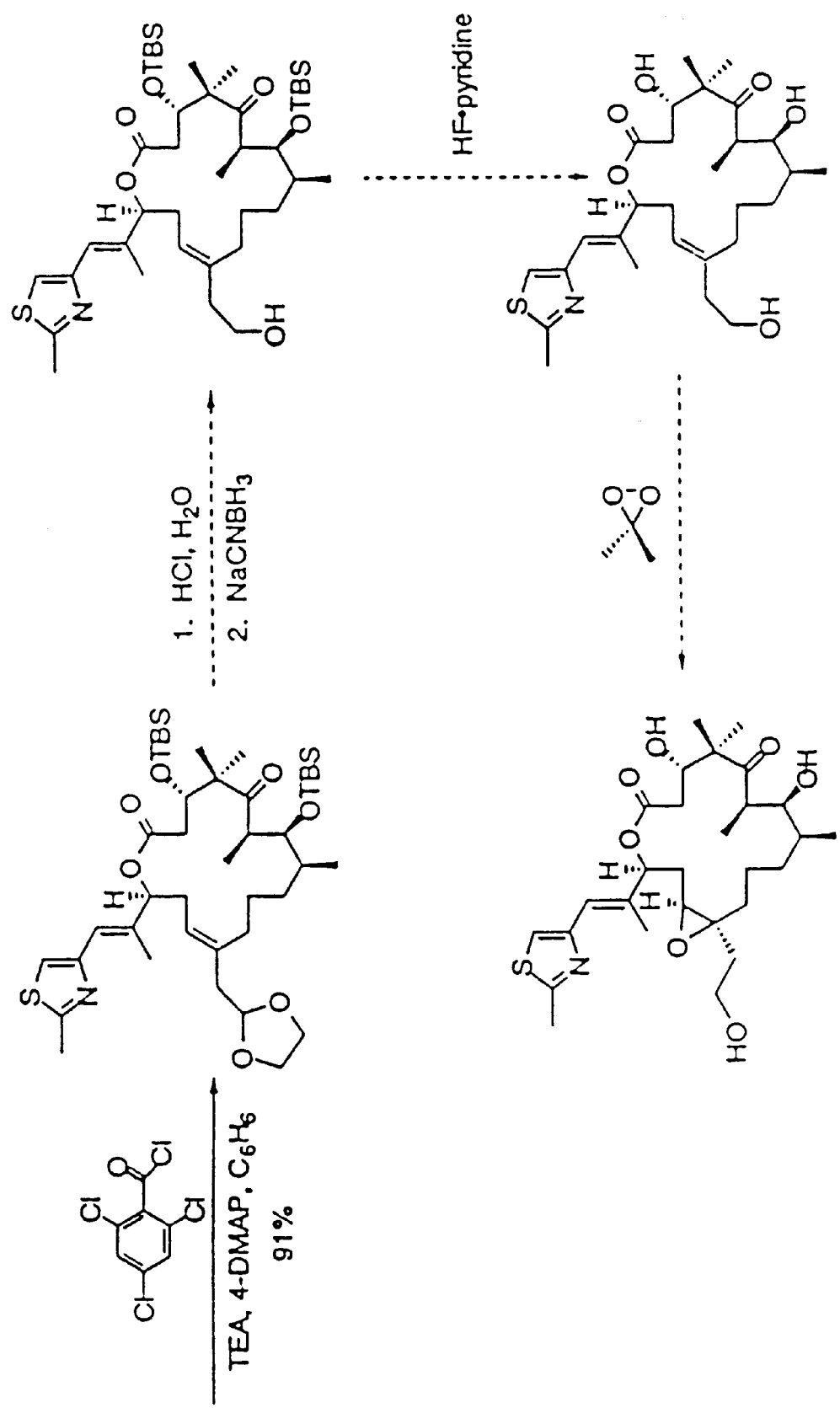
Figure 28A:
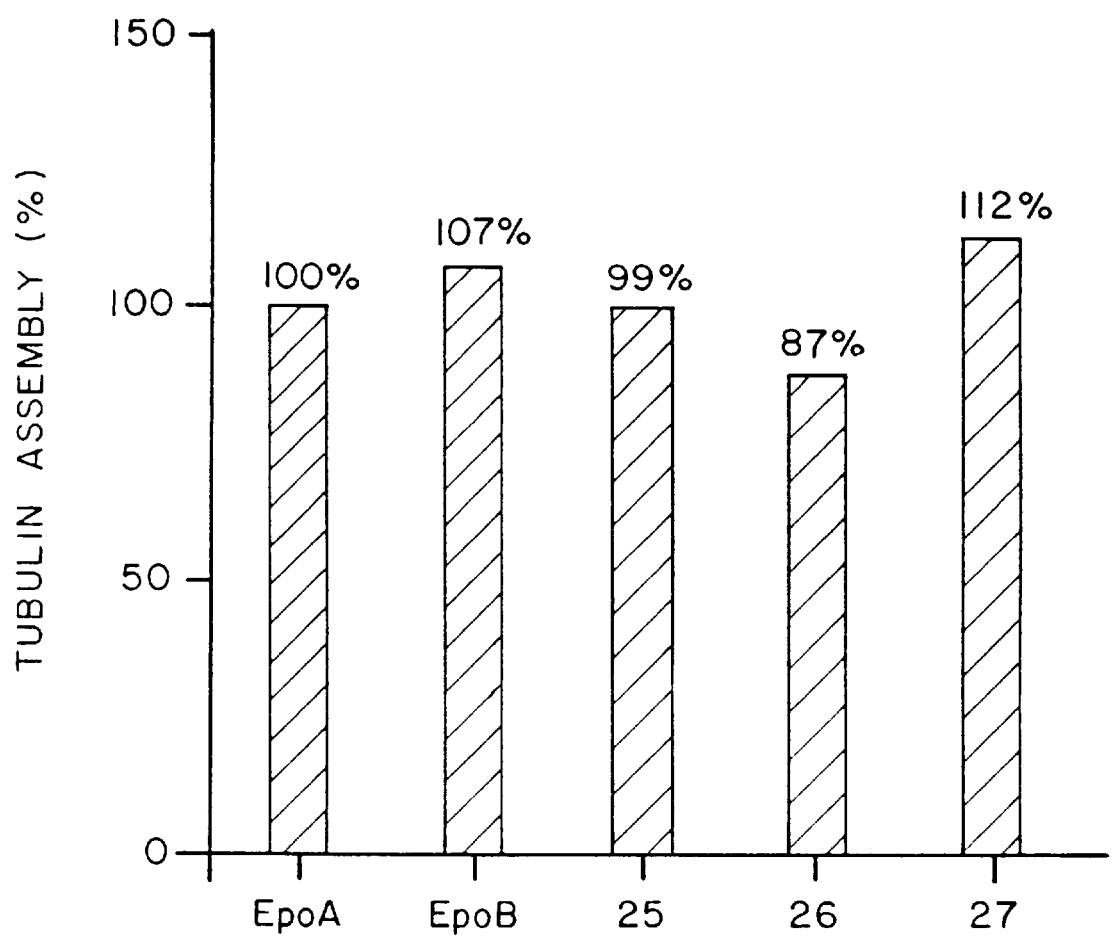
FIGS. 28(A) and 28(B) show the activity of epothilone analogues in a sedimentation test in comparison with DMSO, epothilone A and/or B. Structures 17–20, 22, and 24–27 are shown in FIGS. 29–37, respectively. Compounds were added to tubulin (1 mg/ml) to a concentration of 10 μM. The quantity of microtubules formed with epothilone A was defined as 100%.
Figure 28B:
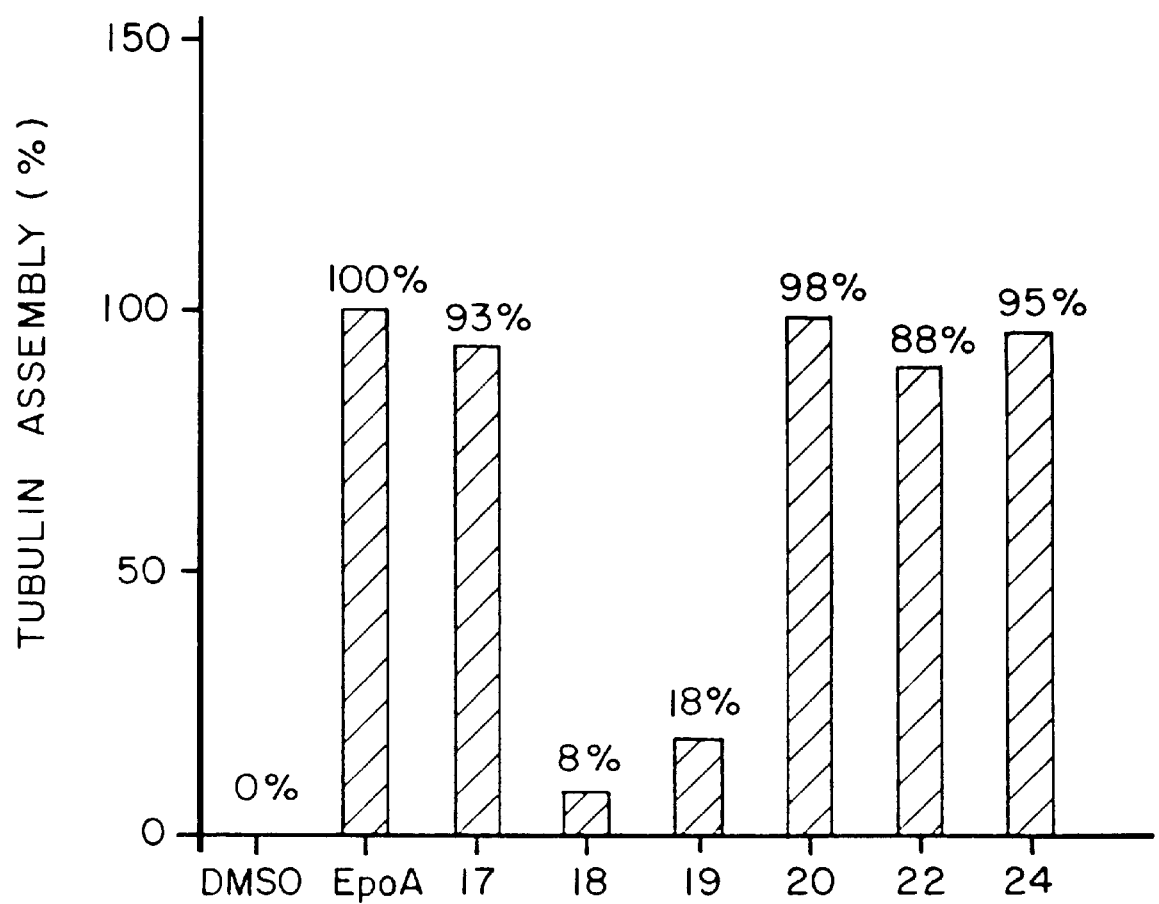
Figure 29:
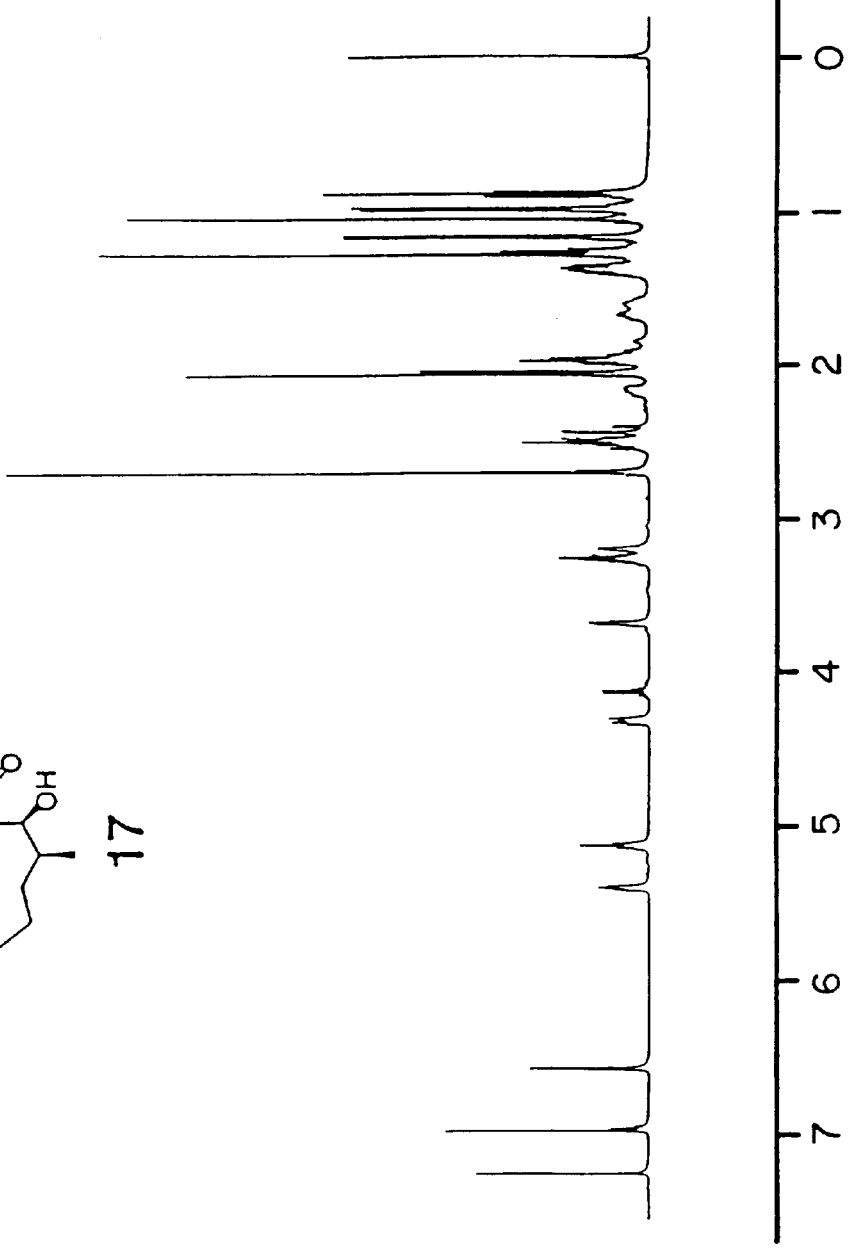
FIG. 29 shows a high resolution $^1H$ NMR spectrum of epothilone analogue #17.
Figure 30:
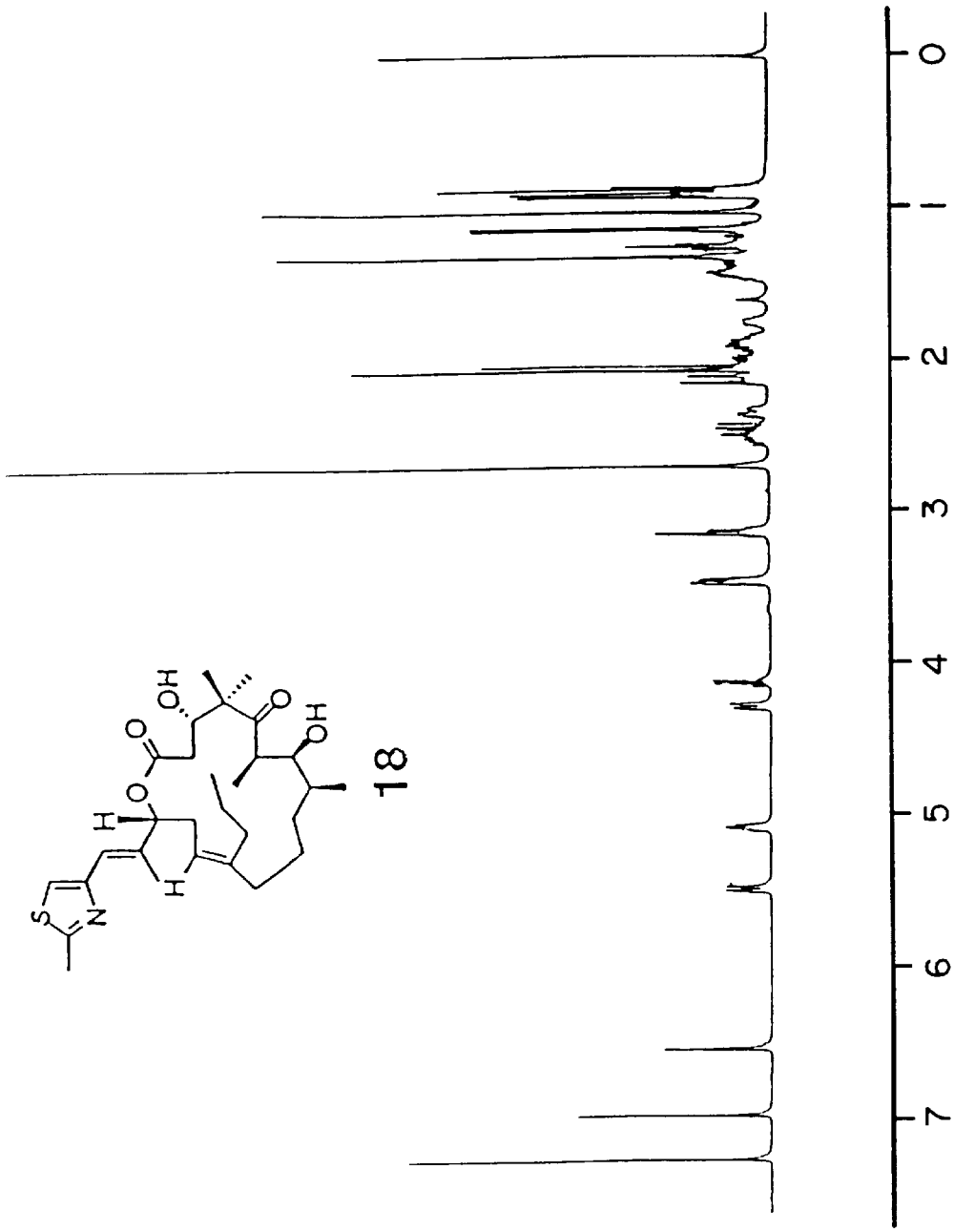
FIG. 30 shows a high resolution $^1H$ NMR spectrum of epothilone analogue #18.
Figure 31:
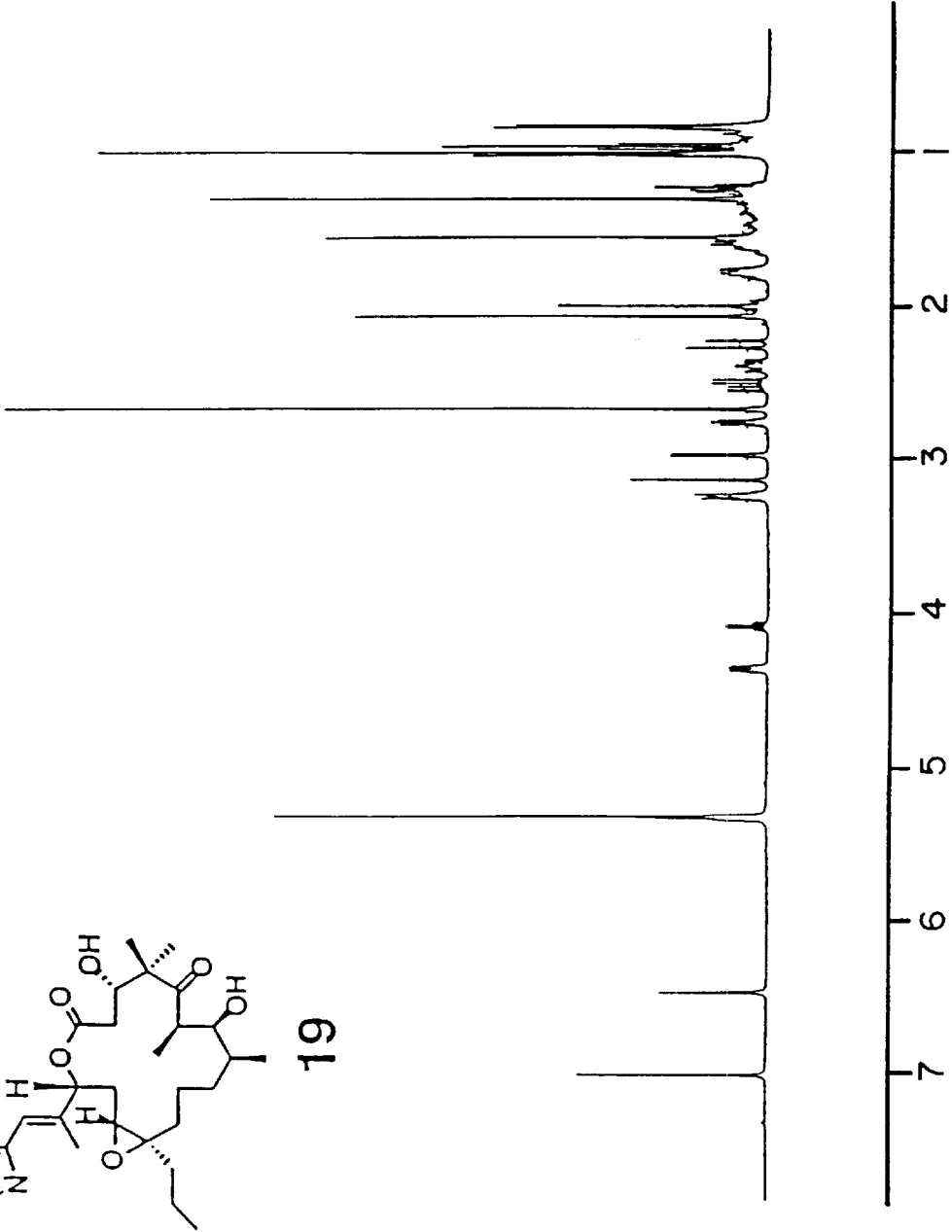
FIG. 31 shows a high resolution $^1H$ NMR spectrum of epothilone analogue #19.
Figure 32:
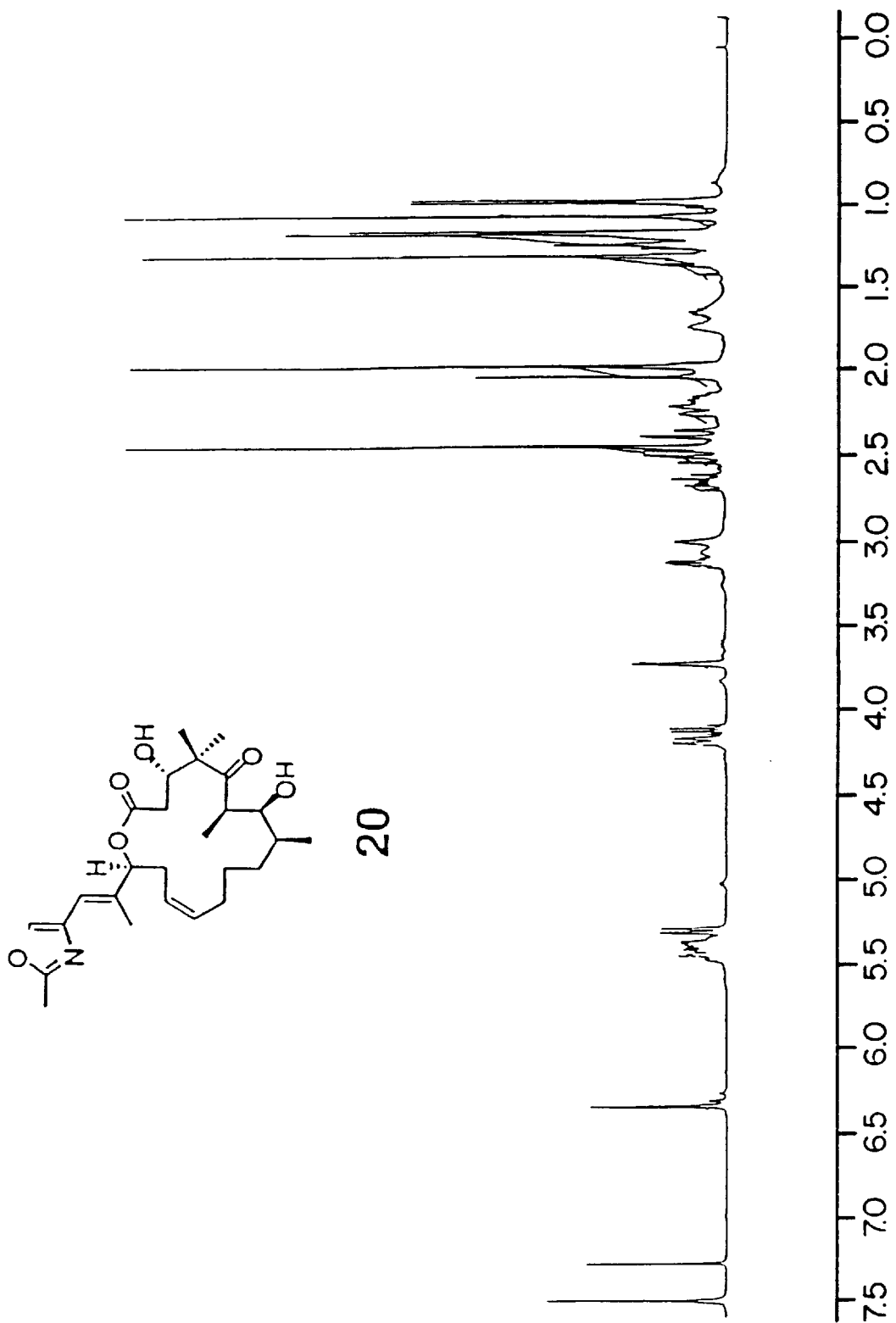
FIG. 32 shows a high resolution $^1H$ NMR spectrum of epothilone analogue #20.
Figure 33:
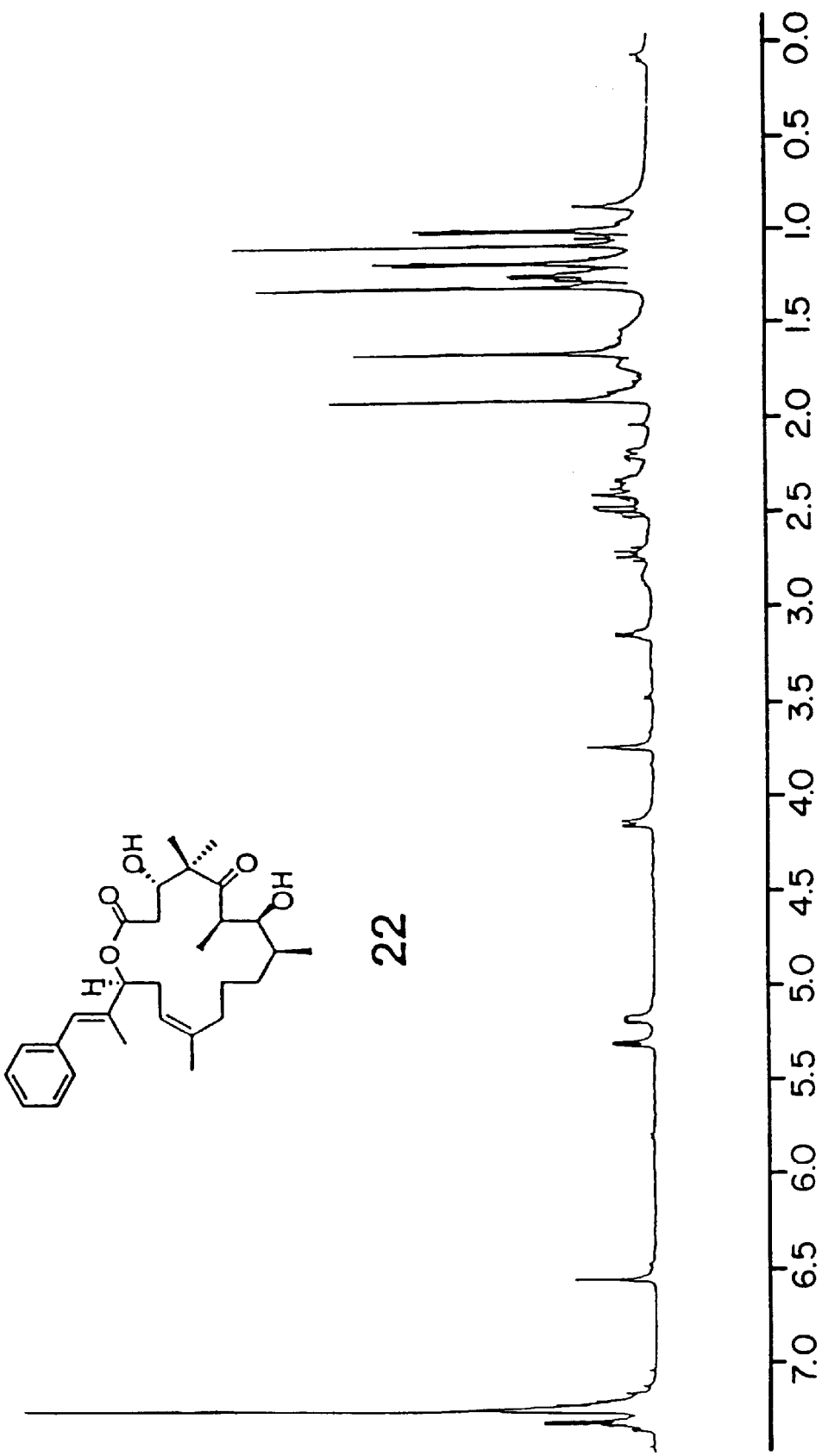
FIG. 33 shows a high resolution $^1H$ NMR spectrum of epothilone analogue #22.
Figure 34:
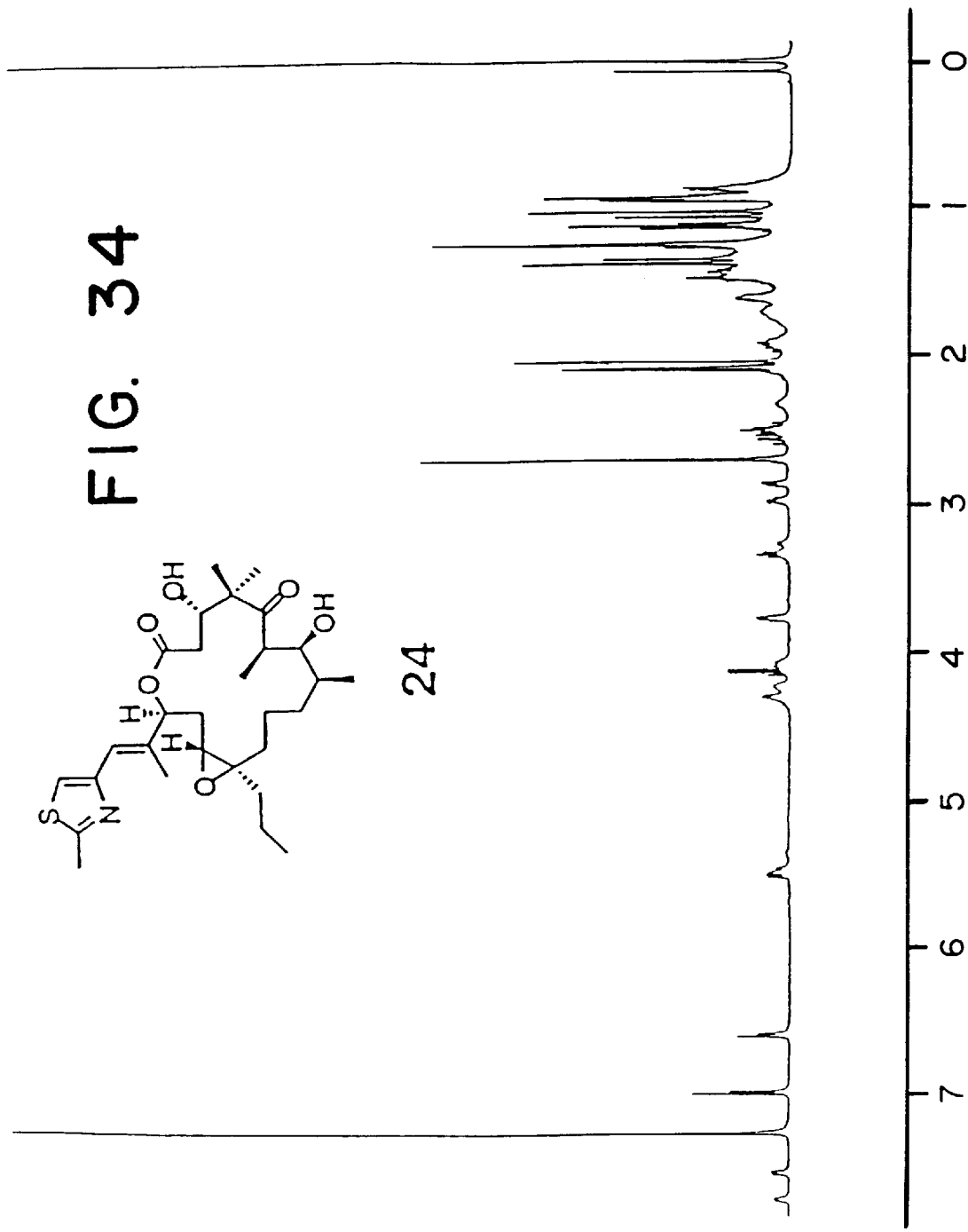
FIG. 34 shows a high resolution $^1H$ NMR spectrum of epothilone analogue #24.
Figure 35:
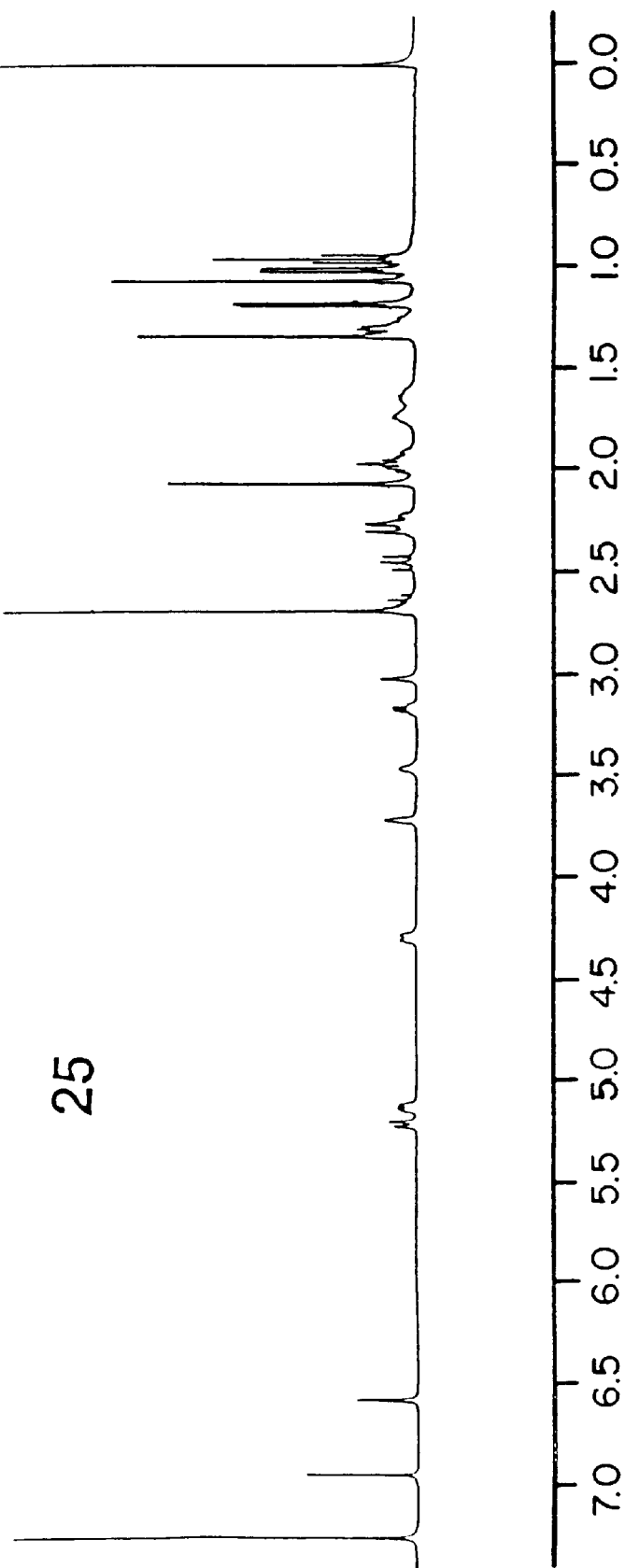
FIG. 35 shows a high resolution $^1H$ NMR spectrum of epothilone analogue #25.
Figure 36:
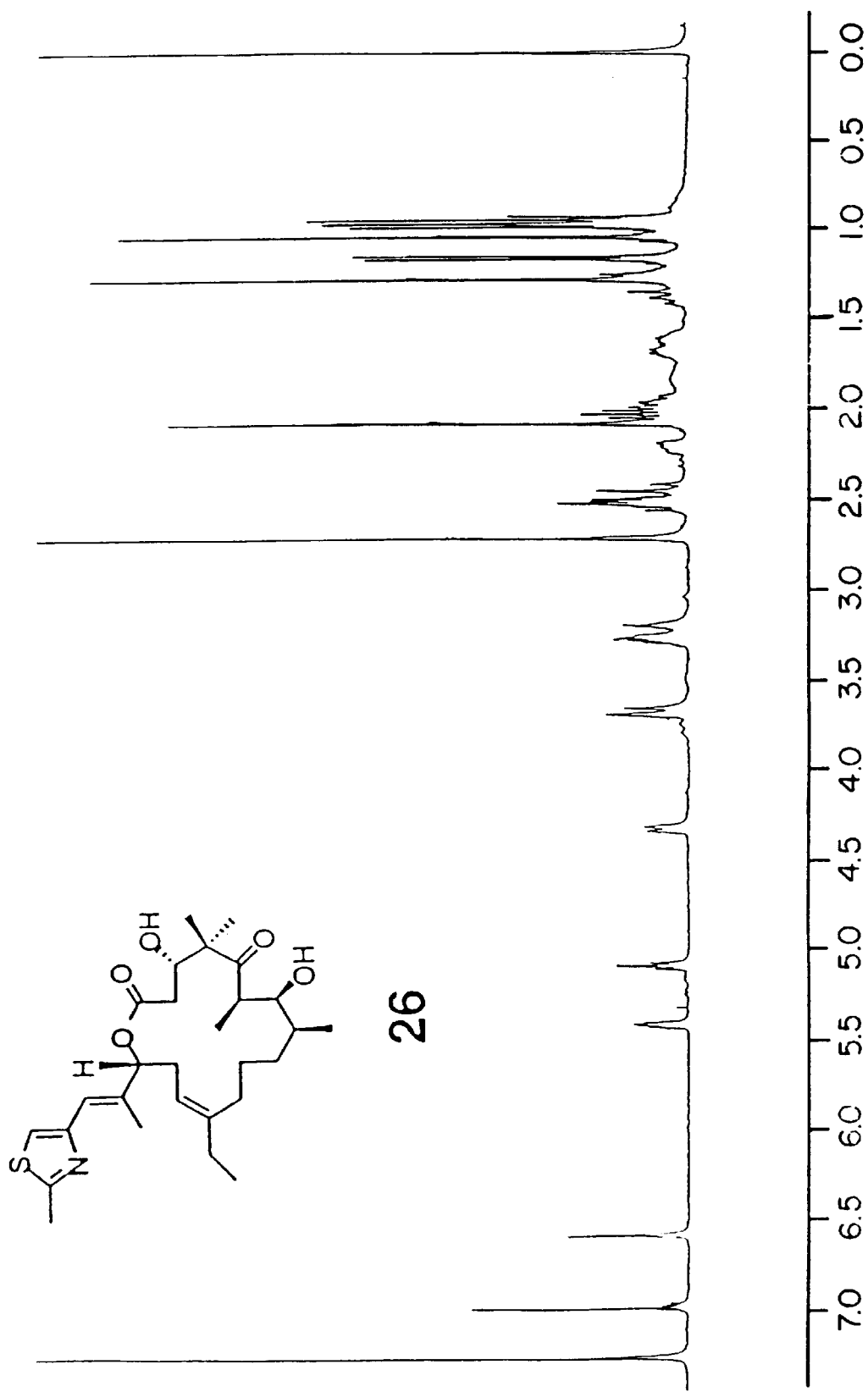
FIG. 36 shows a high resolution $^1H$ NMR spectrum of epothilone analogue #26.
Figure 37:
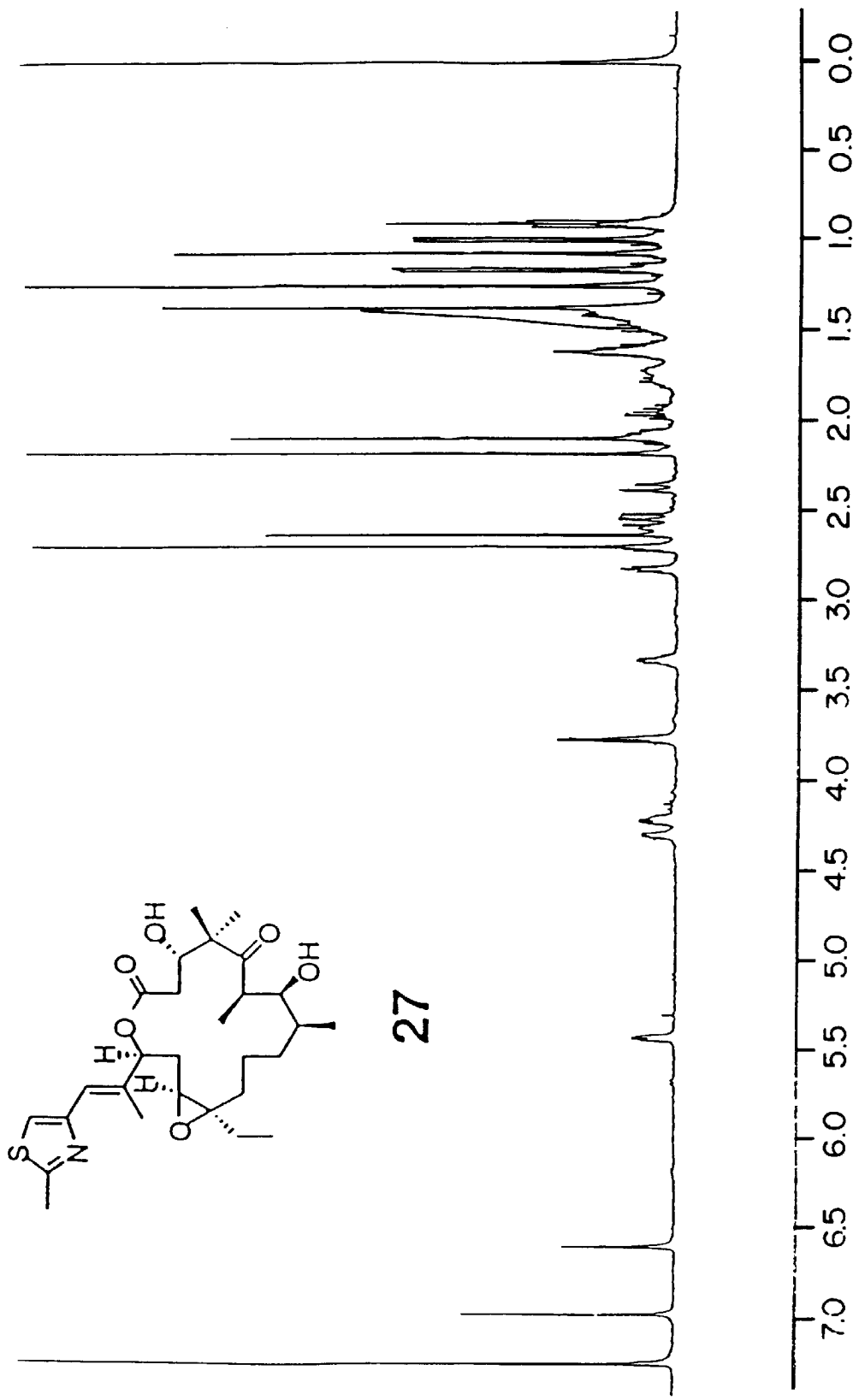
FIG. 37 shows a high resolution $^1H$ NMR spectrum of epothilone analogue #27.
Figure 39A:
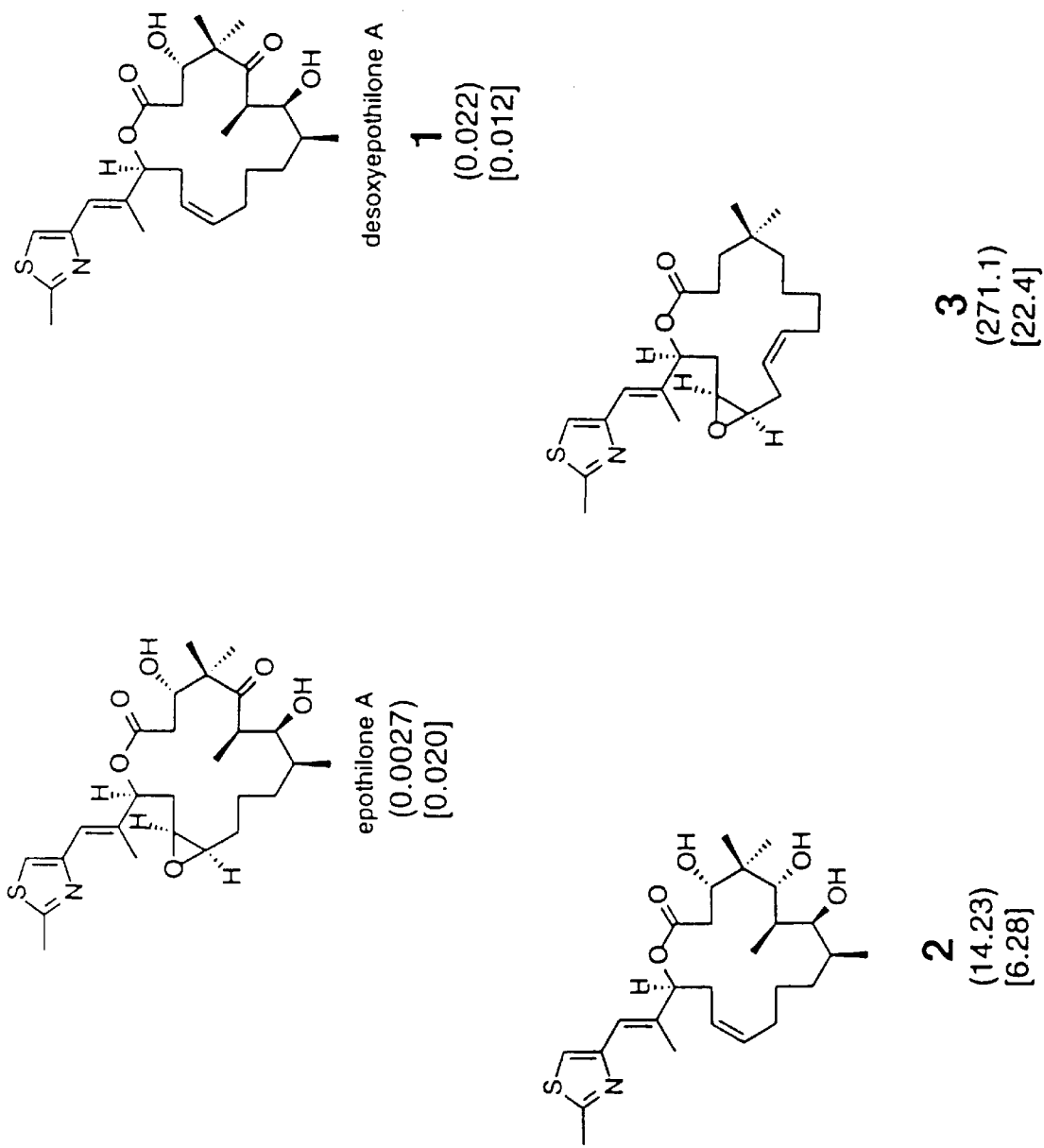
FIGS. 39(A) and 39(B) show epothilone A and epothilone analogues #1–7. Potencies against human leukemia CCRF-CEM (sensitive) and CCRF-CEM/VBL MDR (resistant) sublines are shown in round and square brackets, respectively.
Figure 39B:
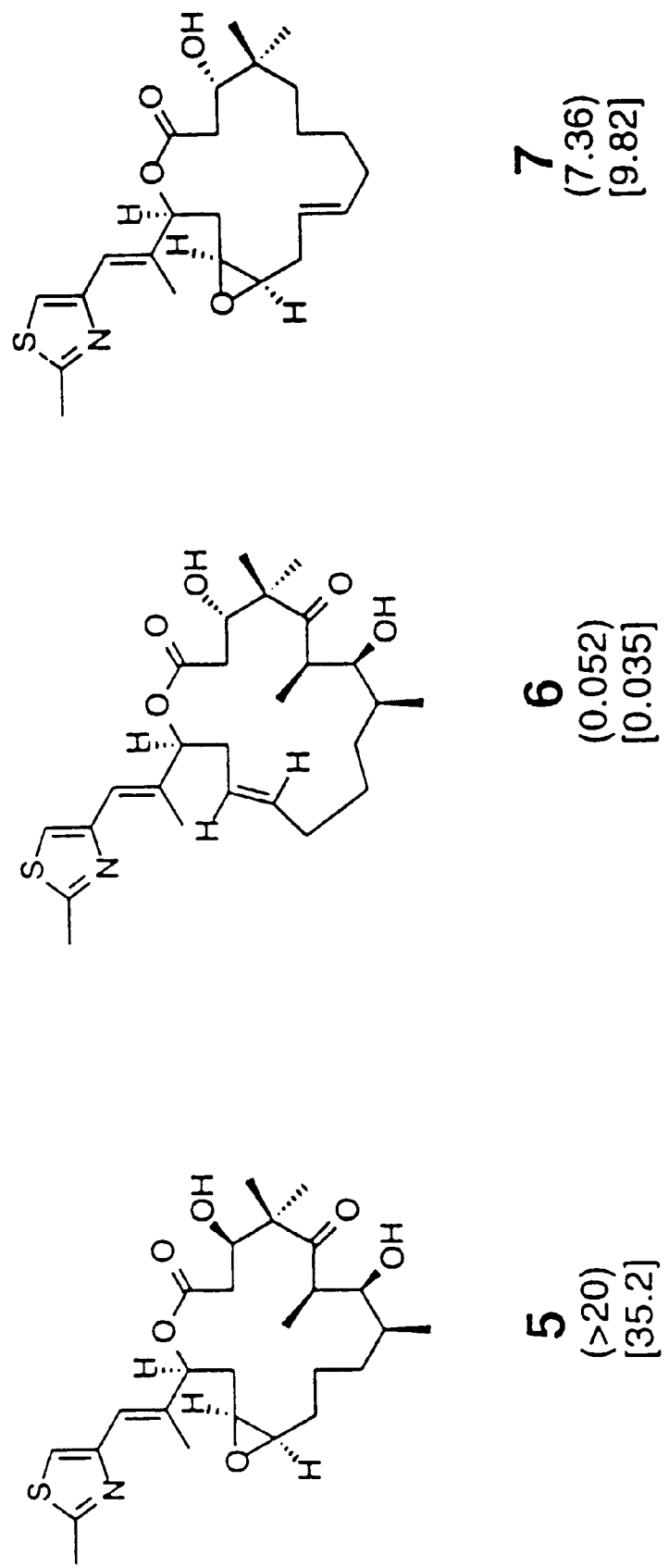
Figure 40A:
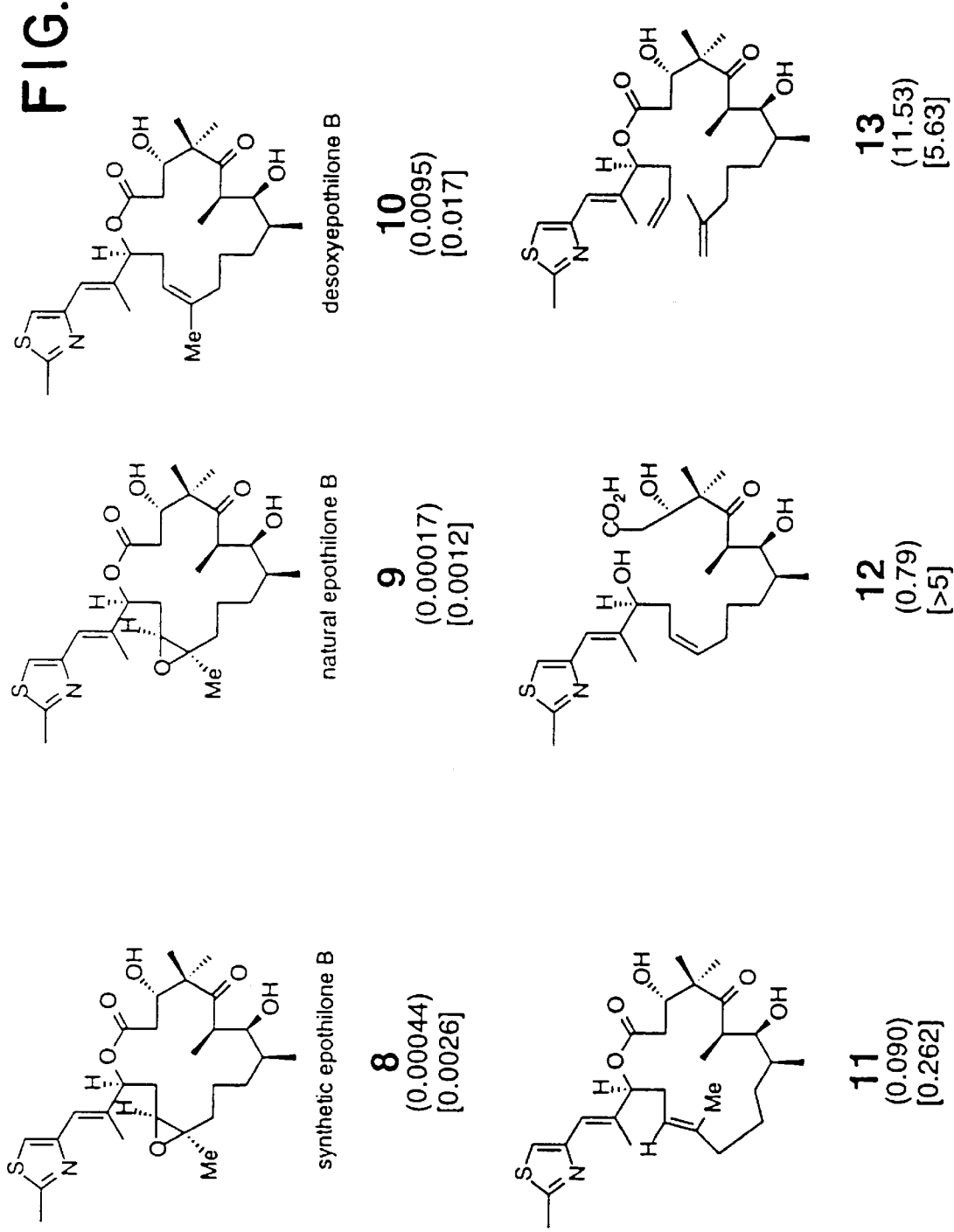
Figure 42D:
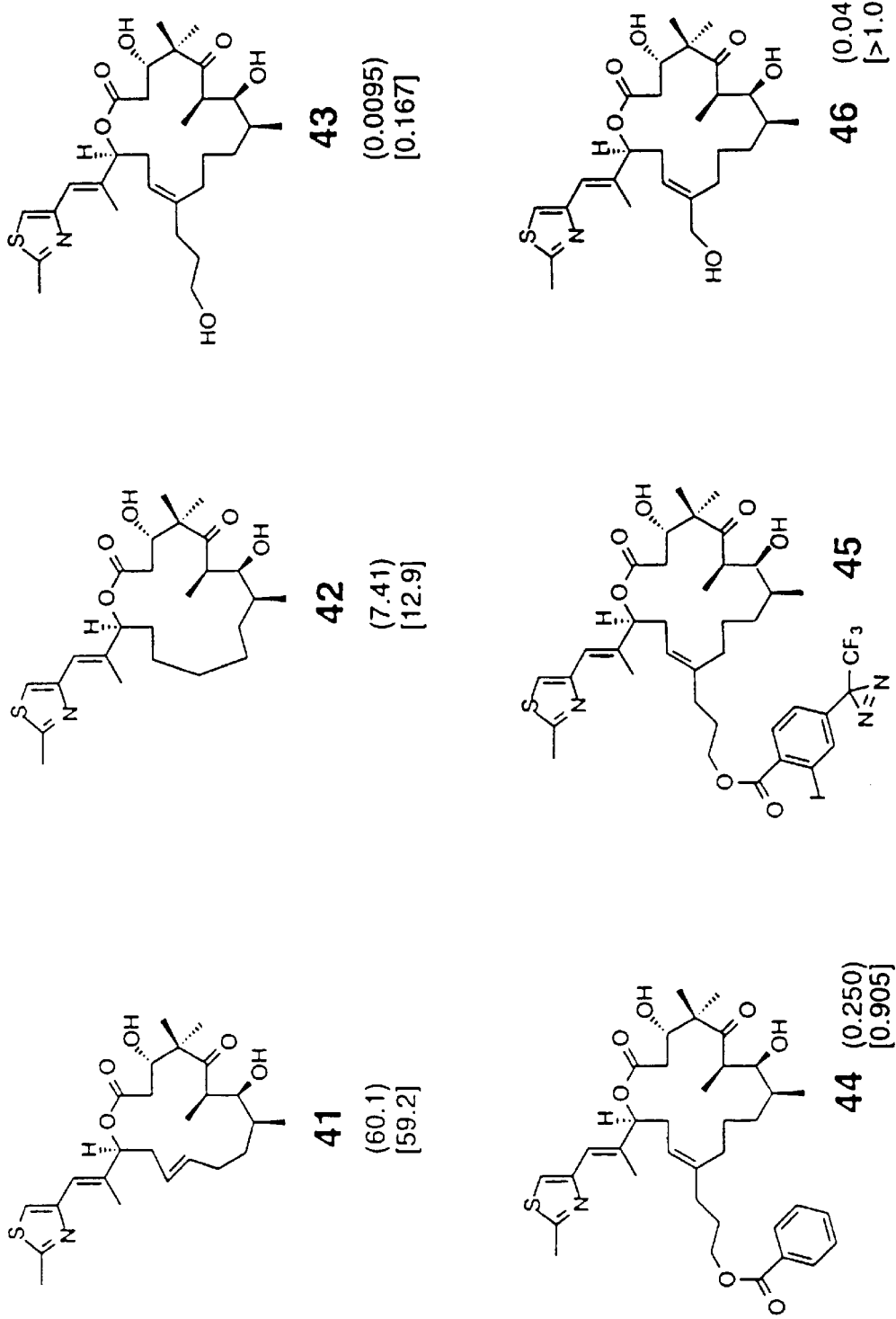
Figure 43A:
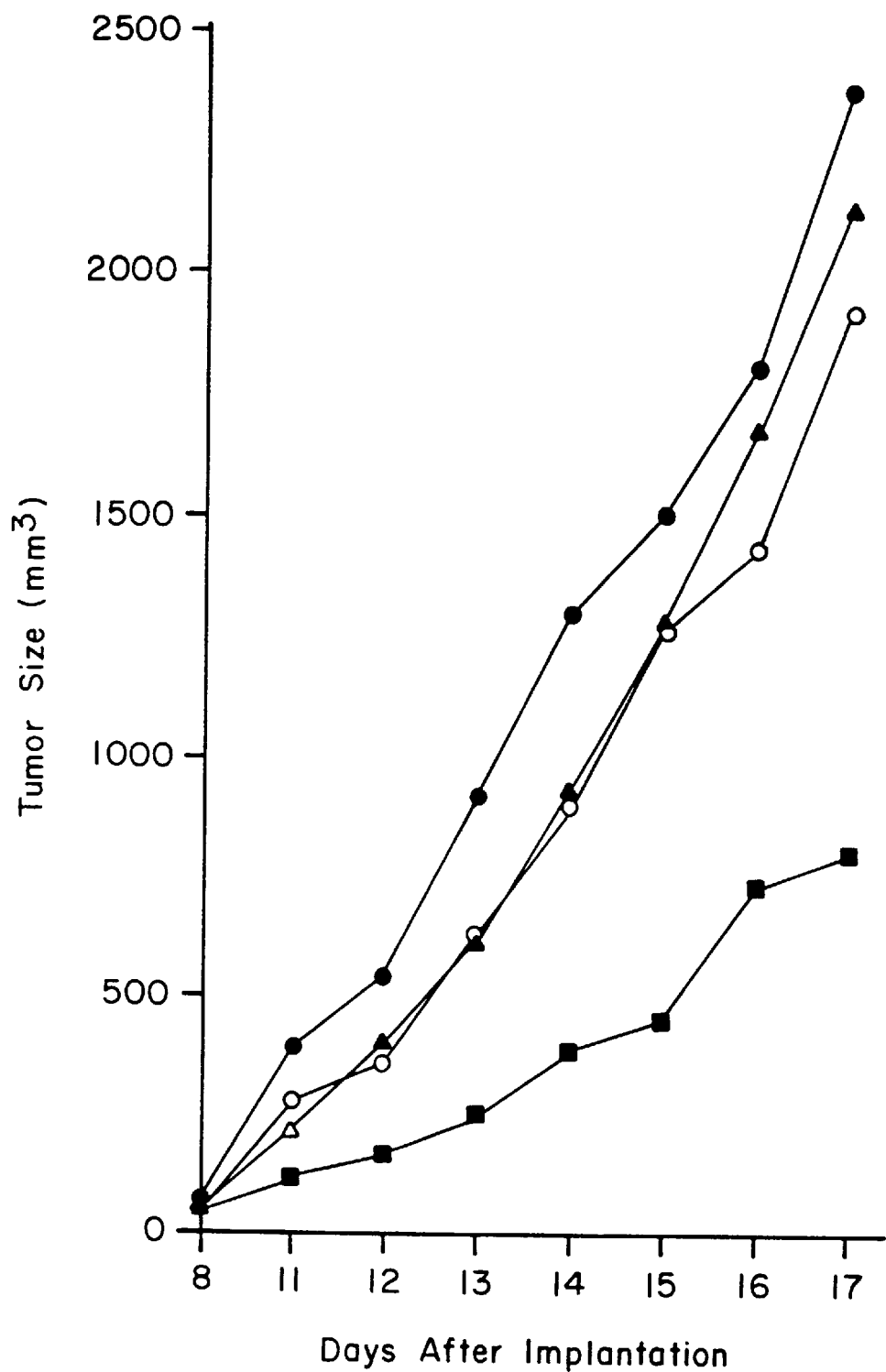
FIG. 43(A) shows antitumor activity of desoxyepothilone B against MDR MCF-7/Adr xenograft in comparison with Taxol®. Control (♦); desoxyepothilone B (■; 35 mg/kg); Taxol® (▲; 6 mg/kg); adriamycin (x;1.8 mg/kg); i.p. Q2Dx5; start on day 8. (B) shows antitumor activity of epothilone B against MDR MCF-7/Adr xenograft in comparison with Taxol®. Control (♦); epothilone B (■; 25 mg/kg; non-toxic dose); Taxol® (▲; 6 mg/kg; half $LD_{50}$); adriamycin (x;1.8 mg/kg); i.p. Q2Dx5; start on day 8.
Figure 43B:
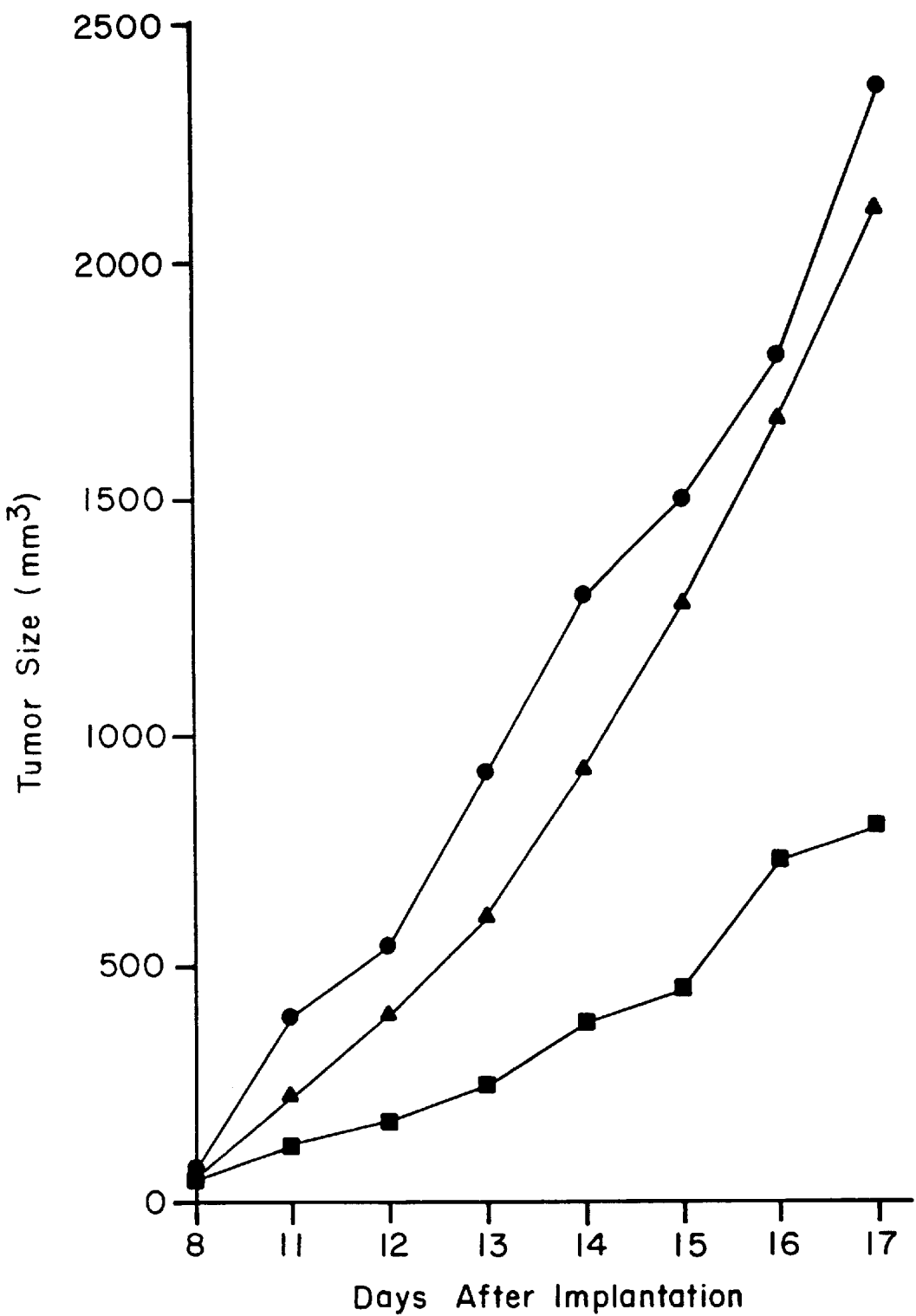

The hydroboration of 10D with 9-BBN produced intermediate 11D which, on coupling with the vinyl iodide 12D and in situ cleavage of the TBS ester led to 13D (FIG. 21). After deacetylation, the hydroxy acid 14D was in hand. Macrolactonization of this compound (Boden, E. P.; Keck, G. E. *J. Org. Chem.* 1985, 50, 2394) produced 15D which, after desilylation, afforded $C_8$-desmethyldesoxyepothilone (16D). Finally, epoxidation of this compound with dimethyldioxirane produced the goal structure 3D. The stereoselectivity of epoxidation was surprisingly poor (1.5:1) given that epoxidation of desoxyepothilone A occurred with >20:1 stereoselectivity. Deletion of the $C_8$ methyl group appears to shift the conformational distribution of 16D to forms in which the epoxidation by dimethyl dioxirane is less β-selective. It is undetermined whether the effect of the $C_8$ methyl on the stereoselectivity of epoxidation by dimethydioxirane and the dramatic reduction of biological activity are related.

Compounds 3D and 16D were tested for cytotoxicity in cell cultures and assembly of tubulin in the absence of GTP. Microtubule protein (MTP) was purified from calf brains by two cycles of temperature dependent assembly and disassembly. Weisenberg, R. C. *Science* 1972, 177, 1104. In control assembly experiments, MTP (1 mg/mL) was diluted in assembly buffer containing 0.1 M MES (2-(N-morpholino) ethanesulfonic acid), 1 mM EGTA, 0.5 mM $MgCl_2$, 1 mM GTP and 3M glycerol, pH 6.6. The concentration of tubulin in MTP was estimated to be about 85%. Assembly was monitored spectrophotometrically at 350 nm, 35° C. for 40 min by following changes in turbidity as a measure of polymer mass. Gaskin, F.; Cantor, C. R.; Shelanksi, M. L. *J. Mol. Biol.* 1974, 89, 737. Drugs were tested at a concentration of 10 μM, in the absence of GTP. Microtubule formation was verified by electron microscopy. To determine the stability of microtubules assembled in the presence of GTP or drug, turbidity was followed for 40 min after the reaction temperature was shifted to 4° C.

Cytotoxicity studies showed drastically reduced activity in the 8-desmethyl series. Compounds 3D and 16D were approximately 200 times less active than their corresponding epothilone A counterparts (see Table 1). Recalling earlier SAR findings at both $C_3$ and $C_5$, in conjunction with the findings disclosed herein, the polypropionate sector of the epothilones emerges as a particularly sensitive locus of biological function. Su, D.-S., et al., *Angew. Chem. Int. Ed. Engl.* 1997, 36, 757; Meng, D., et al., *J. Am. Chem. Soc.* 1997, 119.

TABLE 1

Relative efficacy of epothilone compounds against drug-sensitive and resistant human leukemic CCRF-CEM cell lines.[a]

| Compound | CCRF-CEM $IC_{50}$ (μM)[b] | CCRF-CEM/VBL $IC_{50}$ (μM)[b] | CCRF-CEM/VM$_1$ $IC_{50}$ (μM)[b] |
| --- | --- | --- | --- |
| 16D | 5.00 | 5.75 | 6.29 |
| 3D | 0.439 | 2.47 | 0.764 |
| epothilone A | 0.003 | 0.020 | 0.003 |
| desoxyepothilone A | 0.022 | 0.012 | 0.013 |
| epothilone B | 0.0004 | 0.003 | 0.002 |
| desoxyepothilone B | 0.009 | 0.017 | 0.014 |
| paclitaxel | 0.002 | 3.390 | 0.002 |

[a]The cytotoxicities of test compounds were determined by the growth of human lymphoblastic leukemic cells CCRF-CEM, or their sublines resistant to vinblastine and Taxol ® (CCRF-CEM/VBL) or resistant to etoposide (CCRF-CEM/VM-1). XTT-microculture tetrazolium/formazan assays were used.
[b]The $IC_{50}$ values were calculated from 5–6 concentrations based on the median-effect plot using computer software.

Desoxyepothiline B: an Effective Microtubule-targeted Antitumor Agent with a Promising in Vivo Profile Relative to Epothilone b The epothilones have been synthesized as herein disclosed and evaluated for antitumor potential in vitro and in vivo. Epothilones and paclitaxel are thought to share similar mechanisms of action in stabilizing microtubule arrays as indicated by binding displacement studies, substitution for Taxol® in Taxol®-dependent cell growth, and electron microscopic examinations. Cell growth inhibitory effects have been determined in two rodent and three human tumor cell lines and their drug resistant sublines. While Taxol® showed as much as 1970-fold cross-resistance to the sublines resistant to Taxol®, adriamycin, vinblastine or actinomycin D, most ephothilones exhibit little or no cross-resistance. In multidrug resistant CCRF-CEM/VBL$_{100}$ cells, the 50% cell growth inhibitory concentrations ($IC_{50}$ values) for epothilone A, epothilone B, desoxyepothilone A, desoxy epothilone B and Taxol® were 0.02, 0.002, 0.012, 0.017 and 4.14 μM, respectively. In vivo studies, using i.p. administration, indicate that the parent, epothilone B, is highly toxic to mice with little therapeutic effect when compared with lead compound desoxyepothilone B (25–40 mg/kg, Q2Dx5, i.p.), which showed far superior therapeutic effect and lower toxicity than paclitaxel, doxorubicin, camptothecin or vinblastine (at maximal tolerated doses) in parallel experiments. In nude mice bearing a human mammary carcinoma xenograft (MX-1), marked tumor regression and cures have been obtained with desoxyepothilone B.

The isolation of the naturally occurring macrolides epothilone A and epothilone B from the myoxobacteria *Sorangium cellulosum* (Hoefle, G., et al., *Angew.Chem.Int-.Ed.Engl.* 1996, 35, 567–1569; Gerth, K., et al. *J. Antibiot.* 1996, 49, 560–563) and the subsequent demonstration of their ability to stabilize microtubule arrays in vitro elicited considerable interest in this class of compounds (Bollag, D. M., et al., *Cancer Res.* 1995, 55, 2325–2333; Su, D.-S., et al., *Angew. Chem. Int. Ed. Engl.* 1997, 36, 2093–2096; Meng, D., et al., *J. Am. Chem. Soc.* 1997, 119, 2733–2734; Muhlradt, P. F. & Sasse, F. *Cancer Res.* 1997, 57, 3344–3346; Service, R. E. *Science* 1996, 274, 2009). We have recently conducted the total synthesis of these natural products as well as over 45 related analogs (Meng, D., et al., *J. Am. Chem. Soc.* 1997, 119, 10073–10092; Su, D-S., et al., *Angew. Chem. Int. Ed. Engl.* 1997,36, 757–759; Chou, T.-C., Zhang, X.-G., & Danishefsky, S. J. *Proc. Am. Assoc. Cancer Res.* 1998, 39, 163–164) in order to investigate their chemical structure-biological activity relationships (Su, D.-S, et al., *Agnew. Chem. Int. Ed. Engl.* 1997, 36, 2093–2096). The studies disclosed herein allowed the characterization of the epothilone structure in three zones. Thus, in the C-1~8 acyl sector, the present inventors have determined that structural changes are not tolerated in terms of in vitro cytoxocity and microtubule stabilizing ability. This stands in contrast to the C-9~15 O-alkyl sector and the C-15 pendant aryl sectors wherein considerable modification of structures is tolerated (Su, D.-S., et al., *Angew. Chem. Int. Ed. Engl.* 1997, 36, 2093–2096; Meng, D., et al., 1997, *J.Am.Chem.Soc.* 119, 10073–10092). Described herein are the results of in vitro and in vivo experiments on the Z-12,13 desoxy version of epothilone B (desoxyepothilone B).

It has been shown that the natural epothilones A and B have a similar mechanism of action to paclitaxel (Taxol®) although structurally diverse (Su, D.-S., et al.,*Angew. Chem. Int. Ed. Engl.*1997,36, 2093–2096; Meng, D., et al., *J.Am-.Chem.Soc.* 1997, 19, 2733–2734; Schiff, P. B., Fant, J. & Horwitz, S. B. *Nature* 1979, 277, 665–667; Landino, L. M. & MacDonald, T. L., in: *The Chemistry and Pharmacology of Taxol and Its Derivatives*, Favin, V., ed., Elsevier, New York 1995, Chapter 7, p. 301). Paclitaxel, isolated from the Pacific yew tree (*Taxus brevifolia*), has been widely used clinically to treat a variety of solid cancers including neoplasms of ovary, breast, colon and lung (Landino, L. M. & MacDonald, T. L. id.; Rose, W. C. *Anti-Cancer Drugs*, 1992, 3, 311–321; Rowinsky, E. K., et al., *Seminars Oncol.* 1993, 20, 1–15). Epothilones A and B as well as Taxol® stabilize microtubule assemblies as demonstrated by binding displacement, substitution for paclitaxel in paclitaxel-dependent cell growth, and electron microscopic examinations (Bollag, D. M., et al., *Cancer Res.* 1995, 55, 2325–2333). Despite these similarities, the epothilones are more water soluble than paclitaxel, thereby offering potentially distinct advantages for formulation. Epothilones are more potent than paclitaxel in inhibiting cell growth, especially against cells expressing P-glycoprotein (Pgp) that are multidrug resistant (MDR), including cross-resistance to paclitaxel (Bollag, D. M., id.; Su, D.-S., et al., *Angew. Chem. Int. Ed. Engl.* 1997, 36, 2093–2096).

Materials and Methods

All stock solutions of the above (except VBL in saline) were prepared using dimethylsulfoxide (DMSO) as a solvent and were further diluted to desired concentrations for experimental use. The final concentration of DMSO in tissue culture was 0.25% (v/v) or less to avoid solvent cytotoxicity. For in vivo studies, paclitaxel in Cremophor-EtOH was further diluted with DMSO as needed. Vinblastine sulfate (Velban) (Eli Lilly & Co. Indianapolis, Ind.), and doxorubicin or adriamycin HCl (DX or Adr) (Pharmacia, Columbus, Ohio) in saline were diluted with DMSO as needed. DMSO was used as a vehicle for epothilones. Each mouse received $\leq 40$ $\mu$L DMSO in all experiments.

Cell Lines

The CCRF-CEM human T-cell acute lymphoblastic leukemia cell line and its vinblastine-resistant (CCRF-CEM/VBL$_{100}$) and teniposide-resistant (CCRF-CEM/VM$_1$) sublines (Cass, C. E., et al., 1989, *Cancer Res.* 49, 5798–5804; Danks, M. K., Yalowich, J. C., & Beck, W. T. 1987, *Cancer Res.* 47, 1297–1301) were used. CCRF-CEM/Taxol® was developed by the present inventors following continuous exposure of CCRF-CEM cells with increasing concentrations of paclitaxel (at IC$_{50}$~IC$_{90}$) for ten months. The fresh medium with paclitaxel was replenished every week. The CCRF-CEM/Taxol® exhibited 57-fold resistance to paclitaxel (IC$_{50}$=0.0021 $\mu$M, see Table 1A). The DC-3F hamster lung fibroblast cell line and its actinomycin D-selected sublines (DC-3F/ADII and DC-3F/ADX) were obtained from the Memorial Sloan-Kettering Cancer Center (MSKCC). The murine leukemic P388/0 and its doxorubicin-selected subline (P3881DX) as well as human neuroblastoma SK-N-As and its doxorubicin-selected subline (SK-N-FI/Adr) were obtained from MSKCC.

The drug-resistant cell lines were continuously cultured in the presence of the selecting agent, AD, DX, VBL or VM to maintain the drug resistant phenotypes. Each sub-cell line was cultured for one to two passages in an appropriate concentration (e.g. IC$_{50}$) of the drug, which was then removed from the media and the cells were rested in fresh media for a minimum of 4 days before each assay. All cells were cultured in RPMI 1640–10% FBS at 37° C., 5% CO$_2$ (see below).

Cytotoxicity Assays

The cells were cultured at an initial density of 5×10$^4$ cells/mL. They were maintained in a 5% CO$_2$-humidified atmosphere at 37° C. in RPMI-1640 medium (GIBCO-BRL, Gaithersburg, Md.) containing penicillin (100 U/mL), streptomycin (100 mg/mL) (GIBCO-BRL) and 10% heat inactivate fetal bovine serum. Culture for cell suspension (such as for CCRF-CEM, P388 and sublines), were performed by the XTT-microculture tetrazonium method (Scudiero, D. A. et al., *Cancer Res.* 1988, 48, 4827–4833) in duplicate in 96-well microtiter plates.

2',3'-Bis(methoxy-4-nitro-5-sufophenyl)-5-[(phenylamino)carbonyl]-2H-tetrazolium hyudroxide (XTT) was prepared at 1 mg/mL in prewarmed (37° C.) medium without serum. Phenazine methosulfate (PMS) and fresh XTT were mixed together to obtain 0.025 mM PMS-XTT solution (25$\mu$L of the stock 5 mM PMS was added per 5 mL of 1 mg/mL XTT). Following a 72 h incubation, 50 $\mu$L of the assay aliquots were added to each well of the cell culture. After incubation at 37° C. for 4 h, absorbance at 450 nm and 630 nm was measured with a microplate reader (EL340, Bio-Tek Instruments, Inc., Winooski, Vt.).

The cytotoxicity of the drug toward the monolayer cell cultures (such as DC-3F, MCF-7, SK-N-As and sublines) was determined in 96-well microtiter plates by the SRB method as described by Skehan and co-workers (Skehan, P., et al., *J. Natl. Cancer Inst.* 1990, 82, 1107–1112) for measuring the cellular protein content. Cultures were fixed with trichloroacetic acid and then stained for 30 min with 0.4% suforhodamine B dissolved in 1% acetic acid. Unbound dye was removed by acetic acid washes, and the protein-bound dye was extracted with an unbuffered Tris base (tris(hydroxy-methyl)aminomethane) for determination of absorbance at 570 nm in a 96-well microtiter plate reader. The experiments were carried out in duplicate. Each run entailed six to seven concentrations of the tested drugs. Data were analyzed with the median-effect plot (Chou, T.-C. & Talalay, P. T. (1984) *Adv. Enzyme Regul.* 22, 27–55) using a previously described computer program (Chou, J., & Chou T.-C. 1987, *Dose-effect analysis with microcomputers: Quantitation of ED$_{50}$, synergism, antagonism, low-dose risk, reception-ligand binding and enzyme kinetics,* IBM-PC software and manual, Biosoft, Cambridge, U.K.).

Stability of Desoxyepothilone B in Plasma
HPLC Method.

Sample Preparation. To 300 microliters of spiked plasma are added 30 microliters of methanol. The mixture is agitated and allowed to stand for 2 minutes. Then 600 microliters of methanol are added. The mixture is centrifuged. The supernatant is removed for analysis by HPLC. Analyses were performed under the following chrmotographic conditions: Column: Nova-Pak C18, 15 cm. Eluant: 50% acetonitrile/water with 0.8% triethylamine, 0.2% phosphoric acid. Detection: UV (250 nm).

Animals

Athymic nude mice (nu/nu) were used for MX-1 and MCF-7/Adr human mammary carcinoma xenografts. Mice were obtained from Taconic Laboratory Animals and Service (Germantown, N.Y.: outbred, Swiss background). Male mice 6–8 weeks old, weighing 20–25 g were used.

RESULTS

Structure-activity Relationships

To determine structure-activity relationships of epothilones (Su, D.-S., et al., *Angew. Chem. Int. Ed. Engl.* 1997, 36, 2093–2096), the susceptibility of CCRF-CEM leukemic cells and the respective drug-resistant sublines CCRF-CEM/VBL$_{100}$ (Pgp-MDR cells) (Cass, C. E., el al., *Cancer Res.* 1989, 49, 5798–5804) and CCRF/CEM/VM$_1$ (cells with a mutated topo II gene) (Danks, M. K., Yalowich, J. C., & Beck, W. T. *Cancer Res.* 1987, 47, 1297–1301) to epothilones A and B and desoxyepthilone B (Table 1A) were determined. Although/VBL$_{100}$ is 527-fold resistant to VBL and 1970-fold resistance to paclitaxel, the epothilones A and B exhibited only 6.1~7.4-fold resistance, while desoxyepothilones A and B evidenced only 0.6~1.8-fold resistance. Using paclitaxel as the selecting agent, CCRF-CEM/Taxol® was grown 57-fold resistant and found to be 10.9-fold resistance to VBL. By contrast, DX, AD and VP-16 showed only 2.3–4.5 fold resistance, and epothilones A and B showed very little resistance (i.e., 1.4~3.1-fold) and desoxyepothilones A and B displayed almost no resistance (i.e., 0.7~1.7 fold) (Table 1A). CCRF-CEM/VM₁ cells that were 117-fold resistant to etoposide were sensitive to all epothilones or desoxyepothilones listed in Table 1A with only 0.6–3.6 fold resistance.

i.v. (cremophor and EtOH, 1:1), with Taxol®, i.p. and i.v. (both with clinical samples in cremophor and EtOH as specified by the manufacturer), and with EpoB, i.v. (used cremophor and EtOH, 1:1). As shown in Table 6, for Q2Dx5

TABLE 1A

Susceptibility of CCRF-CEM and its drug resistant sublines to epothilone derivatives.

| Compound | (A) CCRF-CEM | (B) CCRF-CEM/VBL$_{100}$ | (C) CCRF-CEM/Taxol® IC$_{50}$ ($\mu$M) | (D) CCRF-CEM/VM$_1$ | (B)(A) | (C)(A) | (D)(A) |
|---|---|---|---|---|---|---|---|
| Epo A | 0.0027 | 0.020 | 0.0037 | 0.0061 | 7.4 | 1.4 | 2.3 |
| Epo B | 0.00035 | 0.0021 | 0.0011 | 0.0013 | 6.1 | 3.1 | 3.6 |
| dEpo A | 0.0220 | 0.012 | 0.0150 | 0.03 | 0.55 | 0.7 | 0.59 |
| dEpo B | 0.0095 | 0.017 | 0.0162 | 0.014 | 1.8 | 1.7 | 1.5 |
| Taxol® | 0.0021 | 4.140 | 0.120 | 0.0066 | 1971 | 57 | 3.1 |
| Vinblastine | 0.0063 | 0.332 | 0.0069 | 0.00041 | 527 | 10.9 | 0.7 |
| Etoposide | 0.290 | 10.30 | 1.32 | 34.4 | 35 | 4.5 | 117 |
| Adriamycin | 0.036 | 1.74 | 0.082 | 0.128 | 48 | 2.3 | 3.6 |
| Actinomycin D | 0.00035 | 0.038 | 0.0013 | 0.00027 | 109 | 3.7 | 0.8 |

*Cell growth inhibition was measured by XTT tetrazonium assay (Scudiero, D. A. et al., Cancer Res. 1988, 48, 4827–4833) following 72 h incubation for cell growth as described previously. The IC$_{50}$ values were determined with 6–7 concentrations of each drug using a computer program (Chou, T.-C. & Talalay, P.T. (1984) Adv. Enzyme Regul. 22, 27–55); Chou, J., & Chou T.-C., Dose-effect analysis with microcomputers: Quantitation of ED$_{50}$, synergism, antagonism, low-dose risk, reception-ligand binding and enzyme kinetics, 1987, IBM-PC software and manual, Biosoft, Cambridge, U.K.)

Toxicity of dEpoB vs. EpoB

The toxicity of EpoB and dEpoB was compared in normal athymic nude mice on the daily i.p. schedule. EpoB at 0.6 mg/kg, QDX4, i.p. led to lethality in all eight mice. In contrast, in the group treated with dEpoB 25 mg/kg, QDX5, i.p., zero of six mice died. It was also observed that the vehicle treated control group showed a steady increase in body weight and the dEpoB treated mice maintained approximately the same average body weight, whereas the EpoB treated group showed steady decreases in body weight until death. These results indicated a higher toxicity for both EpoB and dEpoB than in tumor bearing nude mice when the treatment schedule was Q2Dx5, i.p. (see Tables 1C and 1D). In the preliminary studies, for the non-tumor bearing nude mice receiving EpoB 0.6 mg/kg or dEpoB 25 mg/kg, QDx4, i.p., there were no apparent changes in hematological cell counts or blood chemistry parameters except for a 43% decrease in lymphocytes. Similar leukopenia was found with paclitaxel. Some obstructive fecal mass in the large intestine was noted following Epo treatments in the preliminary study. No gross pathological abnormalities were observed in other organs.

TABLE 1B

Toxicity of Epothilone B, and Desoxyepothilone B in normal nude mice.

| Group | Dose schedule and route of administration | Number of mice | Number of mice died |
|---|---|---|---|
| Control |  | 4 | 0 |
| Epothilone B | 0.6 mg/kg, QD × 4, i.p. | 8 | 8* |
| Desoxyepothilone B | 25 mg/kg, QD × 4, i.p. | 6 | 0 |

*Mice died of toxicity on day 5,6,6,7,7,7,7,7

Comparison of Different Routes of Administration

Nude mice bearing human ovarian adenocarcinoma, SK-OV3, and human mammary adenocarcinoma, MX-1, were treated with dEpoB, both i.p. (DMSO as solvent) and schedule, dEpoB, i.p. (35 mg/kg) and Taxol® i.v. (15 mg/kg) both yield potent therapeutic effects against MX-1 with tumor-size on day 19, treated/control=0.02 and 0.01, respectively (see Table 1F). For the ovarian tumor a lesser therapeutic effect was seen, tumor size on day 21, treated/control=0.28 for both drugs (see Table 1G). For EpoB i.v., at 0.6 mg/kg there was less therapeutic effect and more toxicity than for dEpoB and Taxol®. In contrast, dEpoB, i.v. (15 mg/kg) and Taxol®, i.p. (5 mg/kg) showed more toxicity and less therapeutic effect against both tumors. Thus, dEpoB showed the best results when given i.p. and Taxol® gave better results when given i.v. in cremophor and EtOH.

In Vitro Effect against Various Tumor Sublines

Further susceptibility evaluations were conducted for epothilones A and B and desoxyepothilones A and B in four additional tumor cell lines and four of their drug resistant sublines (Table 1C). Hamster lung tumor cells DC-3F/ADX, that were selected 13,000-fold resistant to AD, were found to be 328-fold resistant to paclitaxel and 124-fold resistant to DX when compared with the parent cell line (DC-3F). In contrast, epothilones A and B and desoxyepothilone A showed only 3.9~28-fold resistance, and epothilones A and B and desoxyepothilone B showed no cross-resistance (0.9-fold resistance).

Murine leukemic P388/Adr cells that were selected 482-fold resistant to DX, were found to be 111-fold resistant to paclitaxel. However, epothilones A and B showed less than 156-fold resistance, and for desoxyepothilone A and B there was no cross-resistance (<0.6-fold resistance).

Human neuroblastoma cells, SK-N-F1, that were selected as 18-fold resistant to DX, were found to be 80-fold resistant to paclitaxel. By contrast, epothilone B was 25-fold resistant, while the resistance of epothilone A and desoxyepothilones A and B was only between 1.9 and 3.1.

Human mammary carcinoma cells, MCF-7/Adr, that were selected 3.8-fold resistant to DX, were found to be 46-fold resistant to paclitaxel. In contrast, compounds epothilones A and B and desoxyepothilone B was 3.1~5.4-fold resistant, and dEpoB showed only 2.4-fold resistant. Overall, dEpoB was the least cross-resistant among epothilones and desoxyepothilones in various drug-resistant tumor sublines. By contrast, paclitaxel suffers from marked cross-resistance in tumor cells that were selected to be resistant to VBL, DX or AD. In three out of five cell lines studied, cross-resistance to paclitaxel was even greater than that of the selecting agents.

Therapeutic Effects against MX-1 Xenografts

Therapeutic effects of compounds epothilone A and desoxyepothilone B, paclitaxel, VBL and CPT were evaluated in athymic nude mice bearing human mammary adenocarcinoma MX-1 xenografts (Table 1D). Desoxyepothilone B at a 15 mg/kg dose i.p. on days 7, 9, 11, 13 and 15 produced a 50–60% tumor volume reduction when compared to the control group. A higher dose of drug, 25 mg/kg, produced as much as 96% average tumor volume reduction measured two days after the last treatment (i.e., on day 17). These effects were achieved with no lethality nor body weight reduction. Furthermore, with a 25 mg/kg dose, one out of six mice was tumor-free on day 35 after tumor implantation (i.e. on day 35). In contrast, after treatment with EpoB (0.3 mg/kg and 0.6 mg/kg, i.p., on days 7, 9, 11, 13 and 15), the average body weight decreased over 1 g and 2 g, respectively. In the case of 0.6 mg/kg treatment, three out of seven mice died of toxicity. Despite the apparent toxicity at these doses, EpoB appeared to have only marginal therapeutic effect, as only 16% to 26% tumor volume reduction was observed (Table 1D). The parallel experiments for paclitaxel led to a lower therapeutic effect. In animals treated with paclitaxel, 5 mg/kg, there was 55% reduction in tumor volume and no decrease in average body weight. At a dose of 10 mg/kg, paclitaxel showed a 89% tumor reduction, however, four out of seven mice died of toxicity. For DX (2–3 mg/kg) and CPT (1.5~3 mg/kg) i.e., near the maximal tolerated doses, inferior results were obtained when compared with dEpoB. Thus, dEpoB even at non-toxic dose had the best therapeutic effect among the five compounds studied under the same experimental conditions.

Figure 60:
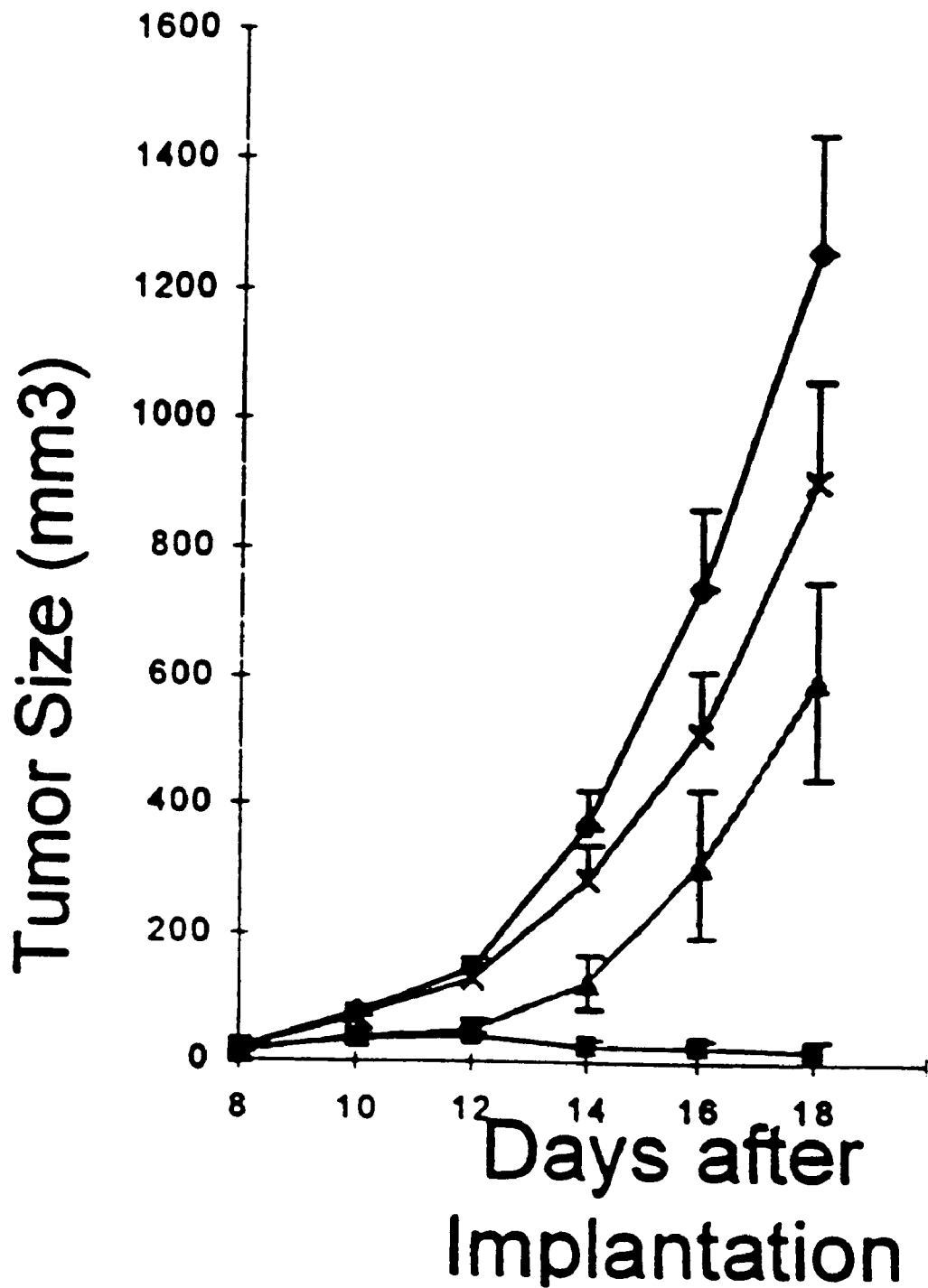
FIG. 60 illustrates the therapeutic effect of dEpoB, Taxol® and adriamycin in nude mice bearing the human mammary carcinoma MX-1 xenograft. MX-1 tissue preparation 100 μl/mouse was implanted s.c. on day 0. Every other day i.p. treatments were given on day 8, 10, 12, 14 and 16 with dEpoB 35 mg/kg (■), Taxol® 5 mg/kg (▲), adriamycin (2 mg/kg (x), and vehicle (DMSO, 30 μl) treated control (♦). For Taxol®, 2/10 mice died of toxicity on day 18. For adriamycin, 1/10 mice died of toxicity on day 22. For dEpoB, 10/10 mice survived and were subjected to the second cycle of treatment at 40 mg/kg on day 18, 20, 22, 24 and 26. This led to 3/10 mice tumor-free up to day 80, whereas 7/10 mice were with markedly suppressed tumors and were sacrificed on day 50.

In a separate experiment, MX-1 xenograft-bearing mice were treated with dEpoB, 35 mg/kg, Q2Dx5, i.p. beginning on day 8 after tumor implantation (FIG. 60). On day 16, two out of ten mice had no detectable tumor. These ten mice were further treated with dEpo B, 40 mg/kg, Q2Dx5 beginning on day 18. At the end of treatment on day 26, five out of ten mice had no detectable tumor, and three remained tumor-free on day 60. There was body weight reduction during treatments but no lethality occurred. In a parallel experiment, ten mice were treated with paclitaxel, 5 mg/kg, Q2Dx5, i.p. from day 8 to day 16, follower by a second cycle of treatment in the same manner from day 18 to day 26. The tumor sizes were reduced but continued to grow during treatment and by day 24, the average tumor size was 2285±597 mm$^3$ (n=10). In a parallel experiment, DX was given 2 mg/kg, Q2Dx5, i.p. (FIG. 60), and reduced therapeutic effect was seen compared to dEpoB or paclitaxel. No data after day 18 is shown because the tumor burden in the control group was excessive and the mice in this group were sacrificed.

Therapeutic Effects against MCF-7/Adr Xenografts

The therapeutic effects of dEpoB, Taxol®, DX and CPT were also evaluated in nude mice bearing xenografts of human mammary adenocarcinoma resistant to DX (MCF-7/Adr) (Table 1E). As indicated earlier in Table 1B for the cytotoxicity results in vitro, MCF-7/Adr cells selected to be 3.8-fold resistant to DX were found to be 46-fold resistant to paclitaxel, and only 2.4-fold resistant to dEpoB. For in vivo studies, each drug was given Q2Dx5, i.p. beginning on day 8 after tumor implantation. Paclitaxel 12 mg/kg and DX 3 mg/kg were highly toxic to the nude mice with 3/7 and 3/6 lethality, respectively. CPT 3 mg/kg led to moderate toxicity without lethality, and dEpoB 35 mg/kg showed negligible toxicity as shown by minimal body weight changes (Table 1E). CPT at 3 mg/kg reduced 57% of tumor size on day 17 ($p<0.05$ when compared with control group). Desoxyepothilone B at 35 mg/kg significantly suppressed tumor size by 66~73% when compared with the control group ($p<0.005$~0.05), without complete tumor regression. In contrast, paclitaxel 5 mg/kg, and DX 2 mg/kg, produced slight growth suppression of this drug-resistant tumor which was not significantly different from the control group (see Table 1D). Thus, dEpoB stands out as the superior drug among the four tested against this drug-resistant tumor.

TABLE 1C

Comparison of in vitro growth inhibition potency of epothilone derivatives against various parent and drug resistant tumor cell lines.

| Compound | DC-3F | DC-3F/ADX | P388/O | P388/Adr | SK-N-As | SK-N-FI | MCF-7 | MCF-7/Adr |
|---|---|---|---|---|---|---|---|---|
| | | | IC$_{50}$ ($\mu$M)* | | | | | |
| Epo A | 0.0037 | 0.053 (14.5x)$^\#$ | 0.0018 | 0.0010 (5.3x)$^\#$ | 0.012 | 0.023 (1.9x)$^\#$ | 0.0030 | 0.0094 (3.1x)$^\#$ |
| Epo B | 0.0006 | 0.017 (28x) | 0.00029 | 0.0016 (5.5x) | 0.004 | 0.010 (25x) | 0.0005 | 0.0027 (5.4x) |
| dEpo A | 0.011 | 0.042 (3.9x) | 0.0213 | 0.0125 (0.59x) | 0.073 | 0.223 (3.1x) | 0.032 | 0.144 (4.5x) |
| dEpo B | 0.00097 | 0.00091 (0.9x) | 0.0068 | 0.0042 (0.62x) | 0.021 | 0.046 (2.2x) | 0.0029 | 0.0071 (2.4x) |
| Taxol ® | 0.095 | 32.0 (338x) | 0.0029 | 0.326 (111x) | 0.0016 | 0.130 (80x) | 0.0033 | 0.150 (46x) |
| Actinomycin D | 0.00044 | 0.572 (13000x) | 0.00015 | 0.0012 (8x) | 0.00085 | 0.0119 (14x) | 0.00068 | 0.00167 (2.5x) |
| Adriamycin | 0.018 | 2.236 (124x) | 0.0055 | 2.65 (482x) | 0.077 | 1.42 (18.4x) | 0.057 | 0.216 (3.8x) |

*Cell growth inhibition was measured by protein staining SRB assay (Skehan, P., et al., J. Natl. Cancer Inst. 1990, 82, 1107–1112) following 72 h incubation as described previously. The IC$_{50}$ values were determined with 6–7 concentrations of each drug using a computer program (Chou, T. C. & Talalay, P. T., Adv. Enzyme Regul. 1984, 22, 27–55; Chou, J., & Chou T. C., Dose-effect analysis with microcomputers:Quantitation of ED$_{50}$, synergism, antagonism, low-dose risk, reception-ligand binding and enzyme kinetics, 1987, IBM-PC software and manual. Biosoft, Cambridge, U.K.).

TABLE 1C-continued

Comparison of in vitro growth inhibition potency of epothilone derivatives against various parent and drug resistant tumor cell lines.

| Compound | DC-3F | DC-3F/ADX | P388/O | P388/Adr | SK-N-As | SK-N-FI | MCF-7 | MCF-7/Adr |
|---|---|---|---|---|---|---|---|---|

Numbers in parentheses are folds of resistance based on the $IC_{50}$ ratio when compared with the corresponding parent cell lines except for P388/O and P388/Adr, XTT assay (Scudiero, D. A., et al., Cancer Res. 1988, 48, 4827–4833) was used.

10

TABLE 1D

Therapeutic effect of desoxyopothilone B, epothilone B, Taxol ®, vinblastine and camptothecin in nude mice bearing human MX-1 zenograft.

| Drug | Dose (mg/kg) | Average Body Weight Change (g) Day | | | | | Average Tumor Size (T/C) Day | | | | Toxicity Death | N |
|---|---|---|---|---|---|---|---|---|---|---|---|---|
| | | 7 | 11 | 13 | 15 | 17 | 11 | 13 | 15 | 17 | | |
| Control | | 27.2 | +0.8 | +1.1 | +1.9 | +0.6 | 1.00 | 1.00 | 1.00 | 1.00 | 0/8 | 8 |
| dEpo B | 15 | 27.1 | +0.8 | +1.1 | +1.6 | +1.5 | 0.65 | 0.46 | 0.49** | 0.41** | 0/6 | 6 |
| | 25# | 27.0 | +0.4 | +0.7 | +1.0 | +0.7 | 0.38* | 0.11** | 0.05*** | 0.04**** | 0/6 | 6 |
| Epo B | 0.3 | 26.9 | +0.5 | +0.4 | −0.3 | −1.2 | 1.00 | 0.71 | 0.71 | 0.84 | 0/7 | 7 |
| | (0.6†) | 27.4 | −0.3 | −1.3 | −2.1 | −2.1 | 1.08 | 0.73 | 0.81 | 0.74 | 3/7)## | 7 |
| Taxol ® | 5 | 26.9 | −0.1 | +0.4 | +1.1 | +1.2 | 0.54 | 0.46 | 0.40* | 0.45** | 0/7 | 7 |
| | 10‡ | 27.6 | −2.7 | −1.1 | −0.3 | +2.2 | 0.43 | 0.37 | 0.12 | 0.11 | 4/7## | 7 |
| Vinblastine | 0.2 | 25.7 | +0.6 | +1.4 | +2.3 | +2.9 | 0.65 | 0.54 | 0.56 | 0.88 | 0/7 | 7 |
| | (0.4¶) | 26.4 | +0.8 | +0.5 | +1.9 | +2.1 | 0.80 | 0.56 | 0.83 | 0.88 | 1/7)## | 7 |
| Campothecin | 1.5 | 27.4 | −0.9 | −0.7 | −0.4 | +1.0 | 0.61 | 0.45* | 0.32* | 0.36** | 0/7 | 7 |

MX-1 tissue 50 µl/mouse was implanted s.c. on day 0. Every other day i.p. treatments were given on days 7, 9, 11, 13, 15; The average tumor volumes of the control group on day 11, 13, 15 and 17 were 386 ± 120, 915 ± 245, 1390 ± 324, and 1903 ± 319 $mm^3$ (mean ± SEM), respectively;
*$P < 0.05$,
**$P < 0.01$,
***$P < 0.005$,
****$P < 0.001$;
One out of six mice with no detectable tumor on day 35;
†Three mice died of drug toxicity on day 17;
‡Four mice died of drug toxicity on day 13, 13, 13, 15;
¶One mouse died of drug toxicity on day 15;
P values were not shown due to toxic lethality.

TABLE 1E

Therapeutic effects of desoxyopothilone B, epothilone B, taxol, adriamycin and camptothecin in nude mice bearing MDR human MCF-7/Adr tumor.

| Drug | Dose (mg/kg) | Average Body Weight Change (g) Day | | | | | Average Tumor Size (T/C) Day | | | | Toxicity Death | N |
|---|---|---|---|---|---|---|---|---|---|---|---|---|
| | | 8 | 11 | 13 | 15 | 17 | 11 | 13 | 15 | 17 | | |
| Control | 0 | 25.0 | +2.0 | +2.6 | +3.1 | +3.7 | 1.00 | 1.00 | 1.00 | 1.00 | 0/8 | 8 |
| dEpo B | 35 | 25.0 | 0.3 | +0.7 | +0.6 | +0.8 | 0.31** | 0.27*** | 0.30*** | 0.34* | 0/8 | 8 |
| Taxol ® | 6 | 25.3 | +1.7 | +1.8 | +0.8 | +0.9 | 0.57 | 0.66 | 0.85 | 0.90 | 0/7 | 7 |
| | (12 | 24.5 | −0.7 | −1.3 | −2.4 | 0 | 0.50 | 0.51 | 0.32 | 0.40 | 3/7 | 7)# |
| Adriamycin | 2 | 25.6 | +0.2 | −0.4 | −0.6 | −0.4 | 0.70 | 0.68 | 0.84 | 0.78 | 0/8 | 8 |
| | (3 | 24.6 | +0.5 | −1.3 | −3.2 | −1.6 | 0.66 | 0.83 | 0.57 | 0.53 | 3/6 | 6)# |
| Campothecin | 1.5 | 24.4 | +1.1 | +0.9 | +1.7 | +1.4 | 1.08 | 0.72 | 0.61 | 0.72 | 0/8 | 8 |
| | (3 | 24.5 | −0.6 | −0.4 | −0.8 | −0.9 | 0.95 | 0.76 | 0.61 | 0.43* | 0/6 | 6 |

MCF-7/Adr cell $3 \times 10^6$/mouse was implanted s.c. on day 0. Every other day ip treatments were given on days 8, 10, 12, 14 and 16. The average tumor size of control group on day 11, 13, 15 and 17 was 392" ± 84, 916 ± 210, 1499 ± 346, and 2373 ± 537 $mm^3$ respectively (mean ± SEM).
*<P 0.05,
**$P < 0.01$,
***$P < 0.005$;
P values were not shown due to lethality.

TABLE 1F

Therapeutic effects of desoxyopothilone B, Epo B and Taxol ® in nude mice bearing MX-1 tumors using different vehicles and different routes of administration.[a]

| Drug/Route | Dose (mg/kg) | Average Body Weight Change (g) Day | | | | | Average Tumor Size (T/C) Day | | | | Tumor Disapp. | Toxicity Death |
|---|---|---|---|---|---|---|---|---|---|---|---|---|
| | | 9 | 13 | 15 | 17 | 19 | 13 | 15 | 17 | 19 | | |
| Control | 0 | 26.4 | −0.2 | −0.4 | +0.2 | +0.8 | 1.00 | 1.00 | 1.00 | 1.00 | 0/6 | 0/6 |
| dEpo B/i.p. | 35 | 27.8 | −1.7 | −2.1 | −2.1 | −2.4 | 0.35 | 0.14 | 0.04 | 0.02 | 3/6 | 0/6 |
| dEpo B/i.v. | 15 | 27.0 | 0 | −0.6 | −1.1 | −2.6 | 0.47 | 0.30 | 0.10 | 0.04 | 0/6 | 4/6[b] |
| Epo B/i.p. | 0.6 | 27.0 | −0.9 | −0.5 | −3.3 | −3.4 | 0.67 | 0.63 | 0.61 | 0.51 | 0/6 | 0/6 |
| Taxol ®/i.p. | 5 | 27.4 | −1.1 | −2.0 | −1.0 | −0.2 | 0.59 | 0.72 | 0.59 | 0.55 | 0/6 | 0/6 |
| Taxol ®/i.v. | 15 | 27.2 | −0.6 | −0.8 | −0.8 | −0.9 | 0.36 | 0.13 | 0.04 | 0.01 | 2/6 | 0/6 |

[a]50 μg tumor tissue was implanted s.c. on day 0. Every other day i.p. or i.v. treatments were given on days 9, 11, 13, 15 and 17. The average tumor size of control group on day 13, 15, 17 and 19 was 274, 378, 677, 1139 mm³ respectively.
[b]4/6 mice died of drug toxicity on day 23, 23, 23, 25.

TABLE 1G

Therapeutic effects of desoxyopothilone B, Epo B and Taxol ® in nude mice bearing SK-OV-3 tumors using different vehicles and different routes of administration.[a]

| Drug/Route | Dose (mg/kg) | Average Body Weight Change (g) Day | | | | | Average Tumor Size (T/C) Day | | | | Tumor Disapp. | Toxicity Death |
|---|---|---|---|---|---|---|---|---|---|---|---|---|
| | | 9 | 13 | 15 | 17 | 19 | 15 | 17 | 19 | 21 | | |
| Control | 0 | 26.4 | −0.2 | −0.4 | +0.2 | +0.8 | 1.00 | 1.00 | 1.00 | 1.00 | 0/6 | 0/6 |
| dEpo B/i.p. | 35 | 27.8 | −1.7 | −2.1 | −2.1 | −2.4 | 0.57 | 0.33 | 0.35 | 0.28 | 0/6 | 0/6 |
| dEpo B/i.v. | 15 | 27.0 | 0 | −0.6 | −1.1 | −2.6 | 0.86 | 0.56 | 0.50 | 0.44 | 0/6 | 4/6[b] |
| Epo B/i.p. | 0.6 | 27.0 | −0.9 | −0.5 | −3.3 | −3.4 | 0.75 | 0.69 | 0.88 | 0.77 | 0/6 | 0/6 |
| Taxol ®/i.p. | 5 | 27.4 | −1.1 | −2.0 | −1.0 | −0.2 | 0.69 | 0.60 | 0.49 | 0.40 | 0/6 | 0/6 |
| Taxol ®/i.v. | 15 | 27.2 | −0.6 | −0.8 | −0.8 | −0.9 | 0.97 | 0.67 | 0.42 | 0.28 | 0/6 | 0/6 |

[a]50 μg tumor tissue was implanted s.c. on day 0. Every other day i.p. or i.v. treatments were given on days 9, 11, 13, 15 and 17. The average tumor size of control group on day 13, 15, 17 and 19 was 274, 378, 677, 1139 mm³ respectively.
[b]4/6 mice died of drug toxicity on day 23, 23, 23, 25.

DISCUSSION

Two classes of naturally occurring compounds, epothilones and paclitaxel, which are apparently structurally dissimilar, show similar modes of action in stabilizing microtubule assemblies. These similarities include binding tubulin, substitution for paclitaxel in maintaining paclitaxel-dependent cell growth in a resistant cell line, and similar morphologic changes as determined by electron microscopic examination of the drug-microtubule complex. There are differences, however, between the two classes of compounds. These differences are most prominently exhibited by the lack of cross-resistance in cytotoxicity between the epothilones and paclitaxel even in CCRF-CEM/Taxol® cells (Table 1A). Furthermore, in CCRF/CEM/VBL$_{100}$, the cells were 527-fold resistant to vinblastine and 1971-fold resistance to paclitaxel, but were only 6.1-fold resistant to EpoB and 1.8-fold resistant to dEpoB (Table 1A). In DC-3F/ADX cells, there was 13,000-fold resistance to actinomycin D and 338-fold resistance to paclitaxel. However, these cells were only 28-fold resistance to EpoB and had no resistance to dEpoB (i.e., 0.9-fold resistance or collateral sensitivity) (Table 1B). Paclitaxel showed a higher degree of cross-resistance in these cell lines than other MDR-drugs such as doxorubicin, actinomycin D, vinblastine or etoposide. In some cases the degrees of resistance to paclitaxel were even greater than those of the resistance-selecting agent (e.g., CCRF-CEM//VBL$_{100}$ in Table 1A, and SK-N-FI and MCF/7-Adr in Table 1B). In contrast, among all compounds tested, dEpoB showed the least cross-resistance in several drug-resistant cell lines (e.g. DC-3F/Adr) and even showed slight collateral sensitivity (e.g. DC-3F/ADX and P388/Adr in Table 1B). Parallel cancer chemotherapeutic studies for EpoB, dEpoB, Taxol® and other drugs were performed under the same experimental conditions (i.e., treatment schedule, Q2D; solvent vehicle, DMSO; and route of administration, i.p.) in animals.

The i.p. route of other formulations for administration of dEpo B is far better tolerated than the i.v. method. Even though EpoB is the most potent, it is by no means the best candidate for cancer therapy in terms of therapeutic index (i.e. the therapeutic efficacy at tolerable dosage, or the ratio of toxic dose vs the therapeutic dose). Desoxyepothilone B, lacking the epoxide functionality, exhibited far superior therapeutic results in vivo as compared to the more potent EpoB. Similarly, the present therapeutic results for dEpoB in MX-1 xenografts were far better than those for EpoB, paclitaxel, doxorubicin, vinblastine or camptothecin. In addition, the effects of dEpo B on MCF-7/Adr xenografts were significantly better than those for paclitaxel, doxorubicin and camptothecin. In view of the finding that the epothilones have little or no cross-resistance against MDR tumor cells in vitro, the special therapeutic advantage of such compounds might be in their use against MDR-resistant tumors.

Figure 53A:
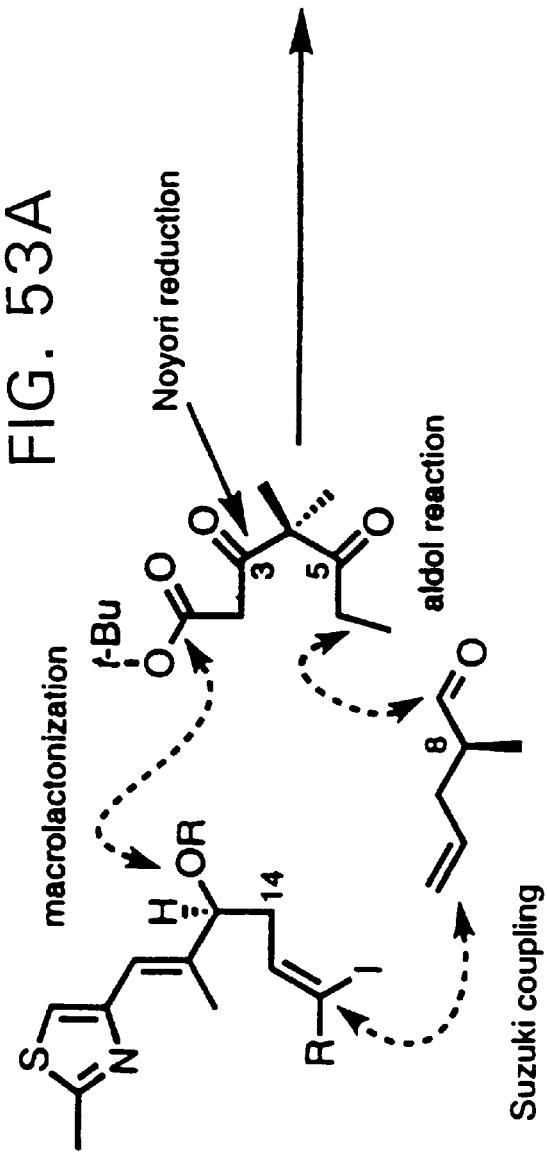
FIG. 53(A) shows an approach to the preparation of desoxyepothilones. (B) represents a key step involving dianion addition to an aldehyde reactant.
Figure 53B:
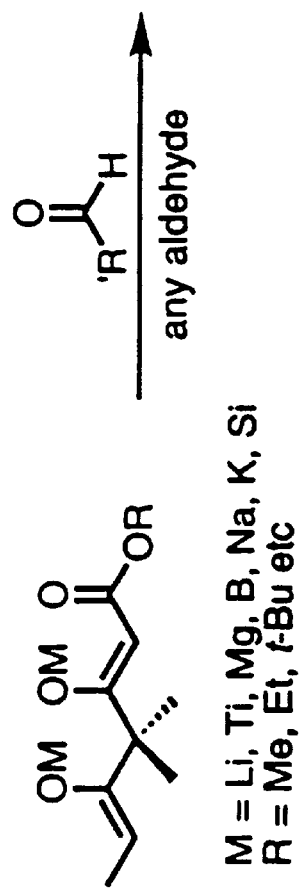
Figure 54:
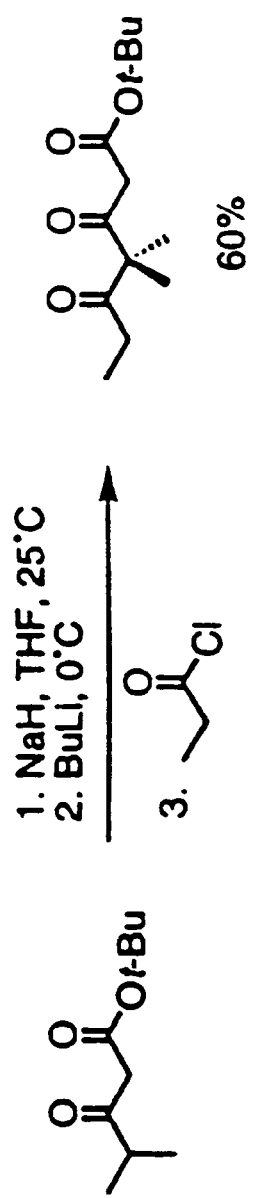
FIG. 54 illustrates the acylation of t-butyl 4-methylpentan-3-on-1-ate to provide t-butyl 4,4-dimethylheptan-3,5-dion-1-ate.
Figure 55:
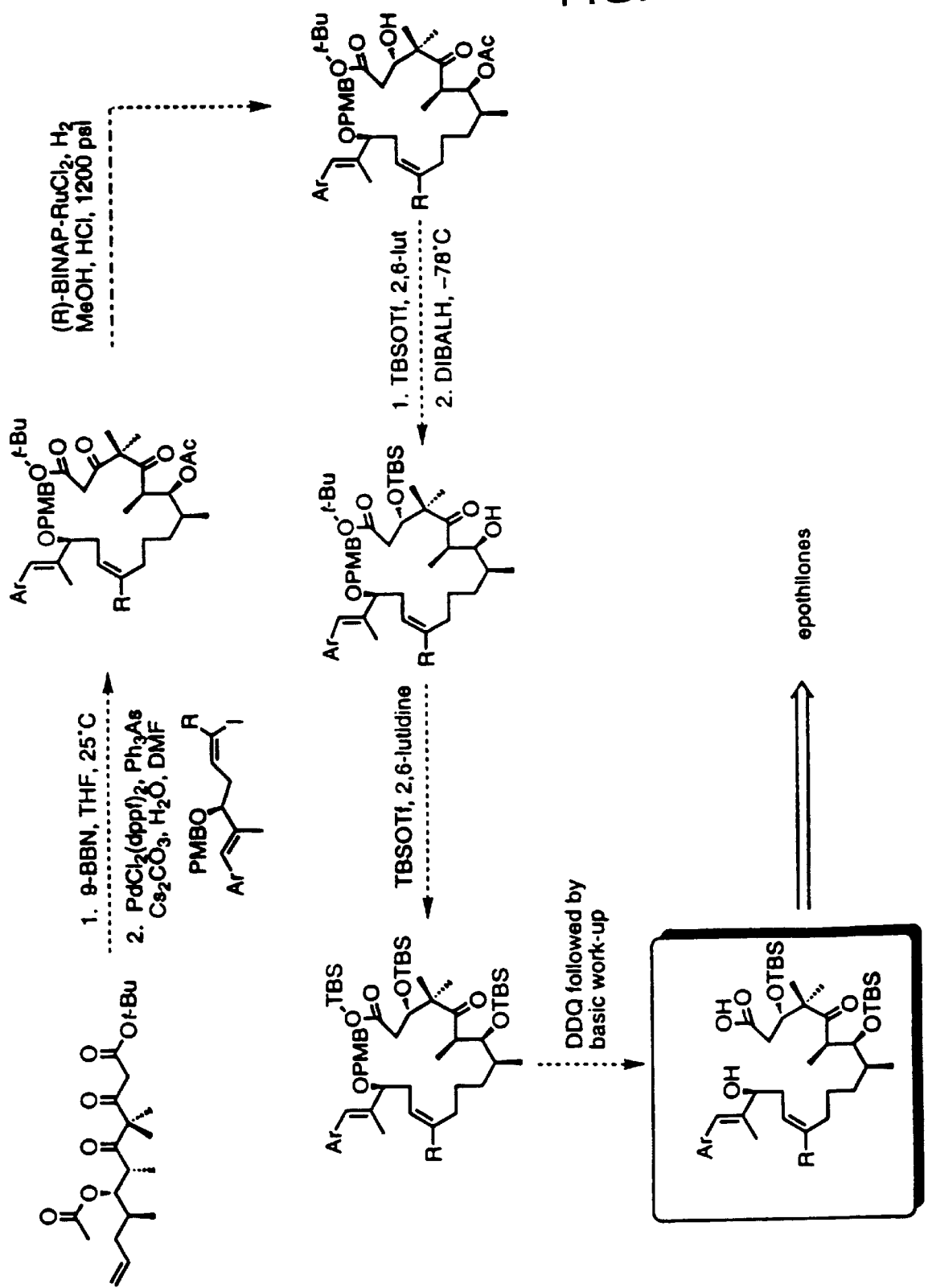
FIG. 55 shows the preparation of a key intermediate hydroxyacid in the preparation of desoxyepothilones. The final synthetic steps leading to various desoxyepothilones from the hydroxyacid are found in, e.g., FIGS. 21–26. R is selected from the group consisting of H, Me, Et, Pr, Hx, $CH_2OH$ and $(CH_2)_3OH$. Ar is selected from the group consisting of phenyl, tolyl, xylyl, thiazolyl, 2-methylthiazolyl, pyrryl and pyridyl, and is either unsubstituted or substituted with an $C_{1-6}$ alkyl, phenyl or benzyl group. Conditions for the Noyori reduction are disclosed in Taber et al., *Tetrahedron Lett.*, 1991, 32, 4227, and Noyori et al., *J.Amer.Chem.Soc.*, 1987, 109, 5856, the contents of which are incorporated herein by reference. Conditions for the DDQ deprotection are disclosed in Horita et al., *Tetrahedron*, 1986, 42, 3021, the contents of which is incorporated herein by reference.
Figure 56:
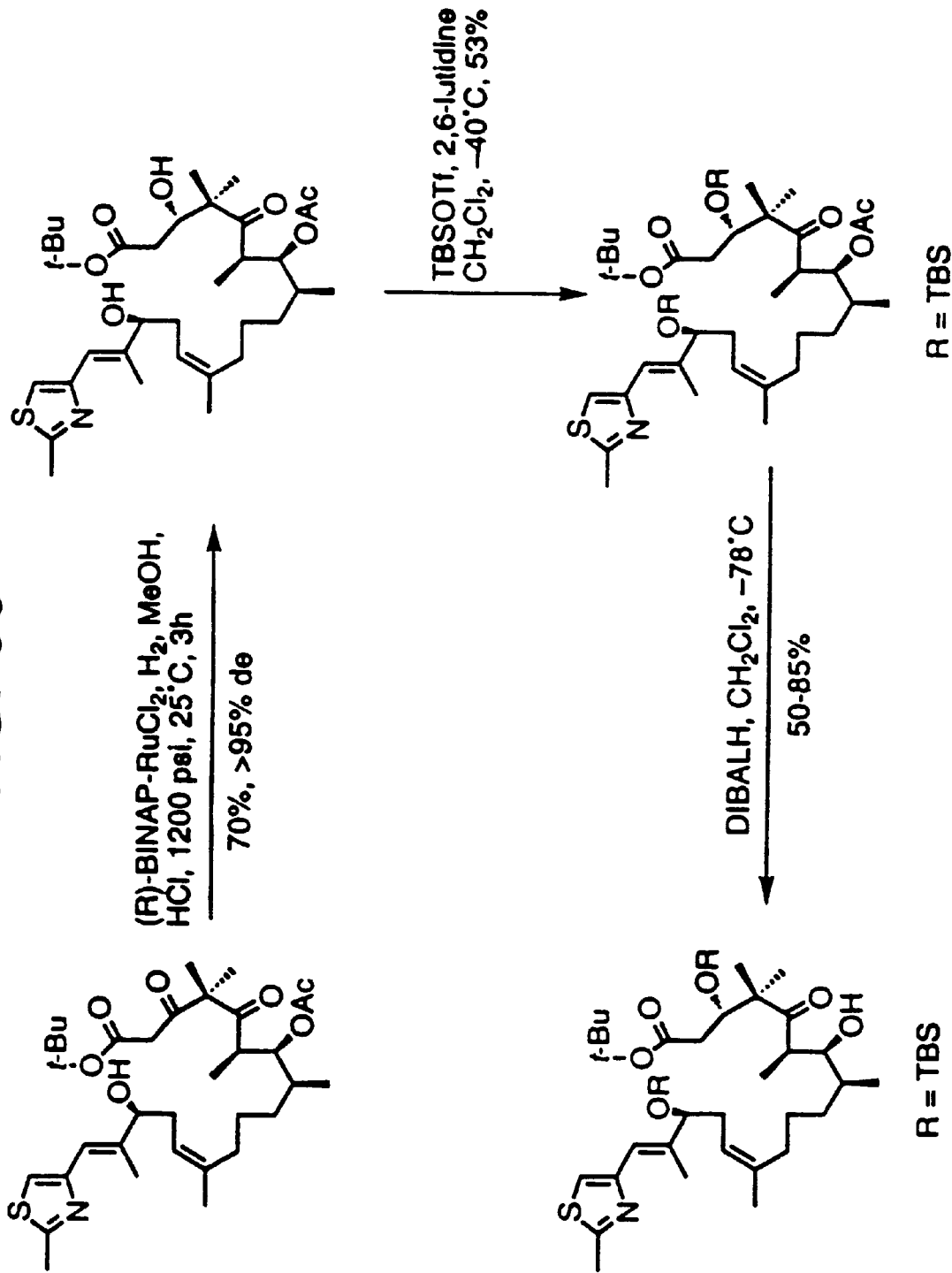
FIG. 56 illustrates an application of the Noyori reduction of a substrate with C-15 hydroxyl useful in the preparation of epothilone analogues.
Figure 57:
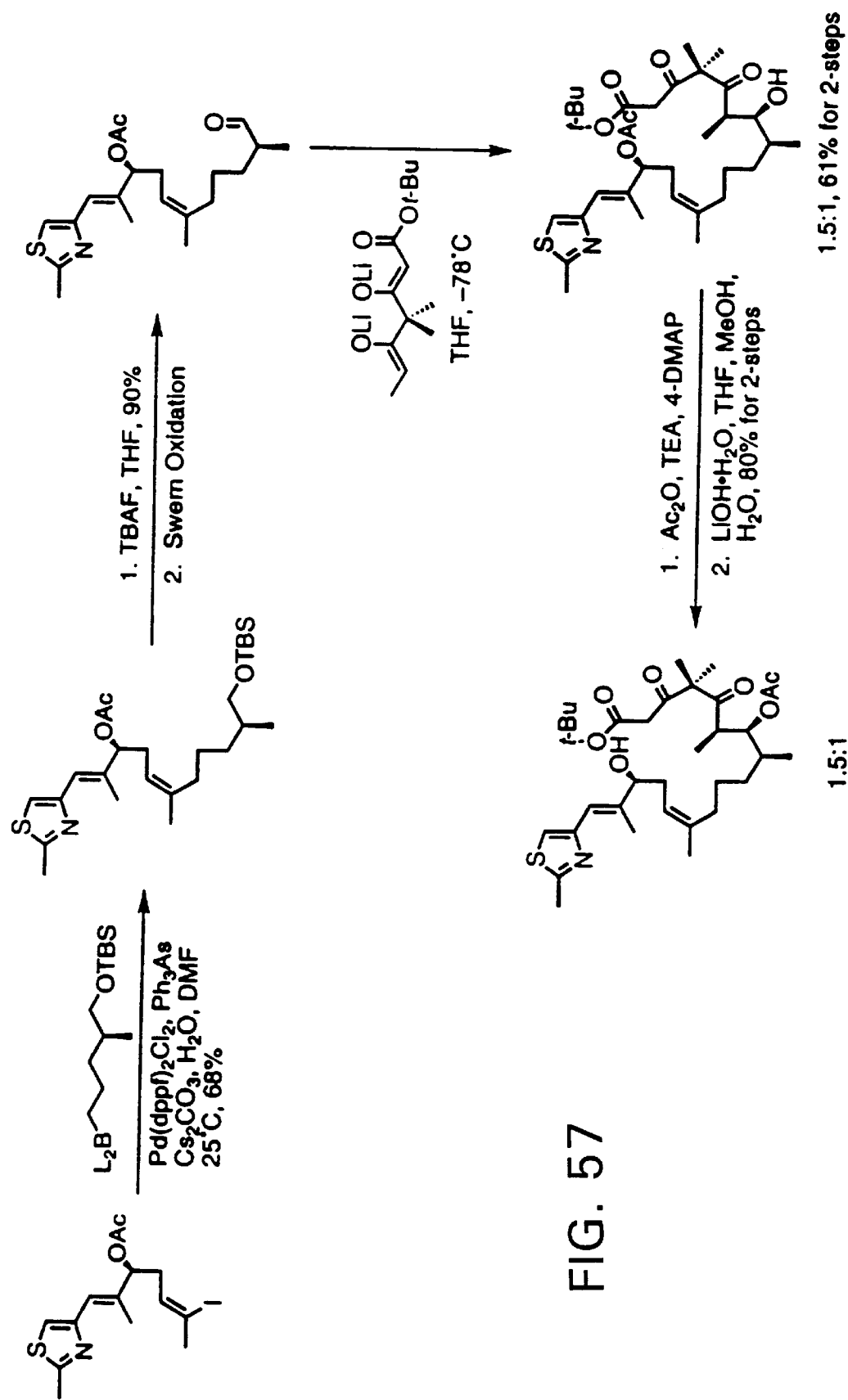
FIG. 57 exemplifies a dianion addition to a coupled aldehyde intermediate useful in the preparation of epothilone analogues.
Figure 58:
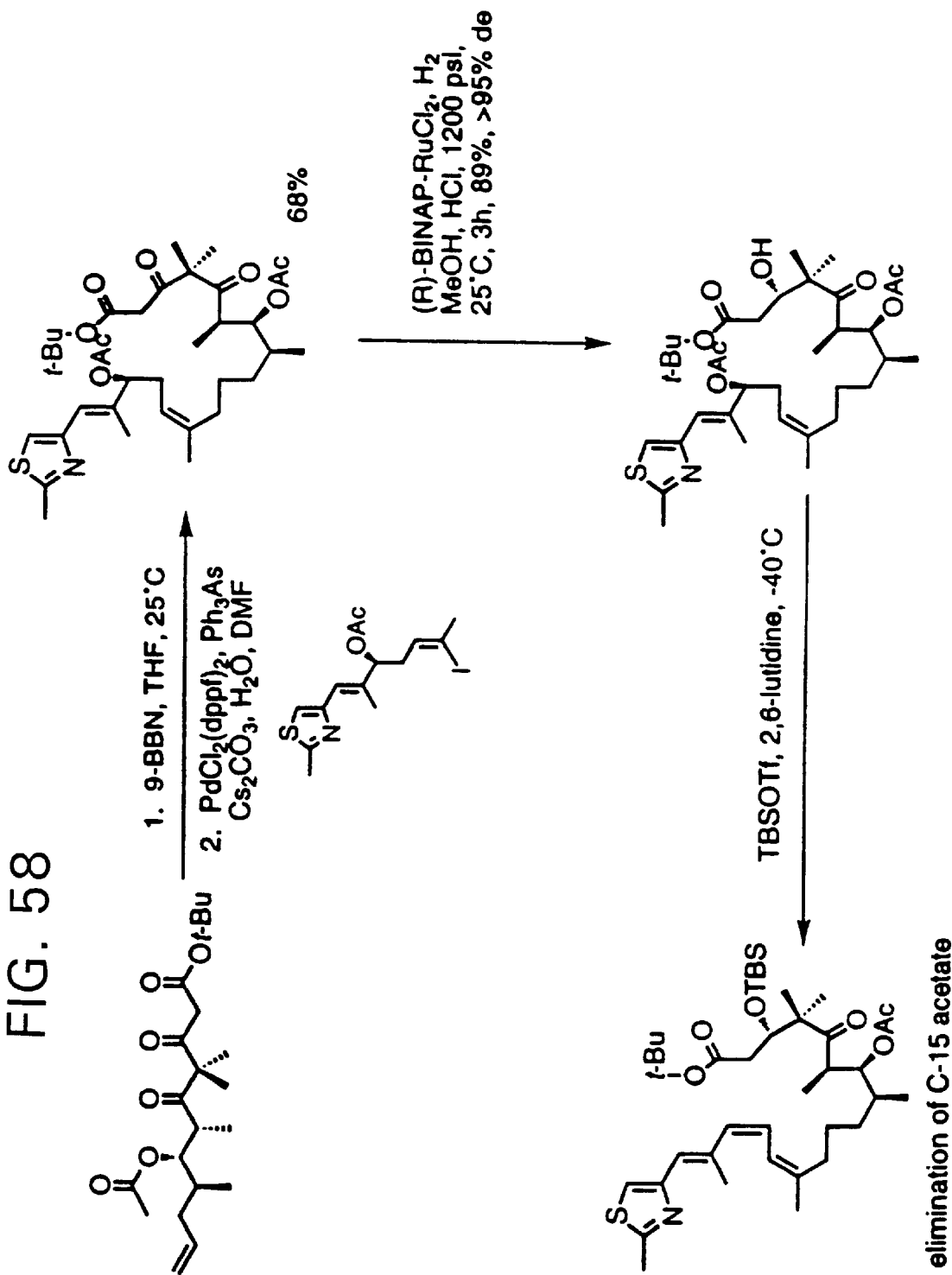
FIG. 58 provides an application of the Noyori reduction of a coupled substrate useful in the preparation of epothilone analogues.
Figure 59:
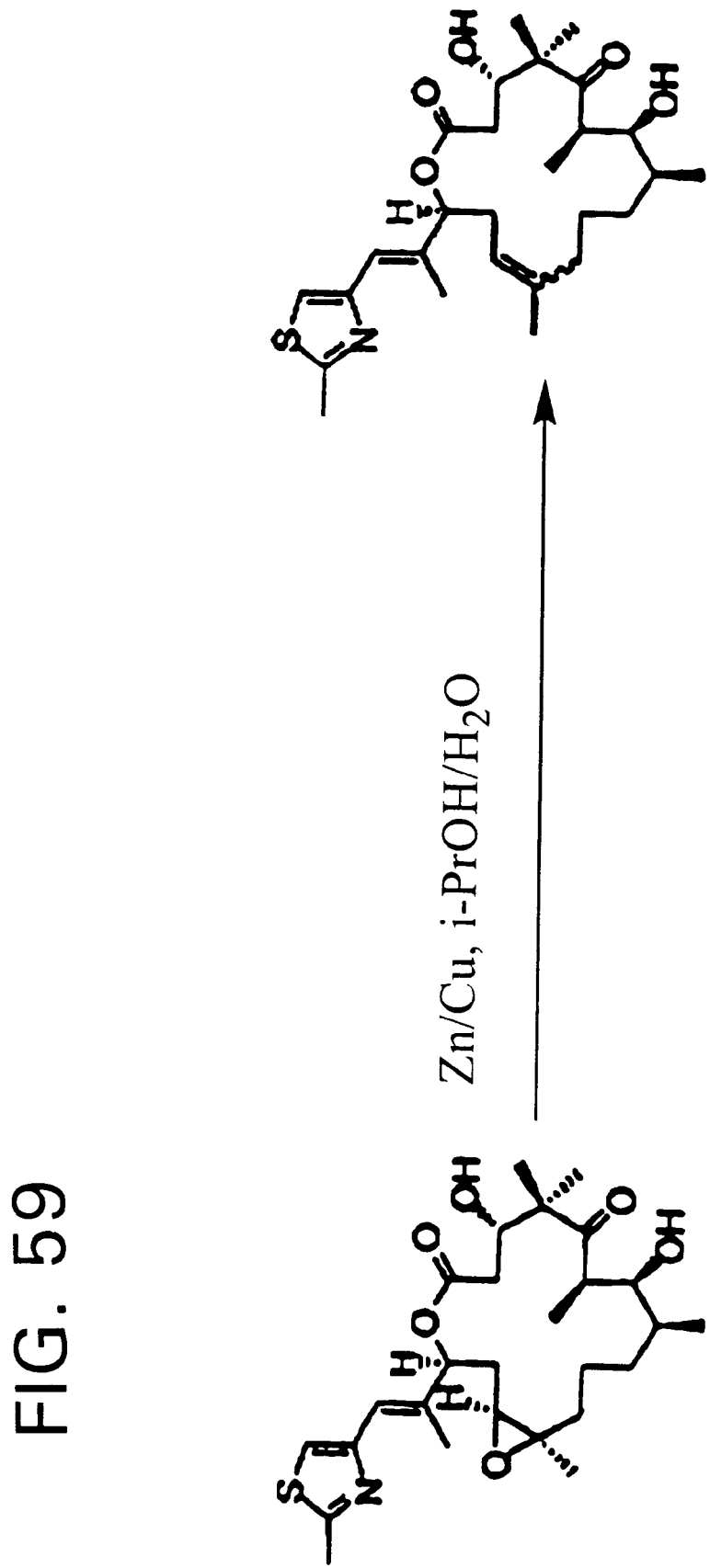
FIG. 59 shows the preparation of desoxyepothilone analogues by deoxygenation of the epoxide using Zn/Cu couple, exemplified by the conversion of desoxyepothilone B from epothilone B. In a sample procedure, Zn/Cu couple is added to a solution of epothilone B (6 mg, 0.012 mmol) in i-PrOH (0.3 mL) and water (3 drops). The suspension was heated to 90° C. for 13 hours, cooled to room temperature, filtered through a pad of Celite™ and concentrated. Flash chromatography afforded 1.5 mg of epothilone B (75% conversion) and 3.2 mg of desoxyepothilone B (73% yield, as a mixture of cis and trans isomers in a 0.7:1 ratio).

Novel Aldol Condensation with 2-Methyl-4-pentenal: Application to Preparation of Epothilone B and Desoxyepothilone B Stereoselectivity poses a potential hindrance to enhancing access to multicomponent libraries. Nicolaou, K. C., et al., *J. Am. Chem. Soc.* 1997, 119, 7960; Nicolaou, K. C., et al., *J. Am. Chem. Soc.* 1997, 119, 7974. Nicolaou, K. C., et al., *Angew. Chem. Int. Ed. Engl.* 1997, 36, 2097. However, stereoselectivity holds the attraction that it allows for accumulation of substantial quantities of fully synthetic key epothilones of correct configuration. Comparable harvesting of needed amounts of material through the stereo-random olefin metathesis route (Yang, Z., Y., et al., *Angew. Chem. Int. Ed. Engl.* 1997, 36, 166; Nicolaou, K. C., et al., *Angew. Chem. Int. Ed. Engl.* 1997, 36, 525; Nicolaou, K. C., et al., *Nature* 1997, 387, 268; Nicolaou, K. C., et al., *J.Am. Chem. Soc.* 1997, 119, 7960; Nicolaou, K. C. et al., *J. Am. Chem. Soc.* 1997, 119, 7974; Nicolaou, K. C., et al., *Angew. Chem. Int. Ed. Engl.* 1996, 35, 2399. Schinzer, D., et al., *Angew. Chem. Int. Ed. Engl.* 1997, 36, 523; Meng, D., et al., *J. Am. Chem. Soc.* 1997, 119, 2733) would be virtually prohibitive. Biological studies in xenograft mice provided herein identified some significant toxicity problems with the highly potent epothilone B. Remarkably, in vivo studies in the intraperitoneal mode of injection demonstrate that the less potent 12,13-deoxyepothilone B is well tolerated and is virtually curative against a variety of xenograft tumors. Chou, T.-C., et al., *Proc. Nat'l Acad. Sci. USA* 1998, 0000. Desoxyepothilone B has clinical advantages relative to paclitaxel, particularly as regards vulnerability to the phenomenon of multiple drug resistance. The preparative route disclosed herein retains the advantages of high stereoselectivity throughout, and provides an improved approach to the previously difficult C1-C11 domain. FIG. 53 provides a global overview of the problem.

Figure 61A:
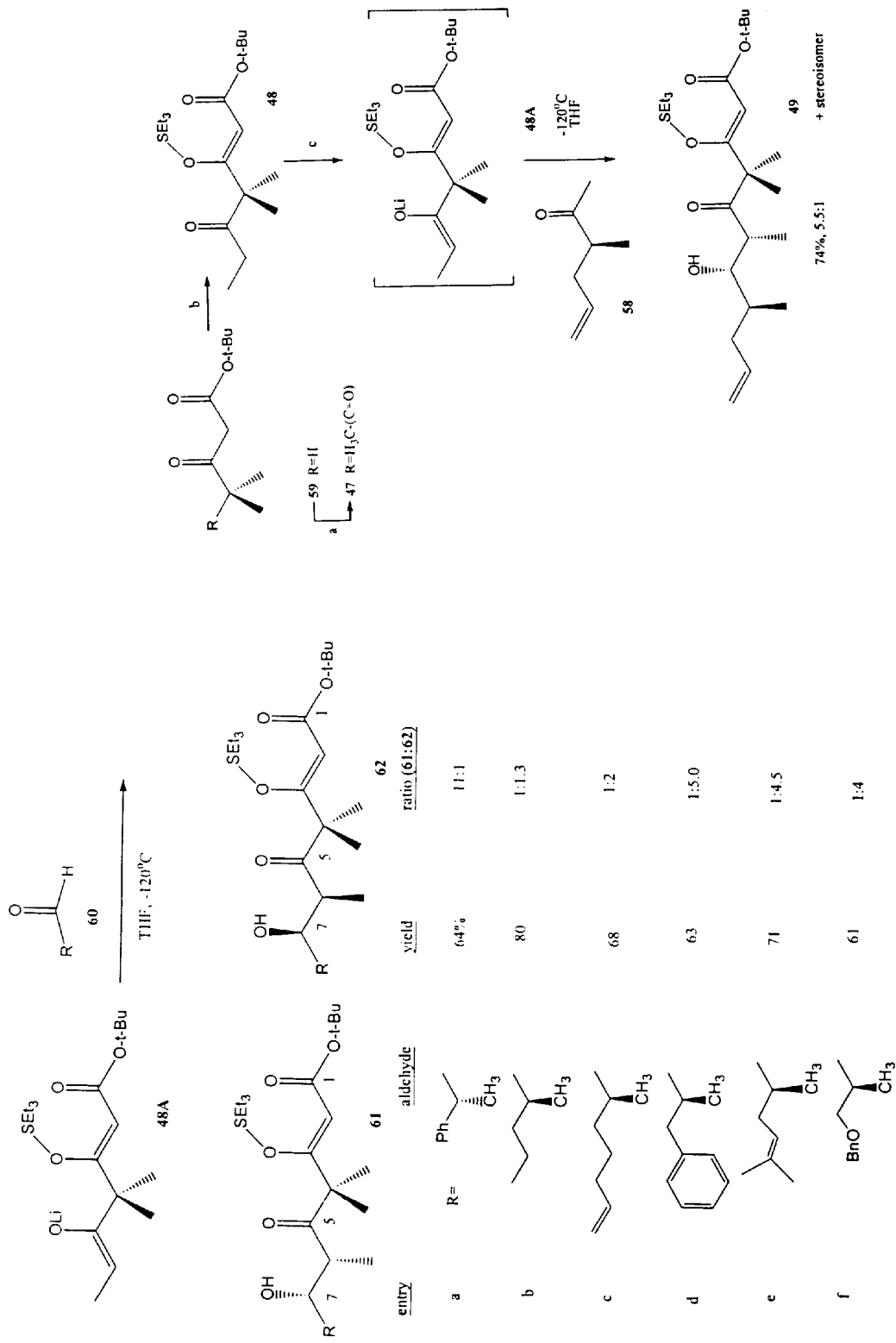
FIG. 61(A) shows a procedure for preparing intermediate 49. ᵃNaH, THF, 25° C., then 0° C., then propionyl chloride, -50° C., 71%; [b]NaH, 0° C. then TESOTf, -50° C., 78%; LDA, THF, -33° C., 5 min.

The route disclosed herein is based on four findings. The first is the ease of formation and the synthetic utility of the Z-lithium enolate (48A) readily produced from 59 as shown in FIG. 61(A). In this easily obtained construct, the critical enolate of the ethyl ketone is fashioned in the context of a putative β,δ-diketoester ensemble embracing carbons 1–6 of the target (cf. structure 47). The advantages of this direct approach for synthetic economy are apparent.

The second and most surprising finding undergirding this synthesis is that the sense of addition of enolate 48A to readily available S-aldehyde 58 provides the desired C7-C8 anti relationship with good diastereofacial selectivity in conjunction with the expected C6-C7 syn relationship (by Ik-addition). C. H. Heathcock, in *Asymmetric Synth.* J. D. Morrison, Ed., Academic Press, New York, 1984, Vol. 3, p.111–212; see compound 49 and its stereoisomer. The stereochemistry of the minor diastereomer was presumed to be C7-C8 syn, but was not rigorously proven. This was based on precedent (Mori, I., et al., *J. Org. Chem.,*1990, 55, 1114), assuming that this isomer arises from facial selectivity in the aldol reaction, not as a consequence of the E-enolate of 48A. Those assignments also rely to varying extents on the Heathcock precedent. The 5.5:1 outcome for the diastereofacial selectivity of this aldol reaction is counter to expectations arising from the traditional models first advanced by Cram and Felkin. (For transition state models in diastereomeric carbonyl addition reactions see: D. J. Cram, F. A. Elhafez, *J. Am. Chem. Soc.* 1952, 74, 5828; D. J. Cram, K. R. Kopecky, *J. Am. Chem. Soc.* 1959, 81, 2748; J. W. Cornforth, R. H., et al., *J. Am. Chem. Soc.* 1959, 81, 112; G. J. Karabatsos, *J. Am. Chem. Soc.* 1967, 89, 1367; M. Cherest, H. Felkin, N. Prudent, *Tetrahedron Lett.* 1968, 2199; N. T. Ahn, O. Eisenstein, *Nouv. J. Chem.* 1977, 1, 61; A. S. Cieplak, *J. Am. Chem. Soc.* 1981, 103, 4540; E. P. Lodge, C. H. Heathcock *J. Am. Chem. Soc.* 1987, 109, 2819.) These extensively invoked formulations, which differ widely in their underlying conformational assumptions and stereochemical treatments, usually converge in terms of their predicted outcome.

The high anti:syn diastereofacial ratio arises from a peculiar characteristic of aldehyde 58 and likely reflects the relationship of its vinyl and formyl groups. It is not, apparently the result of a gross property of enolate 48A. Indeed, the same enolate, with the benchmark aldehyde phenylpropanal 60a, performs in the expected fashion (C. H. Heathcock in *Asymmetric Synth.* J. D. Morrison, ed., Academic Press, New York, 1984, Vol. 3, p.111–212), yielding an 11:1 ratio of 61a:62a. Furthermore, with aldehyde 60b, the dihydro version of 58, the C7 to C8 anti:syn (61b:62b) ratio drops to 1:1.3. Moreover, when the distance between the vinyl and formyl groups is extended, as in 60c, selectivity is also compromised. By contrast the phenyl and dimethylallyl analogs of 58 (60d and 60e) bearing the same relationship of unsaturated groups as in 58, exhibit good anti-antiselectivity (see products 61d and 61e as well as 62d and 62e). Also, aldehyde 60f, a substrate known for its tendency to favor the anti-diastereofacial product (M. T. Reetz, *Angew. Chem. Int. Ed. Engl.* 1984, 23, 556) on the basis of presumed chelation control, performs normally with enolate 48A affording a 1:4 ratio of 61f:62f.

With respect to the impact of the strong anti:syn diastereofacial selectivity in the aldol reaction of 58 and 48A on the overall efficiency of the synthesis, the rather favorable result in establishing the C7-C8 bond opened the possibility that the C1-C7 fragment could be entered into the synthesis as an achiral block. Accordingly, it would be necessary to gain control over the eventual stereochemistry at C3. This subgoal was to be accomplished by the implementation of any asymmetric, reagent controlled Noyori reduction (vide infra). Noyori, R., et al., *J. Am. Chem. Soc.* 1987, 109, 5856; Taber, D. F., Silverbert, L., *Tetrahedron Lett.* 1991, 32, 4227; Ager, D. J., Laneman, S., *Tetrahedron Asymmetry* 1997, 8, 3327.

Figure 61B:
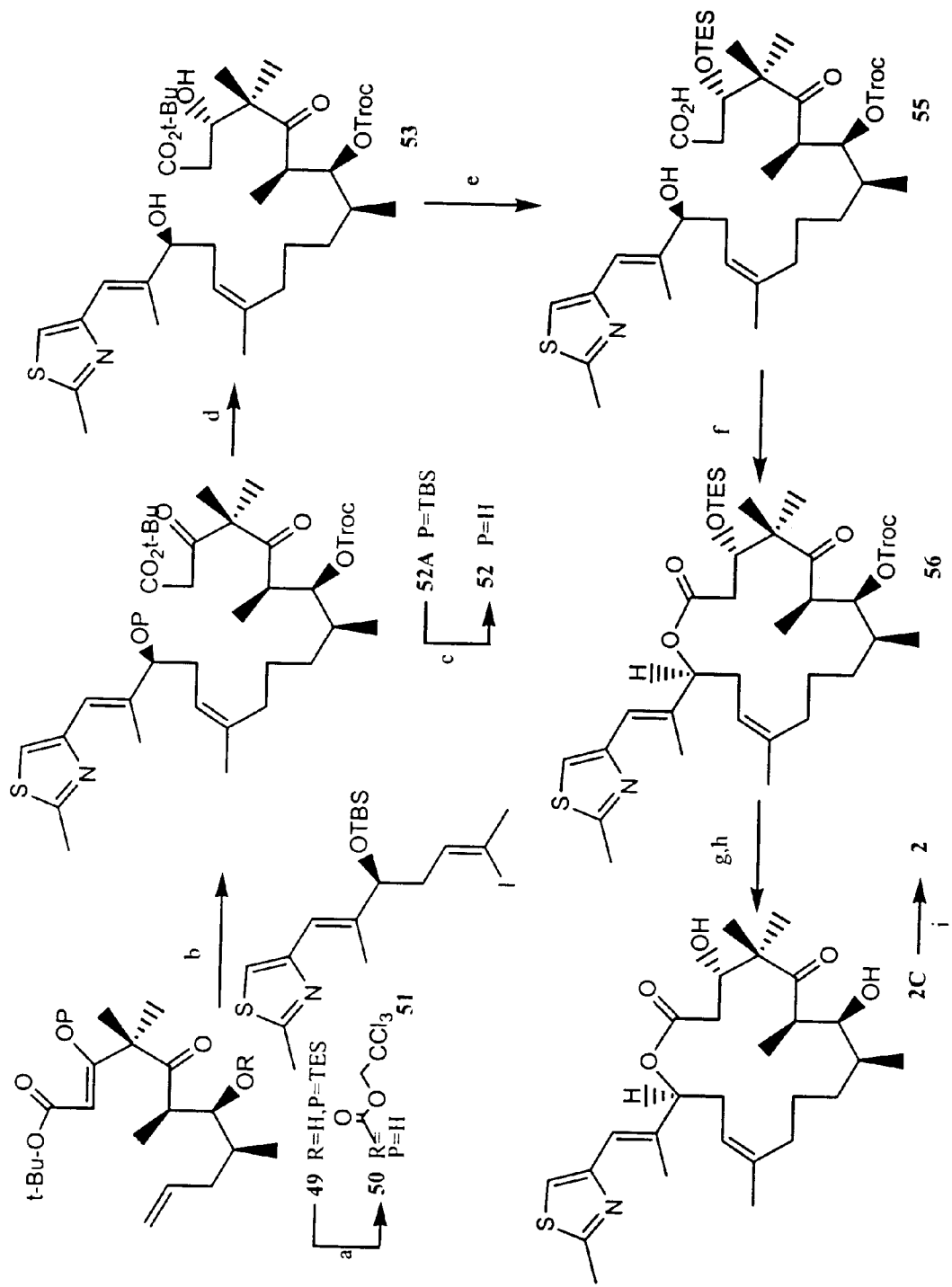
FIG. 61(B) shows a procedure for preparing desoxyepothilone B. [a]TrocCl, pyridine, CH$_2$Cl$_2$, 0° C.→25° C.; then 0.5N HCl in MeOH, 0° C., 87%; [b]9-BBN, THF, 50 then 51, (Pd(dppf)$_2$)Cl$_2$, Ph$_3$As, Cs$_2$CO$_3$, H$_2$O, DMF; [c]0.4N HCl in MeOH (50% for two steps); [d](R)-(BINAP)RuCl$_2$, H$_2$ (1200 psi), MeOH, HCl, 25° C., 7 h, 88%, >95:5; [e]TESOTf, 2,6-lutidine, CH$_2$Cl$_2$, -78→25° C., then HCl/MeOH, 77%; [f]2,4,6-trichlorobenzoyl chloride, TEA, 4-DMAP, toluene, 78%; [g]SmI$_2$, cat. NiI$_2$, THF, -78° C., 95%; [h]HF.pyridine, THF, 98%; [i]2,2-dimethyldioxirane, CH$_2$Cl$_2$, -50° C., 98%, >20:1.
Figure 62:
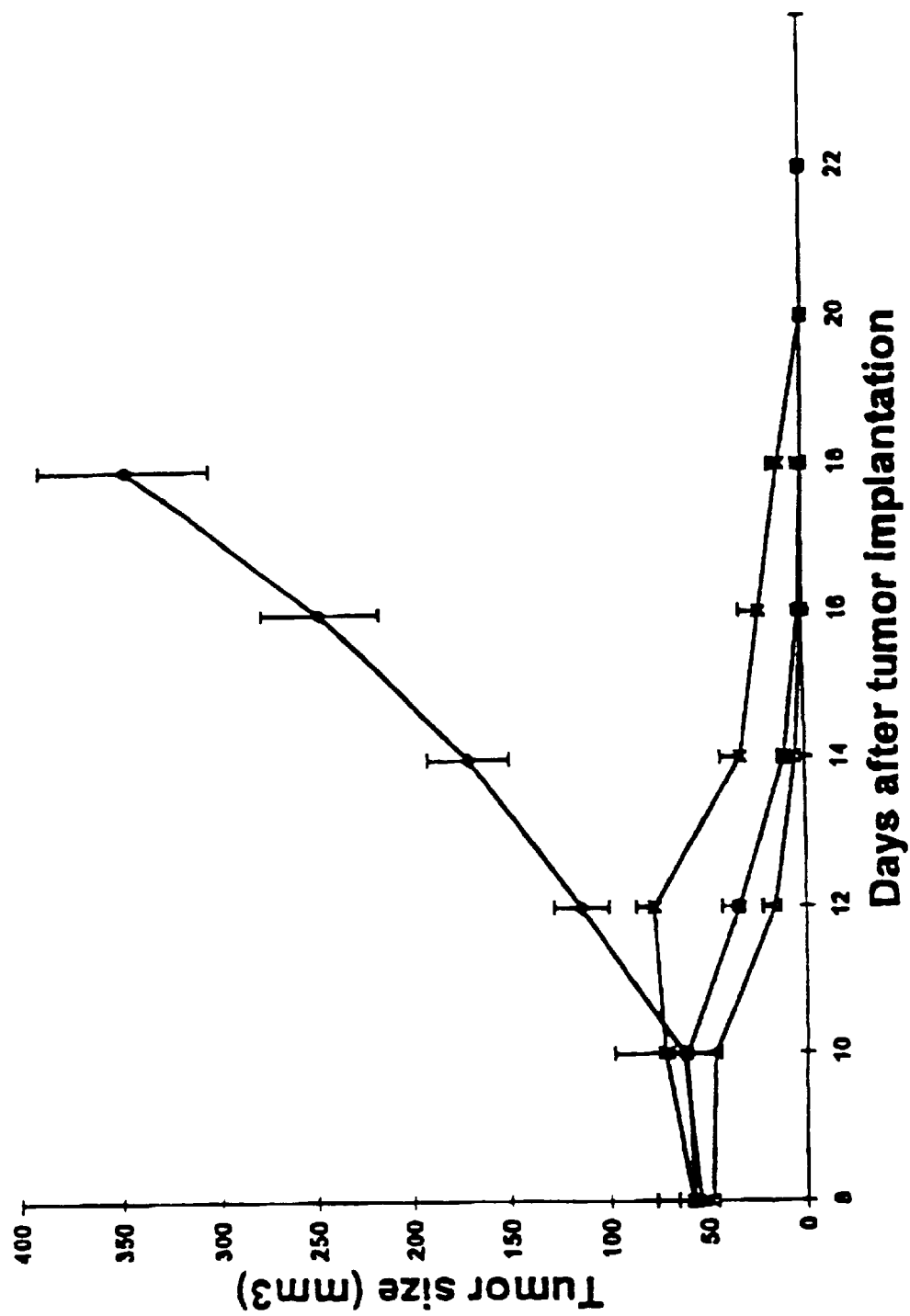
FIG. 62 shows the therapeutic effect of dEpoB and Taxol® in nude mice bearing MX-1 with Q2Dx5 i.v. 6 h infusion, using dEpoB 30 mg/kg (x), Taxol® 15 mg/kg (■), Taxol® 24 mg/kg (Δ) and control (●).
Figure 63:
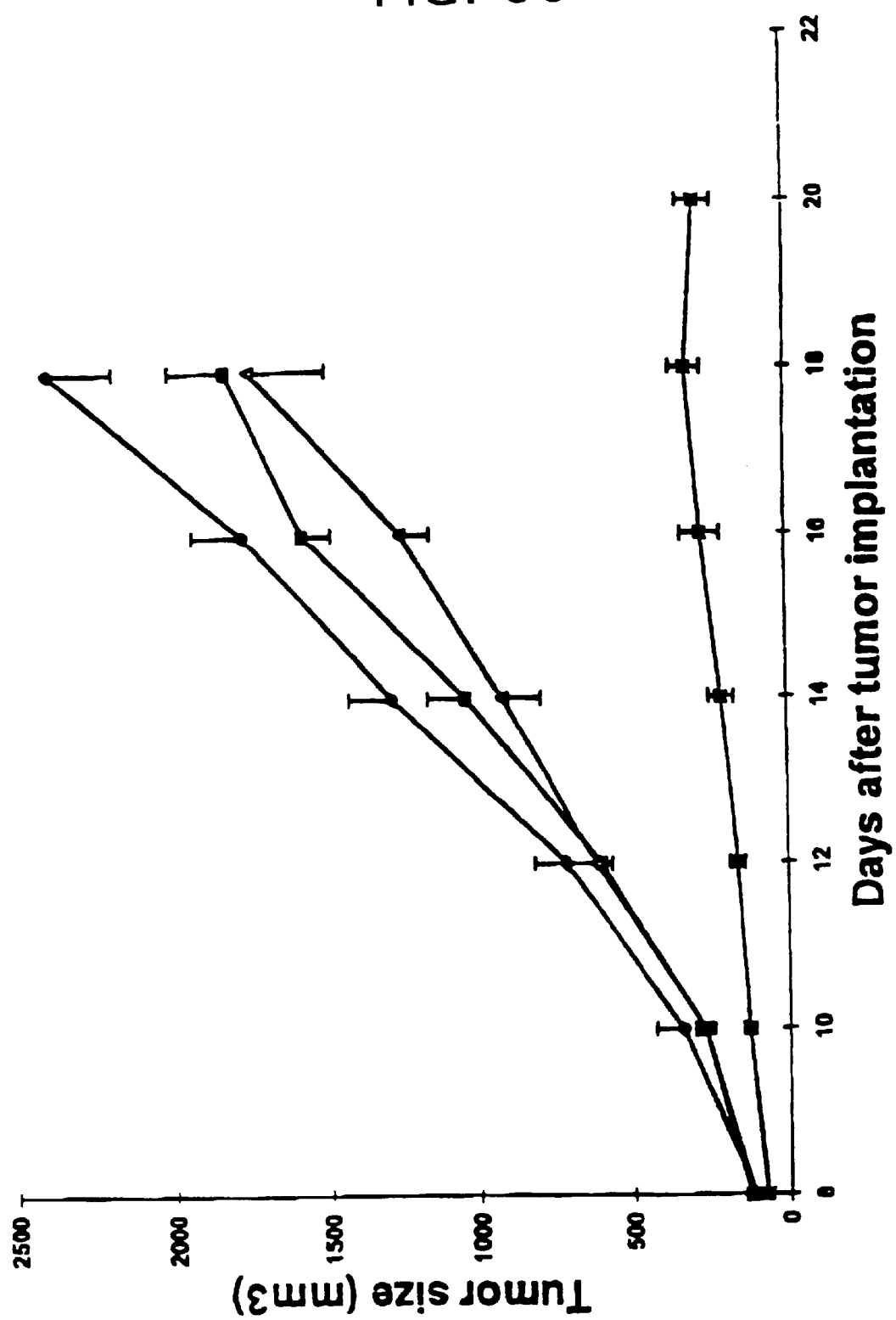
FIG. 63 shows the therapeutic effect of dEpoB and Taxol® in nude mice bearing MCF-7/Adr with Q2Dx5 i.v. 6 h infusion, using dEpoB 30 mg/kg (x), Taxol® 15 mg/kg (■), Taxol® 24 mg/kg (Δ) and control (●).
Figure 64:
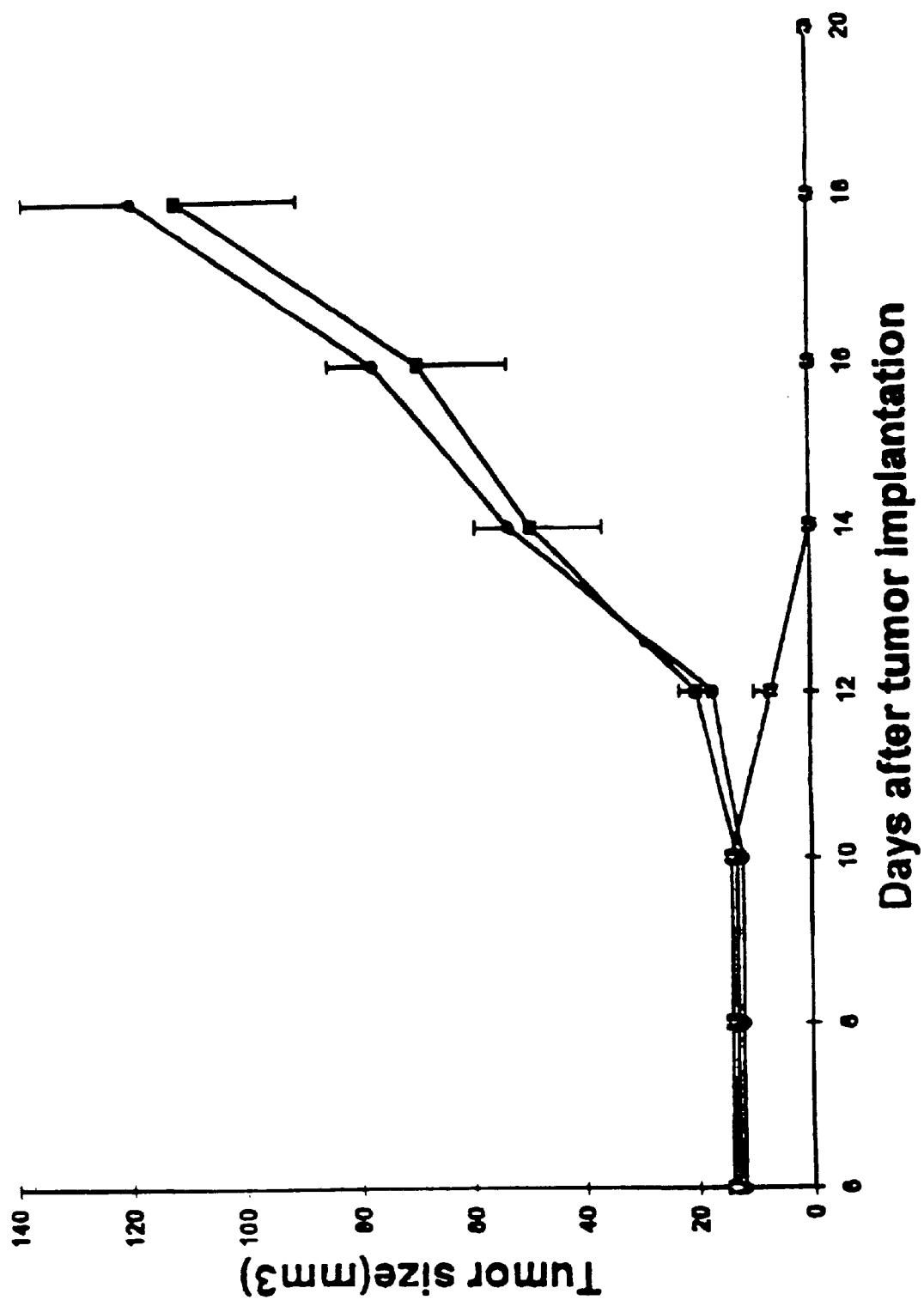
FIG. 64 shows the therapeutic effect of dEpoB and Taxol® in nude mice bearing CCRF/Taxol® with Q2Dx5 i.v. 6 h infusion, using dEpoB 30 mg/kg (x), Taxol® 20 mg/kg (■), Taxol® 24 mg/kg (Δ) and control (●). Treatment on days 6, 8, 10, 12 and 14.
Figure 65A:
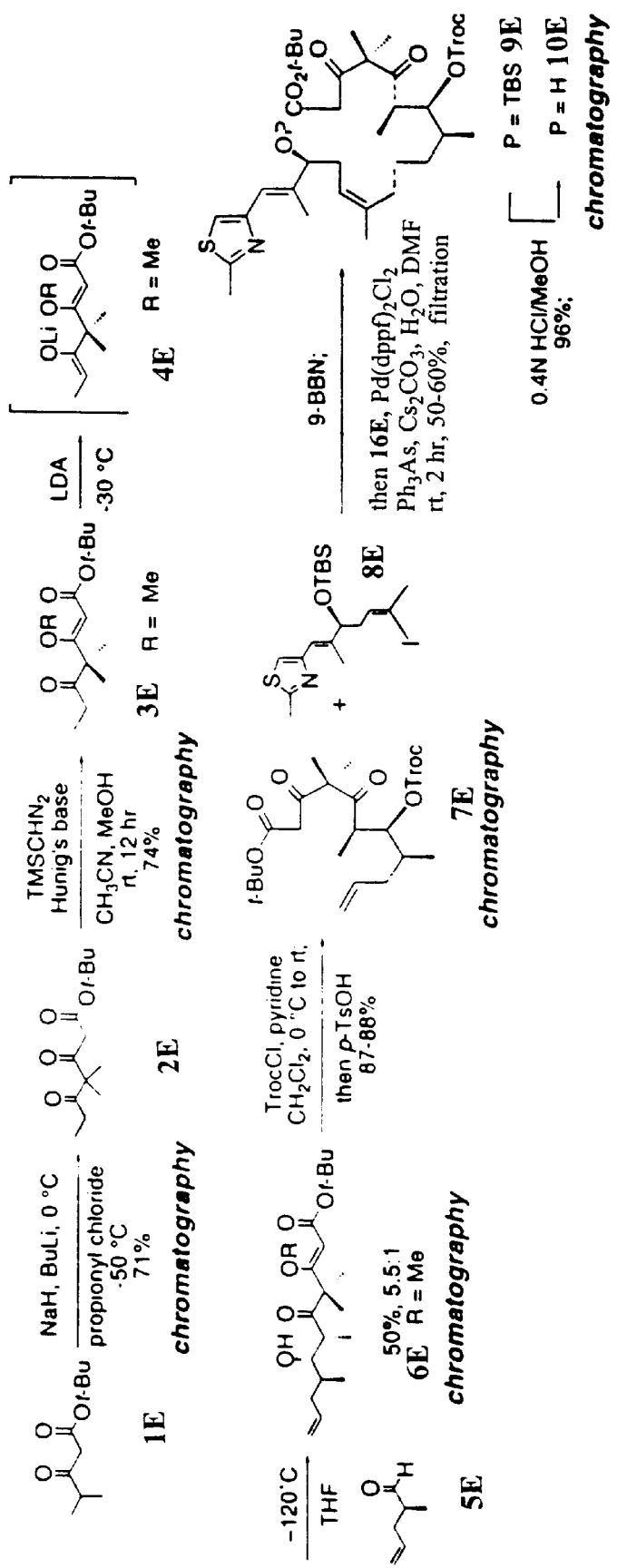
FIGS. 65(A) and 65(B) show a procedure for preparing desoxyepothilone B (14E).
Figure 65B:
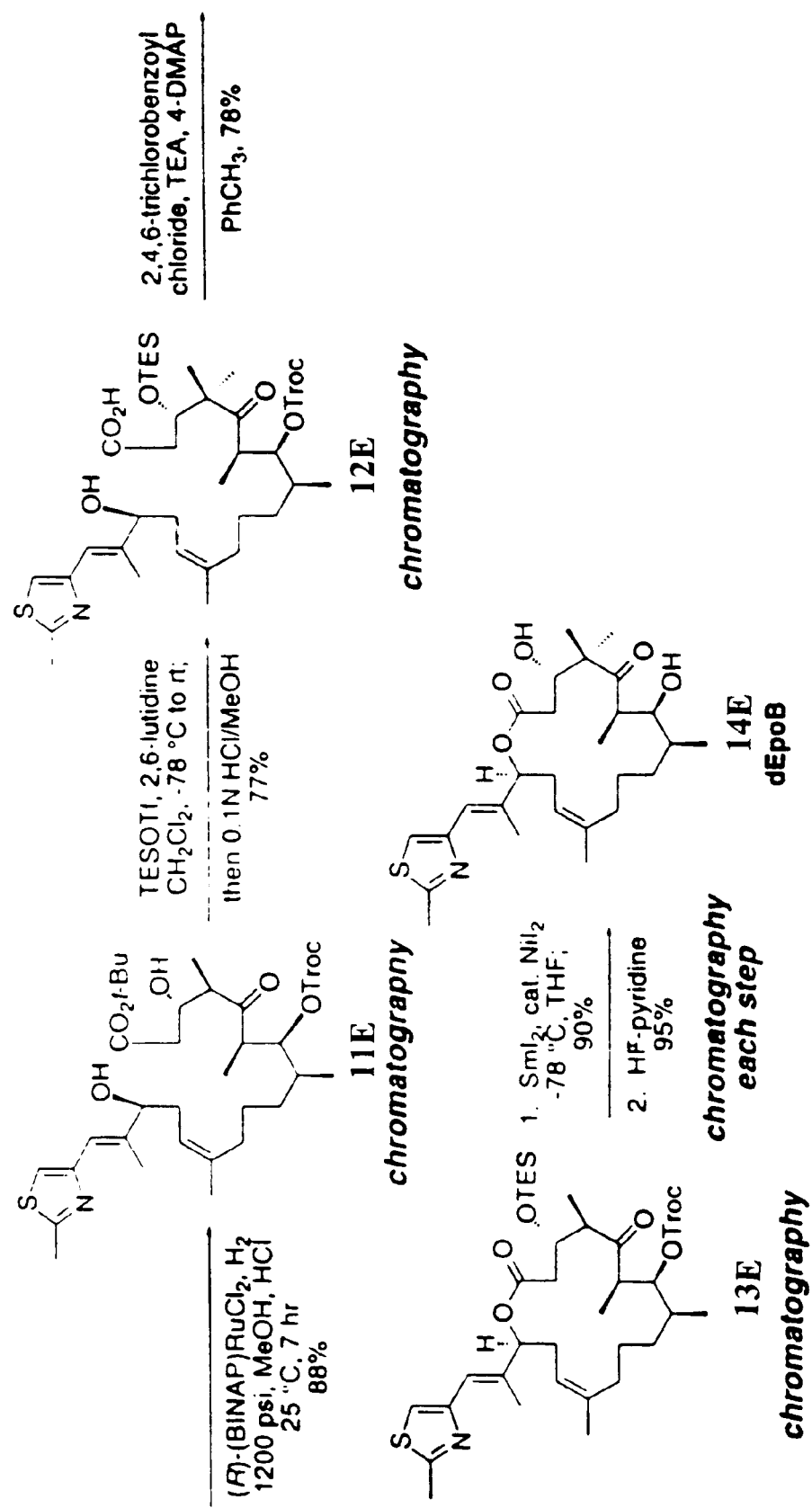
Figure 66A:
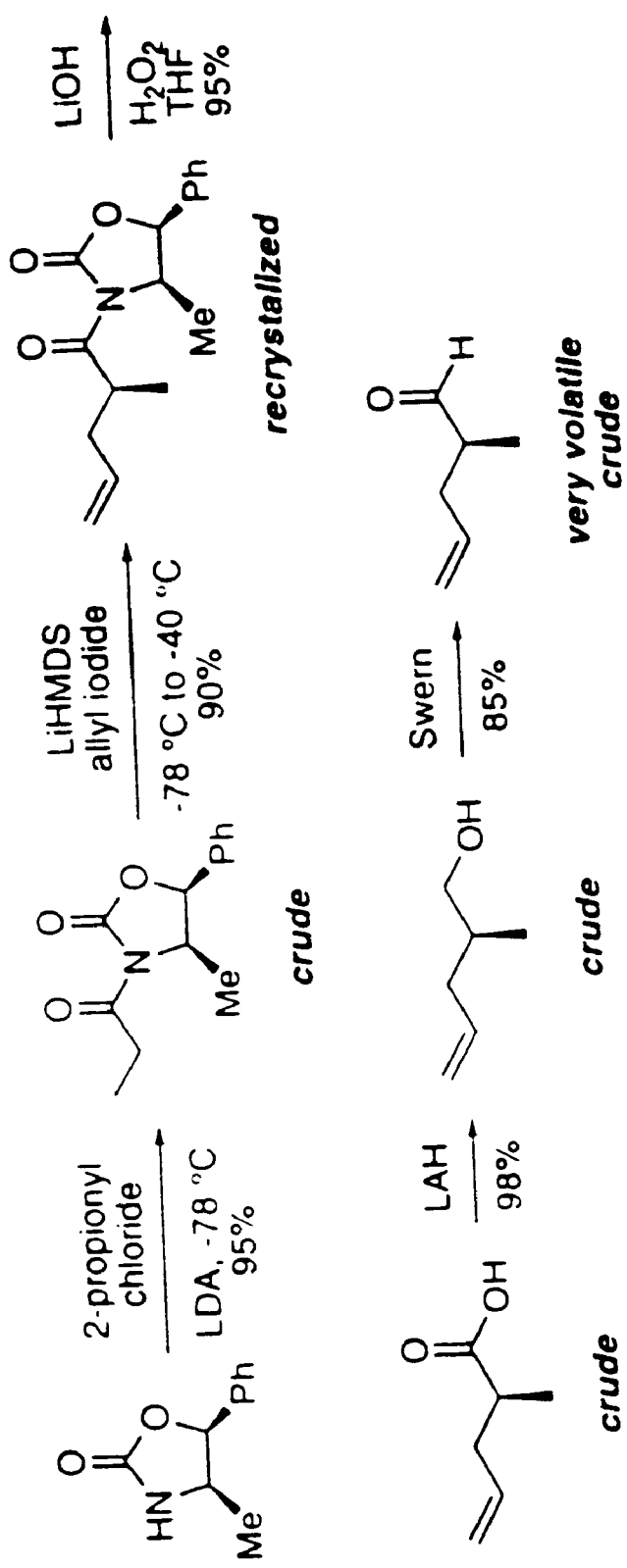
FIGS. 66(A) and 66(B) show a procedure for preparing intermediate 8E.
Figure 66B:
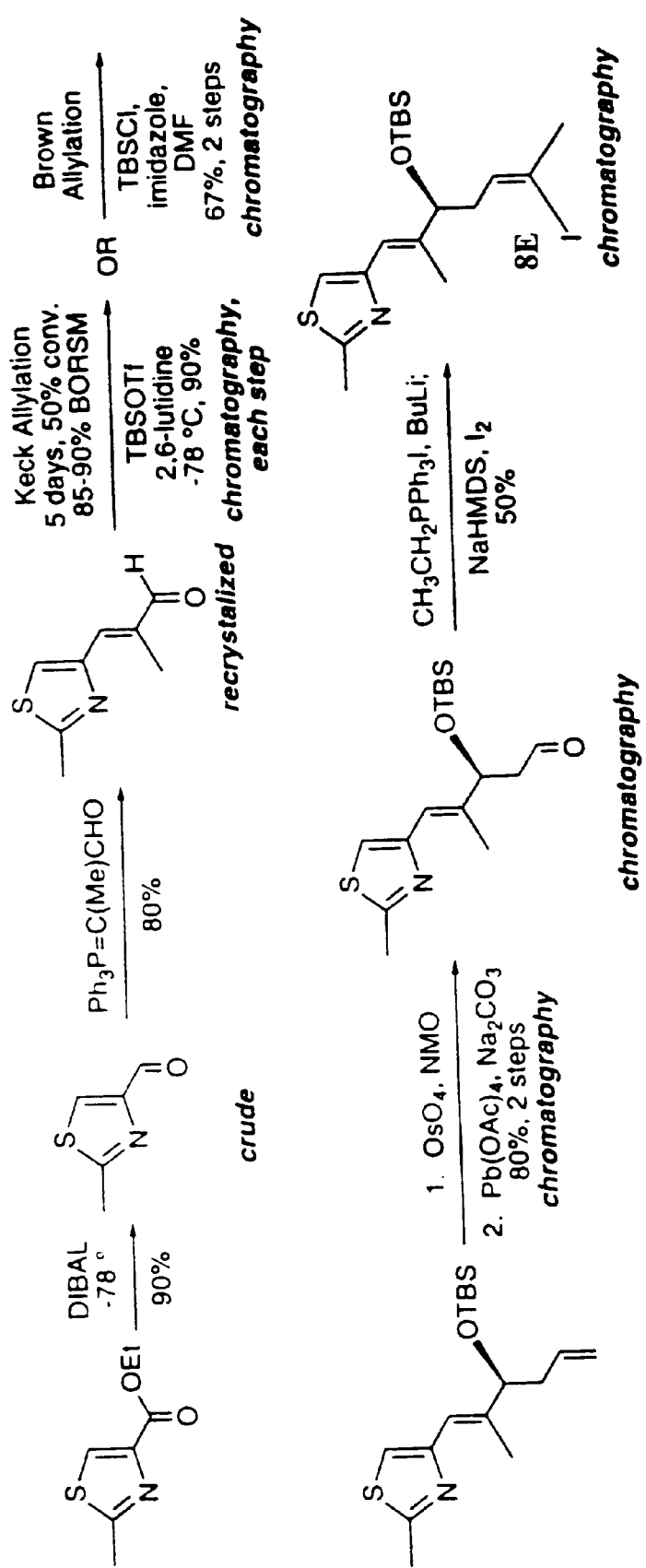
Figure 67:
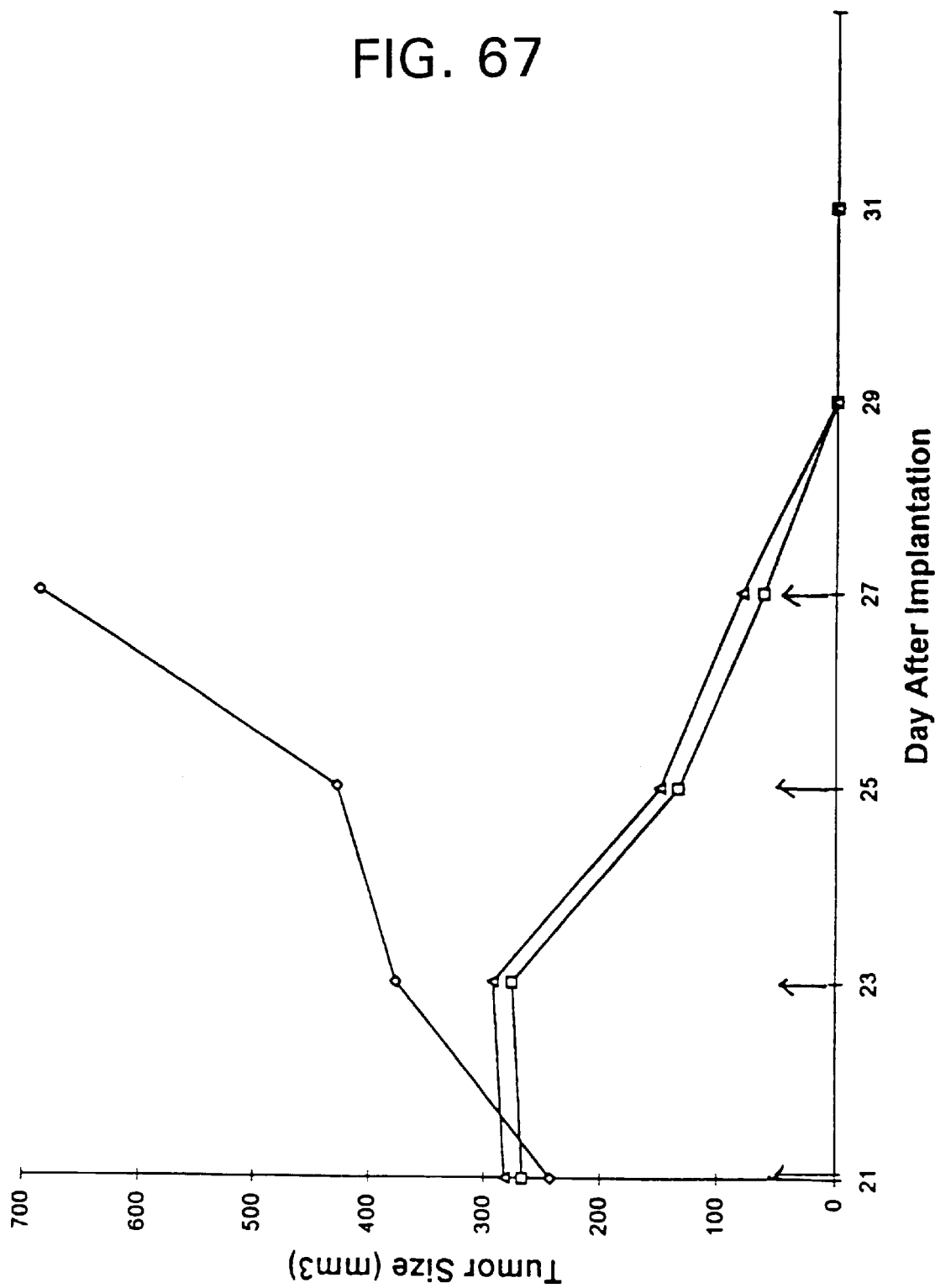
FIG. 67 shows the therapeutic effect of dEpoB and Taxol® in nude mice bearing CCRF/CEM tumor with Q2Dx4 i.v. 6 h infusion, using dEpoB 30 mg/kg (□), Taxol® 20 mg/kg (Δ), and control (◇). Treatment on days 21, 23, 25, and 27.
Figure 68:
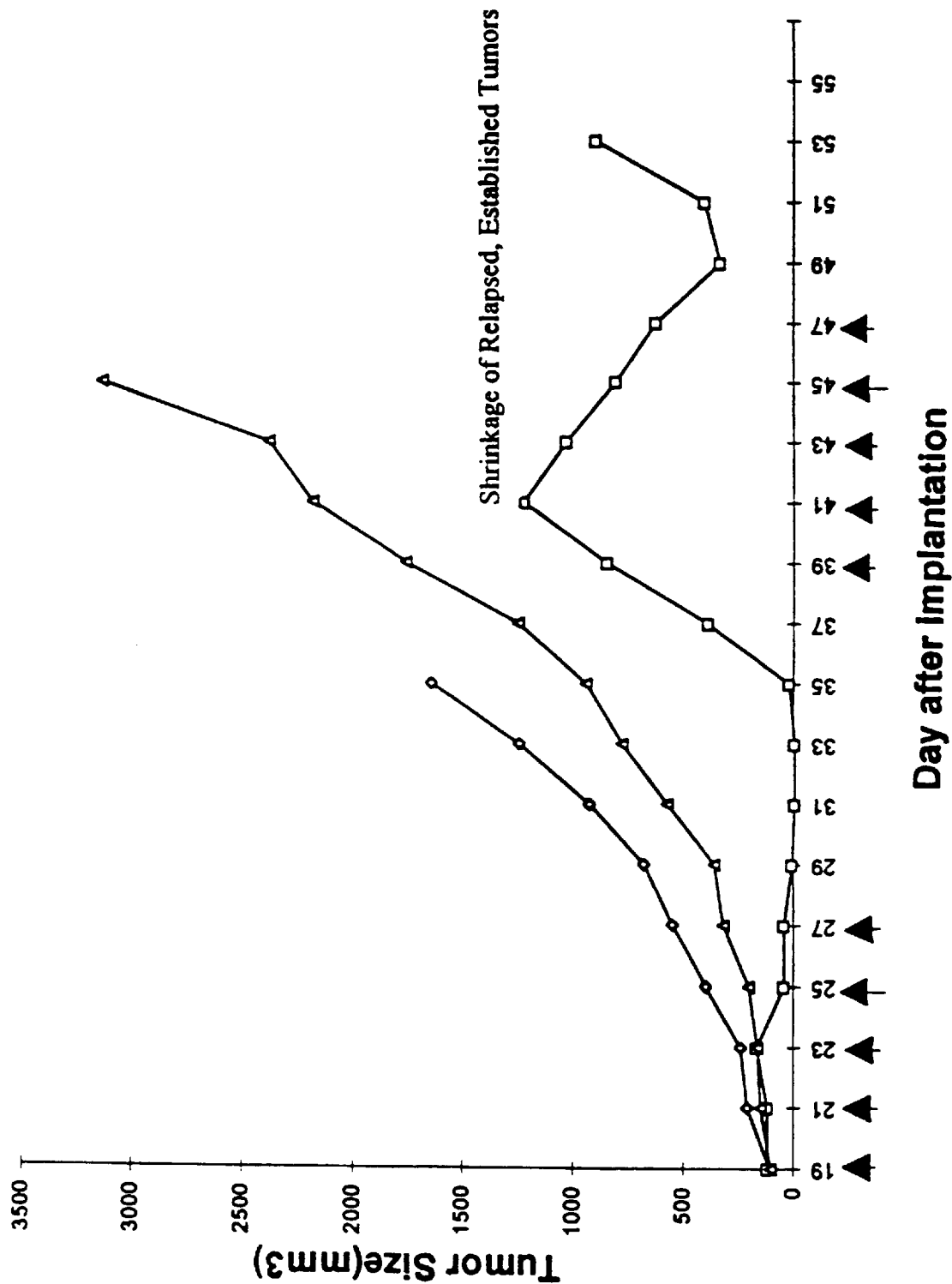
FIG. 68 shows the therapeutic effect of dEpoB and Taxol® in nude mice bearing CCRF/Taxol® with Q2Dx5 i.v. 6 h infusion, using using dEpoB 30 mg/kg (□), Taxol® 20 mg/kg (Δ) and control (◇). Treatment on days 19, 21, 23, 25, 27, 39, 41, 43, 45 and 47.
Figure 69:
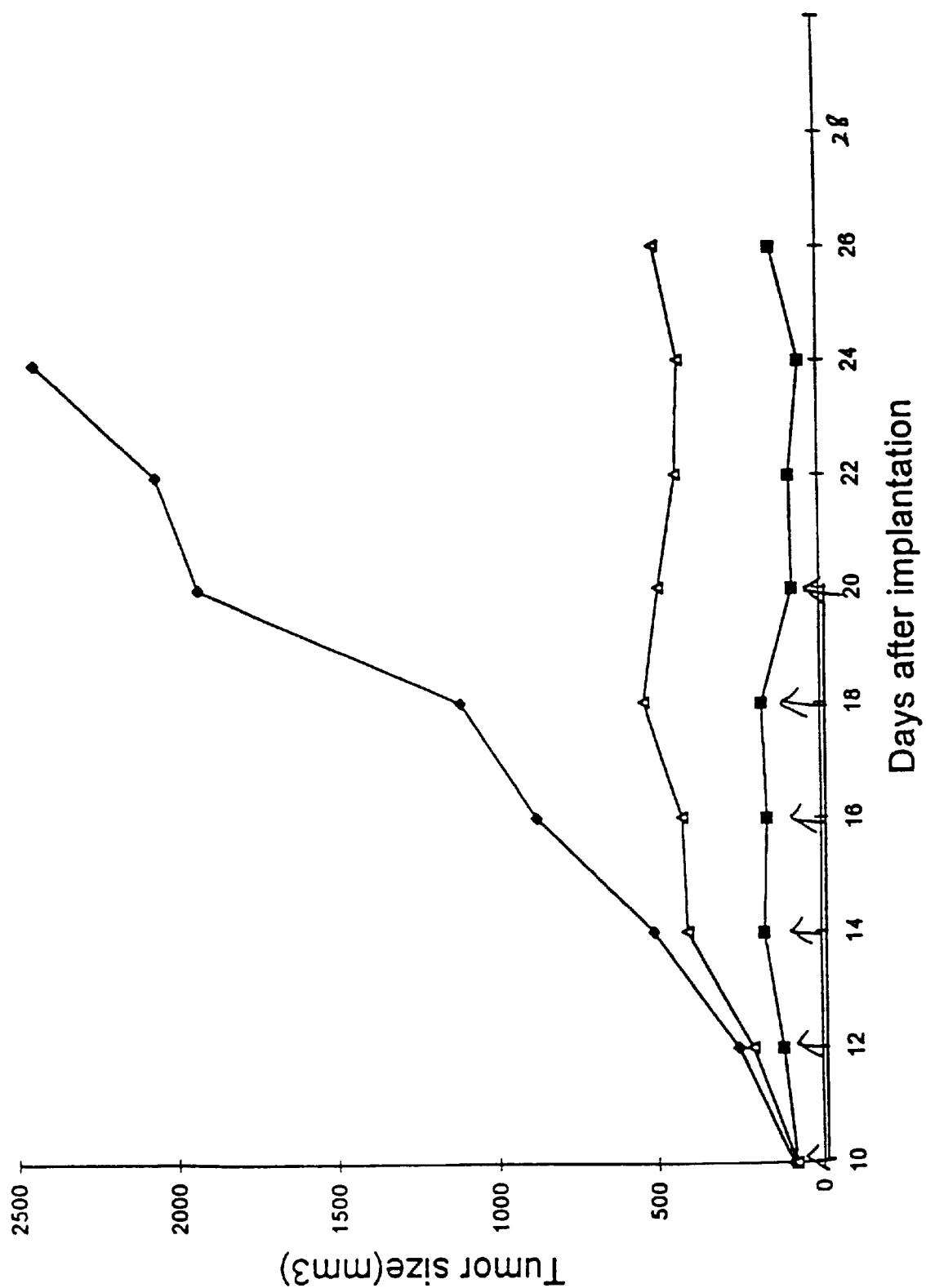
FIG. 69 shows the therapeutic effect of dEpoB and Taxol® in nude mice bearing SK-OV-3 Tumor with Q2Dx6 i.v. 6 h infusion, using dEpoB 30 mg/kg (Δ), Taxol® 15 mg/kg (□), and control (◇). Treatment on days 10, 12, 14, 16, 18 and 20.
Figure 70:
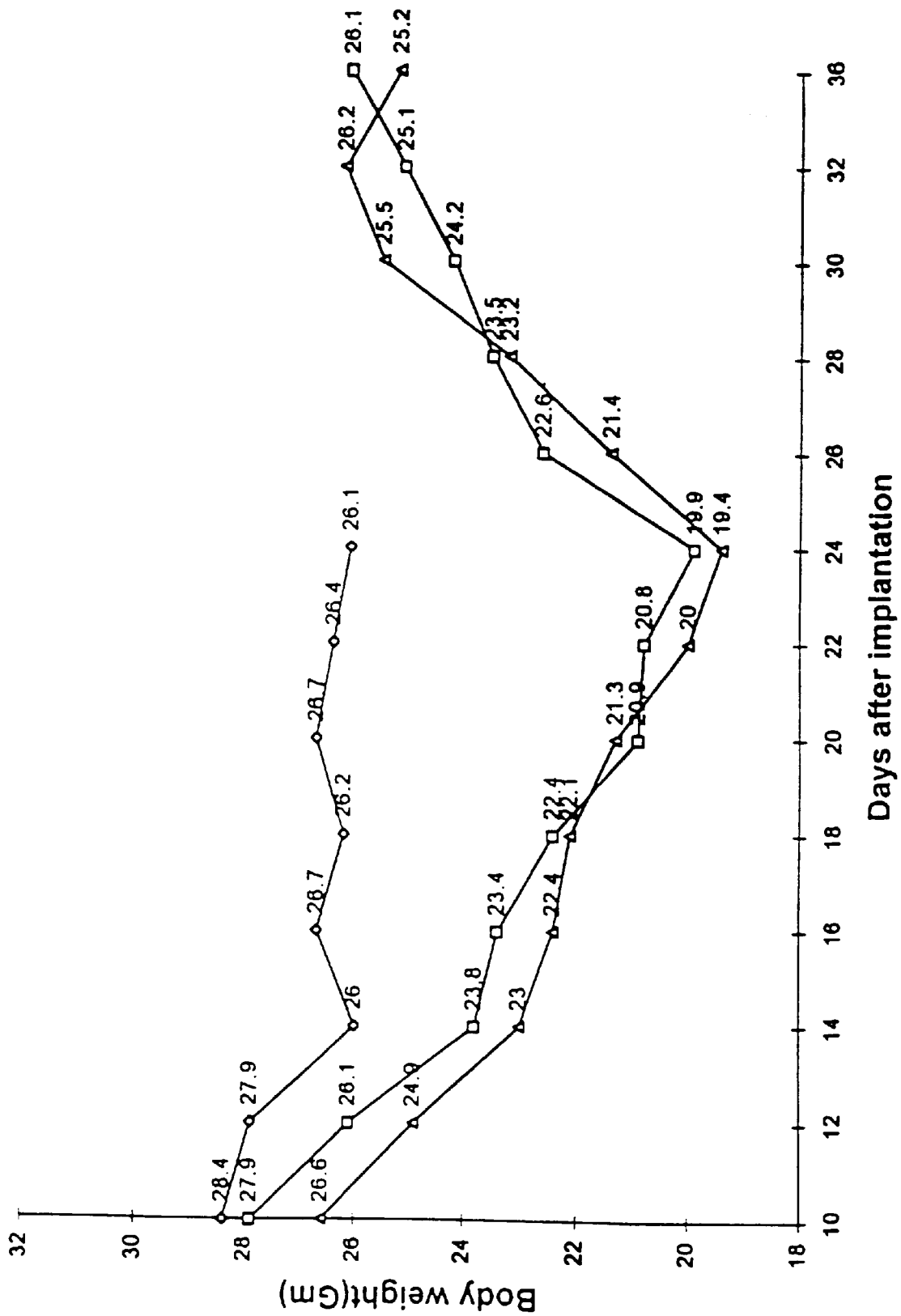
FIG. 70 shows changes in body weight following treatment with desoxyepothilone B and Taxol® in nude mice bearing SK-OV-3 Tumor by i.v. infusion, using dEpoB 30 mg/kg (□), Taxol® 15 mg/kg (Δ) and control (◇).
Figure 71:
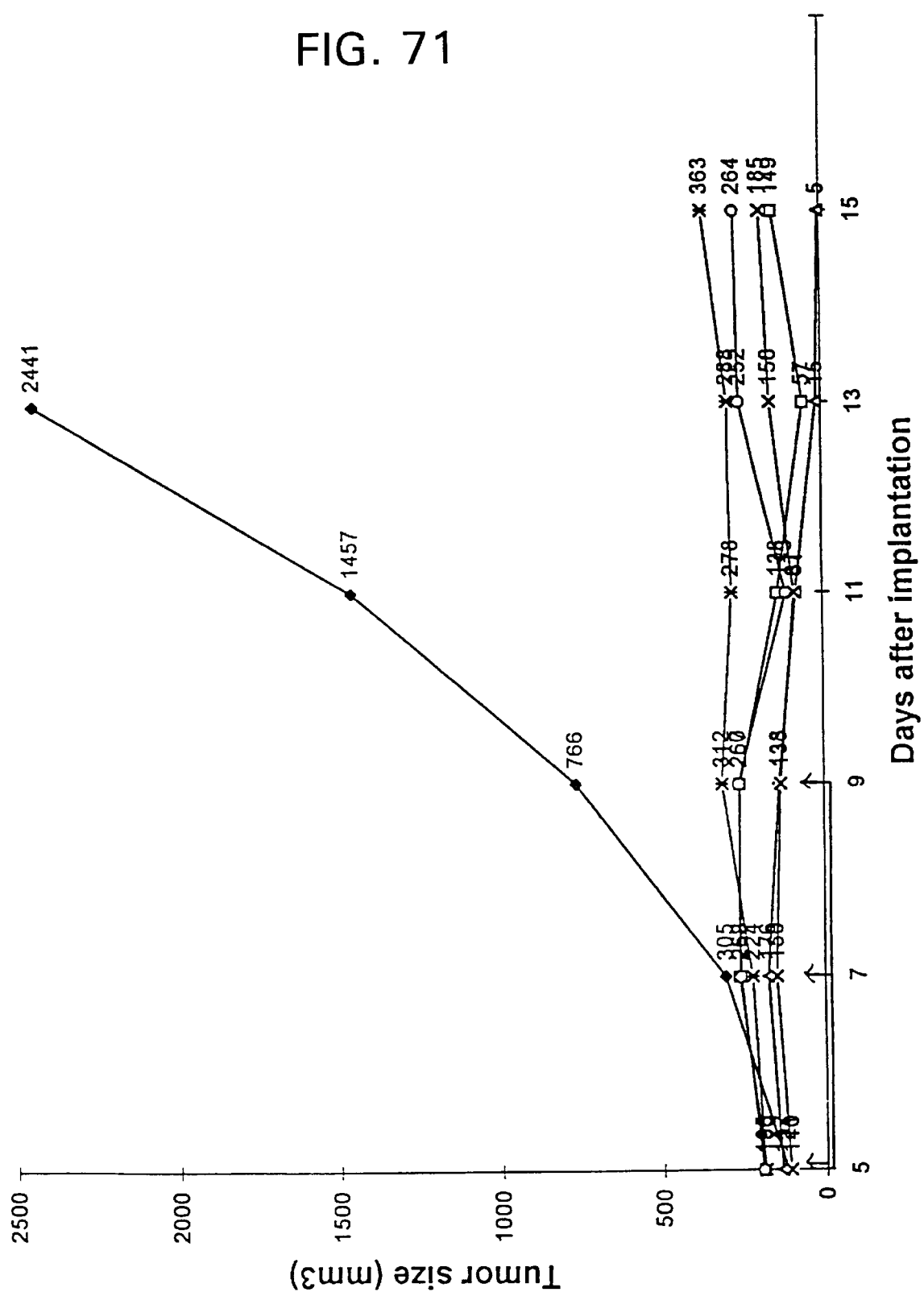
FIG. 71 shows the therapeutic effect of dEpoB and Taxol® in nude mice bearing PC-3 Human Prostate Carcinoma with Q2Dx3 i.v. 6 or 18 h infusion, using dEpoB 30 mg/kg, 18 h (x), dEpoB 40 mg/kg, 6 h (*), dEpoB 50 mg/kg, 6 h (○) Taxol® 15 mg/kg, 6 h (□), Taxol® 24 mg/kg, 6 h (Δ) and control (♦). Treatment on days 5, 7 and 9.
Figure 72:
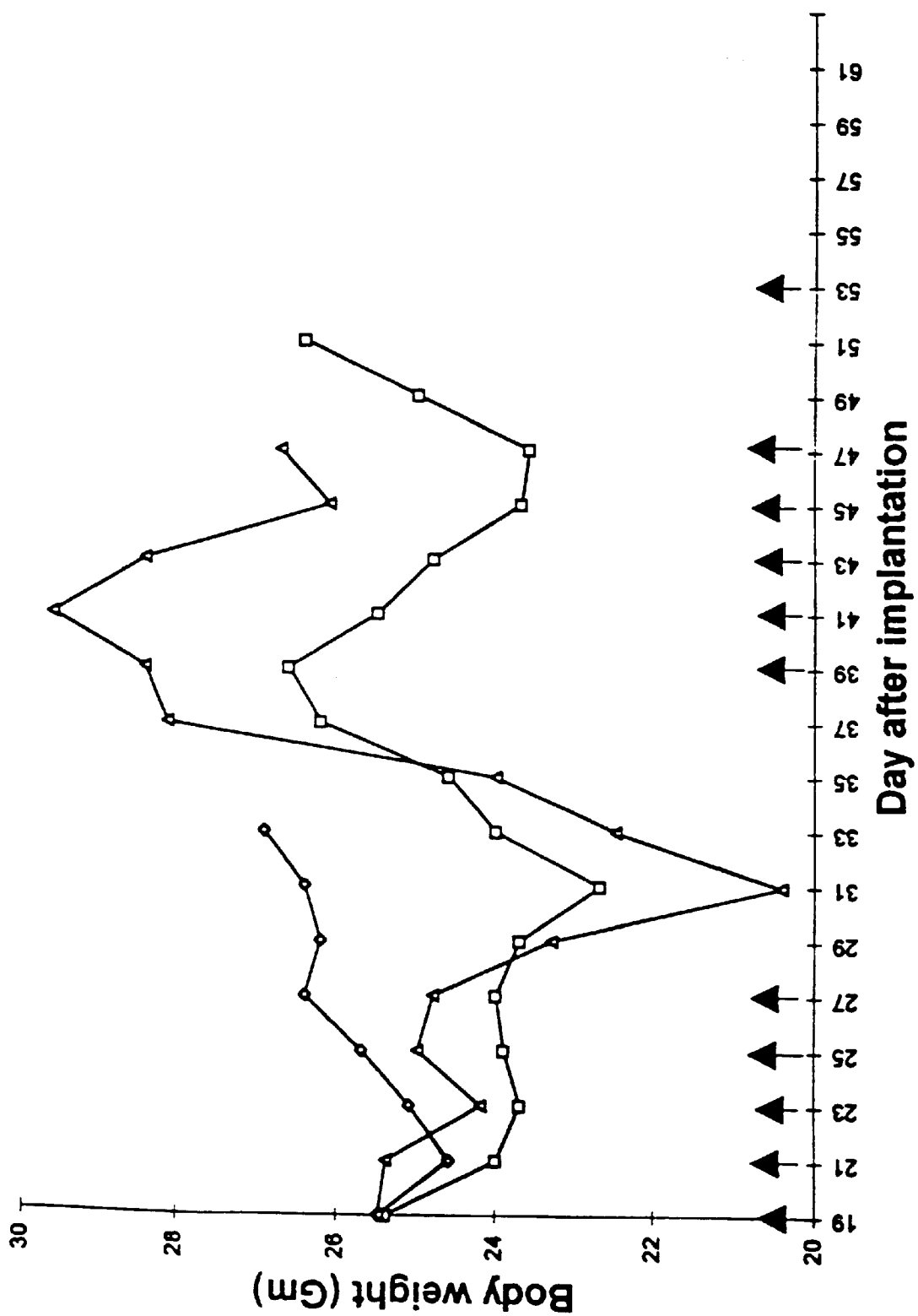
FIG. 72 shows the therapeutic effect of dEpoB and Taxol® in nude mice bearing CCRF-CEM/VBL with Q2Dx5 i.v. 6 h infusion, using using dEpoB 30 mg/kg (□), Taxol® 20 mg/kg (Δ) and control (◇). Treatment on days 19, 21, 23, 25, 27, 39, 41, 43, 45, 47 and 53.
Figure 73:
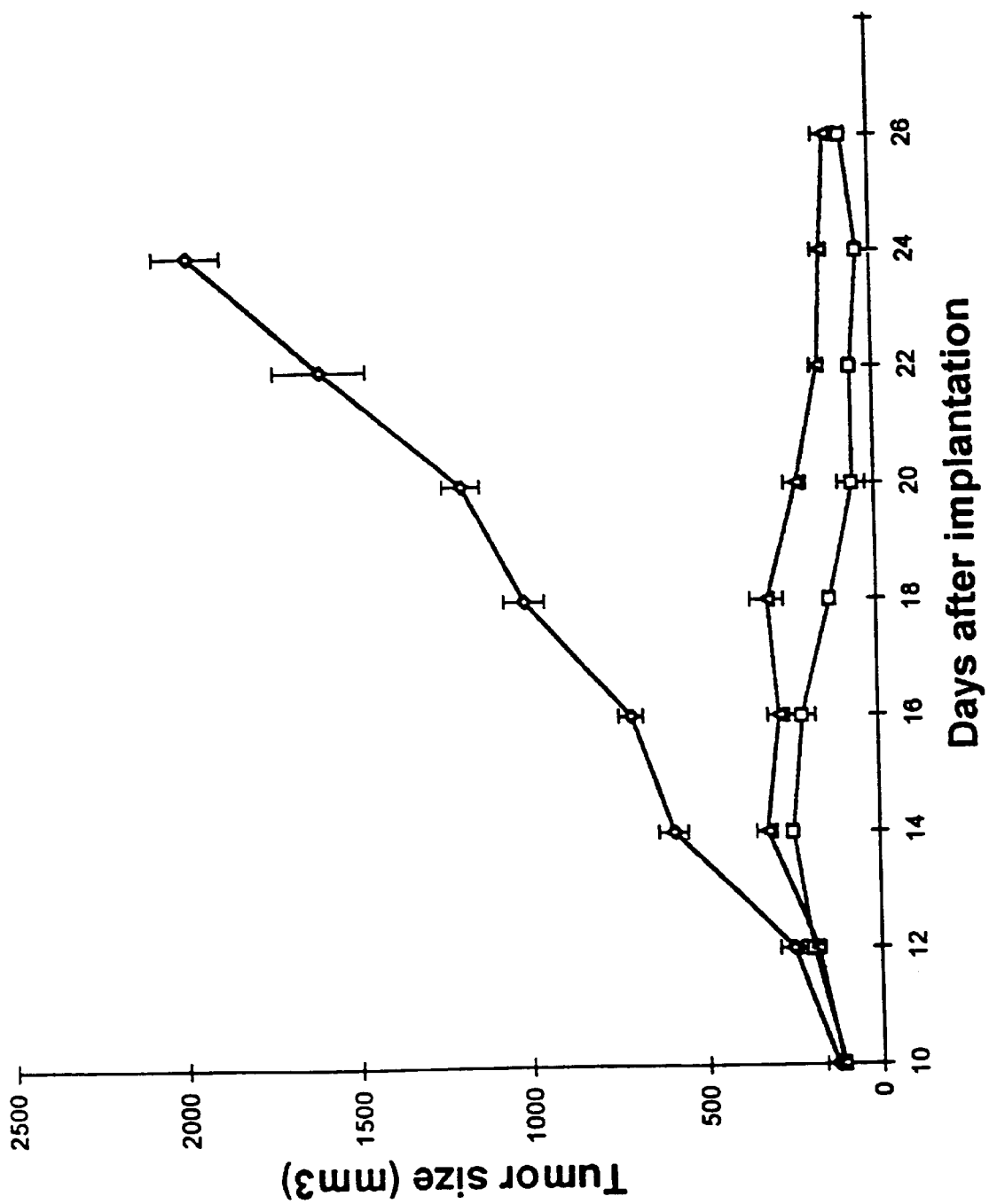
FIG. 73 shows the therapeutic effect of dEpoB and Taxol® in nude mice bearing HT-29 Colon Adenocarcinoma with Q2Dx6 i.v. 6 h infusion, using dEpoB 30 mg/kg (Δ), Taxol® 15 mg/kg (□) and control (◇).
Figure 74:
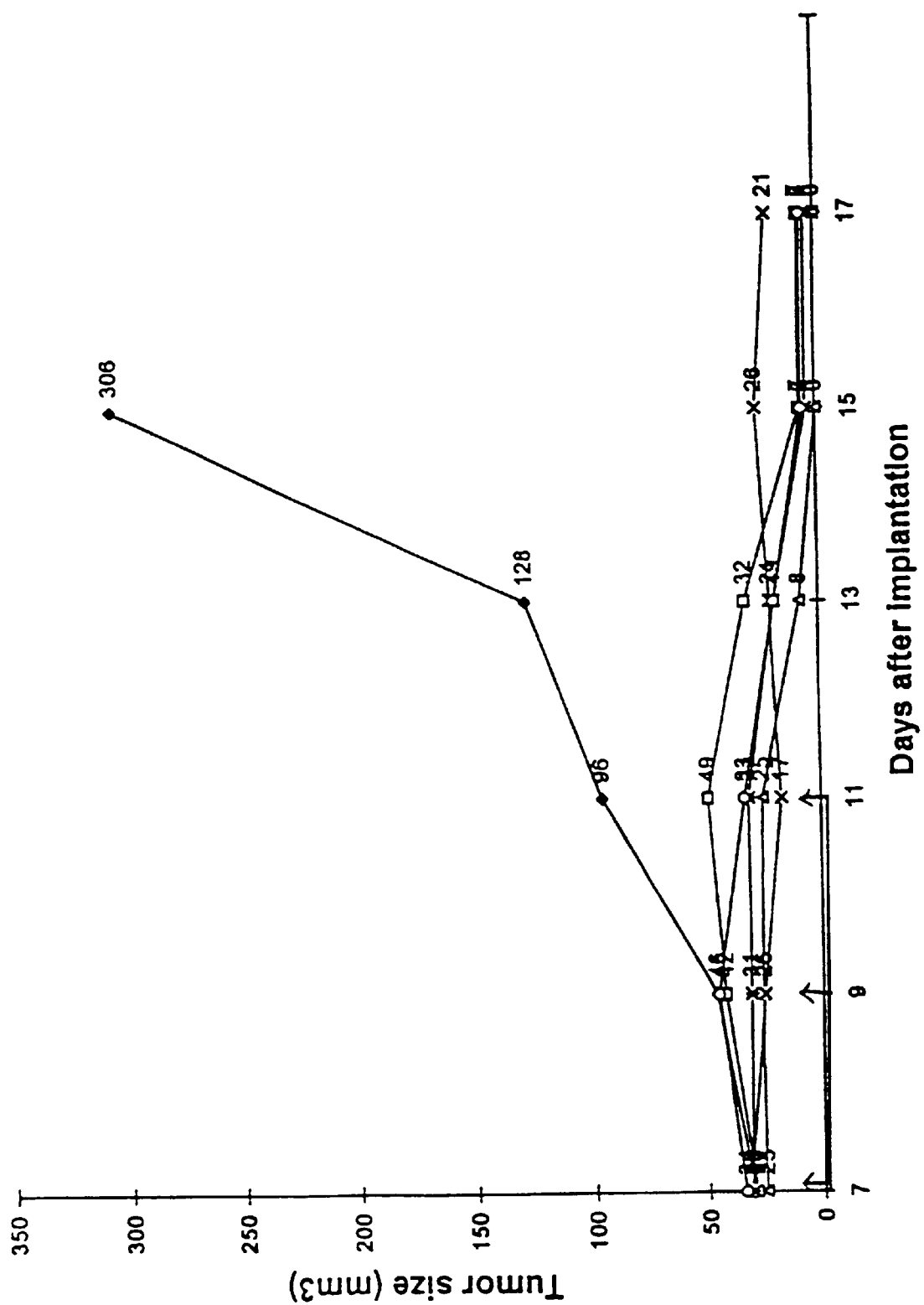
FIG. 74 shows the therapeutic effect of dEpoB and Taxol® in nude mice bearing A549 Human Lung Carcinoma with Q2Dx3 i.v. 6 or 18 h infusion, using dEpoB 30 mg/kg 18 h (x), dEpoB 40 mg/kg, 6 h (*), dEpoB 50 mg/kg, 6 h (○), Taxol® 15 mg/kg, 6 h (□), Taxol® 24 mg/kg, 6 h (Δ) and control (♦). Treatment on days 7, 9 and 11.

The third critical element was the finding that the key B-alkyl Suzuki merger which controls the geometry of the trisubstituted double bond can be conducted successfully ever on the elaborate 51, obtained from 49. The cognate substrate for the Suzuki reaction was the previously described vinyl iodide, 51 (Su, D.-S., et al., *Angew. Chem. Int. Ed. Engl.* 1997, 36, 757). The remarkable coupling step, afforded the Z-olefin 52A and thence, 52 after removal of the C15 silyl protecting group (FIG. 61(B)). The β,δ-disketo ester array in 52 responded well to asymmetric catalytic reduction under modified Noyori conditions (Taber, D., Silverbert, L. J., *Tetrahedron Lett.* 1991, 32, 4227) to give the diol 53 (88%, >95:5). Strict regiochemical and diastereofacial control in the Noyori reduction was very dependent on the amount of acid present in the reaction. Without acid, the rate of reduction dropped off as well as the selectivity in the reduction. Further, the carbonyl at C-5 was never reduced under these conditions but was absolutely necessary for the reduction of the C-3 carbonyl. When C-5 was in the alcohol oxidation state, no reduction was seen. The conversion of 53 to desoxyepothilone B and thus epothilone B was accomplished by methodologies set forth herein. Balog, A., et al., *Angew. Chem. Int. Ed. Engl.* 1996, 35, 2801; Su, D.-S., et al., *Angew. Chem. Int. Ed. Engl.* 1997, 36, 757; Meng, D., et al., *J.Am. Chem Soc.* 1997, 119, 10073.

Biological Results

In the tables which follow, model system I is desoxyepothilone. Model system 2 has the structure:

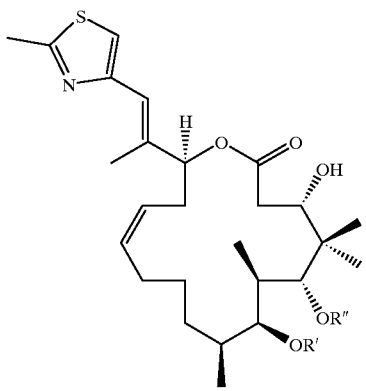

Model system 3 has the structure:

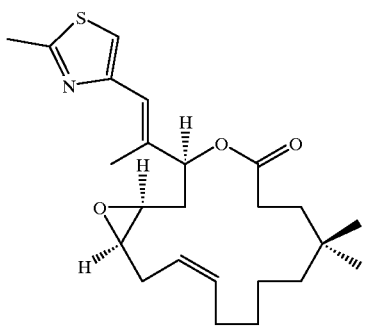

As shown in Table 2A, CCRF-CEM is the parent cell line. CCRF-CEM/VBL (MDR cell line) is 1143-fold resistant to Taxol®. CCRF-CEM/VM (Topo II mutated cell line) only 1.3-fold resistant to Taxol®.

In terms of relative potency, synthetic Epothilone is roughly the same as natural Epothilone A.

For CCRF-CEM cells, the ordering is:

Taxol®≈Epothilone A>Desoxy Epothilone A>>Triol Analog>>Model System I

For CCRF-CEM/VBL, the relative potency ordering is:

Desoxy Epothilone A≧Epothilone A>>Taxol®>Triol Analog>Model System I

For CCRF-CEM/VM, the relative potency ordering is:

Taxol®≈Epothilone A>Desoxy Epothilone A>>Model System I>Triol Analog

It is concluded that CCRF-CEM/VM cells are collaterally sensitive to certain epothilone compounds.

TABLE 2

Relative Efficacy of Epothilone Compound Against HumanLeukemic CCRF-CEM Cell Growth and Against CCRF-CEM MDR Sublines Resistant to Taxol ® or Etoposide

| | $IC_{50}$ in $\mu M$ | | |
|---|---|---|---|
| COMPOUND | CCRF-CEM | CCRF-CEM/VLB | CCRF-CEM/VM-1 |
| EPOTHILONE A NATURAL | 0.0035 | 0.0272 | 0.0034 |
| EPOTHILONE A SYNTHETIC | 0.0029 | 0.0203 | 0.0034 |
| MODEL SYSTEM 1 [3] | 271.7 | 22.38 | 11.59 |
| TRIOL ANALOG [2] | 14.23 | 6.28 | 43.93 |
| DESOXY EPOTHILONE [1] | 0.002 | 0.012 | 0.013 |
| Taxol ® | 0.0023 | 2.63 | 0.0030 |
| VINBLASTINE | 0.00068 | 0.4652 | 0.00068 |
| VP-16 (ETOPOSIDE) | 0.2209 | 7.388 | 34.51 |

TABLE 2A

Relative Potency of Epothilone Compounds Against Human Leukemic CCRF Sublines

| COMPOUND | CCRF-CEM (Parent Cell Line) $IC_{50}$ [$IC_{50}$ ($\mu M$) relative to (A) Epothilone A] | | CCRF-CEM/VBL (MDR Cell Line) (Taxol ® Resistant)-(1143 fold) (Vinblastine Resistant) $IC_{50}$ [$IC_{50}$ ($\mu M$) relative to (B) Epothilone A (B)/(A)] | | | CCRF-CEM/VM$_1$ (Topo II gene mutated cell line) (Taxol ® Sensitive) (VP-16 resistant) $IC_{50}$ [$IC_{50}$ ($\mu M$) relative to (C) Epothilone A (C)/(A)] | | |
|---|---|---|---|---|---|---|---|---|
| Taxol ® | 0.0023 | [0.72] | 2.63 | [109.6] | (1143)[a] | 0.0030 | [0.88] | (1.30)[a] |
| MODEL SYSTEM I | 271.7 | [84906] | 22.38 | [932.5] | (0.082)[b] | 11.59 | [3409] | (0.043)[b] |
| TRIAL ANALOG | 14.23 | [4447] | 6.28 | [261.7] | (0.44)[b] | 43.93 | [12920] | (3.09)[a] |
| DESOXYEPO-THILONE A | 0.022 | [6.9] | 0.012 | [0.5] | (0.55)[b] | 0.013 | [3.82] | (0.59)[b] |
| EPOTHILONE A | 0.0032 | [1] | 0.024 | [1] | (7.5)[a] | 0.0034 | [1] | (1.06)[a] |

[a](B)/(A) or (C)/(A) ratio >1 indicates fold of resistance when compared with the parent cell line.
[b](B)/(A) or (C)/(A) ratio <1 indicates fold of collateral sensitivity when compared with the parent cell line.

TABLE 3

Relative Efficacy of Epothilone Compounds Against The DC-3F Hamster Lung Cell Growth and Against DC-3F MDR Sublines Resistant Actinomylin D

| COMPOUNDS | $IC_{50}$ in $\mu M$ | | |
|---|---|---|---|
| | DC-3F | DC-3F/ADII | DC-3F/ADX |
| EPOTHILONE A NATURAL | 0.00368 | 0.01241 | 0.0533 |
| EPOTHILONE A SYNTHETIC | 0.00354 | 0.0132 | 0.070 |
| MODEL SYSTEM I [3] | 9.52 | 3.004 | 0.972 |
| TRIOL ANALOG [2] | 10.32 | 4.60 | 4.814 |
| DESOXY EPOTHILONE [1] | 0.01061 | 0.0198 | 0.042 |
| Taxol ® | 0.09469 | 3.205 | 31.98 |
| VINBLASTINE | 0.00265 | 0.0789 | 1.074 |
| VP-16 (Etoposide) | 0.03386 | 0.632 | 12.06 |
| ACTINOMYCIN-D | 0.000058 (0.05816 nm) | 0.0082 | 0.486 |

Concerning Table 3, experiments were carried out using the cell lines DC-3F (parent hamster lung cells), DC-3F/ADII (moderate multidrug-resistant (MDR) cells) and DC-3F/ADX (very strong MDR cells).

The relative potency of the compounds are as follows:

DC-3F: Actinomycin D>Vinblastine≧Epothilone A (0.0036 $\mu$M)>Desoxy epothilone>VP-16>Taxol® (0.09 $\mu$M)>Model system I and triol analog DC-3F/ADX: Desoxyepothilone≧Epothilone A (0.06 $\mu$M)>Actinomycin D>Model system I>Vinblastine>triol analog>viablastine>Taxol® (32.0 $\mu$M)

DC-3F/ADX cells (8379-fold resistant to actinomycin D) are >338 fold (ca. 8379 fold) resistant to Taxol®, VP-16, Vinblastine and Actinomycin D but <20 fold resistant to epothilone compounds.

In general, these results are similar to those for CCRF-CEM cells.

TABLE 4

Three Drug Combination Analysis
(Based on the Mutually Exclusive Assumption - Classical Isobologram Method)

Drug A: EPOTHILONE B (#8) ($\mu$M)
Drug B: Taxol ® ($\mu$M)
Drug C: VINBLASTINE ($\mu$M)
Conditions: CCRF-CEM, 3 DRUG COMBINATION, RATIO (A:B:C: 1:5:1); EPOTHILONE + Taxol ® + VINBLASTINE; EXPOSURE TIME 72 HRS; XTT ASSAY.

| Drug | Combination Index* Values at: | | | | | Parameters | |
|---|---|---|---|---|---|---|---|
| | ED50 | ED75 | ED90 | ED95 | Dm ($IC_{50}$) ($\mu$M) | m | r |
| A | | | | | −00061 | 1.71561 | .98327 |
| B | | | | | −00109 | 2.14723 | .98845 |
| C | | | | | −00061 | 1.76186 | .9919 |
| A + B | 1.51545 | 1.38631 | 1.27199 | 1.20162 | −00146 | 2.41547 | .97168 |
| B + C | 1.43243 | 1.33032 | 1.23834 | 1.18091 | .00138 | 2.35755 | .95695 |
| A + C | .74395 | .68314 | .62734 | .59204 | .00045 | 2.0098 | .96232 |
| A + B+ C | 1.37365 | 1.32001 | 1.27285 | 1.24412 | .00122 | 2.11202 | .93639 |

VBL → microtubule depolymerization
Taxol ® → microtubule polymerization
Epo-B → microtubule polymerization
Epothilone B and Taxol ® have a similar mechanism of action (polymerization) but Epothilone B synergizes VBL whereas Taxol ® antagonizes VBL.
Taxol ® + VBL → Antagonism
EpoB + Taxol ® → Antagonism
EpoB + VBL → Synergism
EpoB + Taxol ® + VBL → Antagonism
*Combination index values <1, =1, and >1 indicate synergism, additive effect, and antagonism, respectively.

TABLE 5

Relative cytotoxicity of epothilone compounds in vitro.

| Compounds | | CCRF-CEM | | CCRF-CEM/VLB | | | CCRF-CEM/VM-1 | | |
|---|---|---|---|---|---|---|---|---|---|
| VINBLASTINE | **** | 0.0008 | | 0.44 | | | 0.00049 | | |
| | | 0.0006 | (0.00063 ± | 0.221 | (0.332 ± | (52.7x)§ | 0.00039 | (0.00041 ± | (0.7x) |
| | | 0.0005 | 0.00008) | 0.336 | 0.063 | | 0.00036 | 0.00004) | |
| VP-16 | | 0.259 | | 6.02 | | | 35.05 | | |
| | | 0.323 | (0.293 ± | 9.20 | (10.33 ± | (35.3x) | 42.24 | (34.39 ± | (117.4x) |
| | | 0.296 | 0.019) | 15.76 | 2.87) | | 25.89 | 4.73) | |
| Taxol ® | *** | 0.0021 | | 4.14 | | | 0.0066 | | |
| #17 | * | 0.090 | | | | | 0.254 | | |
| #18 | | 1157.6 | | | | | >>1 | | |
| #19 | | 0.959 | | | | | >>1 | | |
| #20 | * | 0.030 | | | | | 0.049 | | |
| #21 | | — | | | | | — | | |
| #22 | * | 0.098 | | | | | 0.146 | | |
| #23 | | — | | | | | — | | |
| #24 | *** | 0.0078 | | | | | 0.053 | | |
| #25 | * | 0.021 | | | | | 0.077 | | |
| #26 | * | 0.055 | | | | | 0.197 | | |
| #27 | **** | 0.0010 | | | | | 0.0072 | | |
| Epothilone A (Syn) | *** | 0.0021 | | | | | 0.015 | | |
| Epothilone B (Syn) | **** | 0.00042 | | | | | 0.0017 | | |

*Number of asterisks denotes relative potency.
§Number in parentheses indicates relative resistance (fold) when compared with parent cell line.

TABLE 6

Relative potency of epothilone compounds in vitro.

$IC_{50}\ \mu M$

| Compounds | | CCRF-CEM | CCRF-CEM/VBL | CCRF-CEM/VM-1 |
|---|---|---|---|---|
| Desoxy Epo. A | | | | |
| 1 | * | 0.022 | 0.012 | 0.013 |
| 2 | | 14.23 | 6.28 | 43.93 |
| 3 | | 271.7 | 22.38 | 11.59 |
| 4 | | 2.119 | 43.01 | 2.76 |
| 5 | | >20 | 35.19 | 98.04 |
| Trans-A | | | | |
| 6 | | 0.052 | 0.035 | 0.111 |
| 7 | | 7.36 | 9.82 | 9.65 |
| Syn-Epo.-B 8 | **** | 0.00082 | 0.0029 | 0.004 |
| Natural B 9 | **** | 0.00044 | 0.0026 | 0.001 |
| Desoxy Epo. B 10 | *** | 0.0095 | 0.017 | 0.014 |
| Trans. Epo. B | | | | |
| 11 | * | 0.090 | 0.262 | 0.094 |
| 12 | | 0.794 | >5 | >5 |
| 13 | | 11.53 | 5.63 | 14.46 |
| 8-desmethyl desoxy-Epo 14 | | 5.42 | 5.75 | 6.29 |
| 8-desmethyl Mix-cis Epo 15 | | 0.96 | 5.95 | 2.55 |
| 8-desmethyl β-Epo 15 | | 0.439 | 2.47 | 0.764 |
| 8-demethyl α-Epo 16 | | 7.47 | 16.48 | 0.976 |

TABLE 6-continued

Relative potency of epothilone compounds in vitro.

| Compounds | | CCRF-CEM | | CCRF-CEM/VBL | | | CCRF-CEM/VM-1 | | |
|---|---|---|---|---|---|---|---|---|---|
| EPOTHILONE A (Natural) | *** | 0.0024 0.0031 | (0.0027 ± 0.0003) | 0.0211 0.0189 | (0.020 ± 0.001) | (7.4×) | 0.006 0.00625) | } | (0.00611 ± 0.000) (2.3 |
| EPOTHILONE B (Natural) | **** | 0.00017 | | 0.0017 | (7.0×) | | 0.00077 | | |
| EPOTHILONE B (Synthetic) | | 0.00055 | (0.0035 ± 0.0003) | 0.0031 | (0.00213 ± 0.00055) | | 0.0018 | | (0.00126 ± 0.0003) |
| EPOTHILONE B (Synthetic, larger quantity synthesis) (25.9 mg) | | 0.00033 | | 0.0021 | (6.1×) | | 0.0012 | (3.6×) | |

TABLE 7

Relative cytotoxicity of epothilone compounds in vitro.

| | IC$_{50}$ | |
|---|---|---|
| | CEM | CEM/VBL |
| epothilone A | 0.0029 μM | 0.0203 μM |
| desoxyepothilone | 0.022 | 0.012 |
| 2 | 14.2 | 6.28 |
| 3 | 271.7 | 22.4 |
| 4 | 2.1 | 43.8 |
| 5 | >20 | 35.2 |
| 6 | 0.052 | 0.035 |
| 7 | 7.4 | 9.8 |
| synthetic epothilone B | 0.00082 | 0.00293 |
| natural epothilone B | 0.00044 | 0.00263 |
| desoxyepothilone B | 0.0095 | 0.0169 |
| 11 | 0.090 | 0.262 |
| 12 | 0.794 | >5 |
| 13 | 11.53 | 5.63 |
| 14 | 5.42 | 5.75 |
| 15 | 0.439 | 2.47 |
| 16 | 7.47 | 16.48 |
| 17 | 0.090 | 0.254 |
| 18 | 1157.6 | >>1 |
| 19 | 0.959 | >>1 |
| 20 | 0.030 | 0.049 |
| 21 | Not Available | — |
| 22 | 0.098 | 0.146 |
| 23 | Not Available | — |
| 24 | 0.0078 | 0.053 |
| 25 | 0.0212 | 0.077 |
| 26 | 0.0545 | 0.197 |
| 27 | 0.0010 | 0.0072 |

TABLE 8

Chemotherapeutic Effect of Epothilone B, Taxol ® & Vinblastine in CB-17 Scid Mice Bearing Human CCRF-CEM and CCRF-CEM/VBL Xenograft[1]

| Tumor | Drug[2] | Dose | Average weight change | | | | | Average tumor volume | | | |
|---|---|---|---|---|---|---|---|---|---|---|---|
| | | | Day 0 | Day 7 | Day 12 | Day 17 | Day 22 | Day 7 | Day 12 | Day 17 | Day 22 |
| CCRF-CEM | | 0 | 24.4 | +0.2 | +0.4 | +0.1 | +0.5 | 1.0[3] | 1.00 | 1.00 | 1.00 |
| | Epo B | 0.7[4] | 24.7 | −0.1 | −0.7 | −1.4 | +0.3 | 1.0 | 0.53 | 0.48 | 0.46 |
| | | 1.0[5] | 25.0 | +0.1 | −1.5 | −2.4 | +0.1 | 1.0 | 0.46 | 0.35 | 0.43 |
| | Taxol ® | 2.0 | 25.1 | −0.1 | −1.1 | −1.5 | −0.3 | 1.0 | 0.39 | 0.29 | 0.28 |
| | | 4.0 | 25.1 | −0.2 | −1.7 | −1.9 | −0.3 | 1.0 | 0.37 | 0.23 | 0.19 |
| | VBL | 0.2 | 25.9 | +0.2 | −0.8 | −1.5 | −0.3 | 1.0 | 0.45 | 0.25 | 0.29 |
| | | 0.4 | 25.0 | −0.1 | −1.4 | −1.8 | −0.7 | 1.0 | 0.31 | 0.27 | 0.30 |
| CCRF-CEM/VBL | | 0 | 26.3 | −0.3 | +0.1 | −0.3 | +0.4 | 1.0 | 1.00 | 1.00 | 1.00 |
| | EpoB | 0.7 | 25.8 | +0.1 | −0.7 | −1.0 | −0.2 | 1.0 | 0.32 | 0.40 | 0.33 |
| | | 1.0[6] | 26.0 | −0.2 | −1.3 | −2.1 | −0.5 | 1.0 | 0.41 | 0.27 | 0.31 |
| | Taxol ® | 2.0 | 26.1 | 0 | −0.9 | −1.5 | −0.1 | 1.0 | 0.60 | 0.58 | 0.70 |
| | | 4.0 | 26.0 | 0 | −1.4 | −1.6 | −0.9 | 1.0 | 0.79 | 0.55 | 0.41 |
| | VBL | 0.2 | 25.9 | −0.3 | −0.8 | −1.4 | −0.3 | 1.0 | 0.86 | 0.66 | 0.67 |
| | | 0.4 | 25.9 | 0 | −1.2 | −1.8 | −0.5 | 1.0 | 1.02 | 0.57 | 0.62 |

[1]CCRF-CEM and CCRF-CEM/VBL tumor tissue 50 ul/mouse implanted S.C. on day 0, Treatments i.p., QD on day 7, 8, 9, 10, 14 and 15. There were seven CB-17 scid male mice in each dose group and control.
[2]Epo B, epothilone B; VBL, vinblastine.

TABLE 8-continued

Chemotherapeutic Effect of Epothilone B, Taxol ® & Vinblastine
in CB-17 Scid Mice Bearing Human CCRF-CEM and CCRF-CEM/VBL Xenograft[1]

| Tumor | Drug[2] | Dose | Average weight change | | | | | Average tumor volume | | | |
|---|---|---|---|---|---|---|---|---|---|---|---|
| | | | Day 0 | Day 7 | Day 12 | Day 17 | Day 22 | Day 7 | Day 12 | Day 17 | Day 22 |

[3]The tumor volumes for each group on day 7 was about 1 mm$^3$. The average volumes of CCRF-CEM control group on day 12, 17 and 22 were 19, 76 and 171 mm$^3$, and of CCRF-CEM/VBL control group were 35, 107 and 278 mm$^3$, respectively.
[4]Two mice died of drug toxicity on day 19 & 20.
[5]Three mice died of drug toxicity on day 18, 19 and 21.
[6]One mouse died of drug toxicity on day 17.

In summary, epothilones and Taxol® have similar modes of action by stabilizing polymerization of microtubules. However, epothilones and Taxol® have distinct novel chemical structures.

MDR cells are 1500-fold more resistant to Taxol® (CCRF-CEM/VBL cells), epothilone A showed only 8-fold resistance and epothilone B showed only 5-fold resistance. For CCRF-CEM cells, Epo B is 6-fold more potent than Epo A and 10-fold more potent than Taxol®. Desoxyepothilone B and compd #24 are only 3–4-fold less potent than Taxol® and compound #27 is >2-fold more potent than Taxol®. Finally, Taxol® and vinblastine showed antagonism against CCRF-CEM tumor cells, whereas the combination of Epo B+vinblastine showed synergism.

Relative Cytotoxicity of Epothilones against Human Leukemic Cells in Vitro is in the order as follows:

CCRF-CEM Leukemic Cells

Epo B (IC$_{50}$=0.00035 μM; Rel. Value=1)>VBL(0.00063;1/1.8)>#27(0.0010;1/2.9)>Taxol®(0.0021; 1/6)>EpoA (0.0027; 1/7.7)>#24(0.0078; 1122.3)>#10(0.0095; 1/27.1)>#25(0.021; 1/60)>#1(0.022; 1162.8)>#20(0.030; 1/85.7)>#6(0.052; 1/149)>#26 0.055; 1/157)>#17(0.090; 1/257)>VP-16(0.29; 1/8.29)>#15(0.44; 1/1257)>#19 (0.96; 1/2943)

CCRF-CEM/VBL MDR Leukemic Cells

EpoB(0.0021; 1/6*[1]**)>#27(0.0072; 1120.6)>#1(0.012; 1/34.3)>#10(0.017; 1/48.6)>EpoA(0.020; 1/57.1[1/9.5])>#6(0.035)>#20(0.049)>#24(0.053)>#25(0.077)>#22 (0.146)>#26(0.197)>#17(0.254)>#11(0.262)>VBL (0.332; 1/948.6[1/158.1])>Taxol®(4.14; 1/11828 [1/1971.4])>VP-16(10.33; 1/29514[1/4919])

*Potency in parentheses is relative to Epo B in CCRF-CEM cells.
**Potency in square brackets is relative to Epo B in CCRF-CEM/VBL MDR cells.

Figure 46:
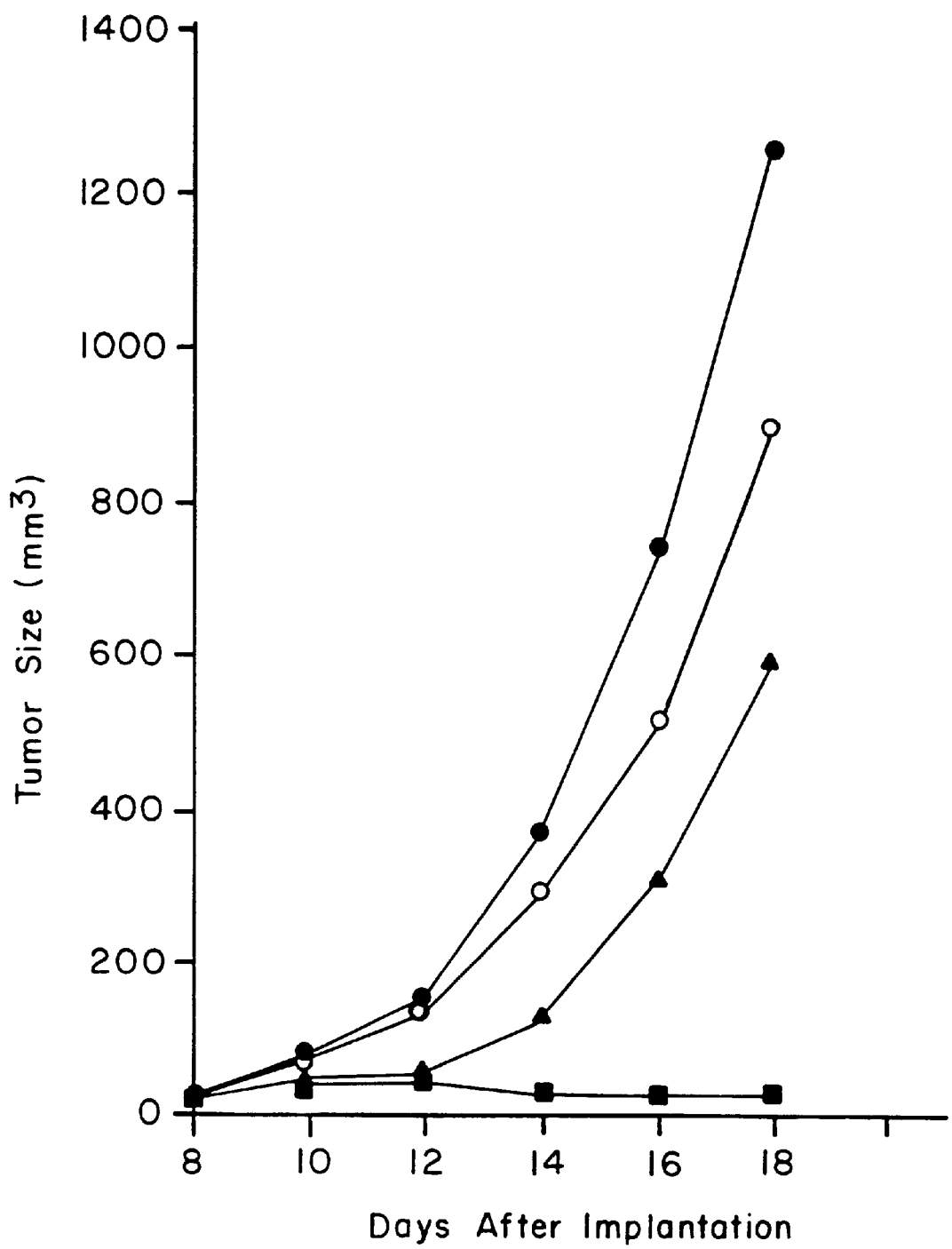
FIG. 46 shows the effect of treatment with desoxyepothilone B (35 mg/kg), Taxol® (5 mg/kg) and adriamycin (2 mg/kg) of nude mice bearing human MX-1 xenograft on tumor size between 8 and 18 days after implantation. Desoxyepothilone B (□), Taxol® (Δ), adriamycin (X), control (♦); i.p. treatments were given on day 8, 10, 12, 14 and 16.

As shown in Table 9, treatment of MX-1 xenograft-bearing nude mice with desoxyepothilone B (35 mg/kg, 0/10 lethality), Taxol® (5 mg/kg, 2/10 lethality; 10 mg/kg, 2/6 lethality) and adriamycin (2 mg/kg, 1/10 lethality; 3 mg/kg, 4/6 lethality) every other day, i.p. beginning day 8 for 5 doses resulted in a far better therapeutic effect for desoxyepothilone B at 35 mg/kg than for Taxol® at 5 mg/kg and adrimycin at 2 mg/kg with tumor volume reduction of 98%, 53% and 28%, respectively. For the desoxyepothilone B-treated group, 3 out of 10 mice were found with tumor non-detectable on day 18. (See FIG. 46)

Extended treatment with desoxyepothilone B (40 mg/kg, i.p.) beginning day 18 every other day for 5 more doses resulted in 5 out of 10 mice with tumor disappearing on day 28 (or day 31). See Table 10. By contrast, the extended treatment with Taxol® at 5 mg/kg for five more doses resulted in continued tumor growth at a moderate rate, and 2 out of 10 mice died of toxicity.

Figure 47:
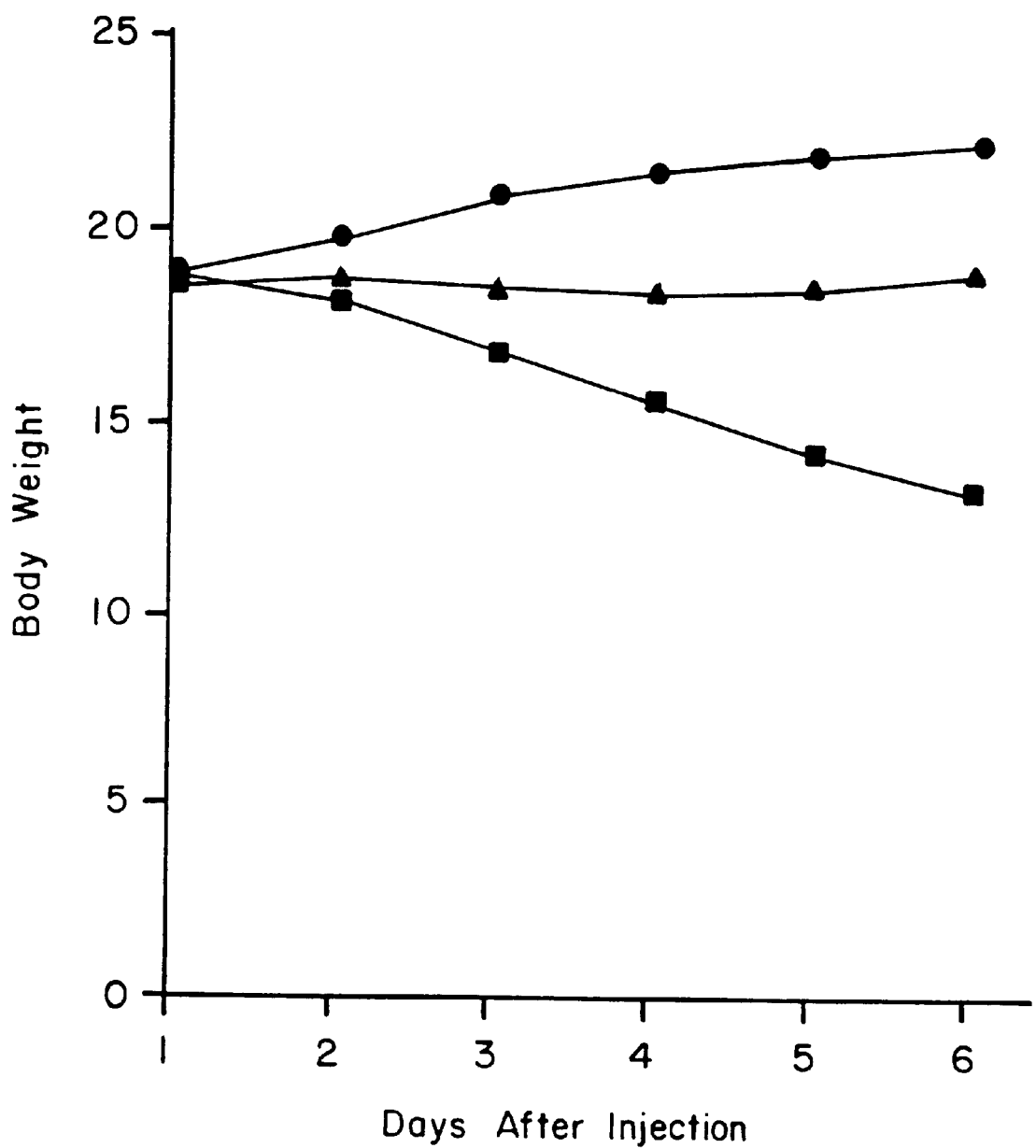
FIG. 47 shows the relative toxicity of epothilone B (□; 0.6 mg/kg QDx4; i.p.) and desoxyepothilone B (Δ; 25 mg/kg QDx4; i.p.) versus control (♦) in normal nude mice. Body weight of mice was determined daily after injection. For epothilone B, 8 of 8 mice died of toxicity on days 5, 6, 6, 7, 7, 7, 7, and 7; for desoxyepothilone B, all six mice survived.
Figure 48:
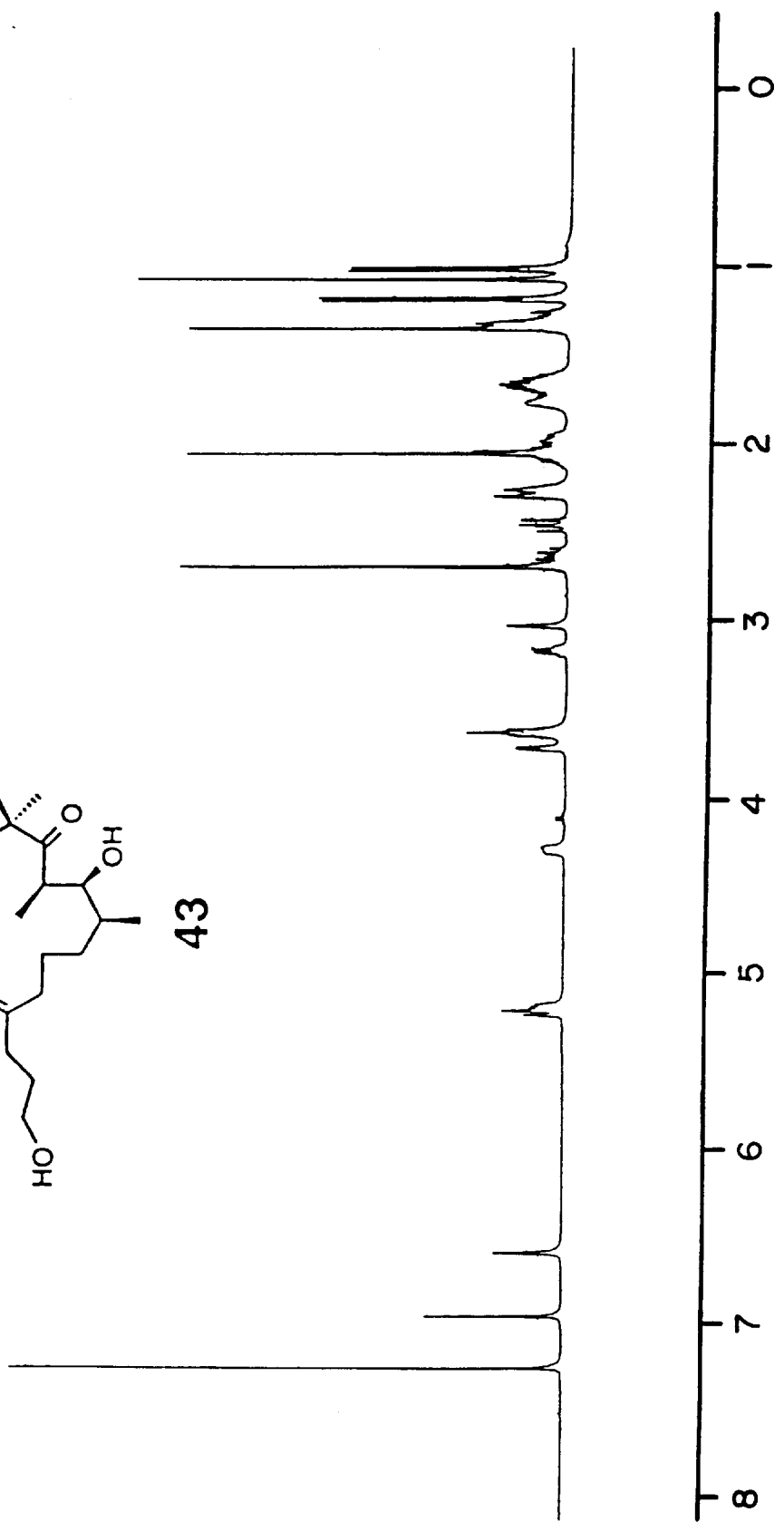
FIG. 48 shows a high resolution $^1$H NMR spectrum of epothilone analogue #43.
Figure 49:
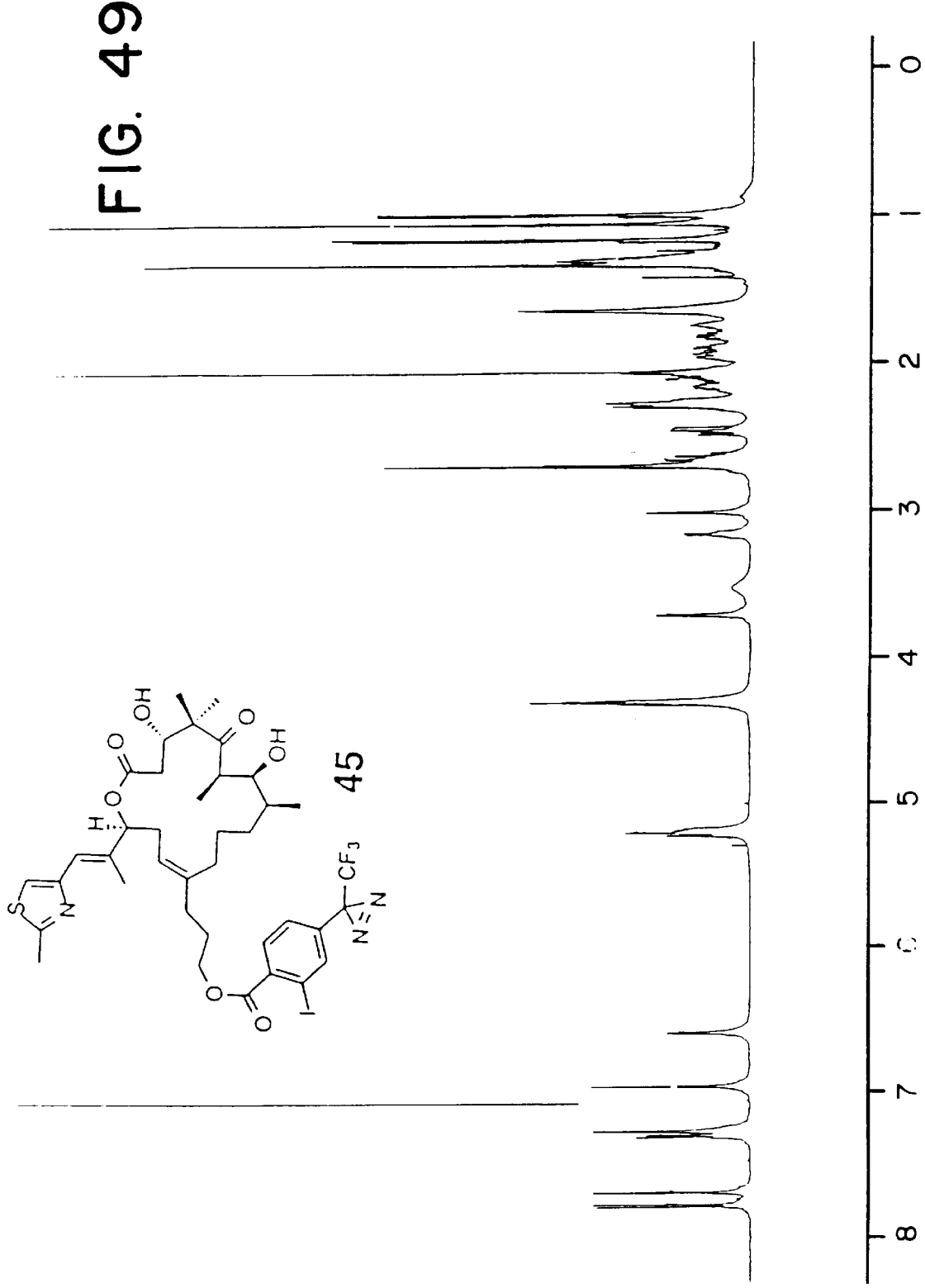
FIG. 49 shows a high resolution $^1$H NMR spectrum of epothilone analogue #45.
Figure 50:
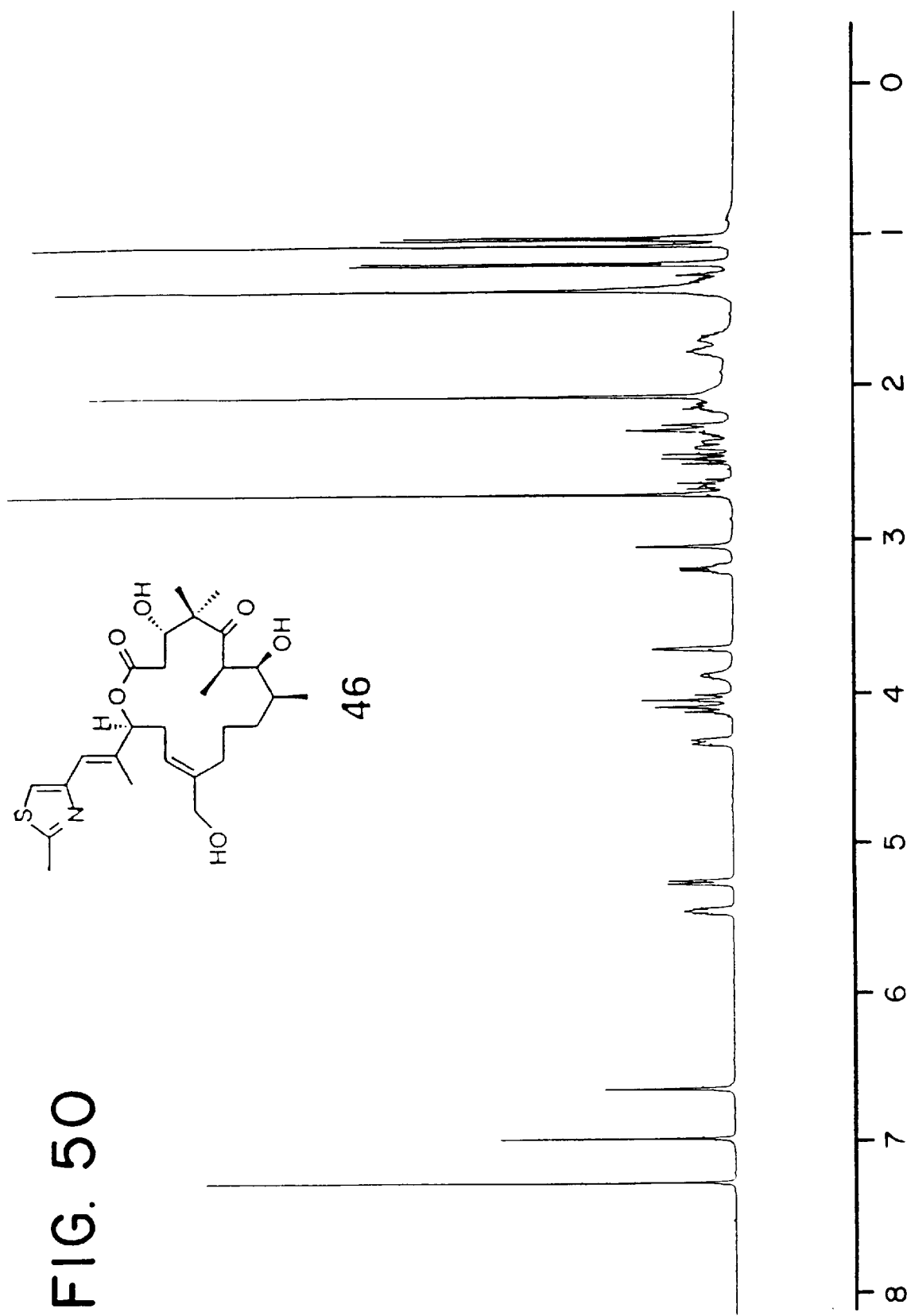
FIG. 50 shows a high resolution $^1$H NMR spectrum of epothilone analogue #46.
Figure 51:
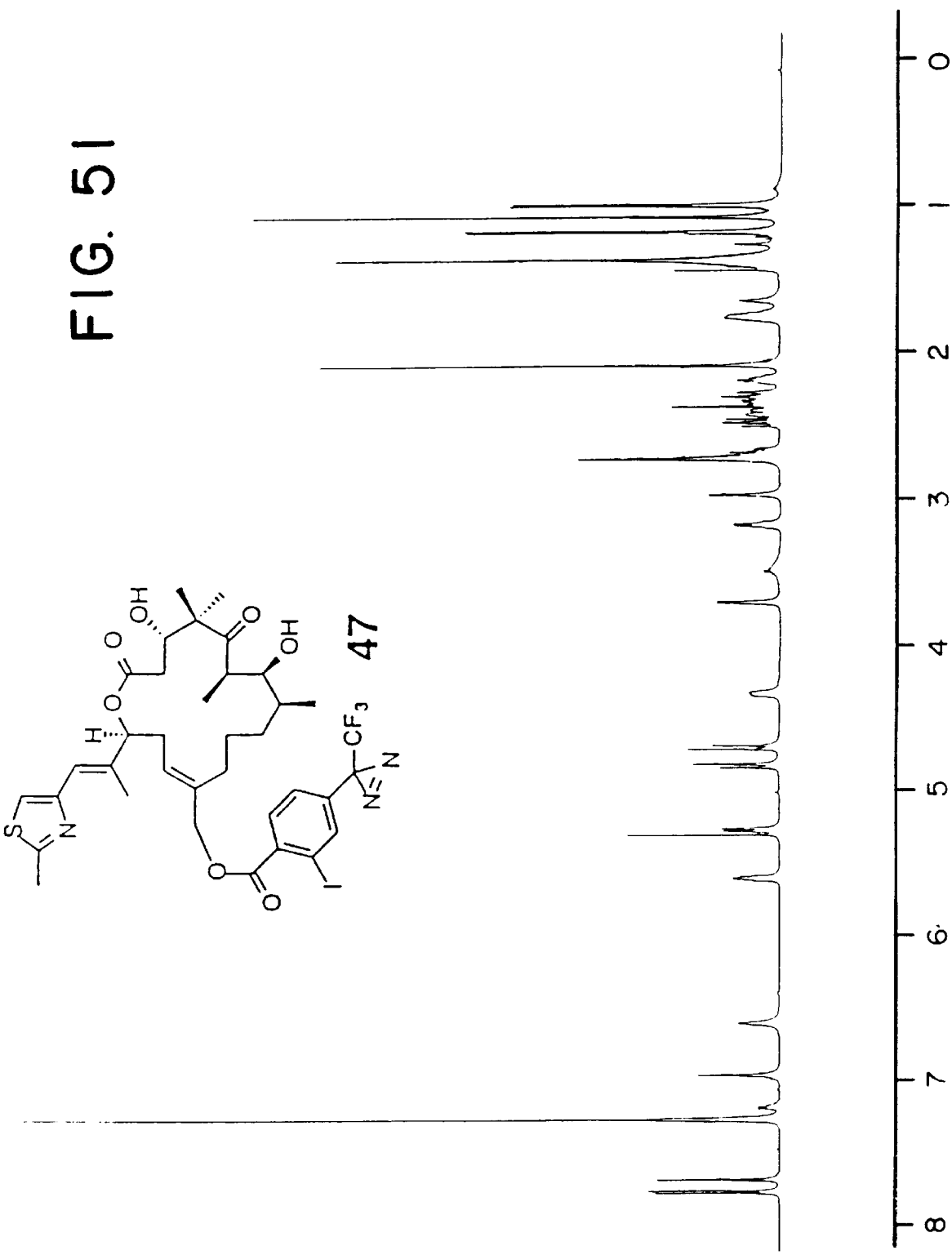
FIG. 51 shows a high resolution $^1$H NMR spectrum of epothilone analogue #47.
Figure 52:
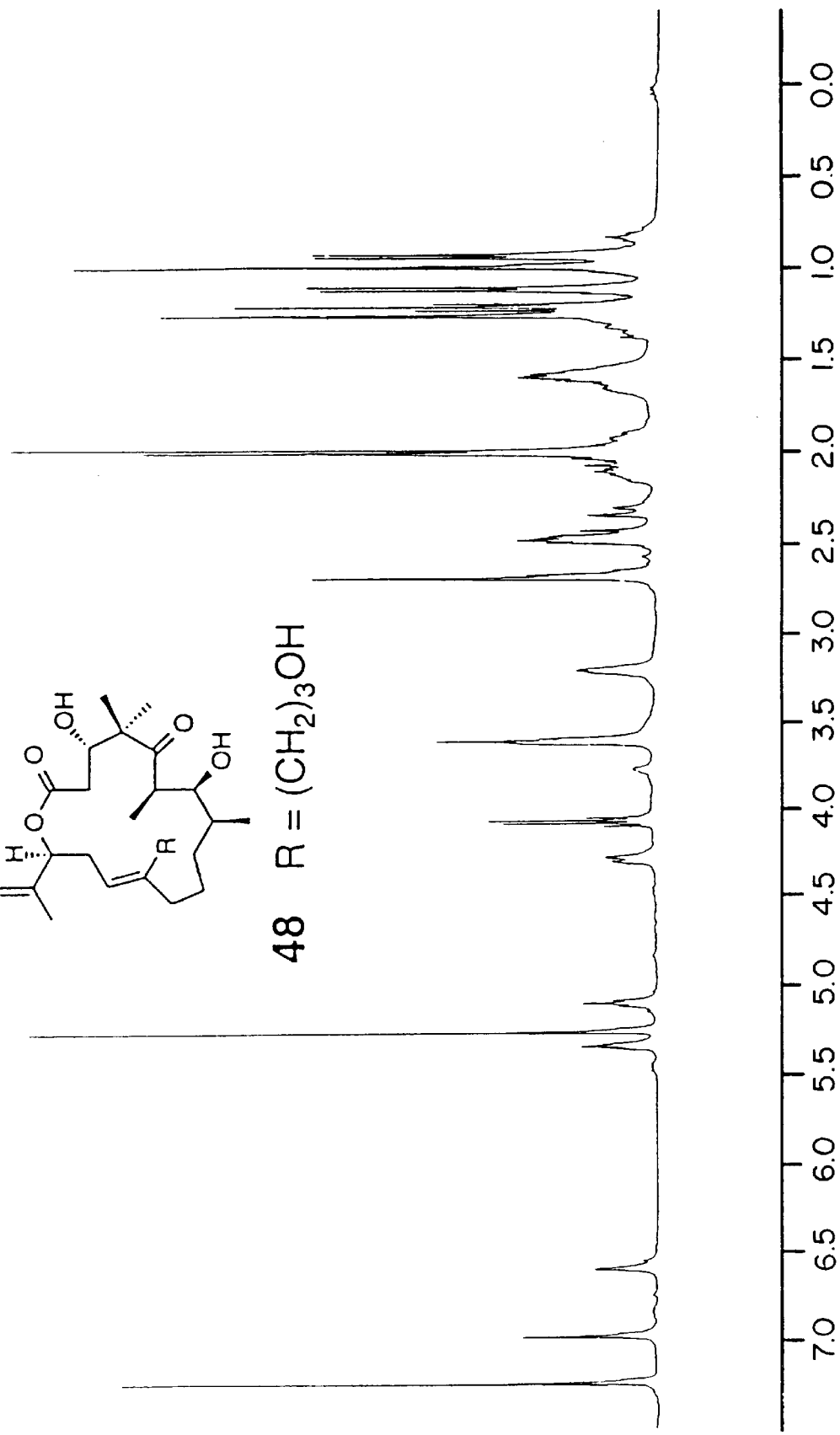
FIG. 52 shows a high resolution $^1$H NMR spectrum of epothilone analogue #48.

Toxicity studies with daily i.p. doses of desoxyepothilone B (25 mg/kg, a very effective therapeutic dose as indicated in earlier experiments) for 4 days to six mice resulted in no reduction in average body weight. (Table 13; FIG. 47) By contrast, epothilone B (0.6 mg/kg, i.p.) for 4 days to eight mice resulted in 33% reduction in average body weight; all eight mice died of toxicity between day 5 and day 7.

As evident from Table 15, desoxyepothilone B performs significantly better than Taxol®, vinblastine, adriamycin and camptothecin against MDR tumor xenografts (human mammary adeoncarcinoma MCF-7/Adr xenografts). This drug-resistant tumor grows very aggressively and is refractory to Taxol® and adriamycin at half their lethal doses. Taxol® at 6 mg/kg i.p. Q2Dx5 reduced tumor size only 10% while adriamycin resulted in only a 22% reduction on day 17. Whereas, desoxyepothilone B at 35 mg/kg reduced tumor size by 66% on day 17 and yet showed no reduction in body weight or apparent toxicity. Even at the LD$_{50}$ dosage for Taxol® (12 mg/kg) or adriamycin (3 mg/kg), desoxyepothilone B still performed more effectively. By comparison, camptothecin at 1.5 and 3.0 mg/kg reduced tumor size by 28% and 57%, respectively. Overall, in comparison with the four important anticancer drugs in current use, i.e., Taxol®, adriamycin, vinblastine and camptothecin, desoxyepothilone B showed superior chemotherapeutic effect against MDR xenografts.

In vivo therapeutic results in nude mice for dEpoB and Taxol® are reported in Tables 19–21. As shown in the Tables, 6 hr i.v. infusion via tail vein provided a good therapeutic profile with remarkably low toxicity.

For mammary MX-1 xenograft (non-MDR), desoxyepothilone B was as effective as Taxol®. Both drugs were administered by 6 hr i.v. infusion and both achieved full cure.

For the MDR-mammary MCF-7/Adr xenograft, the therapeutic effect of desoxyepothilone B was far better than Taxol®, although Q2Dx5 did not achieve a cure.

For CCRF-CEM/Taxol® (57-fold resistant to Taxol® in vitro, in-house developed cell line), Taxol® did not show significant therapeutic effect in this nude mice xenograft whereas desoxyepothilone B achieved a full cure.

Prolonged (6 hr.) i.v. infusion allowed higher doses (e.g., 30 mg/kg, Q2Dx5) to be administered (without lethality) than i.v. bolus injection of desoxyepothilone B, and yet reduced drug toxicity.

Accordingly, the present inventors have found desoxyepothilone B to have excellent properties for therapeutic application as an MDR agent and moreover as a general anticancer agent.

TABLE 9

Therapeutic Effect of Desoxyepothilone B, Taxol ®, and Adriamycin in Nude Mice Bearing Human MX-1 Xenograft[a]

|  | Dose (mg/kg) | Average Body Weight Change (g) Day | | | | | | Average Tumor Volume (T/C) Day | | | | | Tumor Disappear-ance | # Mice Died |
|---|---|---|---|---|---|---|---|---|---|---|---|---|---|---|
|  |  | 8 | 10 | 12 | 14 | 16 | 18 | 10 | 12 | 14 | 16 | 18 |  |  |
| Control | 0 | 24.6 | −0.1 | +1.0 | +1.0 | +1.3 | +1.8 | 1.00 | 1.00 | 1.00 | 1.00 | 1.00 | 0/10 | 0/10 |
| Desoxyepothilone B | 35 | 23.0 | −0.1 | +0.7 | −0.3 | −1.7 | −1.6 | 0.42 | 0.28 | 0.07 | 0.04 | 0.02 | 0/10 | 3/10 |
| Taxol ® | 5 | 24.0 | −1.3 | −0.8 | −1.4 | −1.9 | −1.8 | 0.58 | 0.36 | 0.34 | 0.42 | 0.47 | 2/10 | 0/10 |
|  | 10 | 24.3 | −1.0 | −1.0 | −2.3 | −3.5 | −3.8 | 0.85 | 0.40 | 0.21 | 0.20 | 0.12 | 2/6 | 1/6 |
| Adriamycin | 2[b] | 23.9 | +0.3 | 0 | −1.4 | −1.9 | −2.0 | 0.94 | 0.88 | 1.05 | 0.69 | 0.72 | 1/10 | 0/10 |
|  | 3[c] | 22.4 | +1.3 | −0.2 | −1.5 | −2.1 | −2.3 | 0.72 | 0.54 | 0.56 | 0.51 | 0.36 | 4/6 | 0/6 |

[a]MX-1 tissue 100 μl/mouse was implanted s.c on day 0. Every other day i.p. treatments were given on day 8, 10, 12, 14 and 16. The average tumor volume of control group on day 10, 12, 14, 16 and 18 were 78, 151, 372, 739 and 1257 mm³, respectively.
[b]One mouse died of toxicity on day 22.
[c]Four mice died of toxicity on day 24.

TABLE 10

Extended Experiment of Desoxyepothilone B, Taxol ®, Cisplatin and Cyclophosphamide in Nude Mice Bearing Human MX-1 Xenograft[a]

| Drug | Dose (mg/kg) | Average Body Weight Change (g) Day | | | | | | Tumor Disappearance Day | | | | | Average Tumor Disappearance Duration (Day) | # Died |
|---|---|---|---|---|---|---|---|---|---|---|---|---|---|---|
|  |  | 8 | 20 | 22 | 24 | 26 | 28 | 20 | 22 | 24 | 26 | 28 |  |  |
| Desoxyepo B | 40 | 23.0 | −1.7 | −2.4 | −2.4 | −1.4 | 1.2 | 2/10[b] | 2/10 | 3/10 | 5/10 | 5/10 | 44 (5/10) | 0/10 |
| Taxol ® | 5 | 24.0 | −1.6 | −0.3 | +0.1 | −0.6 | −0.4 | 0/10 | 0/10 | 0/10 | 0/10 | 0/10 | Reappeared on day 38 | 2/10 |
|  | 10 | No extended test | | | | | | 1/6 on day 16 | | | | | | 2/6 |

[a]Extended experiment was carried out after 5 times injection (on day 8, 10, 12, 14 and 16). Every other day i.p. treatments were given continuously: Desoxyepothilone B and Taxol ® on day 18, 20, 22, 24 and 26; control group mice were sacrificed.
[b]One of the mice tumor reappeared on day 20.

TABLE 11

Toxicity of Epothilone B and Desoxyepothilone B in normal nude mice.

| Group Duration | Dose and Schedule (mg/kg) | Number of mice | Died | Disappearance |
|---|---|---|---|---|
| Control |  | 4 | 0 |  |
| Epothilone B[a] | 0.6 QD × 4 | 8 | 8 |  |
| Desoxyepothilone B | 25 QD × 4 | 6 | 0 |  |

[a]Mice died of toxicity on day 5,6,6,7,7,7,7,7

TABLE 12

Therapeutic Effect of Epothilone B, Desoxyepothilone B and Taxol ® in B6D2F₁ Mice Bearing B16 Melanoma[a]

| Drug | Dose (mg/kg) | Average Weight Change (g) Day | | | | | | Average Tumor Volume (T/C) Day | | | | # Mice Died |
|---|---|---|---|---|---|---|---|---|---|---|---|---|
|  |  | 0 | 3 | 5 | 7 | 9 | 11 | 5 | 7 | 9 | 11 |  |
| Control | 0 | 26.5 | −0.2 | 0 | −0.2 | 0 | +1.0 | 1.00 | 1.00 | 1.00 | 1.00 | 0/15 |
| Epothilone B | 0.4 QD × 6[b] | 27.1 | −0.2 | −0.6 | −1.1 | −3.4 | −3.9 | 1.08 | 1.07 | 1.27 | 1.07 | 1/8 |
|  | 0.8 QD × 5[c] | 27.0 | 0 | −0.8 | −3.1 | −4.7 | −4.7 | 0.57 | 0.89 | 0.46 | 0.21 | 5/8 |
| Desoxyepothilone B | 10 QD × 8 | 27.0 | −0.7 | −0.9 | −1.1 | −1.5 | −0.3 | 0.23 | 0.22 | 0.51 | 0.28 | 0/6 |
|  | 20 QD 1–4, 7–8 | 26.9 | −1.3 | −2.2 | −1.3 | −1.6 | −0.8 | 0.59 | 0.63 | 0.58 | 0.33 | 0/6 |

TABLE 12-continued

Therapeutic Effect of Epothilone B, Desoxyepothilone B and Taxol ® in B6D2F$_1$ Mice Bearing B16 Melanoma[a]

| Drug | Dose (mg/kg) | Average Weight Change (g) Day | | | | | | Average Tumor Volume (T/C) Day | | | | # Mice |
|---|---|---|---|---|---|---|---|---|---|---|---|---|
| | | 0 | 3 | 5 | 7 | 9 | 11 | 5 | 7 | 9 | 11 | Died |
| Taxol ® | 4 QD × 8 | 26.7 | +0.1 | +0.2 | +0.3 | +0.4 | +0.8 | 0.62 | 0.39 | 0.56 | 0.51 | 0/8 |
| | 6.5 QD × 8 | 26.7 | +0.1 | +0.3 | +0.3 | +0.4 | +1.7 | 0.19 | 0.43 | 0.20 | 0.54 | 0/8 |

Figure 44A:
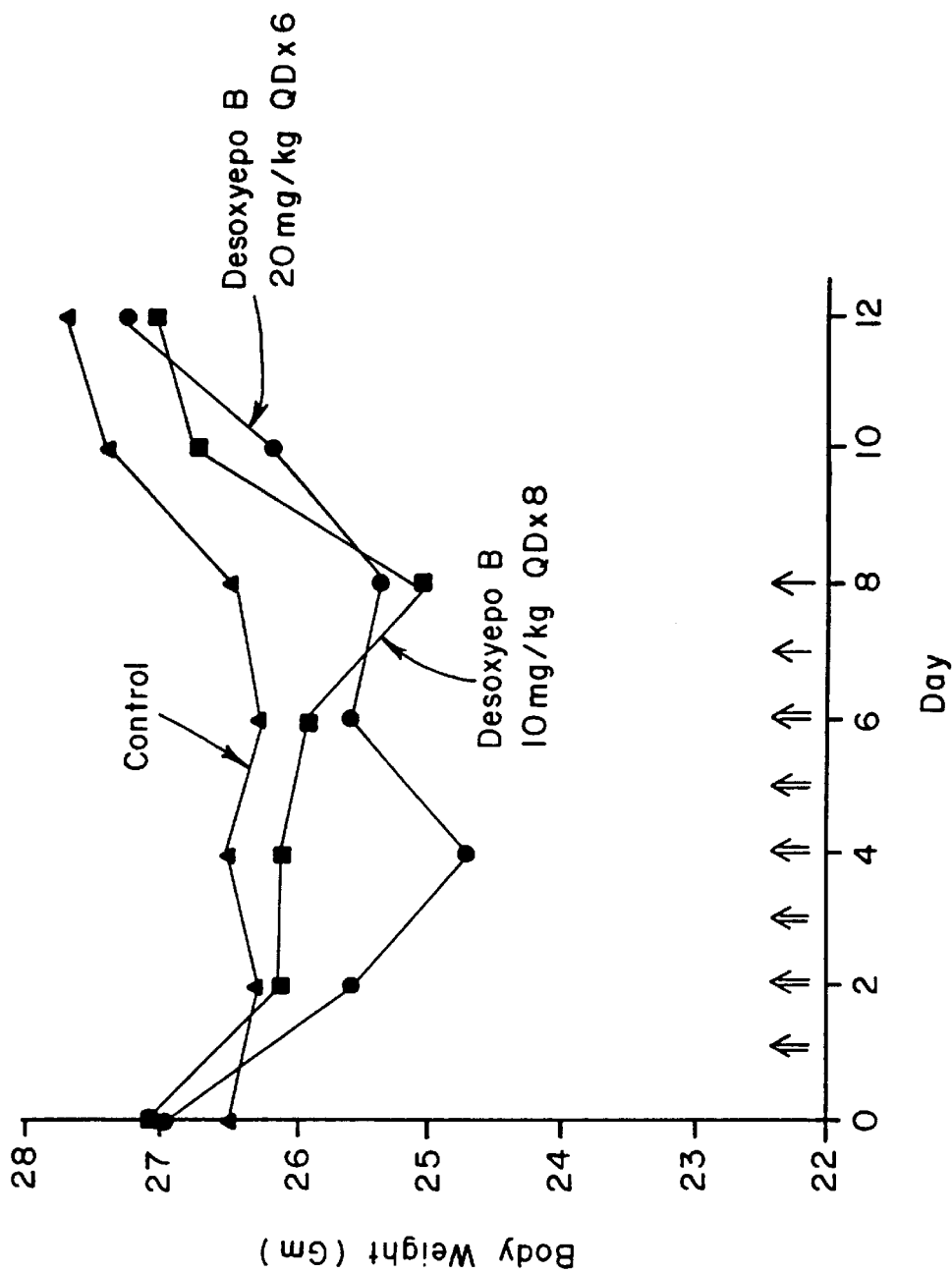
FIG. 44(A) shows toxicity of desoxyepothilone B in $B6D2F_1$ mice bearing B16 melanoma. Body weight was determined at 0, 2, 4, 6, 8, 10 and 12 days. Control (▲); desoxyepothilone B (○; 10 mg/kg QDx8; 0 of 8 died); desoxyepothilone B (●; 20 mg/kg QDx6; 0 of 8 died). Injections were started on day 1. (B) shows toxicity of epothilone B in $B6D2F_1$ mice bearing B16 melanoma. Body weight was determined at 0, 2, 4, 6, 8, 10 and 12 days. Control (▲); epothilone B (○; 0.4 mg/kg QDx6; 1 of 8 died of toxicity); epothilone B (●; 0.8 mg/kg QDx5; 5 of 8 died). Injections were started on day 1.
Figure 44B:
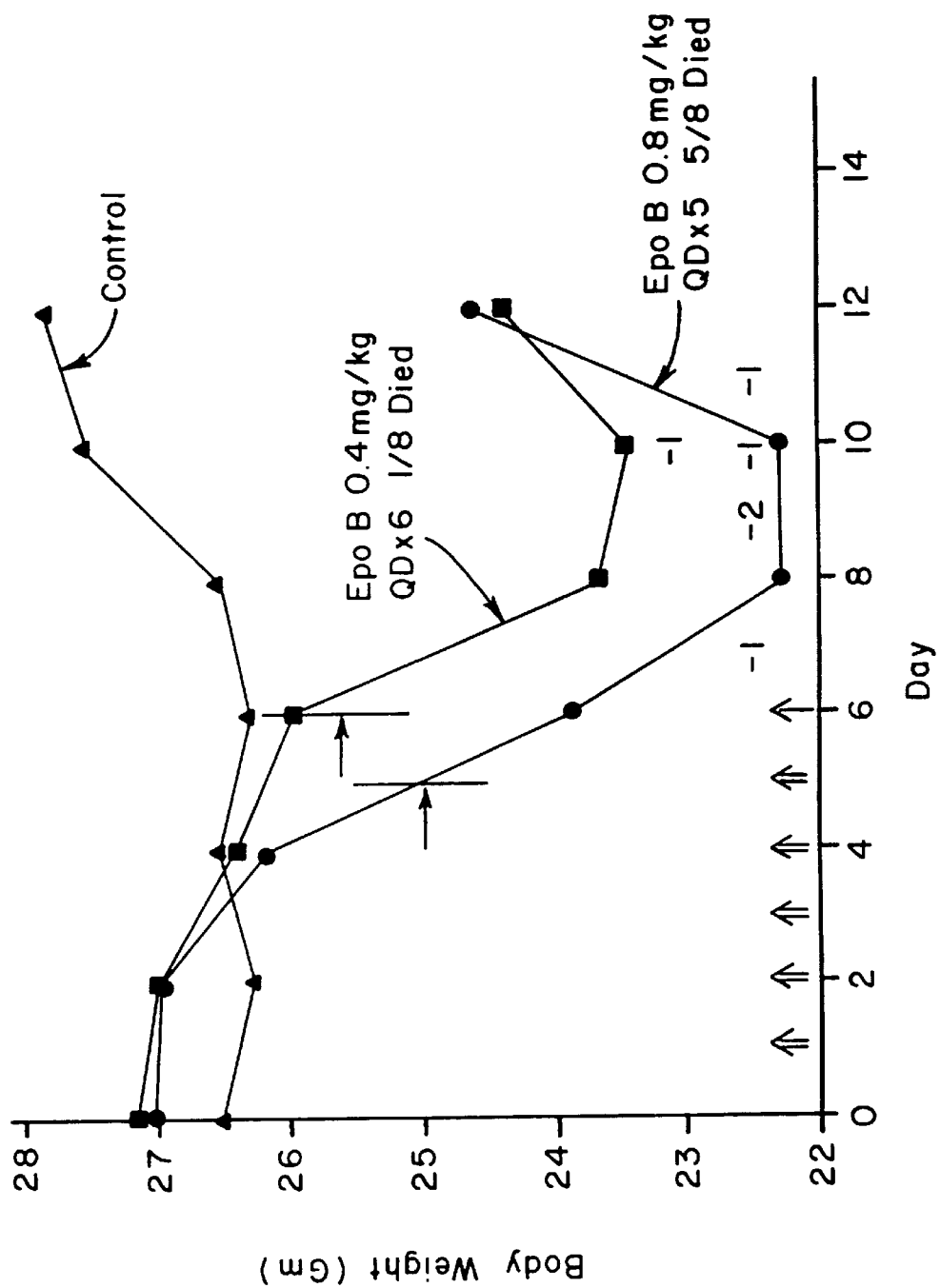

[a]B16 melanoma cells 1.2 × 10$^6$/mouse was implanted S.C. on day 0. Daily treatments start on day 1 after inoculation. Number of mice in each group: Control, 15; Epothilone B, 8; Desoxythilone B, 5 and Taxol ®, 8. The average tumor volume of control group on day 5, 7, 9 and 11 were 16, 138, 436 and 1207 mm$^3$, respectively. See FIGS. 44(a) and (b).
[b]One mouse died of toxicity on day 10.
[c]Five mice died of toxicity on day 8, 10, 10, 11, 12. One moribund mouse was sacrificed for toxicological examinations on day 11.

TABLE 13

Therapeutic Effect of Desoxyepothilone B, Epothilone B, Taxol ® and Vinblastine in Nude Mice Bearing Human MX-1

| Drug | Dose (mg/kg) | Average Body Weight Change (g) Day | | | | | Average Tumor Volume (T/C) Day | | | | Note |
|---|---|---|---|---|---|---|---|---|---|---|---|
| | | 7 | 11 | 13 | 15 | 17 | 11 | 13 | 15 | 17 | |
| Control died | | 27.9 | +0.8 | +1.1 | +1.9 | +0.6 | 1.00 | 1.00 | 1.00 | 1.00 | 0/8 |
| Desoxyepothilone B | 15 | 27.1 | +0.8 | +1.1 | +1.6 | +1.5 | 0.65 | 0.46 | 0.49 | 0.41 | 0/6 died |
| | 25[b] | 27.0 | +0.4 | +0.7 | +1.0 | +0.7 | 0.38 | 0.11 | 0.05 | 0.04 | 0/6 died (1/6 cured on day 35) |
| Epothilone B | 0.3 | 26.9 | +0.5 | +0.4 | −0.3 | −1.2 | 1.00 | 0.71 | 0.71 | 0.84 | 0/7 died |
| | 0.6[c] | 27.4 | −0.3 | −1.3 | −2.1 | −2.1 | 1.08 | 0.73 | 0.81 | 0.74 | 3/7 died |
| Taxol ® | 5 | 26.9 | −0.1 | +0.4 | +1.1 | +1.2 | 0.54 | 0.46 | 0.40 | 0.45 | 0/7 died |
| | 10[d] | 27.6 | −2.7 | −1.1 | −0.3 | +2.2 | 0.43 | 0.37 | 0.12 | 0.11 | 4/7 died |
| Vinblastine | 0.2 | 25.7 | +0.6 | +1.4 | +2.3 | +2.9 | 0.65 | 0.54 | 0.56 | 0.88 | 0/7 died |
| | 0.4[e] | 26.4 | +0.8 | +0.5 | +1.9 | +2.1 | 0.80 | 0.56 | 0.83 | 0.88 | 1/7 died |

Figure 45A:
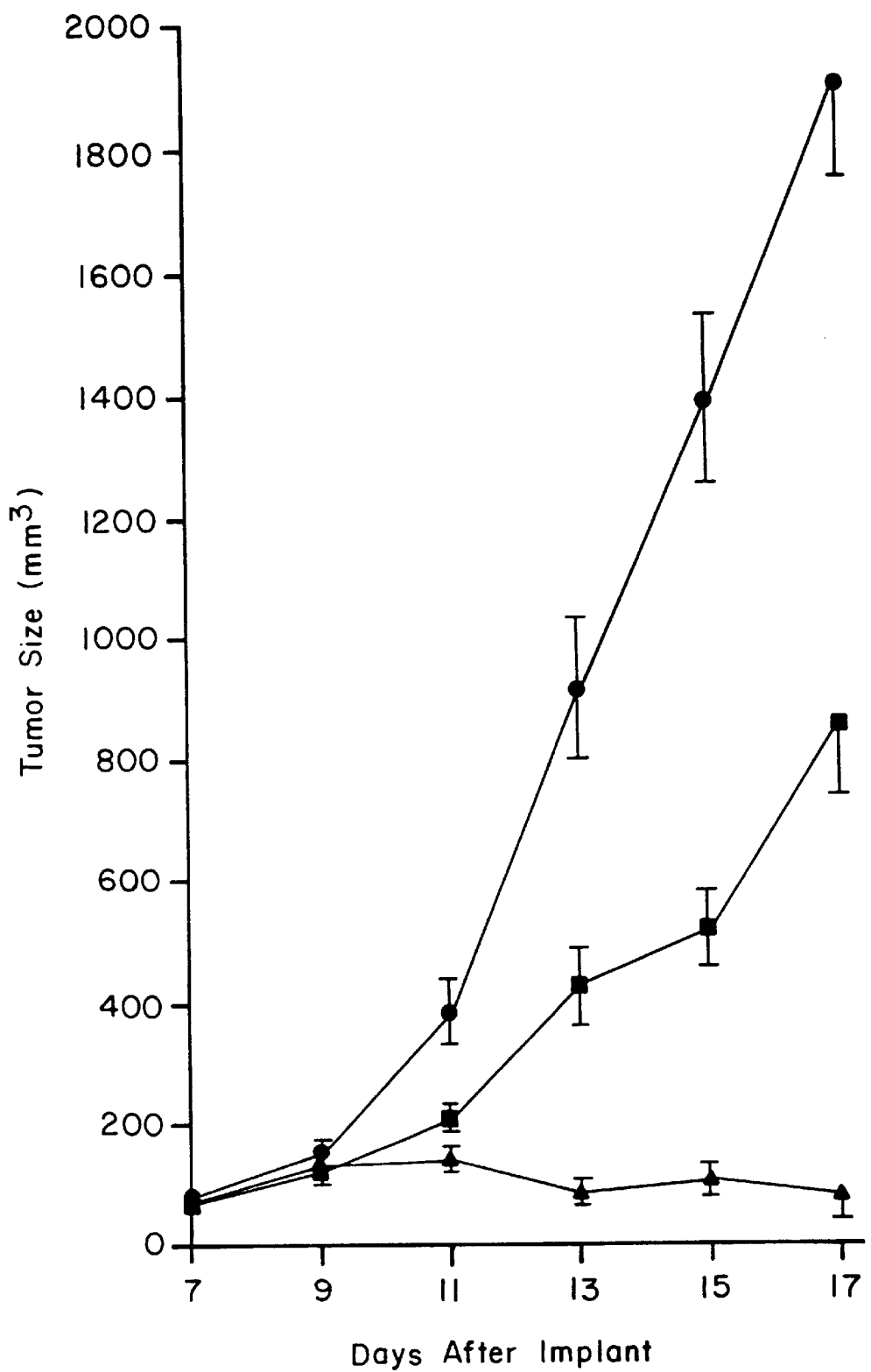
FIG. 45(A) shows comparative therapeutic effect of desoxyepothilone B and Taxol® on nude mice bearing MX-1 xenoplant. Tumor, s.c.; drug administered i.p., Q2Dx5, start on day 7. control (♦); Taxol® (□; 5 mg/kg, one half of $LD_{50}$); desoxyepothilone B (Δ; 25 mg/kg; nontoxic dose). (B) shows comparative therapeutic effect of desoxyepothilone B and Taxol® on nude mice bearing MX-1 xenoplant. Tumor, s.c.; drug administered i.p., Q2Dx5, start on day 7. control (♦); Taxol® (□; 5 mg/kg, one half of $LD_{50}$, given on days 7, 9, 11, 13, 15; then 6 mg/kg, given on days 17. 19, 23, 24, 25); desoxyepothilone B (n=3; Δ, x, *; 25 mg/kg, nontoxic dose, given to three mice on days 7, 9, 11, 13, 15; then 35 mg/kg, given on days 17. 19, 23, 24, 25).

[a]MX-1 tissue 50 μl/mouse was implanted s.c. on day 0. Every other day i.p. treatments were given on day 7, 9, 11, 13 and 15.
Number of mice in each group: Control, 8; Desoxyepothilone B, 6; Epothilone B, 7; Taxol ®, 7 and Vinblastine, 7. The average tumor volume of control group on day 11, 13, 15 and 17 were 386, 915, 1390 and 1903 mm$^3$, respectively. See FIG. 45.
[b]One out of six mice with no detectable tumor on day 35.
[c]Three mice died of drug toxicity on day 17. Every other day i.p. treatments were given except day 15.
[d]Four mice died of drug toxicity on day 13, 13, 13, 15.
[e]One mouse died of drug toxicity on day 15.

TABLE 14

Toxicity of Hematology and Chemistry of Desoxyepothilone B, and Taxol ® in Nude Mice Bearing Human MX-1 Xenograft[a]

| Drug | Dose (mg/kg ip) | Hematology[b] | | | | | Chemistry[b] | |
|---|---|---|---|---|---|---|---|---|
| | | WBC | | | | | | |
| | | Total (10$^3$/mm$^3$) | Neutrophils (%) | Lymph (%) | RBC (10$^3$/mm$^3$) | PLT (10$^6$/mm$^3$) | GOT (U/L) | GPT (U/L) |
| Control | | 12.9 | 38 | 61 | 8.1 | 800 (n = 4) | 203 | 45 (n = 4) |
| Desoxyepothilone B | 25 and 35[c] | 11.8 | 48 | 48 | 8.4 | 700 (n = 6) | 296 | 55 (n = 3) |
| Taxol ® | 5 and 6[d] | 10.9 | 51 | 48 | 6.1 | 1083 (n = 5) | 438 | 79 (n = 5) |
| Normal range[e] | | 6.91 ~ 12.9 | 8.25 ~ 40.8 | 62 ~ 90 | 10.2 ~ 12.0 | 190 ~ 340 | 260 | 138.7 |

[a]Minced MX-1 tumor tissue 50 μl/mouse was implanted s.c. on day 0.
[b]All assays were determined on day 30; averaged values were given.
[c]Desoxyepothilone B 25 mg/kg was given i.p on day 7, 9, 11, 13, 15; 35 mg/kg on day 17, 19, 23, 24, 25.
[d]Taxol ® 5 mg/kg was given i.p. on day 7, 9, 11, 13, 15; 6 mg/kg on day 17, 19, 23, 24, 25.
[e]Normal ranges are for wild type deer mice and C$_3$/HeJ mice (obtained from clinical, biochemical and hematological Reference values in Normal Experimental Animals, Brtjm Mitruka, ed., Masson Publishing USA, Inc., N.Y., 1977, and from Clinical Chemistry of Laboratory Animals, Weter F. Loeb, ed., Pergamon Press, 1989)

TABLE 15

Therapeutic Effect of Desoxyepothilone B, Taxol ®, Adriamycin, and Camptothecin in Nude Mice Bearing MDR Human MCF-7/Adr Tumor.

| Drug | Dose (mg/kg) | Average Body Weight Change (g) | | | | | Average Tumor Volume (T/C) | | | | Died |
|---|---|---|---|---|---|---|---|---|---|---|---|
| | | Day 8 | 11 | 13 | 15 | 17 | Day 11 | 13 | 15 | 17 | |
| Control | 0 | 25.0 | +2.0 | +2.6 | +3.1 | +3.7 | 1.00 | 1.00 | 1.00 | 1.00 | 0/8 |
| DesoxyEpoB | 35 | 25.0 | +0.3 | +0.7 | +0.6 | +0.8 | 0.31 | 0.27 | 0.30 | 0.34 | 0/8 |
| Taxol ® | 6 | 25.3 | +1.7 | +1.8 | +0.8 | +0.9 | 0.57 | 0.66 | 085 | 0.90 | 0/8 |
| | 12 | 24.5 | +0.7 | −1.3 | −2.4 | 0 | 0.50 | 0.51 | 0.32 | 0.40 | 3/6 |
| Adriamycin | 1.8 | 25.6 | +0.2 | −0.4 | −0.6 | −0.4 | 0.70 | 0.68 | 0.84 | 0.78 | 0/8 |
| | 3 | 24.6 | +0.5 | −1.5 | −3.2 | −1.6 | 0.66 | 0.83 | 0.57 | 0.53 | 3/6 |
| Camptothecin | 1.5 | 24.4 | +1.1 | +0.9 | +1.7 | +1.4 | 1.08 | 0.72 | 0.61 | 0.72 | 0/8 |
| | 3.0 | 24.5 | −0.6 | −0.4 | −0.8 | −0.9 | 0.95 | 0.76 | 0.61 | 0.43 | 0/6 |

[a]MCF-7/Adr cell 3 × 10$^6$/mouse was implanted s.c. on day 0. Every other day i.p. treatments were given on day 8, 10, 12, 14 and 16. The average tumor volume of control group on day 11, 13, 15 and 17 were 392, 919, 1499 and 2372 mm$^3$, respectively.

TABLE 16

Extended Experiment of Desoxyepothilone B, Taxol ® in Nude Mice Bearing Human MX-1 Xenograft[a]

| Drug | Dose (mg/kg) | Average Body Weight Change (g) | | | | | | Tumor Disappearance | | | | | Average Tumor Disappearance Duration (Day) | Died |
|---|---|---|---|---|---|---|---|---|---|---|---|---|---|---|
| | | Day 8 | 20 | 22 | 24 | 26 | 28 | Day 20 | 22 | 24 | 26 | 28 | | |
| Desoxyepo B | 40 | 23.0 | −1.7 | −2.4 | −2.4 | −1.4 | −1.2 | 2.10[b] | 2/10 | 3/10 | 5/10 | 5/10 | 44 (5/10) | 0/10 |
| Taxol ® | 5 | 24.0 | −1.6 | −0.3 | +0.1 | −0.6 | −0.4 | 0/10 | 0/10 | 0/10 | 0/10 | 0/10 | | 2/10 |
| | 10 | No Extended Test | | | | | | 1/6 on day 16, | | | | | Reappear on day 38 | 2/6$_{(0/6)}$ |

[a]Extended experiment was going on after 5 times injection (on day 8, 10, 12, 14 and 16). Every other day i.p. treatments were given continuously: Desoxyepothilone B and Taxol ® on day 18, 20, 22, 24 and 26; Control group mice were sacrificed.
[b]In one of the mice, a tumor reappeared on day 20.

As evident from Table 16, extended treatment of nude mice bearing human MX-1 zenografts with desoxyepothilone B results in complete tumor disappearance, with no mortality in any test animals. In conclusion, treatment with desoxyepothilone B shows remarkable specificity with respect to tumor toxicity, but very low normal cell toxicity.

TABLE 17

Therapeutic Effects of Desoxyepothilone B, Taxol ® in Nude Mice Bearing MX-1 Xenograft.

| | Treatment Schedule | # Died of toxicity |
|---|---|---|
| CONTROL | | 0/10 |

| Day | 8 | 10 | 12 | 14 | 16 | 18 | 20 | Sacrificed (n = 10) |
|---|---|---|---|---|---|---|---|---|
| Tumor Size (mm$^3$) | 19 ±2 | 78 ±8 | 151 ±15 | 372 ±55 | 739 ±123 | 1257 ±184 | 1991 ±331 | |

| DESOXYEPOTHILONE B | | 0/10 |
|---|---|---|

| Dose Schedule | 35 mg/kg on day | | | | | 40 mg/kg on day | | | | No Treatment | | | | | | |
|---|---|---|---|---|---|---|---|---|---|---|---|---|---|---|---|---|
| Day | 8 | 10 | 12 | 14 | 16 | 18 | 20 | 22 | 24 | 26 | 28 | 30 | 45 | 47 | 50 | 60 |

Tumor Size

| | 8 | 10 | 12 | 14 | 16 | 18 | 20 | 22 | 24 | 26 | 28 | 30 | 45 | 47 | 50 | 60 |
|---|---|---|---|---|---|---|---|---|---|---|---|---|---|---|---|---|
| Mouse 1 | 15 | 15 | 40 | 40 | 15 | 32 | 30 | 30 | 30 | 30 | 0 | 0 | 0 | 24 | S* | — |
| Mouse 2 | 23 | 23 | 15 | 15 | 15 | 15 | 30 | 48 | 48 | 0 | 30 | 48 | 900 | 1200 | S | — |
| Mouse 3 | 15 | 60 | 90 | 105 | 105 | 126 | 96 | 150 | 180 | 0 | 48 | 64 | 600 | 600 | S | — |
| Mouse 4 | 21 | 38 | 38 | 0 | 0 | 10 | 8 | 8 | 8 | 8 | 0 | 0 | 0 | 0 | 0 | 0 |
| Mouse 5 | 12 | 23 | 50 | 12 | 0 | 4 | 0 | 0 | 0 | 0 | 0 | 0 | 0 | 0 | 0 | 0 |
| Mouse 6 | 15 | 40 | 32 | 8 | 8 | 8 | 8 | 12 | 12 | 12 | 12 | 30 | 120 | 120 | S | — |
| Mouse 7 | 21 | 30 | 15 | 15 | 8 | 8 | 8 | 8 | 8 | 8 | 8 | 8 | 180 | 280 | S | — |
| Mouse 8 | 20 | 48 | 70 | 15 | 15 | 8 | 8 | 0 | 0 | 0 | 0 | 0 | 0 | 8 | S | — |

TABLE 17-continued

Therapeutic Effects of Desoxyepothilone B, Taxol ® in Nude Mice Bearing MX-1 Xenograft.

| | Treatment Schedule | # Died of toxicity |
|---|---|---|
| Mouse 9 | 25 50 40 15 8 0 0 0 0 0 0 0 0 0 4 4 | |
| Mouse 10 | 20 38 38 38 38 25 25 25 0 0 15 15 100 100 S — | |
| Taxol ® | | 2/10 |
| Dose | | |
| Schedule | 5 mg/kg on day     5 mg/kg on day | |
| Day | 8 10 12 14 16 18 20 22 24 26 28 30 45 47 50 60 | |
| Tumor Size | 17 45 54 128 311 596 1114 1930 2285 S (n = 10) | |
| | ±2 ±7 ±13 ±42 ±115 ±151 ±346 ±569 ±597 | |
| | Extended studies → Extended observations → Experiment ended | |

*S: Sacrificed due to tumor burden

TABLE 18

Toxicity of Epothilone B and Desoxyepothilone B in normal nude mice

| Group | Dose and Schedule (mg/kg) | Number of mice | Died |
|---|---|---|---|
| Control | | 4 | 0 |
| Epothilone B[a] | 0.6 QD × 4 | 8 | 8 |
| Desoxyepothilone B | 25 QD × 4 | 6 | 0 |

[a]Mice died of toxicity on day, 5,6,6,7,7,7,7,7

TABLE 19

Therapeutic effects of desoxyepothilone B (dEpo B) and Taxol ® in nude mice bearing MX-1 zenograft[a]

| Drugs | Dose (mg/kg) | Route[b] i.v. infusion | Average Body Weight (g) | | | | | Average Tumor Size (T/C) | | | | Tumor Disappearance |
|---|---|---|---|---|---|---|---|---|---|---|---|---|
| | | | Day 8 | 14 | 16 | 18 | 20 | Day 14 | 16 | 18 | 20 | |
| Control | 0 | | 30.2 | +0.8 | +1.7 | +2.6 | +3.2 | 1.00 | 1.00 | 1.00 | 1.00 | 0/5 |
| dEpo B | 30 | Q2D × 5 | 30.3 | −2.7 | −4.0 | −4.5 | −6.8 | 0.19 | 0.10 | 0.03 | TD[c] | 3/3 |
| Taxol ® | 15 | Q2D × 5 | 30.8 | 0 | −1.1 | −1.6 | −1.4 | 0.06 | 0.01 | TD | TD | 4/4 |
| | 24 | Q2D × 5 | 28.5 | −4.8 | −5.3 | −6.0 | −6.2 | 0.03 | TD | TD | TD | 4/4 |

[a]MX-1 human mammary carcinoma tissue 50 μg was implanted s.c. into mice on day 0. Every other day i.v. infusion were given on day 8, 10, 12, 14 and 16. The average tumor volume of control group on day 14, 16, 18 and 20 were 170 ± 10, 246 ± 29, 345 ± 42 and 529 ± 65 mm³ (mean "SEM"), respectively.
[b]The i.v. infusion was for 6 hrs. The vehicle used was in 100 Fl (Cremophor + EtOH = 1:1) + 4 ml saline.
[c]TD: Tumor disappearance.

TABLE 20

Therapeutic effects of desoxyepoB (dEpo B) and Taxol ® in nude mice bearing MCF-7 Adr xenograft[a]

| Drug | Dose (mg/kg) | Route[b] i.v. infusion | Average Body Weight (g) | | | | Average Tumor Size (T/C) | | | Toxicity death |
|---|---|---|---|---|---|---|---|---|---|---|
| | | | Day 8 | 14 | 16 | 18 | Day 14 | 16 | 18 | |
| Control | 0 | | 30.2 | +0.8 | +1.7 | +2.6 | 1.00 | 1.00 | 1.00 | 0/5 |
| dEpo B | 30 | Q2D × 5 | 30.3 | −2.7 | −4.0 | −4.5 | 0.16*** | 0.15 | 0.13*** | 0/3 |

TABLE 20-continued

Therapeutic effects of desoxyepoB (dEpo B) and Taxol ® in nude mice bearing MCF-7 Adr xenograft[a]

| Drug | Dose (mg/kg) | Route[b] i.v. infusion | Average Body Weight (g) | | | | Average Tumor Size (T/C) | | | Toxicity death |
|---|---|---|---|---|---|---|---|---|---|---|
| | | | Day 8 | 14 | 16 | 18 | Day 14 | 16 | 18 | |
| Taxol ® | 15 | Q2D × 5 | 30.8 | 0 | −1.1 | −1.6 | 0.81 | 0.89 | 0.76 | 0/4 |
| | 24 | Q2D × 5 | 28.5 | −4.8 | −5.3 | −6.0 | 0.73 | 0.71* | 0.73* | 0/4 |

[a]MCF-7/Adr human mammary adenocarcinoma tissue 50 µg was implanted s.c. into mice on day 0. Every other day i.v. infusion were given on a day 8, 10, 12, 14 and 16. The average tumor volume of control group on day 14, 16 and 18 were 1281 ± 145, 1767 ± 161 and 2381 ± 203 mm³ (mean ± SEM), respectively.
[b]The i.v. infusion n was for 6 hrs. The vehicle used was in 100 µl (Cremophor + EtOH = 1:1) + 4 ml saline.

In further tests, desoxyepothilone B showed similar anticancer efficacy as Taxol® in regular human tumor xenographs in nude mice, represented in Table 21. However, in drug-resistant tumors, desoxyepothilone B is by far better cancer therapeutic agent when compared with Taxol® in all tumors tested. Desoxyepothilone B is not only superior to Taxol® in many respects but is also a better therapeutic agent than epothilone B, camptothecin, vinblastine, adriamycin or VP-16 (etoposide) against many other tumors. See Table 21.

Stability of Desoxyepothilone B in Plasma

Figure 75:
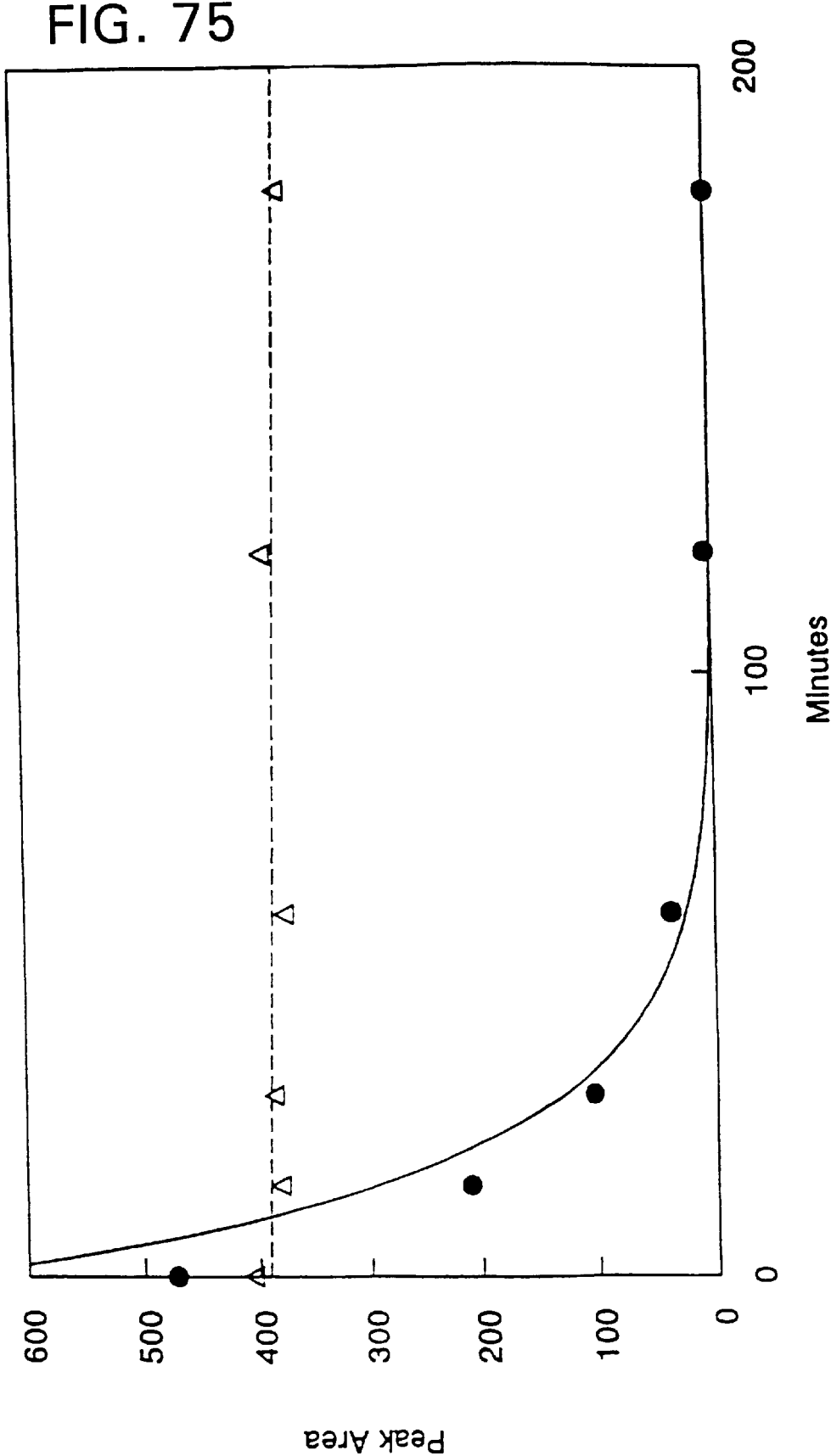
FIG. 75 shows the Epi stability in plasma of dEpoB: human (Δ) and mice (●).

As shown in FIG. 75, desoxyepothilone B is surprisingly and unexpectedly significantly more stable in human serum plasma than in mouse plasma. Desoxyepothilone B is relatively unstable in mouse plasma with a short half-life of about 15 or 20 min, but is very stable in human plasma with a half-life of about 75 hours. It is therefore likely that desoxyepothilone B can be particularly favorable in treating patients in view of the long lasting effects and the absence of a need to use prolonged i.v. infusions.

TABLE 20A

Therapeutic effects of desoxyepoB (dEpo B) and Taxol ® in nude mice bearing human ovarian UL3-C tumor[a].

| Drug | Dose (mg/kg) | Average Body Weight (g) | | | | | Average Tumor Size (T/C) | | | |
|---|---|---|---|---|---|---|---|---|---|---|
| | | Day 19 | 27 | 29 | 31 | 33 | Day 27 | 29 | 31 | 33 |
| Control | 0 | 30.9 | +0.9 | +0.8 | +0.4 | +0.1 | 1.00 | 1.00 | 1.00 | 1.00 |
| dEpo B | 30 | 30.0 | −1.5 | −4.0 | −3.6 | −2.7 | 0.19 | 0.13 | 0.03 | 0.03 |
| Taxol ® | 20 | 31.3 | −2.9 | −3.3 | −2.4 | −2.7 | 0.10 | 0.08 | 0.03 | 0.04 |

[a]UL3-C tissue (50 mg) was implanted s.c. into mice on day 0. I.V. infusions were given on day 19, 21, 23, 25 and 27. The average tumor volume of the control group on day 27, 29, 31 and 33 were 349, 378, 488 and 66 mm³, respectively.

TABLE 21

Comparison Between dEpoB and Taxol ® Chemotherapy in Nude Mice

| Tumor | Drugs | Doses Schedule | Lowest Average Tumor Size (T/C) | Tumor Disappearance | Therapeutic Effects dEpoB vs Taxol ® |
|---|---|---|---|---|---|
| A549 | dEpoB | 40 mg/kg Q2D × 3 | 0.01 | 1/3 | ≅ |
| Lung | Taxol ® | 15 mg/kg Q2D × 3 | 0.01 | 2/4 | |
| MX-1 | dEpoB | 30 mg/kg Q2D × 6 | 0 | 5/5 | ≅ |
| | Taxol ® | 15 mg/kg | 0 | 5/5 | |

TABLE 21-continued

Comparison Between dEpoB and Taxol ® Chemotherapy in Nude Mice

| Tumor | Drugs | Doses Schedule | Lowest Average Tumor Size (T/C) | Tumor Disappearance | Therapeutic Effects dEpoB vs Taxol ® |
|---|---|---|---|---|---|
| HT-29 | dEpoB | Q2D × 6 30 mg/kg | 0.02 | 0 | ≦ |
| Colon | Taxol ® | Q2D × 6 15mg/kg | 0.01 | 0 | |
| UL3-C | dEpoB | Q2D × 6 30 mg/kg | 0.03 | 0 | ≧ |
| Ovary | Taxol ® | Q2D × 5 15 mg/kg | 0.04 | 0 | |
| PC-3 | dEpoB | Q2D × 5 40 mg/kg | 0.12 | 0 | << |
| Prostate | Taxol ® | Q2D × 3 15 mg/kg | 0.02 | 0 | |
| SK-OV-3 | dEpoB | Q2D × 3 30 mg/kg | 0.17 | 0 | << |
| Ovary | Taxol ® | Q2D × 6 15 mg/kg | 0.02 | 1/4 | |
| MCF-7/Adr | dEpoB | Q2D × 6 30 mg/kg | 0.11 | 0 | >> |
| | | Q2D × 5 | | | |

TABLE 21-continued

Comparison Between dEpoB and Taxol ® Chemotherapy in Nude Mice

| Tumor | Drugs | Doses Schedule | Lowest Average Tumor Size (T/C) | Tumor Disappearance | Therapeutic Effects dEpoB vs Taxol ® |
|---|---|---|---|---|---|
| Breast | Taxol ® | 24 mg/kg Q2D × 5 | 0.71 | 0 | |
| CCRF/Taxol | dEpoB | 30 mg/kg Q2D × 6 | 0 | 3/3 | >>> |
| Leukemia | Taxol ® | 15 mg/kg Q2D × 6 | 1.09 | 0 | |
| CCRF/VBL | dEpoB | 30 mg/kg Q2D × 5 | 0 | 2/2 | >>> |
| Leukemia | Taxol ® | 15 mg/kg Q2D × 5 | 0.76 | 0 | |
| CCRF/CEM | dEpoB | 30 mg/kg Q2D × 5 | 0 | 2/2 | ≅ |
| Leukemia | Taxol ® | 15 mg/kg Q2D × 5 | 0 | 2/2 | |

TABLE 22

Comparison of Cancer Chemotherapeutic Effects

| Tumor | Route of Administation | Therapeutic effect Rank Order |
|---|---|---|
| B 16 Melanoma | i.p. | dEpoB > Taxol ® > > EpoB |
| MX-1 | i.p. | dEpoB > Camptothecin > Taxol ® > VBL, EpoB |
| MX-1 | i.p. | dEpoB > Adriamycin > Taxol ® |
| SK-OV-3 | i.v./i.p. | Taxol ® ≈ dEpoB |
| PC-3 | i.v./i.p. | Taxol ® > dEpoB > > Adriamycin |
| MCF-7/Adr | i.p. | dEpoB > > Camptothecin > Adriamycin > Taxol ® |
| MX-1 | i.v. infusion | Taxol ® ≈ dEpoB |
| MCF-7/Adr | i.v. infusion | dEpoB > > VP-16, Taxol ® > VBL, Adriamycin |
| CCRF-CEM | i.v. infusion | dEpoB ≈ Taxol ® |
| CCRF-CEM/Taxol ® | i.v. infusion | dEpoB > > > Taxol ® |
| CCRF-CEM/VBL | i.v. infusion | dEpoB > > > Taxol ® |
| SK-OV-3 | i.v. infusion | Taxol ® > dEpoB |
| HT-29 | i.v. infusion | Taxol ® ≧ dEpoB |
| A549 | i.v. infusion | Taxol ®, dEpoB, VBL > VP-16 |
| PC-3 | i.v. infusion | Taxol ®, VBL ≧ dEpoB > > VP-16 |

TABLE 23

Therapeutic Effects of DesoxyepoB and Taxol ® in Nude Mice Bearing Human Lymphoblastic Leukemia CCRF-CEM[a].

| | | Average Body Weight Changes (g) | | | | | | | | | |
|---|---|---|---|---|---|---|---|---|---|---|---|
| Drug | Dose | Day 21 | 23 | 25 | 27 | 29 | 31 | 33 | 35 | 37 | 39 | 41 |
| Control 1 | 0 | 29.0 | +0.1 | −1.1 | −0.2 | +0.8 | +0.1 | End | End | End | End | End |
| DesoxyepoB | 40 | 26.6 | −1.4 | −3.6 | −3.9 | −5.2 | −4.2 | −3.1 | −2.3 | −1.2 | −0.2 | +0.9 |
| Taxol ® | 20 | 29.0 | −0.1 | −1.9 | −2.9 | −3.0 | −3.6 | −2.6 | −0.5 | +1.2 | +1.3 | +2.1 |

| | | Average Tumor Size (T/C) Proportion of Tumor Disappearance (n/total) | | | | | | | | | |
|---|---|---|---|---|---|---|---|---|---|---|---|
| | | Day 21 | 23 | 25 | 27 | 29 | 31 | 33 | 35 | 37 | 39 | 41 |
| Control | 0 | 1.00 0/5 | 1.00 0/5 | 1.00 0/5 | 1.00 0/5 | 1.00 0/5 | End | End | End | End | End | End |
| DesoxyepoB | 40 | 1.10 0/3 | 0.73 0/3 | 0.31 0/3 | 0.09 0/3 | 0 3/3 | 0 3/3 | 0 3/3 | 0 3/3 | ND[b] 1/3 | ND 1/3 | ND 0/3 |
| Taxol ® | 20 | 1.17 0/4 | 0.78 0/4 | 0.44 0/4 | 0.11 1/4 | 0 4/4 | 0 4/4 | 0 4/4 | 0 1/4 | ND 0/4 | ND 0/4 | ND 0.4 |

[a]CCRF-CEM tissue (50 μg) was implanted s.c. into mice on day 0. I.V. infusion 6 hr were given on day 21, 23, 25 and 27. The average tumor volumes of the control group on day 23, 25, 27, 29 and 31 were 376 ± 100 427 ± 130, 685 ± 144, 850 ± 155, and 1062 ± 165 mm$^3$ (mean ± SEM), respectively.
[b]Tumor reappeared.
"End": Test ended because of tumor burden.

TABLE 24

Therapeutic Effects of dEpoB, Taxol ®, VBL and VP-16 in Nude Mice Bearing Human Lung Carcinoma A549

| Drugs | Dose (mg/kg) Q2D × 3 | i.v. infusion (hrs) | Average Body Weight (g) | | | | Average Tumor Size (mm³) | | | | Tumor Disappearance |
|---|---|---|---|---|---|---|---|---|---|---|---|
| | | | Day 7 | 11 | 13 | 15 | Day 11 | 13 | 15 | 17 | |
| Control | 0 | 6 | 26.4 | +1.3 | +0.6 | +0.2 | 96 | 128 | 306 | 553 | 0/4 |
| dEpoB | 30 | 18 | 29.3 | −2.0 | −5.8 | −5.6 | 17 | 21 | 26 | 21 | 1/3 |
| | 40 | 6 | 27.8 | −1.6 | −3.2 | −2.4 | 31 | 19 | 4 | 4 | 1/3 |
| | 50 | 6 | 27.1 | −2.0 | −3.2 | −2.5 | 33 | 19 | 6 | 6 | 1/2 |
| Taxol ® | 15 | 6 | 27.6 | −1.2 | −0.8 | +0.5 | 49 | 32 | 7 | 6 | 2/4 |
| | 24 | 6 | 28.5 | −2.1 | −2.7 | −0.9 | 14 | 8 | 0 | 0 | 4/4 |
| VBL | 2 | i.v. inj | 25.5 | +13.4 | +2.3 | +3.2 | 11 | 11 | 11 | 7 | 2/3 |
| VP-16 | 25 | i.v. inj | 27.2 | +0.1 | −0.2 | −2.2 | 59 | 150 | 275 | 536 | 0/3 |

TABLE 25

Therapeutic Effects of dEpoB, Taxol ®, VBL and VP-16 in Nude Mice Bearing Human Prostate Adenocarcinoma PC-3

| Drugs | Dose (mg/kg) | i.v. infusion (hrs) | Average Body Weight (g) | | | | Average Tumor Size (T/C) | | | Tumor Disappearance |
|---|---|---|---|---|---|---|---|---|---|---|
| | | | Day 5 | 9 | 11 | 13 | Day 9 | 11 | 13 | |
| Control | 0 | 6 | 26.5 | +1.4 | +0.5 | +0.1 | 1.00 | 1.00 | 1.00 | 0/5 |
| dEpoB | 30 | 18 | 29.4 | −2.2 | −5.9 | −5.8 | 0.17 | 0.06 | 0.06 | 0/3 |
| | 40 | 6 | 28.3 | −1.7 | −3.4 | −2.7 | 0.40 | 0.19 | 0.12 | 0/3 |
| | 50 | 6 | 28.1 | −2.1 | −3.0 | −2.6 | 0.37 | 0.13 | 0.03 | 0/3 |
| Taxol ® | 16 | 6 | 26.6 | −1.1 | −0.9 | +0.4 | 0.34 | 0.09 | 0.02 | 0/4 |
| | 24 | 6 | 28.8 | −2.2 | −2.8 | −0.8 | 0.18 | 0.05 | 0.06 | 2/4 |
| VBL | 2 | i.v. inj | 23.5 | +1.4 | +2.1 | +3.0 | 0.37 | 0.13 | 0.03 | 1/3 |
| VP-16 | 25 | i.v. inj | 24.9 | +0.3 | −0.1 | −2.4 | 1.00 | 1.12 | 0.88 | 0/3 |

PC-3 tissue (50 µg) was implanted s.c into mice on day 0. I.V. infusions were given on day 5, 7 and 9. The average tumor volumes of control group subjects on 9, 11 and 13 day were 766 ± 50, 1457 ± 180 and 2441 ± 221 mm³ (mean ± SEM), respectively.

TABLE 26

Therapeutic Effects of DesoxyepoB and Taxol ® in Nude Mice Bearing Human Lymphoblastic Leukemia CCRF-CEM.

| Drug | Dose Q2D × 4 | Average Body Weight Change (g) | | | | | | Average Tumor Size (T/C) | | | | | Tumor Disappearance |
|---|---|---|---|---|---|---|---|---|---|---|---|---|---|
| | | Day 21 | 23 | 25 | 27 | 29 | 31 | Day 23 | 25 | 27 | 29 | 31 | |
| Control | 0 | 29.0 | +0.1 | −1.1 | −0.2 | +0.8 | +0.1 | 1.00 | 1.00 | 1.00 | 1.00 | 1.00 | 0/5 |
| DesoxyepoB | 40 | 26.6 | −1.4 | −3.6 | −3.9 | −5.2 | −4.2 | 0.68 | 0.30 | 0.09 | 0 | 0 | 3/3 |
| Taxol | 20 | 29.0 | −0.1 | −1.9 | −2.9 | −3.0 | −3.6 | 0.78 | 0.44 | 0.11 | 0 | 0 | 4/4 |

CCRF-CEM tissue (50 µg) was implanted s.c into mice on day 0. I.V. infusion 6 hr were given on day 21, 23, 25 and 27. The average tumor volume of the control group on day 23, 25, 27, 29 and 31 were 376 ± 100 427 ± 130, 685 ± 144, 850 ± 155, and 1062 ± 165 mm³ (mean ± SEM), respectively.

TABLE 27

Comparison of Therapeutic Effects and Toxicity of dEpoB and Paclitaxel with Different Solvents, Routes and Schedules of Administration Using a Non-MDR MX-1 Xenograft[a]

| Route | Solvent[b] | Dose (mg/kg)[c] | Therapeutic Effect against MX-1 Xenograft[d] | | Toxicity toward Nude Mice[e] | |
|---|---|---|---|---|---|---|
| | | | dEpoB | Paclitaxel | DepoB | Paclitaxel |
| i.p | DMSO | 35 Q2D × 5 | + + + + + | + + + + + | + + | + + |
| | Cremophor-EtOH | 15 Q2D × 5 | + | + + | + + + + + | + + + + |
| i.v. injection | DMSO | 15 Q2D × 5 | + + | + + + + | + + + | + + |
| | | 24 Q2D × 5 | + + | + + + + | + + + | + + |
| i.v. infusion | Cremophor-EtOH | | | | | |
| | 6 hr | 30 Q2D × 5 | + + + + + | + + + + + | + + | + + |
| | 24 hr | 60 Q4D × 2 | + + + + + | ND[f] | + + + | ND[f] |

[a]Approximate relative scale: +, marginal; + +, little; + + +, moderate; + + + +, substantial; + + + + +, marked.
[b]DMSO: dimethylsulfoxide; Cremophor: EtOH (1:1).
[c]The dose of dEpoB.
[d]Based on tumor volume reduction when compared with the untreated control.
[e]Based on body weight decrease or lethality.
[f]Not done.

What is claimed is:

1. A method of preparing a protected ketoester desoxyepothilone precursor having the structure:

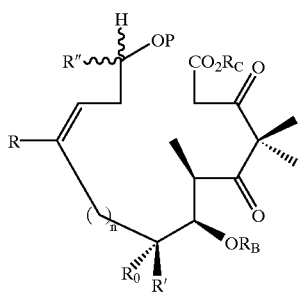

wherein P is a linear or branched alkyl, alkoxyalkyl, substituted or unsubstituted aryloxyalkyl, trialkylsilyl, aryldialkylsilyl, diarylalkylsilyl or triarylsilyl; wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyl-oxycarbonyl, (dialkylarylsilyl)alkyloxycarbonyl, benzyl, trialkylsilyl, dialkylarylsilyl, alkyldiarylsilyl, triarysilyl, a linear or branched acyl, substituted or unsubstituted aroyl or benzoyl; and wherein $R_C$ is tertiary-alkyl; which comprises coupling a terminal vinyl enol ether ester having the structure:

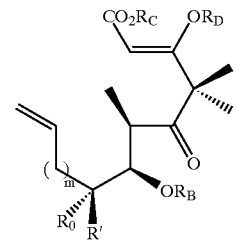

wherein R, $R_0$, $R_B$, $R_C$, and R' are defined as above; wherein m is 0, 1 or 2; and wherein $R_D$ is linear or branched alkyl, benzyl, trialkylsilyl, dialkylarylsilyl, alkyldiarylsilyl, linear or branched acyl, substituted or unsubstituted aroyl or benzoyl; with a protected halovinyl or metalvinyl compound having the structure:

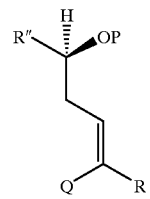

wherein R, P and R" are defined as above; and wherein Q is a halide or a metal; under suitable conditions to form the protected ketoester desoxyepothilone precursor.

2. The method of claim 1 wherein n is 3 and R" is 2-methyl-1,3-thiazolinyl.

3. The method of claim 1 wherein $R_A$ is TES and $R_B$ is Troc.

4. The method of claim 1 wherein P is TBS or TES.

5. The method of claim 1 wherein Q is iodine or bromine.

6. The method of claim 1 wherein $R_D$ is methyl or TES.

7. The method of claim 1 wherein the coupling step comprises contacting the terminal vinyl enol ether ester and the protected halovinyl compound with noble metal complex capable of effecting a Suzuki coupling.

8. The method of claim 1 wherein the noble metal complex is $Pd(dppf)_2Cl_2$ in the presence of $Ph_3As$ and $Cs_2CO_3$.

9. A method of preparing a hydroxy ester desoxyepothilone precursor having the structure:

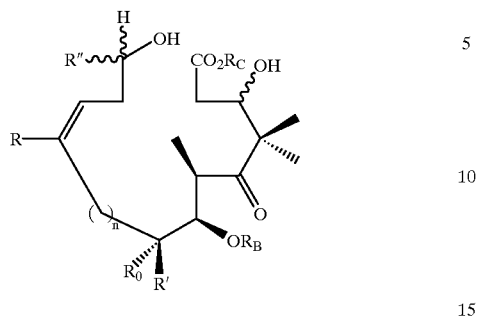

wherein R, R₀, and R' are independently H, linear or branched chain alkyl, optionally substituted by hydroxy, alkoxy, carboxy, carboxaldehyde, linear or branched alkyl or cyclic acetal, fluorine, NR₁R₂, N-hydroximino, or N-alkoxyimino, wherein R₁ and R₂ are independently H, phenyl, benzyl, linear or branched chain alkyl; wherein R'' is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyloxycarbonyl, (dialkylarylsilyl)alkyloxycarbonyl, benzyl, trialkylsilyl, dialkylarylsilyl, alkyldiarylsilyl, triarysilyl, linear or branched acyl, substituted or unsubstituted aroyl or benzoyl; and wherein $R_C$ is tertiary-alkyl; which comprises:

(1) preparing a terminal vinyl enol ether ester having the structure:

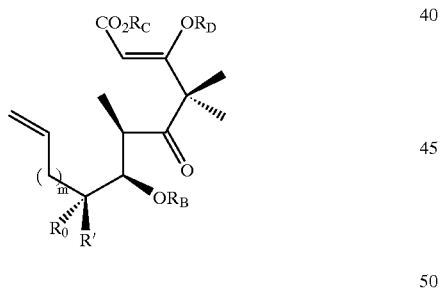

wherein R₀ and R' are independently H, linear or branched chain alkyl, optionally substituted by hydroxy, alkoxy, carboxy, carboxaldehyde, linear or branched alkyl or cyclic acetal, fluorine, NR₁R₂, N-hydroximino, or N-alkoxyimino, wherein R₁ and R₂ are independently H, phenyl, benzyl, linear or branched chain alkyl; wherein m is 0, 1 or 2; wherein $R_B$ is hydrogen, t-butyloxycarbonyl, amyloxycarbonyl, (trialkylsilyl)alkyl-oxycarbonyl, (dialkylarylsilyl)alkyloxycarbonyl, benzyl, trialkylsilyl, dialkylarylsilyl, alkyldiarylsilyl, triarysilyl, linear or branched acyl, substituted or unsubstituted aroyl or benzoyl; wherein $R_C$ is tertiary-alkyl; and wherein $R_D$ is linear or branched alkyl, benzyl, trialkylsilyl, dialkylarylsilyl, alkyldiarylsilyl, triarysilyl, linear or branched acyl, substituted or unsubstituted aroyl or benzoyl; which comprises:

(a) treating a keto enol ester having the structure,

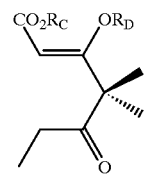

under suitable conditions to form an enolate enol ester having the structure:

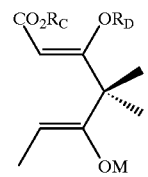

wherein M is Li, Na or K; and (b) coupling the enolate enol ester with a vinyl aldehyde having the structure:

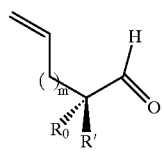

wherein m, and R₀ and R' are as defined above; under suitable condition, to form the terminal vinyl enol ether ester;

(2) preparing a protected ketoester desoxyepothilone precursor having the structure:

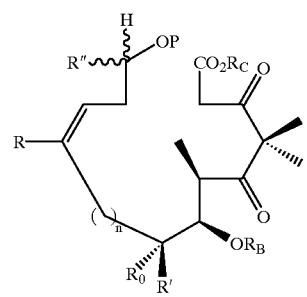

wherein P is a linear or branched alkyl, alkoxyalkyl, substituted or unsubstituted aryloxyalkyl, trialkylsilyl, aryldialkylsilyl, diarylalkylsilyl or triarylsilyl; wherein R, R₀, and R' are independently H, linear or branched chain alkyl, optionally substituted by hydroxy, alkoxy, carboxy, carboxaldehyde, linear or branched alkyl or cyclic acetal, fluorine, NR₁R₂, N-hydroximino, or N-alkoxyimino, wherein R₁ and R₂ are independently H, phenyl, benzyl, linear or branched chain alkyl; wherein R'' is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyl-oxycarbonyl, (dialkylarylsilyl) alkyloxycarbonyl, benzyl, trialkylsilyl, dialkylarylsilyl, alkyldiarylsilyl, triarysilyl, a linear or branched acyl, substituted or unsubstituted aroyl or benzoyl; and wherein $R_C$ is tertiary-alkyl; which comprises coupling the terminal vinyl enol ether ester having the structure:

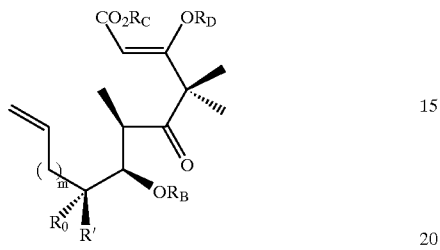

wherein R, $R_0$, $R_B$, $R_C$, and R' are defined as above; wherein m is 0, 1 or 2; and wherein $R_D$ is linear or branched alkyl, benzyl, trialkylsilyl, dialkylarylsilyl, alkyldiarylsilyl, linear or branched acyl, substituted or unsubstituted aroyl or benzoyl; with a protected halovinyl or metalvinyl compound having the structure:

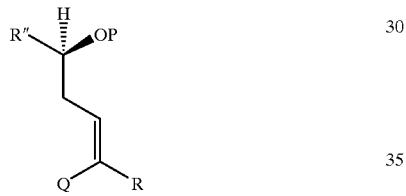

wherein R, P and R" are defined as above; and wherein Q is a halide or a metal; under suitable conditions to form the protected ketoester desoxyepothilone precursor, (3) preparing a hydroxy ketoester desoxyepothilone precursor having the structure:

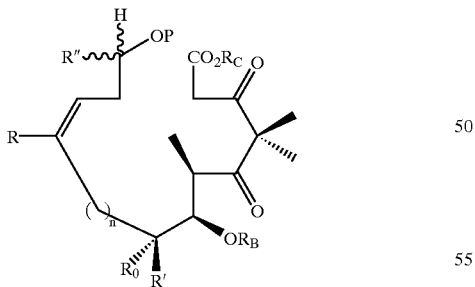

wherein P is H; wherein R, $R_0$, and R' are independently H, linear or branched chain alkyl, optionally substituted by hydroxy, alkoxy, carboxy, carboxaldehyde, linear or branched alkyl or cyclic acetal, fluorine, $NR_1R_2$, N-hydroximino, or N-alkoxyimino, wherein $R_1$ and $R_2$ are independently H, phenyl, benzyl, linear or branched chain alkyl; wherein R" is —CY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein n is 2 or 3; wherein $R_B$ is hydrogen, t-butyloxycarbonyl, amyloxycarbonyl, (trialkylsilyl)alkyloxycarbonyl, (dialkylarylsilyl) alkyloxycarbonyl, benzyl, trialkylsilyl, dialkylarylsilyl, alkyldiarylsilyl, triarysilyl, a linear or branched acyl, substituted or unsubstituted aroyl or benzoyl; and wherein $R_C$ is tertiary-alkyl; which comprises deprotecting the protected ketoester desoxyepothilone precursor having the structure:

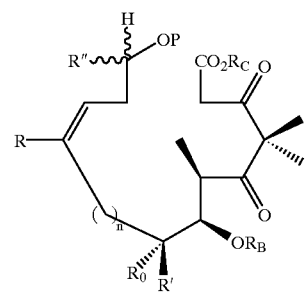

wherein R, $R_0$, $R_A$, $R_B$, $R_C$, R', R" and n are defined as above; and wherein P is a linear or branched alkyl, alkoxyalkyl, substituted or unsubstituted aryloxyalkyl, trialkylsilyl, aryldialkylsilyl, diarylalkylsilyl or triarylsilyl; under suitable conditions to form the hydroxy ketoester desoxyepothilone precursor; and (4) reducing the hydroxy ketoester desoxyepothilone precursor having the structure:

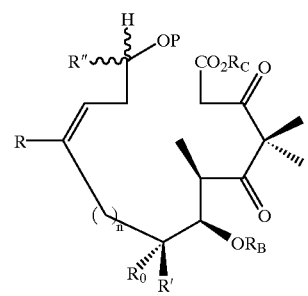

wherein P, R, $R_0$, $R_B$, $R_C$, R', R" and n are defined as above; under suitable conditions to form the hydroxy ester desoxyepothilone precursor.

* * * * *

UNITED STATES PATENT AND TRADEMARK OFFICE
CERTIFICATE OF CORRECTION

| | | |
|---|---|---|
| PATENT NO. | : 6,204,388 B1 | Page 1 of 1 |
| APPLICATION NO. | : 09/257072 | |
| DATED | : March 20, 2001 | |
| INVENTOR(S) | : Samuel Danishefsky | |

It is certified that error appears in the above-identified patent and that said Letters Patent is hereby corrected as shown below:

In the Specification

In column 1, beginning at line 17 and ending at line 21, please delete:

"This invention was made with government support under grants CA-28824, CA-39821, CA-GM 72231, GM-18248, CA-62948, and AI0-9355 from the National Institutes of Health, and grant CHE-9504805 from the National Science Foundation."

and insert:

--This invention was made with government support under grant numbers: AI009355, CA028824, CA062948, CA081704, GM072231, GM199721 awarded by National Institutes of Health and DAMD17-98-1-8155 awarded by the Army Medical Research and Materiel Command. The government has certain rights in the invention.--

Signed and Sealed this
Twenty-ninth Day of March, 2016

Michelle K. Lee
*Director of the United States Patent and Trademark Office*